(12) United States Patent
Sah et al.

(10) Patent No.: US 11,542,506 B2
(45) Date of Patent: Jan. 3, 2023

(54) COMPOSITIONS AND METHODS OF TREATING AMYOTROPHIC LATERAL SCLEROSIS (ALS)

(71) Applicant: VOYAGER THERAPEUTICS, INC., Cambridge, MA (US)

(72) Inventors: Dinah Wen-Yee Sah, Cambridge, MA (US); Jinzhao Hou, Lexington, MA (US); Mathieu E. Nonnenmacher, Cambridge, MA (US); Pengcheng Zhou, Lexington, MA (US); Markus Hossbach, Kulmbach (DE); Jochen Deckert, Bayreuth (DE)

(73) Assignee: Voyager Therapeutics, Inc., Cambridge, MA (US)

( * ) Notice: Subject to any disclaimer, the term of this patent is extended or adjusted under 35 U.S.C. 154(b) by 176 days.

(21) Appl. No.: 17/143,036

(22) Filed: Jan. 6, 2021

(65) Prior Publication Data

US 2021/0139915 A1 May 13, 2021

Related U.S. Application Data

(62) Division of application No. 16/774,493, filed on Jan. 28, 2020, now Pat. No. 10,920,227, which is a division of application No. 15/526,690, filed as application No. PCT/US2015/060562 on Nov. 13, 2015, now Pat. No. 10,597,660.

(60) Provisional application No. 62/234,466, filed on Sep. 29, 2015, provisional application No. 62/211,992, filed on Aug. 31, 2015, provisional application No. 62/079,588, filed on Nov. 14, 2014.

(51) Int. Cl.
*C12N 15/11* (2006.01)
*C12N 15/113* (2010.01)

(52) U.S. Cl.
CPC .. *C12N 15/1137* (2013.01); *C12Y 115/01001* (2013.01); *C12N 2310/14* (2013.01); *C12N 2330/51* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,064,764 A | 11/1991 | Besnainon |
| 5,171,680 A | 12/1992 | Mullenbach et al. |
| 5,474,935 A | 12/1995 | Chatterjee |
| 5,587,308 A | 12/1996 | Carter |
| 5,652,224 A | 7/1997 | Wilson |
| 5,658,785 A | 8/1997 | Johnson |
| 5,688,676 A | 11/1997 | Zhou |
| 5,691,176 A | 11/1997 | Lebkowski |
| 5,693,531 A | 12/1997 | Chiorini |
| 5,741,683 A | 4/1998 | Zhou |
| 5,756,283 A | 5/1998 | Wilson |
| 5,856,152 A | 1/1999 | Wilson |
| 5,858,351 A | 1/1999 | Podsakoff |
| 5,858,775 A | 1/1999 | Johnson |
| 5,866,552 A | 2/1999 | Wilson |
| 5,866,696 A | 2/1999 | Carter |
| 5,871,982 A | 2/1999 | Wilson |
| 5,952,221 A | 9/1999 | Kurtzman |
| 5,962,313 A | 10/1999 | Podsakoff |
| 5,989,540 A | 11/1999 | Carter |
| 6,083,716 A | 7/2000 | Wilson |
| 6,143,548 A | 11/2000 | O'Riordan |
| 6,143,567 A | 11/2000 | Van Agthoven |
| 6,146,874 A | 11/2000 | Zolotukhin |
| 6,156,303 A | 12/2000 | Russell |
| 6,174,527 B1 | 1/2001 | Wilson |
| 6,180,613 B1 | 1/2001 | Kaplitt |
| 6,194,191 B1 | 2/2001 | Zhang |
| 6,200,560 B1 | 3/2001 | Couto |
| 6,204,059 B1 | 3/2001 | Samulski |
| 6,211,163 B1 | 4/2001 | Podsakoff |
| 6,251,677 B1 | 6/2001 | Wilson |
| 6,258,595 B1 | 7/2001 | Gao |
| 6,261,551 B1 | 7/2001 | Wilson |
| 6,265,389 B1 | 7/2001 | Burke |
| 6,270,996 B1 | 8/2001 | Wilson |
| 6,274,354 B1 | 8/2001 | Wilson |
| 6,281,010 B1 | 8/2001 | Gao |
| 6,325,998 B1 | 12/2001 | Podsakoff |
| 6,335,011 B1 | 1/2002 | Podsakoff |
| 6,365,394 B1 | 4/2002 | Gao |
| 6,387,368 B1 | 5/2002 | Wilson |
| 6,399,385 B1 | 6/2002 | Croyle |

(Continued)

FOREIGN PATENT DOCUMENTS

| | | | |
|---|---|---|---|
| AU | 2007201330 A1 | 4/2007 | |
| CA | 2453183 A1 | 1/2003 | |

(Continued)

OTHER PUBLICATIONS

U.S. Appl. No. 15/526,690, filed May 12, 2017, Dinah Wen-Yee Sah, U.S. Pat. No. 10,597,660.
U.S. Appl. No. 16/774,493, filed Jan. 28, 2020, Dinah Wen-Yee Sah, U.S. Pat. No. 10,920,227.
U.S. Appl. No. 16/756,586, filed Apr. 16, 2020, Dinah Wen-Yee Sah, US 2020-0239912.
U.S. Appl. No. 16/611,054, filed Nov. 5, 2019, Dinah Wen-Yee Sah, US 2020-0123574.
U.S. Appl. No. 16/756,595, filed Apr. 16, 2020, Dinah Wen-Yee Sah, US 2020-0237799.

(Continued)

*Primary Examiner* — Ekaterina Poliakova-Georgantas
(74) *Attorney, Agent, or Firm* — Nelson Mullins Riley & Scarborough LLP; Jane E. Remillard, Esq.; Cynthia L. Kanik

(57) ABSTRACT

The present invention relates to small interfering RNA (siRNA) molecules against the SOD1 gene, adeno-associated viral (AAV) vectors encoding siRNA molecules and methods for treating amyotrophic lateral sclerosis (ALS) using the siRNA molecules and AAV vectors.

30 Claims, 12 Drawing Sheets
Specification includes a Sequence Listing.

(56) References Cited

U.S. PATENT DOCUMENTS

| | | |
|---|---|---|
| 6,410,300 B1 | 6/2002 | Samulski |
| 6,416,992 B1 | 7/2002 | Mejza |
| 6,428,988 B1 | 8/2002 | Wilson |
| 6,436,392 B1 | 8/2002 | Engelhardt |
| 6,436,394 B1 | 8/2002 | Henderson |
| 6,468,524 B1 | 10/2002 | Chiorini |
| 6,468,771 B1 | 10/2002 | Einerhand |
| 6,475,769 B1 | 11/2002 | Wilson |
| 6,482,634 B1 | 11/2002 | Wilson |
| 6,485,966 B2 | 11/2002 | Gao |
| 6,503,888 B1 | 1/2003 | Kaplitt |
| 6,509,150 B1 | 1/2003 | Salvetti |
| 6,521,426 B1 | 2/2003 | Ciliberto |
| 6,555,525 B2 | 4/2003 | Burke |
| 6,566,118 B1 | 5/2003 | Atkinson |
| 6,582,692 B1 | 6/2003 | Podsakoff |
| 6,593,123 B1 | 7/2003 | Wright |
| 6,610,290 B2 | 8/2003 | Podsakoff |
| 6,642,051 B1 | 11/2003 | Lynch |
| 6,660,514 B1 | 12/2003 | Zolotukhin |
| 6,660,521 B2 | 12/2003 | Brough |
| 6,670,176 B1 | 12/2003 | Samulski |
| 6,676,935 B2 | 1/2004 | Henderson |
| 6,699,706 B1 | 3/2004 | Brooks |
| 6,710,036 B2 | 3/2004 | Kurtzman |
| 6,723,551 B2 | 4/2004 | Kotin |
| 6,726,907 B1 | 4/2004 | Zhang |
| 6,753,419 B1 | 6/2004 | Toniatti |
| 6,759,237 B1 | 7/2004 | Wilson |
| 6,846,665 B1 | 1/2005 | Horer |
| 6,855,314 B1 | 2/2005 | Chiorini |
| 6,887,463 B2 | 5/2005 | Wilson |
| 6,897,045 B2 | 5/2005 | Engelhardt |
| 6,933,310 B1 | 8/2005 | Ikeda |
| 6,943,019 B2 | 9/2005 | Wilson |
| 6,953,690 B1 | 10/2005 | Gao |
| 6,984,517 B1 | 1/2006 | Chiorini |
| 6,995,006 B2 | 2/2006 | Atkinson |
| 7,015,026 B2 | 3/2006 | O'Riordan |
| 7,022,519 B2 | 4/2006 | Gao |
| 7,048,920 B2 | 5/2006 | Yu |
| 7,056,502 B2 | 6/2006 | Hildinger |
| 7,070,998 B2 | 7/2006 | Johnson |
| 7,091,030 B2 | 8/2006 | Setiawan |
| 7,094,604 B2 | 8/2006 | Snyder |
| 7,097,980 B2 | 8/2006 | Barany et al. |
| 7,105,345 B2 | 9/2006 | Wilson |
| 7,112,321 B2 | 9/2006 | Wang |
| 7,125,705 B2 | 10/2006 | Colosi |
| 7,125,706 B2 | 10/2006 | Zhang |
| 7,166,434 B2 | 1/2007 | Barany et al. |
| 7,169,612 B2 | 1/2007 | Kostenis |
| 7,186,552 B2 | 3/2007 | Wilson |
| 7,198,951 B2 | 4/2007 | Gao |
| 7,223,585 B2 | 5/2007 | Coffey |
| 7,235,393 B2 | 6/2007 | Gao |
| 7,238,526 B2 | 7/2007 | Wilson |
| 7,241,447 B1 | 7/2007 | Engelhardt |
| 7,247,472 B2 | 7/2007 | Wilson |
| 7,271,002 B2 | 9/2007 | Kotin |
| 7,282,199 B2 | 10/2007 | Gao |
| 7,291,498 B2 | 11/2007 | Roy |
| 7,300,797 B2 | 11/2007 | Van Agthoven |
| 7,306,794 B2 | 12/2007 | Wilson |
| 7,312,039 B2 | 12/2007 | Barany et al. |
| 7,319,002 B2 | 1/2008 | Wilson |
| 7,320,865 B2 | 1/2008 | Barany et al. |
| 7,326,555 B2 | 2/2008 | Konz |
| 7,332,285 B2 | 2/2008 | Barany et al. |
| 7,342,111 B2 | 3/2008 | Lewin et al. |
| 7,344,872 B2 | 3/2008 | Gao |
| 7,364,858 B2 | 4/2008 | Barany et al. |
| 7,419,817 B2 | 9/2008 | Chiorini |
| 7,419,956 B2 | 9/2008 | Ohtaki |
| 7,429,453 B2 | 9/2008 | Barany et al. |
| 7,445,930 B2 | 11/2008 | Zhang |
| 7,459,547 B2 | 12/2008 | Zamore et al. |
| 7,465,583 B2 | 12/2008 | Samulski et al. |
| 7,479,554 B2 | 1/2009 | Chiorini |
| 7,491,508 B2 | 2/2009 | Roy |
| 7,498,316 B2 | 3/2009 | Xu et al. |
| 7,510,872 B2 | 3/2009 | Clark |
| 7,510,875 B2 | 3/2009 | Zhang |
| 7,556,924 B2 | 7/2009 | Barany et al. |
| 7,579,181 B2 | 8/2009 | O'Riordan |
| 7,625,570 B1 | 12/2009 | Schaffer |
| 7,632,938 B2 | 12/2009 | Khvorova et al. |
| 7,638,120 B2 | 12/2009 | Liu |
| 7,662,627 B2 | 2/2010 | Johnson |
| 7,678,895 B2 | 3/2010 | Bennett et al. |
| 7,691,995 B2 | 4/2010 | Zamore et al. |
| 7,704,492 B2 | 4/2010 | Podsakoff |
| 7,704,721 B2 | 4/2010 | Wright |
| 7,732,129 B1 | 6/2010 | Zhang |
| 7,732,593 B2 | 6/2010 | Zamore et al. |
| 7,772,203 B2 | 8/2010 | Zamore et al. |
| 7,790,154 B2 | 9/2010 | Samulski et al. |
| 7,790,449 B2 | 9/2010 | Gao |
| 7,794,443 B2 | 9/2010 | Nelson et al. |
| 7,794,692 B2 | 9/2010 | Chakrabartty et al. |
| 7,803,622 B2 | 9/2010 | Engelhardt |
| 7,838,277 B2 | 11/2010 | Gao |
| 7,867,484 B2 | 1/2011 | Samulski et al. |
| 7,887,803 B2 | 2/2011 | Cashman |
| 7,888,096 B2 | 2/2011 | Wu |
| 7,892,809 B2 | 2/2011 | Bowles et al. |
| 7,893,036 B2 | 2/2011 | Zamore et al. |
| 7,901,921 B2 | 3/2011 | Coffey |
| 7,906,111 B2 | 3/2011 | Wilson |
| 7,951,784 B2 | 5/2011 | Rana et al. |
| 7,968,333 B2 | 6/2011 | Yu |
| 7,977,314 B2 | 7/2011 | Cashman |
| 8,008,271 B2 | 8/2011 | Xu et al. |
| 8,039,610 B2 | 10/2011 | Khvorova et al. |
| 8,090,542 B2 | 1/2012 | Khvorova et al. |
| 8,105,574 B2 | 1/2012 | Wilson |
| 8,110,351 B2 | 2/2012 | Bosnes |
| 8,137,948 B2 | 3/2012 | Qu |
| 8,163,543 B2 | 4/2012 | Urabe |
| 8,173,614 B2 | 5/2012 | Burright et al. |
| 8,183,219 B2 | 5/2012 | Burright |
| 8,231,880 B2 | 7/2012 | Roy |
| 8,232,260 B2 | 7/2012 | Zamore et al. |
| 8,236,495 B2 | 8/2012 | Nochumson |
| 8,241,622 B2 | 8/2012 | Englehardt |
| 8,273,344 B2 | 9/2012 | Wang |
| 8,283,151 B2 | 10/2012 | Schmidt |
| 8,304,530 B2 | 11/2012 | Zamore et al. |
| 8,309,533 B2 | 11/2012 | Xu |
| 8,309,705 B2 | 11/2012 | Zamore et al. |
| 8,318,480 B2 | 11/2012 | Gao |
| 8,318,687 B2 | 11/2012 | Tabira |
| 8,329,892 B2 | 12/2012 | Zamore et al. |
| 8,361,457 B2 | 1/2013 | Samulski et al. |
| 8,394,386 B2 | 3/2013 | Wilson |
| 8,409,842 B2 | 4/2013 | Clark |
| 8,470,310 B2 | 6/2013 | Roy |
| 8,476,418 B2 | 7/2013 | Mueller |
| 8,512,981 B2 | 8/2013 | Hermens |
| 8,513,387 B2 | 8/2013 | Chakrabartty et al. |
| 8,524,219 B2 | 9/2013 | Roy |
| 8,524,446 B2 | 9/2013 | Gao |
| 8,530,438 B2 | 9/2013 | Zamore et al. |
| 8,557,785 B2 | 10/2013 | Zamore et al. |
| 8,586,554 B2 | 11/2013 | Bhanot et al. |
| 8,603,459 B2 | 12/2013 | Wilson |
| 8,614,101 B2 | 12/2013 | VanDine |
| 8,632,764 B2 | 1/2014 | Xiao et al. |
| 8,637,255 B2 | 1/2014 | Wilson |
| 8,642,314 B2 | 2/2014 | Bakker |
| 8,685,734 B2 | 4/2014 | Coffey |
| 8,697,417 B2 | 4/2014 | Bakker |
| 8,697,665 B2 | 4/2014 | Rom? |
| 8,709,422 B2 | 4/2014 | Cashman et al. |

(56) References Cited

U.S. PATENT DOCUMENTS

| | | |
|---|---|---|
| 8,734,809 B2 | 5/2014 | Gao et al. |
| 8,778,885 B2 | 7/2014 | Cashman et al. |
| 8,784,799 B2 | 7/2014 | Samulski et al. |
| 8,834,863 B2 | 9/2014 | Roy |
| 8,846,030 B2 | 9/2014 | Engelhardt |
| 8,846,389 B2 | 9/2014 | Chiorini |
| 8,906,387 B2 | 12/2014 | Kay |
| 8,906,675 B2 | 12/2014 | Gao |
| 8,927,514 B2 | 1/2015 | Chatterjee |
| 8,962,330 B2 | 2/2015 | Gao |
| 8,962,332 B2 | 2/2015 | Gao |
| 8,999,678 B2 | 4/2015 | Vandenberghe |
| 9,012,224 B2 | 4/2015 | Bowles et al. |
| 9,051,542 B2 | 6/2015 | Wright |
| 9,056,892 B2 | 6/2015 | Pun |
| 9,080,183 B2 | 7/2015 | Klein |
| 9,089,667 B2 | 7/2015 | Bankiewicz |
| 9,101,645 B2 | 8/2015 | Watts |
| 9,102,943 B2 | 8/2015 | Shinmura |
| 9,102,949 B2 | 8/2015 | Gao et al. |
| 9,107,884 B2 | 8/2015 | Chedotal |
| 9,115,373 B2 | 8/2015 | Herm |
| 9,163,260 B2 | 10/2015 | Wilson |
| 9,169,483 B2 | 10/2015 | Davidson |
| 9,175,287 B2 | 11/2015 | Zamore et al. |
| 9,186,419 B2 | 11/2015 | Xiao et al. |
| 9,217,155 B2 | 12/2015 | Gao |
| 9,217,159 B2 | 12/2015 | Roy |
| 9,228,174 B2 | 1/2016 | Noordman |
| 9,233,174 B2 | 1/2016 | Chen |
| 9,238,800 B2 | 1/2016 | Bossis |
| 9,260,724 B2 | 2/2016 | Bakker |
| 9,284,357 B2 | 3/2016 | Gao et al. |
| 9,402,921 B2 | 8/2016 | Xiao et al. |
| 9,434,776 B2 | 9/2016 | Ando |
| 9,434,930 B2 | 9/2016 | Doudna |
| 9,439,979 B2 | 9/2016 | Chiorini |
| 9,441,206 B2 | 9/2016 | Grieger |
| 9,441,244 B2 | 9/2016 | Schaffer |
| 9,447,433 B2 | 9/2016 | Hirsch |
| 9,457,103 B2 | 10/2016 | Schaffer |
| 9,458,517 B2 | 10/2016 | Schaffer |
| 9,464,119 B2 | 10/2016 | Sonntag |
| 9,475,845 B2 | 10/2016 | Asokan |
| 9,487,779 B2 | 11/2016 | Davidson |
| 9,493,788 B2 | 11/2016 | Gao |
| 9,506,068 B2 | 11/2016 | Inturrisi |
| 9,506,083 B2 | 11/2016 | Arbetman |
| 9,523,093 B2 | 12/2016 | Davidson |
| 9,528,126 B2 | 12/2016 | Qu |
| 9,539,307 B2 | 1/2017 | Kaspar |
| 9,540,659 B2 | 1/2017 | Davidson |
| 9,546,112 B2 | 1/2017 | Voit |
| 9,546,369 B2 | 1/2017 | Gao |
| 9,567,376 B2 | 2/2017 | Cronin |
| 9,567,607 B2 | 2/2017 | Wilson |
| 9,580,691 B2 | 2/2017 | Bakker |
| 9,585,971 B2 | 3/2017 | Deverman |
| 9,587,250 B2 | 3/2017 | Gao |
| 9,587,282 B2 | 3/2017 | Schaffer |
| 9,593,346 B2 | 3/2017 | Roy |
| 9,596,835 B2 | 3/2017 | Gao |
| 9,597,363 B2 | 3/2017 | Roy |
| 9,598,468 B2 | 3/2017 | Weigel-Van Aken |
| 9,598,703 B2 | 3/2017 | Garcia |
| 9,611,302 B2 | 4/2017 | Srivastava |
| 9,617,561 B2 | 4/2017 | Roy |
| 9,623,120 B2 | 4/2017 | Chatterjee |
| 9,624,274 B2 | 4/2017 | Lux |
| 9,636,370 B2 | 5/2017 | McCown |
| 9,650,631 B2 | 5/2017 | Davidson |
| 9,670,507 B2 | 6/2017 | Xiao |
| 9,677,088 B2 | 6/2017 | Nakai |
| 9,677,089 B2 | 6/2017 | Gao |
| 9,682,193 B2 | 6/2017 | Anand |
| 9,695,220 B2 | 7/2017 | Vandenberghe |
| 9,701,984 B2 | 7/2017 | Gao |
| 9,708,627 B2 | 7/2017 | Christi |
| 9,719,070 B2 | 8/2017 | Vandenberghe |
| 9,719,106 B2 | 8/2017 | Wilson |
| 9,725,485 B2 | 8/2017 | Srivastava |
| 9,732,345 B2 | 8/2017 | Martin |
| 9,733,237 B2 | 8/2017 | Wichterle |
| 9,737,618 B2 | 8/2017 | Wilson |
| 9,745,590 B2 | 8/2017 | Kay |
| 9,775,918 B2 | 10/2017 | Zhong |
| 9,777,291 B2 | 10/2017 | Chatterjee |
| 9,783,824 B2 | 10/2017 | Kay |
| 9,783,825 B2 | 10/2017 | Chatterjee |
| 9,790,472 B2 | 10/2017 | Gao |
| 9,803,218 B2 | 10/2017 | Chatterjee |
| 9,850,487 B2 | 12/2017 | Zamore et al. |
| 10,035,825 B2 | 7/2018 | Gao et al. |
| 10,041,090 B2 | 8/2018 | Gao |
| 10,047,377 B2 | 8/2018 | Piedras-Renteria |
| 10,584,337 B2 | 3/2020 | Sah et al. |
| 10,689,420 B2 | 6/2020 | Gao et al. |
| 10,731,155 B2 | 8/2020 | Zamore et al. |
| 10,731,178 B2 | 8/2020 | Gao et al. |
| 10,920,227 B2 | 2/2021 | Sah et al. |
| 2001/0006955 A1 | 7/2001 | Wilson |
| 2001/0049144 A1 | 12/2001 | Rivera |
| 2002/0019050 A1 | 2/2002 | Gao |
| 2002/0037867 A1 | 3/2002 | Wilson |
| 2002/0081721 A1 | 6/2002 | Allen |
| 2002/0090717 A1 | 7/2002 | Gao |
| 2002/0102714 A1 | 8/2002 | Wilson |
| 2002/0131961 A1 | 9/2002 | Wilson |
| 2003/0013189 A1 | 1/2003 | Wilson |
| 2003/0032613 A1 | 2/2003 | Gao |
| 2003/0092161 A1 | 5/2003 | Gao |
| 2003/0100115 A1 | 5/2003 | Raj |
| 2003/0119191 A1 | 6/2003 | Gao |
| 2003/0138772 A1 | 7/2003 | Gao |
| 2003/0180756 A1 | 9/2003 | Shi et al. |
| 2004/0043490 A1 | 3/2004 | Shimada |
| 2004/0057931 A1 | 3/2004 | Wilson |
| 2004/0136963 A1 | 7/2004 | Wilson |
| 2004/0171807 A1 | 9/2004 | Gao |
| 2005/0059005 A1 | 3/2005 | Tuschl |
| 2005/0064489 A1 | 3/2005 | Zhang |
| 2005/0130184 A1 | 6/2005 | Xu et al. |
| 2005/0255086 A1 | 11/2005 | Davidson et al. |
| 2005/0255487 A1 | 11/2005 | Khvorova et al. |
| 2005/0261218 A1 | 11/2005 | Esau |
| 2006/0003451 A1 | 1/2006 | Gao |
| 2006/0009402 A1 | 1/2006 | Zamore et al. |
| 2006/0041022 A1 | 2/2006 | Pasinetti |
| 2006/0204479 A1 | 9/2006 | Wilson |
| 2006/0229268 A1 | 10/2006 | Benjamin et al. |
| 2006/0246517 A1 | 11/2006 | Cashman |
| 2007/0003977 A1 | 1/2007 | Cashman et al. |
| 2007/0004042 A1 | 1/2007 | Gao et al. |
| 2008/0008684 A1 | 1/2008 | Wilson |
| 2008/0020992 A1 | 1/2008 | Rao |
| 2008/0050343 A1 | 2/2008 | Wilson |
| 2008/0050345 A1 | 2/2008 | Wilson |
| 2008/0075737 A1 | 3/2008 | Gao |
| 2008/0113375 A1 | 5/2008 | Khvorova |
| 2009/0098151 A1 | 4/2009 | Cashman |
| 2009/0143764 A1 | 6/2009 | Nelson |
| 2009/0215871 A1 | 8/2009 | Wilson |
| 2009/0275107 A1 | 11/2009 | Lock |
| 2009/0317417 A1 | 12/2009 | Vandenberghe |
| 2010/0004320 A1 | 1/2010 | Elmen |
| 2010/0013351 A1 | 1/2010 | Gas et al. |
| 2010/0036107 A1 | 2/2010 | Clawson |
| 2010/0130594 A1 | 5/2010 | Barkats |
| 2010/0132060 A1 | 5/2010 | Burright |
| 2010/0240739 A1 | 9/2010 | Barkats |
| 2010/0247490 A1 | 9/2010 | Roy |
| 2010/0278791 A1 | 11/2010 | Wilson |
| 2010/0286378 A1 | 11/2010 | Li |
| 2011/0020816 A1 | 1/2011 | Chen |

(56) References Cited

U.S. PATENT DOCUMENTS

| | | |
|---|---|---|
| 2011/0039914 A1 | 2/2011 | Pavco et al. |
| 2011/0104120 A1 | 5/2011 | Xiao et al. |
| 2011/0105517 A1 | 5/2011 | Ikeda et al. |
| 2011/0111496 A1 | 5/2011 | Li |
| 2011/0124018 A1 | 5/2011 | Cashman et al. |
| 2011/0135673 A1 | 6/2011 | Cashman |
| 2011/0136227 A1 | 6/2011 | Bakker |
| 2011/0171262 A1 | 7/2011 | Bakker |
| 2011/0223135 A1 | 9/2011 | Roy |
| 2011/0229971 A1 | 9/2011 | Knop |
| 2011/0251258 A1 | 10/2011 | Samarsky et al. |
| 2011/0263680 A1 | 10/2011 | Khvorova et al. |
| 2012/0015850 A1 | 1/2012 | Khvorova et al. |
| 2012/0046349 A1 | 2/2012 | Bell |
| 2012/0058102 A1 | 3/2012 | Wilson |
| 2012/0077212 A1 | 3/2012 | Cashman |
| 2012/0093853 A1 | 4/2012 | Wilson |
| 2012/0093916 A1 | 4/2012 | Kaemmerer |
| 2012/0137379 A1 | 5/2012 | Gao |
| 2012/0258046 A1 | 10/2012 | Mutzke |
| 2012/0309050 A1 | 12/2012 | Kumon |
| 2013/0019580 A1 | 1/2013 | Anderson et al. |
| 2013/0023033 A1 | 1/2013 | Wilson |
| 2013/0045186 A1 | 2/2013 | Gao |
| 2013/0101558 A1 | 4/2013 | Gao |
| 2013/0171726 A1 | 7/2013 | Roelvink |
| 2013/0195801 A1 | 8/2013 | Gao |
| 2013/0225642 A1 | 8/2013 | Inoue et al. |
| 2013/0267582 A1 | 10/2013 | Kollipara |
| 2013/0296532 A1 | 11/2013 | Herm |
| 2013/0323226 A1 | 12/2013 | Wilson |
| 2013/0323302 A1 | 12/2013 | Constable |
| 2014/0031418 A1 | 1/2014 | Wilson |
| 2014/0044680 A1 | 2/2014 | Roy |
| 2014/0065105 A1 | 3/2014 | Wilson |
| 2014/0087361 A1 | 3/2014 | Dobbelaer |
| 2014/0099666 A1 | 4/2014 | Rossomando |
| 2014/0107186 A1 | 4/2014 | Garcia |
| 2014/0234274 A1 | 8/2014 | Xiao et al. |
| 2014/0243783 A1 | 8/2014 | Raghavan et al. |
| 2014/0335054 A1 | 11/2014 | Gao et al. |
| 2014/0335538 A1 | 11/2014 | Cashman |
| 2014/0336245 A1 | 11/2014 | Mingozzi |
| 2014/0341852 A1 | 11/2014 | Srivastava |
| 2014/0342434 A1 | 11/2014 | Herm |
| 2014/0348822 A1 | 11/2014 | Cashman et al. |
| 2015/0005369 A1 | 1/2015 | Muzyczka |
| 2015/0023924 A1 | 1/2015 | High |
| 2015/0065562 A1 | 3/2015 | Yazicioglu |
| 2015/0111955 A1 | 4/2015 | High et al. |
| 2015/0118201 A1 | 4/2015 | Xiao et al. |
| 2015/0118287 A1 | 4/2015 | Hammond |
| 2015/0139952 A1 | 5/2015 | Webster |
| 2015/0159173 A1 | 6/2015 | Vandenberghe |
| 2015/0164906 A1 | 6/2015 | Zack |
| 2015/0197751 A1 | 7/2015 | Roelvink |
| 2015/0232840 A1 | 8/2015 | Aronin |
| 2015/0238610 A1 | 8/2015 | Sista |
| 2015/0267189 A1 | 9/2015 | Angel et al. |
| 2015/0275193 A1 | 10/2015 | Angel et al. |
| 2015/0307898 A2 | 10/2015 | Herm |
| 2015/0315610 A1 | 11/2015 | Nishie |
| 2015/0322813 A1 | 11/2015 | Tralshawala et al. |
| 2015/0335708 A1 | 11/2015 | Froelich |
| 2015/0374803 A1 | 12/2015 | Wolfe |
| 2016/0032319 A1 | 2/2016 | Wright |
| 2016/0102309 A1 | 4/2016 | Zamore et al. |
| 2016/0108373 A1 | 4/2016 | Bennett |
| 2016/0153992 A1 | 6/2016 | Buening |
| 2016/0166709 A1 | 6/2016 | Davidson |
| 2016/0251653 A1 | 9/2016 | Davidson |
| 2016/0264994 A1 | 9/2016 | Lawrence |
| 2016/0271192 A1 | 9/2016 | Roy |
| 2016/0272976 A1 | 9/2016 | Kaspar |
| 2016/0273058 A1 | 9/2016 | Akashika |
| 2016/0281084 A1 | 9/2016 | Davidson |
| 2016/0289275 A1 | 10/2016 | Chiorini |
| 2016/0289676 A1 | 10/2016 | Kaspar |
| 2016/0296694 A1 | 10/2016 | Bankiewicz |
| 2016/0319278 A1 | 11/2016 | Khvorova |
| 2016/0326524 A1 | 11/2016 | Flotte |
| 2016/0331897 A1 | 11/2016 | Anand |
| 2016/0333372 A1 | 11/2016 | Srivastava |
| 2016/0333373 A1 | 11/2016 | Farley |
| 2016/0333375 A1 | 11/2016 | Chen |
| 2016/0340393 A1 | 11/2016 | Schaffer |
| 2016/0340692 A1 | 11/2016 | Wang |
| 2016/0346359 A1 | 12/2016 | Buchlis |
| 2016/0348106 A1 | 12/2016 | Harper |
| 2016/0354487 A1 | 12/2016 | Zhang |
| 2016/0355577 A1 | 12/2016 | Kelley |
| 2016/0355796 A1 | 12/2016 | Davidson |
| 2016/0355808 A1 | 12/2016 | Khvorova |
| 2016/0361439 A1 | 12/2016 | Agbandje-Mckenna |
| 2016/0369298 A1 | 12/2016 | Marsic |
| 2016/0369299 A1 | 12/2016 | Boye |
| 2016/0375151 A1 | 12/2016 | Schaffer |
| 2016/0376323 A1 | 12/2016 | Schaffer |
| 2016/0376608 A1 | 12/2016 | Chou |
| 2017/0000904 A1 | 1/2017 | Wilson |
| 2017/0004254 A1 | 1/2017 | Rossi |
| 2017/0007669 A1 | 1/2017 | Sarkar |
| 2017/0007720 A1 | 1/2017 | Boye |
| 2017/0009304 A1 | 1/2017 | Zhuo |
| 2017/0022498 A1 | 1/2017 | Cullen |
| 2017/0028082 A1 | 2/2017 | Wilson |
| 2017/0029849 A1 | 2/2017 | Harper |
| 2017/0037410 A1 | 2/2017 | Swayze |
| 2017/0044504 A1 | 2/2017 | Schaffer |
| 2017/0044530 A1 | 2/2017 | Kay |
| 2017/0067028 A1 | 3/2017 | Ballon |
| 2017/0071972 A1 | 3/2017 | Buj Bello |
| 2017/0073703 A1 | 3/2017 | Chatterjee |
| 2017/0088819 A1 | 3/2017 | Vandendriessche |
| 2017/0088858 A1 | 3/2017 | Gao |
| 2017/0096646 A1 | 4/2017 | Roy |
| 2017/0105927 A1 | 4/2017 | Thome |
| 2017/0107536 A1 | 4/2017 | Zhang |
| 2017/0112946 A1 | 4/2017 | Ikeda |
| 2017/0114340 A1 | 4/2017 | Mueller |
| 2017/0121734 A1 | 5/2017 | Cairns |
| 2017/0128594 A1 | 5/2017 | Wright |
| 2017/0130208 A1 | 5/2017 | Potter |
| 2017/0130245 A1 | 5/2017 | Kotin |
| 2017/0145440 A1 | 5/2017 | Herm |
| 2017/0151348 A1 | 6/2017 | Kaspar |
| 2017/0151416 A1 | 6/2017 | Kutikov |
| 2017/0152517 A1 | 6/2017 | Barkats |
| 2017/0152525 A1 | 6/2017 | Herm |
| 2017/0157267 A1 | 6/2017 | Kay |
| 2017/0159026 A1 | 6/2017 | Kay |
| 2017/0159027 A1 | 6/2017 | Wilson |
| 2017/0159072 A9 | 6/2017 | Arbeit |
| 2017/0165377 A1 | 6/2017 | Gao |
| 2017/0166871 A1 | 6/2017 | Nishie |
| 2017/0166925 A1 | 6/2017 | Gao |
| 2017/0166926 A1 | 6/2017 | Deverman |
| 2017/0166927 A1 | 6/2017 | Gao |
| 2017/0183636 A1 | 6/2017 | Roy |
| 2017/0191039 A1 | 7/2017 | Gao |
| 2017/0191079 A1 | 7/2017 | Vandenberghe |
| 2017/0198304 A1 | 7/2017 | Wilson |
| 2017/0204144 A1 | 7/2017 | Deverman |
| 2017/0211092 A1 | 7/2017 | Chatterjee |
| 2017/0211093 A1 | 7/2017 | Chatterjee |
| 2017/0211094 A1 | 7/2017 | Chatterjee |
| 2017/0211095 A1 | 7/2017 | Chatterjee |
| 2017/0216458 A1 | 8/2017 | Kaspar |
| 2017/0218395 A1 | 8/2017 | Byrne |
| 2017/0226160 A1 | 8/2017 | Sonntag |
| 2017/0232072 A1 | 8/2017 | Ikeda |
| 2017/0232117 A1 | 8/2017 | Arbetman |
| 2017/0240885 A1 | 8/2017 | Deverman |
| 2017/0240921 A1 | 8/2017 | Gao |

(56) References Cited

U.S. PATENT DOCUMENTS

| | | |
|---|---|---|
| 2017/0246322 A1 | 8/2017 | Mendell |
| 2017/0247664 A1 | 8/2017 | Wright |
| 2017/0258996 A1 | 9/2017 | Anand |
| 2017/0260545 A1 | 9/2017 | Qu |
| 2017/0274024 A1 | 9/2017 | McCown |
| 2017/0275337 A1 | 9/2017 | Srivastava |
| 2017/0298323 A1 | 10/2017 | Vandenberghe |
| 2017/0304464 A1 | 10/2017 | Sebastian |
| 2017/0306354 A1 | 10/2017 | Gao |
| 2017/0306355 A1 | 10/2017 | Davidson |
| 2017/0321290 A1 | 11/2017 | Lubelski |
| 2018/0230490 A1 | 8/2018 | O'Riordan |
| 2018/0237772 A1 | 8/2018 | Yu |
| 2018/0282732 A1 | 10/2018 | Sah et al. |
| 2018/0298380 A1 | 10/2018 | Gao |
| 2019/0038777 A1 | 2/2019 | Donsante |
| 2019/0194688 A1 | 6/2019 | Gao et al. |
| 2019/0194689 A1 | 6/2019 | Gao et al. |
| 2019/0276848 A1 | 9/2019 | Gao et al. |
| 2019/0276849 A1 | 9/2019 | Gao et al. |
| 2020/0123574 A1 | 4/2020 | Sah et al. |
| 2020/0149045 A1 | 5/2020 | Sah et al. |
| 2020/0157547 A1 | 5/2020 | Sah et al. |
| 2020/0237799 A1 | 7/2020 | Sah et al. |
| 2020/0239912 A1 | 7/2020 | Sah et al. |
| 2020/0270635 A1 | 8/2020 | Hou et al. |
| 2020/0377554 A1 | 12/2020 | Gao et al. |
| 2021/0139915 A1 | 5/2021 | Sah et al. |
| 2021/0163985 A1 | 6/2021 | Sah et al. |
| 2021/0230632 A1 | 7/2021 | Sah et al. |
| 2021/0254103 A1 | 8/2021 | Sah |
| 2021/0361318 A1 | 11/2021 | Patzke et al. |

FOREIGN PATENT DOCUMENTS

| | | |
|---|---|---|
| CA | 3077426 A1 | 4/2019 |
| CN | 102016036 A | 4/2011 |
| EP | 1015619 A1 | 7/2000 |
| EP | 1078096 A1 | 2/2001 |
| EP | 1183380 A1 | 3/2002 |
| EP | 1218035 A2 | 7/2002 |
| EP | 1240345 A2 | 9/2002 |
| EP | 1279740 A1 | 1/2003 |
| EP | 1412371 A1 | 4/2004 |
| EP | 1692262 B1 | 8/2006 |
| EP | 1046711 B1 | 12/2006 |
| EP | 1847614 A1 | 10/2007 |
| EP | 1849872 A1 | 10/2007 |
| EP | 1857552 A1 | 11/2007 |
| EP | 1944043 A1 | 7/2008 |
| EP | 1696036 B1 | 4/2010 |
| EP | 2186283 | 5/2010 |
| EP | 2213738 A2 | 8/2010 |
| EP | 1164195 B1 | 10/2010 |
| EP | 2250256 B1 | 11/2010 |
| EP | 2292780 B1 | 3/2011 |
| EP | 2301582 B1 | 3/2011 |
| EP | 2311967 B1 | 4/2011 |
| EP | 2524037 A1 | 11/2012 |
| EP | 2561073 A1 | 2/2013 |
| EP | 2572661 A1 | 3/2013 |
| EP | 2359866 B1 | 7/2013 |
| EP | 2660325 A3 | 2/2014 |
| EP | 2699270 B1 | 2/2014 |
| EP | 2383346 B1 | 10/2014 |
| EP | 2814958 A1 | 12/2014 |
| EP | 2826860 A1 | 1/2015 |
| EP | 2198016 B1 | 5/2015 |
| EP | 2871239 A9 | 6/2015 |
| EP | 2879719 A1 | 6/2015 |
| EP | 2164967 B1 | 7/2015 |
| EP | 2453735 B1 | 7/2015 |
| EP | 2172549 B1 | 8/2015 |
| EP | 2906580 A2 | 8/2015 |
| EP | 2943567 B1 | 11/2015 |
| EP | 3058959 A1 | 8/2016 |
| EP | 1453547 B1 | 9/2016 |
| EP | 1900815 B1 | 9/2016 |
| EP | 2220241 B1 | 9/2016 |
| EP | 2360251 B1 | 9/2016 |
| EP | 2497500 B1 | 9/2016 |
| EP | 2325298 B1 | 10/2016 |
| EP | 2007795 B1 | 11/2016 |
| EP | 2176283 | 11/2016 |
| EP | 2292779 B1 | 11/2016 |
| EP | 3067417 A3 | 11/2016 |
| EP | 2220242 B1 | 12/2016 |
| EP | 3108000 | 12/2016 |
| EP | 3117005 A1 | 1/2017 |
| EP | 2737071 B1 | 3/2017 |
| EP | 2933336 B1 | 3/2017 |
| EP | 3134431 A1 | 3/2017 |
| EP | 2531604 B1 | 4/2017 |
| EP | 3168298 A1 | 5/2017 |
| EP | 3174981 A1 | 6/2017 |
| EP | 3209311 A1 | 8/2017 |
| EP | 3215602 A1 | 9/2017 |
| EP | 3221453 A1 | 9/2017 |
| EP | 3221456 A2 | 9/2017 |
| EP | 3224376 A1 | 10/2017 |
| EP | 3230441 A1 | 10/2017 |
| EP | 3235827 A2 | 10/2017 |
| JP | 2013-143917 A | 7/2013 |
| WO | 1989012677 A1 | 12/1989 |
| WO | 1993009239 | 5/1993 |
| WO | 1995028493 A1 | 10/1995 |
| WO | 1995034670 | 12/1995 |
| WO | 1996023810 A1 | 8/1996 |
| WO | 1996030540 A2 | 10/1996 |
| WO | 1997045559 A1 | 12/1997 |
| WO | 1998010088 | 3/1998 |
| WO | 1999027110 A1 | 6/1999 |
| WO | 1999043360 A1 | 9/1999 |
| WO | 1999058700 A1 | 11/1999 |
| WO | 1999061595 A2 | 12/1999 |
| WO | 1999060146 | 5/2000 |
| WO | 2000024916 | 5/2000 |
| WO | 2000066780 A2 | 11/2000 |
| WO | 2000075353 A1 | 12/2000 |
| WO | 2001014539 A2 | 3/2001 |
| WO | 2001023001 | 4/2001 |
| WO | 2001025465 A1 | 4/2001 |
| WO | 2001036623 A2 | 5/2001 |
| WO | 2001068888 A2 | 9/2001 |
| WO | 2001075164 A1 | 10/2001 |
| WO | 2001092551 A2 | 12/2001 |
| WO | 2001096587 A2 | 12/2001 |
| WO | 2001032711 B1 | 1/2002 |
| WO | 2001042444 A3 | 1/2002 |
| WO | 2002012525 A2 | 2/2002 |
| WO | 2002014487 A2 | 2/2002 |
| WO | 2002020748 A2 | 3/2002 |
| WO | 2002070719 A2 | 9/2002 |
| WO | 2002071843 A1 | 9/2002 |
| WO | 2003/006477 A1 | 1/2003 |
| WO | 2003010320 A2 | 2/2003 |
| WO | 2003024502 | 3/2003 |
| WO | 2003042397 A2 | 5/2003 |
| WO | 33080807 A2 | 10/2003 |
| WO | 2003087382 A1 | 10/2003 |
| WO | 2003087383 A1 | 10/2003 |
| WO | 2004027030 A2 | 4/2004 |
| WO | 2004044003 | 5/2004 |
| WO | 2004045543 A2 | 6/2004 |
| WO | 2004083441 A2 | 9/2004 |
| WO | 2004108922 A2 | 12/2004 |
| WO | 2004111191 A2 | 12/2004 |
| WO | 2004111248 A2 | 12/2004 |
| WO | 2005001043 A2 | 1/2005 |
| WO | 2005005610 | 1/2005 |
| WO | 2005007875 A2 | 1/2005 |
| WO | 2005012537 | 2/2005 |
| WO | 2005019828 A1 | 3/2005 |
| WO | 2005027980 A1 | 3/2005 |

(56) References Cited

FOREIGN PATENT DOCUMENTS

| | | |
|---|---|---|
| WO | 2005062937 A2 | 7/2005 |
| WO | 2005096781 A2 | 10/2005 |
| WO | 2005111220 A2 | 11/2005 |
| WO | 2006006948 A2 | 1/2006 |
| WO | 2006066066 A2 | 6/2006 |
| WO | 2006066203 A2 | 6/2006 |
| WO | 2006075434 A1 | 7/2006 |
| WO | 2006102072 | 9/2006 |
| WO | 2007044362 A2 | 4/2007 |
| WO | 2007089632 A2 | 8/2007 |
| WO | 2007/109097 A2 | 9/2007 |
| WO | 2007098607 A1 | 9/2007 |
| WO | 2007130519 | 11/2007 |
| WO | 2008086079 A2 | 7/2008 |
| WO | 2007148971 | 7/2009 |
| WO | 2009102427 A2 | 8/2009 |
| WO | 2009134681 | 11/2009 |
| WO | 2009137006 A2 | 11/2009 |
| WO | 2010011346 A1 | 1/2010 |
| WO | 2010138263 A2 | 12/2010 |
| WO | 2011038187 | 3/2011 |
| WO | 2011054976 A2 | 5/2011 |
| WO | 2011122950 | 10/2011 |
| WO | 2011133890 A1 | 10/2011 |
| WO | 2010109053 | 11/2011 |
| WO | 2012057363 | 5/2012 |
| WO | 2012114090 | 8/2012 |
| WO | 2012144446 | 10/2012 |
| WO | 2012149646 A1 | 11/2012 |
| WO | 2013078199 | 5/2013 |
| WO | 2013123503 A1 | 8/2013 |
| WO | 2013164793 | 11/2013 |
| WO | 2013170078 A1 | 11/2013 |
| WO | 2014016817 A2 | 1/2014 |
| WO | 2014071219 A1 | 5/2014 |
| WO | 2014107763 A1 | 7/2014 |
| WO | 2014144486 A2 | 9/2014 |
| WO | 2014160092 | 10/2014 |
| WO | 2014168953 | 10/2014 |
| WO | 2014170470 | 10/2014 |
| WO | 2014170480 | 10/2014 |
| WO | 2014172669 | 10/2014 |
| WO | 2014186579 | 11/2014 |
| WO | 2014194132 | 12/2014 |
| WO | 2014201252 | 12/2014 |
| WO | 2015012924 | 1/2015 |
| WO | 2015013313 A2 | 1/2015 |
| WO | 2015018503 | 2/2015 |
| WO | 2015023503 A2 | 2/2015 |
| WO | 2014186746 | 3/2015 |
| WO | 2015031686 | 4/2015 |
| WO | 2015044292 | 4/2015 |
| WO | 2015060722 | 4/2015 |
| WO | 2015069647 A1 | 5/2015 |
| WO | 2015031392 A9 | 6/2015 |
| WO | 2015084254 A1 | 6/2015 |
| WO | 2015106273 A2 | 7/2015 |
| WO | 2015108610 | 7/2015 |
| WO | 2015114365 | 8/2015 |
| WO | 2015121501 | 8/2015 |
| WO | 2015124546 | 8/2015 |
| WO | 2015137802 | 9/2015 |
| WO | 2015143078 A1 | 9/2015 |
| WO | 2015153800 A2 | 10/2015 |
| WO | 2015127128 | 11/2015 |
| WO | 2015196179 | 12/2015 |
| WO | 2016/016449 A1 | 2/2016 |
| WO | 2016019364 | 2/2016 |
| WO | 2016054554 | 4/2016 |
| WO | 2016054557 | 4/2016 |
| WO | 2016065001 | 4/2016 |
| WO | 2016077607 A1 | 5/2016 |
| WO | 2016077687 A1 | 5/2016 |
| WO | 2016077689 A1 | 5/2016 |
| WO | 2016081811 | 5/2016 |
| WO | 2016081927 | 5/2016 |
| WO | 2016102664 A1 | 6/2016 |
| WO | 2016109649 A1 | 7/2016 |
| WO | 2016115382 | 7/2016 |
| WO | 2016115503 A1 | 7/2016 |
| WO | 2016122791 | 8/2016 |
| WO | 2016126857 | 8/2016 |
| WO | 2016130589 A2 | 8/2016 |
| WO | 2016130591 | 8/2016 |
| WO | 2016154055 | 9/2016 |
| WO | 2016154344 | 9/2016 |
| WO | 2016137949 A1 | 10/2016 |
| WO | 2016161374 A1 | 10/2016 |
| WO | 2016164609 | 10/2016 |
| WO | 2016168728 | 10/2016 |
| WO | 2016172008 | 10/2016 |
| WO | 2016172155 | 10/2016 |
| WO | 2016179496 | 11/2016 |
| WO | 2016183297 A1 | 11/2016 |
| WO | 2016191418 | 12/2016 |
| WO | 2016196328 A1 | 12/2016 |
| WO | 2016196507 | 12/2016 |
| WO | 2017004514 | 1/2017 |
| WO | 2017005806 | 1/2017 |
| WO | 2017015102 | 1/2017 |
| WO | 2017019876 | 2/2017 |
| WO | 2017019994 | 2/2017 |
| WO | 2017024111 A1 | 2/2017 |
| WO | 2017058892 | 4/2017 |
| WO | 2017062983 A1 | 4/2017 |
| WO | 2017070476 | 4/2017 |
| WO | 2017070516 | 4/2017 |
| WO | 2017070525 | 4/2017 |
| WO | 2017070678 | 4/2017 |
| WO | 2017075335 | 5/2017 |
| WO | 2017079768 A1 | 5/2017 |
| WO | 2017083423 | 5/2017 |
| WO | 2017093330 | 6/2017 |
| WO | 2017096039 | 6/2017 |
| WO | 2017100671 | 6/2017 |
| WO | 2017100674 | 6/2017 |
| WO | 2017100676 | 6/2017 |
| WO | 2017100704 | 6/2017 |
| WO | 2017106236 A1 | 6/2017 |
| WO | 2017112948 A1 | 6/2017 |
| WO | 2017122789 A1 | 7/2017 |
| WO | 2017136202 A1 | 8/2017 |
| WO | 2017136536 A1 | 8/2017 |
| WO | 2017139381 A1 | 8/2017 |
| WO | 2017143100 A1 | 8/2017 |
| WO | 2017147477 A1 | 8/2017 |
| WO | 2017152149 A1 | 9/2017 |
| WO | 2017155973 A1 | 9/2017 |
| WO | 2017160360 A2 | 9/2017 |
| WO | 2017165859 A1 | 9/2017 |
| WO | 2017172733 A1 | 10/2017 |
| WO | 2017172772 A1 | 10/2017 |
| WO | 2017173043 A1 | 10/2017 |
| WO | 2017173283 A1 | 10/2017 |
| WO | 2017180854 A1 | 10/2017 |
| WO | 2017181162 A1 | 10/2017 |
| WO | 2017184879 A1 | 10/2017 |
| WO | 2017/201258 A1 | 11/2017 |
| WO | 2017189963 A1 | 11/2017 |
| WO | 2017190031 A1 | 11/2017 |
| WO | 2017192699 A1 | 11/2017 |
| WO | 2017192750 A1 | 11/2017 |
| WO | 2018/204786 A1 | 11/2018 |
| WO | 2018/204797 A1 | 11/2018 |
| WO | 2018220211 A1 | 12/2018 |
| WO | 2019/028306 A2 | 2/2019 |
| WO | 2019/079242 A1 | 4/2019 |
| WO | 2019079240 A1 | 4/2019 |
| WO | 2019222329 A1 | 11/2019 |
| WO | 2020/010035 A1 | 1/2020 |
| WO | 2020/010042 A1 | 1/2020 |

(56) References Cited

FOREIGN PATENT DOCUMENTS

| WO | 2020077165 A1 | 4/2020 |
|---|---|---|
| WO | 2020223296 A1 | 11/2020 |

OTHER PUBLICATIONS

U.S. Appl. No. 17/252,584, filed Dec. 15, 2020, Dinah Wen-Yee Sah, US 2021-0254103.
U.S. Appl. No. 17/606,733, filed Oct. 26, 2021, Dinah Wen-Yee Sah.
U.S. Appl. No. 17/257,418, filed Dec. 31, 2020, Dinah Wen-Yee Sah, US 2021-0361318.
U.S. Appl. No. 15/526,697, filed May 12, 2017, Jinzhao Hou, U.S. Pat. No. 10,570,395.
U.S. Appl. No. 16/302,146, filed Nov. 16, 2018, Dinah Wen-Yee Sah, U.S. Pat. No. 10,584,337.
Loring HS, et al. Development of rAAV2-CFTR: History of the First rAAV Vector Product to be Used in Humans. Hum Gene Ther Methods. Apr. 2016;27(2):49-58.
Ly CV and Miller TM. Emerging antisense olgionucleotide and viral therapies for amyotrophic lateral sclerosis. Curr Dpin. Neurol. Jul. 1, 20189 Epub ahead of print.
Giles AR, et al. Mapping an adeno-associated virus 9-specific neutralizing epitope to develop next-generation gene delivery vectors. J Virol. Aug. 8, 2018 Epub ahead of print.
Larson TC, et al. Amyotrophic Lateral Sclerosis Mortality in the United States, 2011-2014 Neuroepidemiology Jul. 10, 2018;51(1-2):96-103.
Hudry E, et al. Efficient gene transfer to the central nervous system by single stranded Anc80L65. Mol Ther Meth Clin Dev. Jul. 15, 2018.
McCampbell A, et al. Antisense oligonucleotides extend survival and reverse decrement in muscle response in ALS models. J Clin Invest. Jul. 16, 2018 Epub ahead of print.
Conlon EG, et al. Unexpected similarities between C9ORF72 and sporadic forms of ALS/FTD suggest a common disease mechanism. Elife Jul. 13, 2018;7.
Iannitti T, et al. Translating SOD1 Gene Silencing toward the Clinic: A Highly Efficacious, Off-Target-free, and Biomarker-Supported Strategy for fALS. Mol Ther Nucleic Acids. Sep. 7, 2018.
McGurk L, et al. Poly(ADP-Ribose) Prevents Pathological Phase Separation of TDP-43 by Promoting Liquid Demixing and Stress Granule Localization. Molecular Cell. Aug. 9, 2018.
Wang D, et al. A Rationally Engineered Capsid Variant of AAV9 for Systemic CNS-Directed and Peripheral Tissue-Detargeted Gene Delivery in Neonates. Mol Ther Methods Clin Dev. Mar. 16, 2018;9:234-246.
Chandran JS, et al. Gene therapy in the nervous system: failures and successes. Adv Exp Med Biol. 2017;1007:241-257.
Tse LV, et al. Mapping and engineering function domains of the assembly-activating protein of adeno-associated viruses. J. Virol. Jun. 29, 2018;92(14).
Albright BH, et al. Mapping the Structural Determinants Required for AAVrh. 10 Transport across the Blood-Brain Barrier. Mol Ther. Feb. 7, 2018;26(2):510-523.
Gaj T, et al. In vivo genome editing improves motor function and extends survival in a mouse model of ALS. Sci Adv. Dec. 20, 2017;3(12):eaar3952.
Auyeung VC, et al. Beyond secondary structure: primary sequence determinants license pri-miRNA hairpins for processing. Cell Feb. 2013;152(4):844-858.
Fellman C, et al. An optimized microRNA backbone for effective single-copy RNAi. Cell Rep. Dec. 2013;5(6):1704-1713.
Medinas DB, et al. Endoplasmic reticulum stress leads to accumulation of wild-type SOD1 aggregates associated with sporadic amyotrophic lateral sclerosis. Proc Natl Acad Sci USA Aug. 17, 2018;115(32):8209-8214.
Balendra R and ISSACS AM. C9orf72-mediated ALS and FTD: multiple pathways to disease. Nat Rev Neurol. Aug. 17, 2018 Epub ahead of print.
Pourshafie N, et al. Systemic Delivery of MicroRNA Using Recombinant Adeno-associated Virus Serotype 9 to Treat Neuromuscular Diseases in Rodents. J Vis Exp Aug. 10, 2018;(138).
Denard J, et al. AAV-8 and AAV-9 Vectors Cooperate with Serum Proteins Differently Than AAV-1 and AAV-6. Mol Ther Methods Clin Dev. Aug 8;10:291-302.
Gowanlock D, et al. A designer AAV variant permits efficient retrograde access to projection neurons. Neuron. Oct. 19, 2016;92(2):372-382.
Ha et al., Regulation of microRNA biogenesis. Nat Rev Mol Cell Bio, Aug. 2014, vol. 15, No. 8, pp. 509-524.
Hardcastle N. AAV gene delivery to the spinal cord: serotypes, methods, candidate diseases and clinical trials. Expert Opinion on Biological Therapy. Mar. 2018;18(3):293-307.
Boudreau RL, et al. Artificial microRNAs as siRNA shuttles: improved safety as compared to shRNAs in vitro and in vivo. The American Society of Gene Therapy 2009; 17(1):169-175.
Dirren JA, et al. SOD1 silencing in motor neurons or glia rescues neuromuscular function in ALS mice. Annals of Clinical and Translational Neurology 2015;2(2):167-184.
Federici T, et al. Surgical technique for spinal cord delivery of therapies: demonstration of procedure in gottingen minipigs. J Vis Exp Dec. 7, 2012;(70):e4371.
Foust KD et al. Therapeutic AAV9 mediated suppression of mutant SOD1 slows disease progression and extends survival in models of inherited ALS. Mol Ther Dec. 21, 2013(12):2148-59.
Ralph GS et al. Silencing mutant SOD1 using RNAi protects against neurodegeneration and extends survival in an ALS model. Nature Medicine. Apr. 11, 2005(4):429-33.
Raoul C et al. Lentiviral-mediated silencing of SOD1 through RNA interference retards disease onset and progression in a mouse model of ALS. Nature Medicine, vol. 11, No. 4, Apr. 2005, pp. 423-428.
Wang H, et al. Widespread spinal cord transduction by intrathecal injection of rAAV delivers efficacious RNAi therapy for amyotrophic lateral sclerosis. Hum Mol Genet Feb. 1, 2014; 23(3):668-81.
Maier M, et al. A human-derived antibody targets misfolded SOD1 and ameliorates motor symptoms in mouse models of amyotrophic lateral sclerosis. Sci Transl Med. Dec. 5, 2018;10(470):1-14.
Borel, F et al. Safe and effective superoxide dismutase 1 silencing using artificial microRNA in macaques. Sci Transl Med. Oct. 31, 2018;10(465).
Paré B, et al. Misfolded SOD1 pathology in sporadic Amyotrophic Lateral Sclerosis. Sci Rep. Sep. 2, 20181;8(1):14223.
Mondo E, et al. Selective Neuronal Uptake and Distribution of AAVrh8, AAV9, and AAVrh10 in Sheep After Intra-Striatal Administration. Selective Neuronal Uptake and Distribution of AAVrh8, AAV9, and AAVrh10 in Sheep After Intra-Striatal Administration. J Huntingtons Dis. 2018;7(4):309-319.
Wang D, et al. Adeno-associated virus vector as a platform for gene therapy delivery. Nat Rev Drug Discov. Feb. 1, 2019. doi: 10.1038/s41573-019-0012-9. [Epub ahead of print] Review.
Martier R, et al. Artificial microRNAs targeting C9ORF72 have the potential to reduce accumulation of the intra-nuclear transcripts in ALS and FTD patients. Molecular Therapy Nucleic Acids. Jan. 22, 2019. DOI: https.//doi.org/10.1016 [Epub ahead of print] Review.
Shen YH etl a., Viral vectors for Gene Transfer. Curr Protoc Mouse Biol. Dec. 2018;8(4):e58.
Büning and Srivastava. Capsid Modifications for Targeting and Improving the Efficacy of AAV Vectors. vol. 12, p. 248-265, Mar. 15, 2019.
Swarup V et al. Identification of evolutionarily conserved gene networks mediating neurodegenerative dementia. Nat Med Jan. 2019;25(1):152-164.
Hudry E, Vandenberghe LH. Therapeutic AAV Gene Transfer to the Nervous System: A Clinical Reality. Neuron. Mar. 6, 2019;101(5):839-862.
Betancur JG et al., miRNA-like duplexes as RNAi triggers with improved specificity. Front Genet. Jul. 12, 2012;3:127.
Chung et al., Polycystronic RNA polymerase II expression vectors for RNA interference based on BIC/miR-155. Nucleic Acids Res. Apr. 13, 2006;34(7):e53.

(56) References Cited

OTHER PUBLICATIONS

Cullen BR. Induction of stable RNA interference in mammalian cells. Gene Ther. Mar. 2006;13(6):503-8.
Dow LE et al., A pipeline for the generation of shRNA transgenic mice. Nat Protoc. Feb. 2, 2012;7(2):374-93.
Fellmann C. et al., Functional identification of optimized RNAi triggers using a massivelyparallel sensor assay. Mol Cell. Mar. 18, 2011;41(6):733-46.
Gu S et al., The loop position of shRNAs and pre-miRNAs is critical for the accuracy of dicer processing in vivo. Cell. Nov. 9, 2012;151(4):900-911.
Han J. et al., Molecular basis for the recognition of primary microRNAs by the Drosha-DGCR8 complex. Cell. Jun. 2, 2006;125(5):887-901.
Ketley A. et al., The miR-20 microRNA family targets smoothened to regulate hedgehog signalling in zebrafish early muscle development. PLoS One. Jun. 5, 2013;8(6):e65170.
Liu YP et al., Inhibition of HIV-1 by multiple siRNAs expressed from a single microRNApolycistron. Nucleic Acids Res. May 2008;36(9):2811-24.
Cirulli ET, et al. Exome sequencing in amyotrophic lateral sclerosis identifies risk genes and pathways. Science. Mar. 27, 2015;347(6229):1436-41.
Häggmark A, et al. Plasma profiling reveals three proteins associated to amyotrophic lateral sclerosis. Ann Clin Transl Neurol. Aug. 2014;1(8):544-53.
Jackson KL, et al. Preservation of forelimb function by UPF1 gene therapy in a rat model of TDP-43-induced motor paralysis. Gene Ther.Jan. 2015, 22(1):20-8.
Herranz-Martin S, et al. Viral delivery of C9ORF72 hexanucleotide repeat expansions in mice lead to repeat length dependent neuropathology and behavioral deficits. Dis Model Meeh 10:859-868. May 26, 2017. Epub ahead of print.
Jara JH, et al. Healthy and diseased corticospinal motor neurons are selectively transduced upon direct AAV2-2 injection into the motor cortex. Gene Ther. Mar. 2016;23(3):272-82.
Borel F et al.Therapeutic rAAVrh10 Mediated SOD1 Silencing in Adult SOD1(G93A) Mice and Nonhuman Primates. Hum Gene Ther. Jan. 2016;27(1):19-31.
Frakes AE, et al. Additive amelioration of ALS by co-targeting independent pathogenic mechanisms. Ann Clin Transl Neurol. Jan. 2017;4(2):76-86.
Stoica L et al. Adeno Associated Viral Vector Delivered RNAi for Gene Therapy of SOD1 Amyotrophic Lateral Sclerosis. Front Mol Neurosci. Aug. 2, 2016;9:56.
Van Zundert B et al. Silencing Strategies for Therapy of SOD1-Mediated ALS. 2017 Neurosci Lett 636:32-39, Aug. 6, 2016.
Stoica et al. Adeno-associated virus-delivered artificial microRNA extends survival and delays paralysis in an amyotrophic lateral sclerosis mouse model. Ann Neurol. Apr. 2016;79(4):687-700.
Picher-Martel V et al. From Animal Models to Human Disease: A Genetic Approach for Personalized Medicine in ALS. Acta Neuropathol Commun. Jul. 11, 2016;4(1):70.
Hocquemiller M et al. Adeno-Associated Virus-Based Gene Therapy for CNS Diseases. Hum Gene Ther. Jul. 2016;27(7):478-96.
Bisset DR, et al. Therapeutic impact of systemic AAV-mediated RNA interference in a mouse model of myotonic dystrophy. Hum Mol Genet. Sep. 2015;24(17):4971-83.
Darambazar G, et al. Paraventricular NUCB2/nesfatin-1 is directly targeted by leptin and mediates its anorexigenic effect. Biochem Biophys Res Commun Jan. 2015, 456(4):913-8.
He X, et al. Recombinant adeno-associated virus-mediated inhibition of microRNA-21 protects mice against the lethal schistosome infection by repressing both IL-13 and transforming growth factor beta 1 pathways. Hepatology. Jun. 2015, 61(6):2008-17. d.
Huang WD, et al. miR-134 Regulates Ischemia/Reperfusion Injury-Induced Neuronal Cell Death by Regulating CREB Signaling. J Mol Neurosci. Apr. 2015, 55(4):821-9.
Keiser MS et al. RNAi Prevents and Reverses Phenotypes Induced by Mutant Human Ataxin-1. Ann Neurol. Sep. 30, 2016.
Knabel MK, et al. Systemic Delivery of scAAVS-Encoded MiR-29a Ameliorates Hepatic Fibrosis in Carbon Tetrachloride-Treated Mice. PLoS One.Oct. 2014,10(4):e0124411.
Miyamoto Y, et al. Knockdown of Dopamine D-2 Receptors in the Nucleus Accumbens Core Suppresses Methamphetamine-Induced Behaviors and Signal Transduction in Mice. Int J Neuropsychopharmacol.Feb. 2015, 18(4).
Valdmanis PN, et al. RNA interference-induced hepatotoxicity results from loss of the first synthesized isoform of microRNA-122 in mice. Nat Med. May 2016;22(5):557-62.
Weinberg MS, et al. Viral Vector Reprogramming of Adult Resident Striatal Oligodendrocytes into Functional Neurons. Mol Ther. Apr. 2017,25(4):928-934.
Xie J et al. Adeno-Associated Virus-Mediated MicroRNA Delivery and Therapeutics. Semin Liver Dis. Feb. 2015, 35(1):81-8.
Xu PW, et al. Estrogen receptor-alpha in medial amygdala neurons regulates body weight. J Clin Invest.Jul. 2015, 125(7):2861-76.
Keiser MS et al. Broad distribution of ataxin 1 silencing in rhesus cerebella for spinocerebellar ataxia type 1 therapy. Brain. Dec. 2015;138(Pt 12):3555-66.
Enomoto M, et al. Efficient Gene Suppression in Dorsal Root Ganglia and Spinal Cord Using Adeno-Associated Virus Vectors Encoding Short-Hairpin RNA. Methods Mol Biol. 2016;1364:277-290.
Fan AM, et al. Virus mediated knockdown of Nav1.3 in dorsal root ganglia of STZ-Induced diabetic rats alleviates tactile allodynia. Mol Med. Jun. 2015;21:544-52.
Chali F, et al. Inhibiting cholesterol degradation induces neuronal sclerosis and epileptic activity in mouse hippocampus. Eur J Neurosci. May 2015, 41(10):1345-55.
Kao JH, et al. Effect of naltrexone on neuropathic pain in mice locally transfected with the mutant mu-opioid receptor gene in spinal cord. Br J Pharmacol Jan. 2015, 172(2):630-41.
Sun J, et al. Gene delivery of activated Factor VII Using Alternative AAV Serotype Improves Hemostasis in Hemophiliac Mice with FVIII Inhibitors and AAV Neutralizing antibodies. Hum Gene Ther. May 6, 2017. Epub ahead of print.
Tse LV, et al. Structure-guided evolution of antigenically distinct adeno-associated virus variants for immune evasion. Proc Natl Acad Sci USA May 30, 2017. Epub ahead of print.
Vandamme C, et al. Unraveling the complex story of immune responses to AAV vectors trial after trial. Hum Gene Ther. Aug. 23, 2017.
Fu H, et al. Differential prevalence of antibodies against adeno-associated virus in healthy children and patients with mucopolysaccharidosis III: perspective for AAV-mediated gene therapy. Human Gene Ther Clin Dev Sep. 19, 2017 Epub ahead of print.
Mingozzi F, et al. Overcoming the Host Immune Response to Adeno-Associated Virus Gene Delivery Vectors: The Race Between Clearance, Tolerance, Neutralization, and Escape. Annu Rev Virol Sep. 29, 2017;4(1):511-534.
Majowicz A, et al. Successful Repeated Hepatic Gene Delivery in Mice and Non-human Primates Achieved by Sequential Administralion of AAV5ch and AAV1. Mol Ther. Jun. 5, 2017. Epub ahead of print.
Kim Y, et al. Mutagenic Analysis of an Adeno-Associated Virus Variant Capable of Simultaneously Promoting Immune Resistance and Robust Gene Delivery. Hum Gene Ther. Jun. 24, 2017. Epub ahead of print.
Gil-Farina I, et al. Recombinant AAV Integration is not Associated With Hepatic Genotoxicity in Nonhuman Primates and Patients. Mol Ther. Jun. 2016;24(6):1100-5.
Logan GJ, et al. Identification of liver-specific enhancer-promoter activity in the 3' untranslated region of the wild-type AAV2 genome. Nat Genet. Jun. 19, 2017. Epub ahead of print.
Pillay S, et al. AAV serotypes have distinctive interactions with domains of the cellular receptor AAVR. J Virol. Jul. 5, 2017. Epub ahead of print.
Wang M, Sun J, Crosby A, Woodard K, Hirsch ML, Samulski RJ, Li C. Direct interaction of human serum proteins with AAV virions to enhance AAV transduction: immediate impacton clinical applications. Gene Ther. Jan. 2017;24(1):49-59. doi: 10.1038/gt.2016.75. Epub Nov. 11, 2016.

(56) References Cited

OTHER PUBLICATIONS

Lu J, et al. A 5' Noncoding Exon Containing Engineered Intron Enhances Transgene Expression from Recombinant AAV Vectors in vivo. Hum Gene Ther. Jan. 2017;28(1):125-134.
Bennett A, et al. Thermal Stability as a Determinant of AAV Serotype Identity. Mol Ther Methods Clin Dev. Jul. 24, 2017;6:171-182. doi: 10.1016/j.omtm.2017.07.003.
Gray-Edwards H, et al. AAV gene therapy in a sheep model of Tay-Sachs disease. Human Gene Therapy. Sep. 19, 2017 Epub ahead of print.
Guggino W, et al. A Preclinical Study in Rhesus Macaques for Cystic Fibrosis To Assess Gene Transfer and Transduction by AAV1 and AAV5 With a Dual-Luciferase Reporter System. Hum Gene Ther Clin Dev. Jul. 20, 2017.
Eichler F, et al. Hematopoietic Stem-Cell Gene Therapy for Cerebral Adrenoleukodystrophy. N Engl J Med Oct. 4, 2017 Epub ahead of print.
Bennett A, et al. Understanding capsid assembly and genome packaging for adeno-associated viruses. Future Virology Jun. 2017; 12(6): 283-297.
Grimm D, et al. Small but increasingly mightly—latest advances in AAV vector research, design and evolution. Hum Gene Ther. Aug. 23 Epub ahead of print.
Pillay S, et al. Host determinants of adeno-associated viral vector entry. Curr Opin Virol. Jun. 30, 2017;24:124-131. Epub ahead of print.
Smith LJ, et al. Gene transfer properties and structural modeling of human stem cell-derived AAV. Molecular Therapy. Sep. 2014;22(9):1625-1634.
Wooley DP, et al. A directed evolution approach to select for novel Adeno-associated virus capsids on an HIV-1 producer T cell line. J Virol. Methods. Sep. 13, 2017 Epub ahead of print.
Biferi MG, et al. A New AAV10-U7-Mediated Gene Therapy Prolongs Survival and Restores Function in an ALS Mouse Model. Mol Ther. Jun. 26, 2017. Epub ahead of print.
Adachi K, et al. Drawing a high-resolution functional map of adeno-associated virus capsid by massively parallel sequencing. Nat Commun 2014;5:3075. doi: 10 1038/ncomms4075.
Ahmed SS, et al. rAAV gene therapy in a Canavan's disease mouse model reveals immune impairments and an extended pathology beyond the central nervous system. Mol Ther. Jun. 2016;24(6):1030-41.
Al J, et al. Adeno-associated virus serotype rh.10 displays strong muscle tropism following intraperitoneal delivery. Sci Rep. Jan. 2017;7:40336.
Altschul SF, et al. Basic local alignment search tool. J Mol Biol. Oct. 5, 1990;215(3):403-10.
Aoyama Y, et al. Wnt11 gene therapy with adeno-associated virus 9 improves the survival of mice with myocarditis induced by coxsackievirus B3 through the suppression of the inflammatory reaction. J Mol Cell Cardiol. Jul. 2015;84:45-51.
Aubourg P. Gene therapy for rare central nervous system diseases comes to age. Endocr Dev. 2016;30:141-6.
Aydemir F, et al. Mutants at the 2-fold interface of AAV2 structural proteins suggest a role in viral transcription for AAV capsids. J Virol. Jul. 2016;90(16):7196-204.
Bankiewicz KS et al. AAV Viral Vector Delivery to the Brain by Shape-conforming MR-guided Infusions. J Control Release. Oct. 28, 2016;240:434-442.
Bantel-Schaal U, et al. Human adeno-associated virus type 5 is only distantly related to other known primate helper-dependent parvoviruses. J Virol. Feb. 1999;73(2):939-47.
Baum BJ, et al. Advances in salivary gland gene therapy—oral and systemic implications. Expert Opinion on Biological Therapy. 2015;15(10):1443-54.
Bell P, et al. Effects of self-complementarity, codon optimization, transgene, and dose on liver transduction with AAV8. Hum Gene Ther Methods. Dec. 2016;27(6):228-237.
Berge SM Pharmaceutical salts. J Pharm Sci. Jan. 1977;66(1):1-19.
Berry GE, et al. Cellular transduction mechanisms of adeno-associated viral vectors. Curr Opin Virol. Dec. 2016;21:54-60.
Chiorini JA, et al. Adeno-associated virus (AAV) type 5 Rep protein cleaves a unique terminal resolution site compared with other AAV serotypes. J Virol. May 1999;73(5):4293-8.
Bey K, et al. Efficient CNS targeting in adult mice by intrathecal infusion of single-stranded AAV9-GFP for gene therapy of neurological disorders. Gene Ther. Apr. 20, 2017. Epub ahead of print.
Brulet R, et al. NEUROD1 Instructs Neuronal Conversion in Non-Reactive Astrocytes. Stem Cell Reports. May 11, 2017. Epub ahead of print.
Cabral-Miranda F, et al. rAAV8-733-Mediated Gene Transfer of CHIP/Stub-1 Prevents Hippocampal Neuronal Death in Experimental Brain Ischemia. Mol Ther. Feb. 2017;25(2):392-400.
Carillo H, et al. The Multiple Sequence Alignment Problem in Biology. SIAM J. Appl. Math. 48-5 (1988), pp. 1073-1082.
Carter BJ. Adeno-associated virus and the development of adeno-associated virus vectors: a historical perspective. Mol Ther. Dec. 2004;10(6):981-9.
Chandler RJ, et al. Systemic AAV9 gene therapy improves the lifespan of mice with Niemann-Pick disease, type C1. Hum Mol Genet. Jan. 2017;26(1):52-64.
Chiorini JA, et al. Adeno-associated virus (AAV) type 5 Rep protein cleaves a unique terminal resolution site compared with other AAV serotypes. J Virol. May 1999;73(5):4293-8.
Chiorini JA, et al. Cloning and characterization of adeno-associated virus type 5. J Virol. Feb. 1999;73(2):1309-19.
Chiorini JA, et al. Cloning of adeno-associated virus type 4 (AAV4) and generation of recombinant AAV4 particles. J Virol. Sep. 1997;71(9):6823-33.
Dang CH, et al. In vivo dynamics of AAV-mediated gene delivery to sensory neurons of the trigeminal ganglia. Sci Rep. Apr. 19, 2017;7(1):927.
Dashkoff J, et al. Tailored transgene expression to specific cell types in the central nervous system after peripheral injection with AAV. Mol Ther Methods Clin Dev. Dec. 2016;3:16081.
Devereux J A comprehensive set of sequence analysis programs for the VAX. Nucleic Acids Res. Jan. 11, 1984;12(1 Pt 1):387-95.
Dimidschsien J, et al. A viral strategy for targeting and manipulating interneurons across vertebrate species. Nat Neurosci. Dec. 2016;19(12):1743-1749.
Ding C, et al., Biochemical Characterization of Junonia Coenia Densovirus Nonstructural Protein NS-1. J. Virol., 76(1):338-345 2002.
Donsante A et al. Intracerebroventricular delivery of self-complementary adeno-associated virus serotype 9 to the adult rat brain. Gene Ther. May 2016;23(5):401-7.
Earley LF, et al. Adeno-Associated Virus Assembly-Activating Protein is not an Essential Requirement for Capsid Assembly of AAV Serotypes 4, 5 and 11. J Virol. Jan. 2017;91(3):pii:e0198-16.
El-Shamayleh Y, et al. Strategies for targeting primate neural circuits with viral vectors. J Neurophysiol. Jul. 2016; 116(1):122-34.
Fargnoli AS, et al. Liquid jet delivery method featuring S100A1 gene therapy in the rodent model following acute myocardial infarction. Gene Ther. Feb. 2016;23(2):151-7.
Foust KD, et al. Intravascular AAV9 preferentially targets neonatal neurons and adult astrocytes. Nat Biotechnol. Jan. 2009;27(1):59-65. doi: 10.1038/nbt.1515. Epub Dec. 21, 2008.
Gessler DJ et al. Gene Therapy for the Treatment of Neurological Disorders: Metabolic Disorders. Methods Mol Biol. 2016;1382:429-65.
Gilkes JA et al. Preferred Transduction with AAV8 and AAV9 Via Thalamic Administration in the MPS IIIB Model: A Comparison of Four rAAV Serotypes. Mol Genet Metab Rep. Dec. 7, 2015;6:48-54.
Gombash SE, et al. Systemic Gene Therapy for Targeting the CNS. Methods Mol Biol. 2016;1382:231-7.
Greig JA, et al. Impact of intravenous infusion time on AAV8 vector pharmacokinetics, safety, and liver transduction in cynomolgus macaGruntman AM, et al. Delivery of Adeno-associated virus gene therapy by intravascular limb infusion methods Hum Gene Ther Clin Dev Sep. 2015;26(3):159-64. ques. Mol Ther Methods Clin Dev. Dec. 2016;3:16079.

(56) References Cited

OTHER PUBLICATIONS

Greig JA, et al. Intramuscular administration of AAV overcomes pre-existing neutralizing antibodies in rhesus macaques. Vaccine. Dec. 2016;34(50):6323-6329.
Gribskov M, et al. Sequence Analysis Primer. M Stockton Press, New York, 1991.
Grimm D, et al. Progress in adeno-associated virus type 2 vector production: promises and prospects for clinical use. Hum Gene Ther. Oct. 10, 1999;10(15):2445-50.
Grimson A, et al. MicroRNA targeting specificity in mammals: determinants beyond seed pairing. Mol Cell. Jul. 6, 2007;27(1):91-105.
Gruntman AM, et al. Delivery of Adeno-associated virus gene therapy by intravascular limb infusion methods. Hum Gene Ther Clin Dev Sep. 2015;26(3):159-64.
Gruntman AM, et al. Retro-Orbital Venous Sinus Delivery of rAAV9 Mediates High-Level Transduction of Brain and Retina Compared with Temporal Vein Delivery in Neonatal Mouse Pups. Hum Gene Ther. Mar. 2017;28(3):228-230.
Gurda BL, et al. Evaluation of AAV-mediated gene therapy for central nervous system disease in canine mucopolysaccharidosis VII. Mol Ther. Feb. 2016;24(2):206-16.
Hagg A, et al. Using AAV vectors expressing the beta 2-adrenoceptor or associated G alpha proteins to modulate skeletal muscle mass and muscle fiber size. Sci Rep. Mar. 2016;6:23042.
Hai B, et al. Long-term transduction of miniature pig parotid glands using serotype 2 adeno-associated viral vectors. J Gene Med. Jun. 2009;11(6):506-14.
Hastie E, et al. Adeno-Associated Virus at 50: A Golden Anniversary of Discovery, Research, and Gene Therapy Success—A Personal Perspective. Hum Gene Ther. May 2015, 26(5):257-65.
Hastie E, et al. Recombinant adeno-associated virus vectors in the treatment of rare diseases. Expert Opin Orphan Drugs. 2015;3(6):675-689.
Heim et al., Wavelength mutations and posttranslational autoxidation of green fluorescent protein. Proc. Natl. Acad. Sci. USA (1994).
Powell et al., Viral Expression Cassette Elements to Enhance Transgene Target Specificity and Expression in Gene Therapy. Discov Med. Jan. 2015;19(102):49-57.
Bensimon G et al., "A study of riluzole in the treatment of advanced stage or elderly patients with amyotrophic lateral sclerosis," J Neurol., vol. 249: 609-615 (2002).
Brown, J. et al., Intraparenchymal Spinal Cord Delivery of AAV VY-SOD102 Reduces Disease Burden in the G93A Mouse Model of ALS-SOD1, ASGCT—2020 Annual Meeting, May 12-15, 2020, 1 page.
Ding H et al., "Design of functional small interfering RNAs targeting amyotrophic lateral sclerosis-associated mutant alleles," Chinese Medical J , vol. 124(1): 106-110 (2011).
Fujita, Y. et al., "The Golgi apparatus is fragmented in spinal cord motor neurons of amyotrophic lateral sclerosis with basophilic inclusions," Acta Neuropathol, vol. 103:243-247 (2002).
Ghatak et al., "Anterior horn changes of motor neuron disease associated with demyelinating radiculopathy" J Neuropathol Exp Neurol., vol. 45: 385-395 (1986).
Griffin AM, et al. Computer Analysis of Sequence Data, Part I. Humana Press, New Jersey, 1994.
Holger Patzke, "Robust SOD1 Knockdown in Large Mammal Spinal Cord Using a Novel Delivery Paradigm With AAV Gene Therapy Targeting SOD1 for the Treatment of SOD1-ALS," ALSMND Dec. 7-9, 2018.
Kawamata, T. et al., "Immunologic reactions in amyotrophic lateral sclerosis brain and spinal cord tissue," Am J Pathol., vol. 140:691-707 (1992).
Kim C., et al., "Amyotrophic lateral sclerosis—cell based therapy and novel therapeutic development," Exp. Neurobiol., vol. 23(3): 207-214 (2014).
Lepore. et al., "Intraparenchymal spinal cord delivery of adeno-associated virus IGF-1 is protective in the SOD1 G93A model of ALS," Brain Research, vol. 1185: 256-265 (2007).
Maekawa, S. et al., Cortical selective vulnerability in motor neuron disease: a morphometric study Brain, vol. 27:1237-1251 (2004).
Matsumoto et al., "Ubiquitin-positive inclusion in anterior horn cells in subgroups of motor neuron diseases: a comparative study of adult-onset amyotrophic lateral sclerosis, juvenile amyotrophic lateral sclerosis and Werdnig-Hoffmann disease," J Neurol Sci., vol. 115: 208-213 (1993).
Maxwell MM et al., "RNA interference-mediated silencing of mutant superoxide dismutase rescues cyclosporin A-induced death in cultured neuroblastoma cells," PNAS, vol. 101(9):3178-3183 (2004).
McBride, J. et al., "Preclinical Safety of RNAi-Mediated HTT Suppression in the Rhesus Macaque as a Potential Therapy for Huntington's Disease," Molecular Therapy, vol. 19(12):2152-2162 (2011).
Mitroshina, EV et al., "Ration of Recombinant Adenoassociated Viruses for Transduction of Dell Cultures," The State University of Nizhny Novgorod (2013) No English Translation available.
Partial European Search Report, European Application No. 18794385, dated Feb. 1, 2021, 13 pages.
Philips, T, and J D Rothstein. "Glial cells in amyotrophic lateral sclerosis." Experimental Neurology, vol. 262 Pt B (2014): 111-20 doi:10.1016/j.expneurol.2014.05.015.
Renton, A. et al., "State of play in amyotrophic lateral sclerosis genetics," Nat. Neurosci., vol. 17:17-23 (2014).
Rizvanov AA et al., "Retrogradely transported siRNA silences human mutant SOD1 in spinal cord motor neurons," Exp. Brain Res., vol. 195(1): 1-4 (2009).
Robberecht and Philip, "The changing scene of amyotrophic lateral sclerosis," Nat. Rev. Neurosci., vol. 14: 248-264 (2013).
Rosen DR et al., "Mutations in Cu/Zn superoxide dismutase gene are associated with familial amyotrophic lateral sclerosis," Nature, vol. 362: 59-62 (1993).
Rotunno MS and Bosco DA, "An emerging role for misfolded wild-type SOD1 in sporadic ALS pathogenesis," Front Cell Neurosci., vol. 16 (7): 253 (2013).
Rowland LP and Shneibder, "Amyotrophic lateral sclerosis," NA, N Engl. J. Med., vol. 344: 1688-1700 (2001).
Sasaki and Maruyama, "Immunocytochemical and ultrastructural studies of the motor cortex in amyotrophic lateral sclerosis" Acta Neuropathol., vol. 87: 578-585 (1994).
Schiffer D. et al., "Reactive astrogliosis of the spinal cord in amyotrophic lateral sclerosis," J Neurol Sci., vol. 139: 27-33 (1996).
Schwarz DS et al., "Designing siRNA that distinguish between genes that differ by a single nucleotide," Plos Genet., vol. 2(9): e140 (2006).
Thomsen, G.M., et al.,"Delayed Disease Onset and Extended Survival in the SOD1G93A Rat Model of Amyotrophic Lateral Sclerosis after Suppression of Mutant SOD1 in the Motor Cortex," The Journal of Neuroscience, vol. 34 (47):15587-15600 (2014).
Udaka et al., "Degeneration of Betz cells in motor neuron disease. A Golgi study," Acta Neuropathol., vol. 70:289-295 (1986).
Vehvilainen P et al., "Mechanisms of mutant SOD1 induced mitochondrial toxicity in amyotrophic lateral sclerosis," Front Cell Neurosci., vol. 8: 126 (2014).
Voyager Therapeutics: "Intravenous Delivery of Novel AAV Capsids," Oct. 20, 2017 (Oct. 20, 2017), XP055630466, Retrieved from the Internet: URL:https://www.voyagertherapeutics.com/wp-content/uploads/2017/10/ESGCT_slides.pdf [retrieved on Oct. 9, 2019].
Wang H et al., "Therapeutic gene silencing delivered by a chemically modified small interfering RNA against mutant SOD1 slows amyotrophic lateral sclerosis progression," J Biol. Chem., vol. 283(23):15845-15852 (2008).
Wang, H. et al., "Widespread spinal cord transduction by intrathecal injection of rAAV delivers efficacious RNAi therapy for amyotrophic lateral sclerosis," Human Molecular Genetics, vol. 23(3):668-681 (2014).
Wroe R et al., "ALSOD: the Amyotrophic Lateral Sclerosis Online Database," Amyotroph Lateral Scler., vol. 9:249-250 (2008).
Wu, R. et al., "Nerve Injection of Viral Vectors Efficiently Transfers Transgenes into Motor Neurons and Delivers RNAi Therapy Against ALS," Antioxidantsand Redox Signaling, vol. 11 (7):1523-1534 (2009).

(56) References Cited

OTHER PUBLICATIONS

Xue, J. et al., "Epigenetics: Principles, Protocols and practices," 121-122 (2006) No English Translation available.

Yacila and Sari, "Potential therapeutic drugs and methods for the treatment of amyotrophic lateral sclerosis," Curr Med Chem., vol. 21(31): 3583-3593 (2014).

Lee SH et al., Intrathecal delivery of recombinant AAV1 encoding hepatocyte growth factor improves motor functions and protects neuromuscular system in the nerve crush and SOD1-G93A transgenic mouse models. Acta Neuropathol Commun. Jun. 12, 2019;7(1):14.

Leyton-Jaimes et al., AAV2/9-mediated overexpression of MIF inhibits SOD1 misfolding, delays disease onset, and extends survival in mouse models of ALS. Proc Natl Acad Sci U S A. Jul. 1, 2019.

Bofill-De Ros et al. Guidelines for the optimal design of miRNA-based shRNAs. Methods. Jul. 1, 2016;103:157-66.

Miyagishi et al. Optimization of an siRNA-expression system with an improved hairpin and its significant suppressive effects in mammalian cells. The Journal of Gene Medicine: A cross-disciplinary journal for research on the science of gene transfer and its clinical applications. Jul. 2004;6(7):715-23.

Du et al. Design of expression vectors for RNA interference based on miRNAs and RNA splicing. The FEBS journal. Dec. 2006;273(23):5421-7.

Calloni et al. Scaffolds for artificial miRNA expression in animal cells Human gene therapy methods Aug. 27, 2015;26(5):162-74.

Schopman et al. Optimization of shRNA inhibitors by variation of the terminal loop sequence. Antiviral research. May 1, 2010;86(2):204-11.

Bravo-Hernandez et al., Spinal subpial delivery of AAV9 enables widespread gene silencing and blocks motoneuron degeneration in ALS. Nat Med. Dec. 23, 2019.

Lim et al., Treatment of a Mouse Model of ALS by in Vivo Base Editing. Mol Ther. Jan. 14, 2020. [Epub ahead of print].

Cornetta et al., The National Gene Vector Biorepository: Eleven Years of Providing Resources to the Gene Therapy Community. Hum Gene Ther. Feb. 2020;31(3-4):145-150.

Khosravi et al., Cell-to-cell transmission of C9orf72 poly-(Gly-Ala) triggers key features of als/ftd. embo J. Mar. 16, 2020:e102811. [Epub ahead of print].

Bey et al., Intra-CSF AAV9 and AAVrh10 administration in non-human primates: promising routes and vectors for what neurological diseases? Molecular Therapy Methods & Clinical Development Apr. 11, 2020.

Hinderer et al., Translational feasibility of lumbar puncture for intrathecal AAV administration. Molecular Therapy Methods & Clinical Development. Apr. 17, 2020.

Lind et al., Intralingual administration of AAVrh10-miR SOD1 improves respiratory but not swallowing function in a SOD1 mouse model of ALS. Human Gene Therapy. Jun. 5, 2020.

Mueller et al., SOD1 Suppression With Adeno-Associated Virus and MicroRNA in Familial ALS. N Engl J Med. Jul. 9, 2020;383(2):151-158.

Kotin RM, et al. Manufacturing clinical grade recombinant adeno-associated virus using invertebrate cell lines. Hum Gene Ther. Mar. 28, 2017. Epub ahead of print.

Kotterrman MA, et al. Enhanced cellular secretion of AAV2 by expression of foreign viral envelope proteins. Biochemical Engineering Journal, vol. 93, Jan. 15, 2015, pp. 108-114.

Methods in Molecular Biology, ed. Richard, Humana Press, NJ (1995).

Mietzsch M, et al. OneBac 2.0: Sf9 Cell Lines for Production of AAV1, AAV2 and AAV8 Vectors with Minimal Encapsidation of Foreign DNA. Hum Gene Ther Methods. Feb. 2017;28(1):15-22.

Mietzsch M, et al. OneBac 2.0: Sf9 cell lines for production of AAV5 vectors with enhanced infectivity and minimal encapsidation of foreign DNA. Hum Gene Ther. Oct. 26, 2015(10):688-97.

Nambiar B, et al. Characteristics of minimally oversized adeno-associated virus vectors encoding human Factor VIII generated using producer cell lines and triple transfection. Hum Gene Ther Methods. Feb. 2017;28(1):23-38.

Pacouret S, et al. AAV-ID: A Rapid and Robust Assay for Batch-to-Batch Consistency Evaluation of AAV Preparations. Mol Ther. Apr. 17, 2017. Epub ahead of print.

Penaud-Budloo M, et al. Accurate identification and quantification of DNA species by next-generation sequencing in adeno-associated viral vectors produced in insect cells. Hum Gene Ther Methods. May 2, 2017. Epub ahead of print.

Ruffing M, et al. Assembly of viruslike particles by recombinant structural proteins of adeno-associated virus type 2 in insect cells. J Virol. Dec. 1992;66(12):6922-30.

Samulski RJ, et al. Helper-free stocks of recombinant adeno-associated viruses: normal integration does not require viral gene expression. J Virol. Sep. 1989;63(9):3822-8.

Smith RH, et al. A simplified baculovirus-AAV expression vector system coupled with one-step affinity purification yields high-titer rAAV stocks from insect cells. Mol Ther. Nov. 2009;17(11):1888-96. doi: 10.1038/mt.2009.128. Epub Jun. 16, 2009.

Urabe M, et al. Scalable generation of high-titer recombinant adeno-associated virus type 5 in insect cells. J Virol. Feb. 2006;80(4):1874-85.

Van Der Loo Jcm, et al. Progress and challenges in viral vector manufacturing. Hum Mol Genet. Apr. 2016;25(R1):R42-52.

Wasilko DJ, et al. The titerless infected-cells preservation and scale-up (TIPS) method for large-scale production of NO-sensitive human soluble guanylate cyclase (sGC) from insect cells infected with recombinant baculovirus. Protein Expr Purif. Jun. 2009;65(2):122-32. doi: 10.1016/j.pep.2009.01.002. Epub Jan. 11, 2009.

Zhao KN, et al. BPV1 E2 protein enhances packaging of full-length plasmid DNA in BPV1 pseudovirions. Virology. Jul. 5, 2000;272(2):382-93.

Pierson EE, et al. Resolving adeno-associated viral particle diversity with charge detection mass spectrometry. Anal Chem. Jul. 2016;88(13):6718-25.

Rashnonejad A, et al. Large-Scale Production of Adeno-Associated Viral Vector Serotype-9 Carrying the Human Survival Motor Neuron Gene. Mol Biotechnol Jan. 2016;58(1):30-6.

Ling C, et al. Strategies to generate high-titer, high-potency recombinant AAV3 serotype vectors. Mol Ther Methods Clin Dev. May 2016;3:16029.

Afione S, et al. Identification and Mutagenesis of the Adeno-Associated Virus 5 Sialic Acid Binding Region.J Virol. Feb. 2015, 89(3):1660-72.

Drouin LM, et al. Cryo-electron microscopy reconstruction and stability studies of Wild-Type and R432A Variant of AAV2 Reveals Capsid Structural Stability is a Major Factor in Genome Packaging. J Virol. Sep. 2016;90(19):8542-51.

Halder S, et al. Structure of neurotropic adeno-associated virus AAVrh.8. J Struct Biol. Oct. 2015;192(1):21-36.

Huang LY, et al. Characterization of the adeno-associated virus 1 and 6 sialic acid binding site. J Virol. May 2016;90 (11):5219-30.

Mao Y, et al. Single point mutation in adeno-associated viral vectors—DJ capsid leads to improvement for gene delivery in vivo BMC Biotechnol. Jan. 2016;16:1.

Tu My, et al. Role of capsid proteins in parvoviruses infection. Virol J. Aug. 2015, 4;12:114.

Zeng C, et al. Probing the Link between Genomic Cargo, Contact Mechanics and Nanoindentation in Recombinant Adeno-Associated Virus 2. J Phys Chem B. Mar. 2017;121(8):1843-1853.

Zinn E, et al. In Silico Reconstruction of the Viral Evolutionary Lineage Yields a Potent Gene Therapy Vector. Cell Rep. Aug. 2015, 12(6):1056-68.

Grimm D, et al. E Pluribus Unum: 50 years of research, millions of viruses and one goal—tailored acceleration of AAV evolution. Mol Ther. Dec. 2015;23(12):1819-1831.

Karamuthil-Melethil S, et al. Novel Vector Design and Hexosaminidase Variant Enabling Self-Complementary Adeno-Associated Virus for the Treatment of Tay-Sachs Disease. Hum Gene Ther. Jul. 2016;27(7):509-21.

(56) References Cited

OTHER PUBLICATIONS

Pillay S, et al. An essential receptor for adeno-associated virus infection. Nature. Feb. 2016;530(7588):108-12.
Li Bz, et al. Site directed mutagenesis of surface-exposed lysine residues leads to improved transduction by AAV2 but not AAV8 vectors in murine hepatocytes in vivo. Hum Gene Ther Methods. Dec. 2015;26(6):211-20.
Shen S, et al. Functional Analysis of the Putative Integrin Recognition Motif on Adeno-associated virus 9. J Biol Chem. Jan. 2015, 290(3):1496-504.
Steines B, et al. CFTR gene transfer with AAV improves early cystic fibrosis pig phenotypes. JCI Insight. Sep. 2016;1 (14):e88728.
Bensky MJ, et al. Targeted gene delivery to the enteric nervous system using AAV: a comparison across serotypes and capsid mutants.Mol Ther Mar. 2015,23(3):488-500.
Castle MJ, et al. Controlling AAV Tropism in the Nervous System with Natural and Engineered Capsids. Methods Mol Biol. 2016;1382:133-49.
Choudhury SR, et al. Widespread CNS gene transfer and silencing after systemic delivery of novel AAV-AS vectors. Mol Ther. Apr. 2016;24(4):726-35.
Davis AS, et al. Rational design and engineering of a modified adeno-associated virus (AAV1)-based vector system for enhanced retrograde gene delivery. Neurosurgery Feb. 2015;76(2):216-25.
Deverman BE et al. Cre-dependent selection yields AAV variants for widespread gene transfer to the adult brain. Mat Biotechnol. Feb. 2016;34(2):204-9.
Powell SK et al. Characterization of a novel adeno-associated viral vector with preferential oligodendrocyte tropism. Gene Ther Sep. 15, 2016.
Tervo et al. A Designer AAV Variant Permits Efficient Retrograde Access to Projection Neurons. Neuron. Oct. 19, 2016;92(2):372-382.
Choudhury et al. In Vivo Selection Yields AAV-B1 Capsid for Central Nervous System and Muscle Gene Therapy. Mol Ther. Aug. 2016;24(7):1247-57.
Keravala A, et al. Evaluating AAV Hybrid Variants for Improved Tropism after Intravitreal Gene Delivery to the Retina. Molecular Therapy, vol. 23, Supplement 1, May 2015, pp. S127-S128.
Vercauteren K, et al. Superior in vivo Transduction of Human Hepatocytes Using Engineered AAV3 Capsid. Mol Ther. Jun. 2016;24(6):1042-9.
Chen M, et al. Efficient Gene Delivery and Expression in Pancreas and Pancreatic Tumors by Capsid-optimized AAV8 Vectors. Hum Gling C, et al. High-Efficiency Transduction of Primary Human Hematopoietic Stem/Progenitor Cells by AAV6 Vectors: Strategies for Overcoming Donor-Variation and Implications in Genome Editing. Sci Rep. Oct. 2016;6:35495. Gene Ther Methods Feb. 2017;28(1):49-59.
Ling C, et al. High-Efficiency Transduction of Primary Human Hematopoietic Stem/Progenitor Cells by AAV6 Vectors: Strategies for Overcoming Donor-Variation and Implications in Genome Editing Sci Rep. Oct. 2016;6:35495.
Earley LF, et al. Identification and Characterization of Nuclear and Nucleolar Localization Signals in the Adeno-Associated Virus Serotype 2 Assembly-Activating Protein. J Virol. Mar. 2015, 89(6):3038-48.
Zou W, et al. Nonstructural protein NP1 of human bocavirus 1 plays a critical role in the expression of viral capsid proteins. J Virol. Apr. 2016;90(9):4658-69.
Mingozzi F, et al. Adeno-associated viral vectors at the frontier between tolerance and immunity. Front Immunol. Mar. 2015, 6:120.
Ling C, et al. Enhanced Transgene Expression from Recombinant Single-Stranded D-Sequence-Substituted Adeno-Associated Virus Vectors in Human Cell Lines In Vitro and in Murine Hepatocytes In Vivo. J Virol. Jan. 2015, 89(2):952-61.
Huang W, et al. Targeting Visceral Fat by Intraperitoneal Delivery of Novel AAV Serotype Vector Restricting Off-Target Transduction in Liver. Mol Ther Methods Clin Dev. Jun. 19, 2017;6:68-78.

Herrera-Carrillo E, et al. Improving miRNA delivery by optimizing miRNA expression cassettes in viral vectors. Hum Gene Ther Methods. Jul. 16, 2017.
Krhac Levacic A, et al. Minicircle versus plasmid DNA delivery by receptor-targeted polyplexes. Hum Gene Ther. Aug. 21, 2017 Epub ahead of print.
Moffett HF, et al. Hit-and-run programming of therapeutic cytoreagents using mRNA nanocarriers. Nat Commun. Aug. 30, 2017;8(1):389.
Ly CV and Miller TM. Emerging antisense olgionucleotide and viral therapies for amyotrophic lateral sclerosis. Curr Opin. Neurol. Jul. 19, 2018 Epub ahead of print.
Raoul C et al. Lentiviral-mediated silencing of SOD1 through RNA interference retards disease onset and progression in a mouse model of ALS.
Paré B, et al. Misfolded SOD1 pathology in sporadic Amyotrophic Lateral Sclerosis. Sci Rep. Sep. 21, 2018;8(1):14223.
Martier R, et al. Artificial microRNAs targeting C9ORF72 have the potential to reduce accumulation of the intra-nuclear transcripts in ALS and FTD patients. Molecular Therapy Nucleic Acids. Jan. 22, 2019.
BY999593, GenBank EST No. BY999593, BY999593 human cDNA library, immortalized cell line of corneal epithelial cells *Homo sapiens* cDNA clone cp1739 3-, mRNA sequence, Apr. 14, 2008 [online], [Retrived on Apr. 5, 2016]. Retrieved from the internet ,URL: http://www.ncbi.nlm.nih.gov/nucest/BY999593. Entire document.
International Search Report dated Apr. 19, 2016 received in corresponding PCT Application No. PCT/US2015/060562.
Park JE et al., Dicer recognizes the 5' end of RNA for efficient and accurate processing. Nature. Jul. 13, 2011;475(7355):201-5.
Schwarz DS et al., Asymmetry in the assembly of the RNAi enzyme complex. Cell. Oct. 17, 2003; 115(2):199-208.
Seitz H et al., A 5'-uridine amplifies miRNA/miRNA* asymmetry in *Drosophila* by promoting RNA-induced silencing complex formation. Silence. Jun. 7, 2011;2:4.
Wang D et al., Adeno-associated virus vector as a platform for gene therapy delivery. Nat Rev Drug Discov. Feb. 1, 2019.
Maniatis S et al., Spatiotemporal dynamics of molecular pathology in amyotrophic lateral sclerosis.Science Apr. 5, 2019: vol. 364, Issue 6435, pp. 89-93.
Borel F et al., Recombinant AAV as a platform for translating the therapeutic potential of RNA interference. Mol Ther. Apr. 2014;22(4):692-701.
Pfeifer A et al., Pharmacological potential of RNAi-focus on miRNA. Pharmacol Ther. Jun. 2010;126(3):217-27.
Xie J et al., Short DNA Hairpins Compromise Recombinant Adeno-Associated Virus Genome Homogeneity. Mol Ther. Jun. 7, 2017;25(6):1363-1374.
Poesen et al., Neurofilament markers for ALS correlate with extent of upper and lower motor neuron disease. Neurology Jun. 13, 2017; 88(24):2302-2309. Epub May 12, 2017.
Toedebusch et al., Cerebrospinal Fluid Levels of Phosphorylated Neurofilament Heavy as a Diagnostic Marker of Canine Degenerative Myelopathy. J Vet Intern Med. Mar.-Apr. 2017; 31(2): 513-520. Published online Feb. 10, 2017.
Nardone et al., Canine degenerative myelopathy: a model of human amyotrophic lateral sclerosis. Zoology (Jena). Feb. 2016; 119(1):64-73. Epub Sep. 21, 2015.
Crisp et al., Canine degenerative myelopathy: Biochemical characterization of superoxide dismutase 1 in the first naturally occurring. Exp Neurol Oct. 2013; 248:1-9 Epub May 25, 2013.
Awano et al., Genome-wide association analysis reveals a SOD1 mutation in canine degenerative myelopathy that resembles amyotrophic lateral sclerosis. Proc Natl Acad Sci U S A. Feb. 24, 2009; 106(8): 2794-2799. Published online Feb. 2, 2009.
Al-Chalabi et al., Deletions of the heavy neurofilament subunit tail in amyotrophic lateral sclerosis. Hum Mol Genet. Feb. 1999;8(2):157-64.
Al-Chalabi et al., The epidemiology of ALS: a conspiracy of genes, environment and time. Nat Rev Neurol. Nov. 2013;9(11):617-28.
Alonso et al., Incidence and lifetime risk of motor neuron disease in the United Kingdom: a population-based study. Eur J Neurol. Jun. 2009;16(6):745-51.

(56) References Cited

OTHER PUBLICATIONS

Armon et al., Sports and trauma in amyotrophic lateral sclerosis revisited. J Neurol Sci. Nov. 15, 2007;262(1-2):45-53.
Arnold et al., ALS-linked TDP-43 mutations produce aberrant RNA splicing and adult-onset motor neuron disease without aggregation or loss of nuclear TDP-43. Proc Natl Acad Sci U S A. Feb. 19, 2013;110(8):E736-45.
Ayala et al., TDP-43 regulates retinoblastoma protein phosphorylation through the repression of cyclin-dependent kinase 6 expression. Proc Natl Acad Sci U S A. Mar. 11, 2008;105(10):3785-9.
Bali et al., Defining SOD1 ALS natural history to guide therapeutic clinical trial design. J Neurol Neurosurg Psychiatry. Feb. 2017;88(2):99-105.
Battistini et al., SOD1 mutations in amyotrophic lateral sclerosis. Results from a multicenter Italian study. J Neurol. Jul. 2005;252(7):782-8.
Berry JD et al., New considerations in the design of clinical trials for amyotrophic lateral sclerosis. Clin Investig (Lond). Oct. 2011;1(10):1375-1389.
Bevan AK et al., Systemic gene delivery in large species for targeting spinal cord, brain, and peripheral tissues for pediatric disorders. Mol Ther. Nov. 2011;19(11):1971-80.
Van Blitterswijk et al., Anti-superoxide dismutase antibodies are associated with survival in patients with sporadic amyotrophic lateral sclerosis. Amyotroph Lateral Scler. Nov. 2011;12(6):430-8.
Boillee S et al., Onset and progression in inherited ALS determined by motor neurons and microglia. Science. Jun. 2, 2006;312(5778):1389-92.
Borchelt DR et al., Superoxide dismutase 1 with mutations linked to familial amyotrophic lateral sclerosis possesses significant activity. Proc Natl Acad Sci USA. Aug. 16, 1994;91(17):8292-6.
Bosco DA et al., Wild-type and mutant SOD1 share an aberrant conformation and a common pathogenic pathway in ALS. Nat Neurosci. Nov. 2010;13(11):1396-403.
Brown et al. Analysis of mutant SOD1 electrophoretic mobility by Blue Native gel electrophoresis; evidence for soluble multimeric assemblies. PLoS One. Aug. 14, 2014;9(8):e104583.
Cedarbaum JM et al., The ALSFRS-R: a revised ALS functional rating scale that incorporates assessments of respiratory function. BDNF ALS Study Group (Phase III). J Neurol Sci. Oct. 31, 1999;169(1-2):13-21.
Chung et al., Cu/Zn superoxide dismutase can form pore-like structures. Biochem Biophys Res Commun. Dec. 26, 2003;312(4):873-6.
Clement et al., Wild-type nonneuronal cells extend survival of SOD1 mutant motor neurons in ALS mice. Science. Oct. 3, 2003;302(5642):113-7.
Cudkowicz et al., Epidemiology of mutations in superoxide dismutase in amyotrophic lateral sclerosis. Ann Neurol. Feb. 1997;41(2):210-21.
De Boer et al., Genetic validation of a therapeutic target in a mouse model of ALS. Sci Transl Med. Aug. 6, 2014;6 (248):248ra104.
De la Maza. Molecular sturcture of adeno-associated virus variant DNA. JBC. Apr. 1980;255(7):3194-3203.
Deng et al., FUS-immunoreactive inclusions are a common feature in sporadic and non-SOD1 familial amyotrophic lateral sclerosis. Ann Neurol. Jun. 2010;67(6):739-48.
Deng HX et al., Mutations in UBQLN2 cause dominant X-linked juvenile and adult-onset ALS and ALS/dementia. Nature. Aug. 21, 2011;477(7363):211-5.
Di Giorgio et al., Non-cell autonomous effect of glia on motor neurons in an embryonic stem cell-based ALS model. Nat Neurosci. May 2007;10(5):608-14.
Dirren et al., SOD1 silencing in motoneurons or glia rescues neuromuscular function in ALS mice. Ann Clin Transl Neurol. Feb. 2015; 2(2):167-184.
Dupuis L et al., Differential screening of mutated SOD1 transgenic mice reveals early up-regulation of a fast axonal transport component in spinal cord motor neurons. Neurobiol Dis. Aug. 2000;7(4):274-85.

Elchuri et al., CuZnSOD deficiency leads to persistent and widespread oxidative damage and hepatocarcinogenesis later in life Oncogene. Jan. 13, 2005;24(3):367-80.
Epstein et al., Transgenic mice with increased Cu/Zn-superoxide dismutase activity: animal model of dosage effects in Down syndrome. Proc Natl Acad Sci U S A. Nov. 1987;84(22):8044-8.
Estévez et al., Induction of nitric oxide-dependent apoptosis in motor neurons by zinc-deficient superoxide dismutase. Science. Dec. 24, 1999;286(5449):2498-500.
Gurney et al., Motor neuron degeneration in mice that express a human Cu,Zn superoxide dismutase mutation. Science. Jun. 17, 1994;264(5166):1772-5.
Haidet-Phillips et al., Astrocytes from familial and sporadic ALS patients are toxic to motor neurons. Nat Biotechnol. Aug. 11, 2011;29(9):824-8.
Johnston et al., Amyotrophic lateral sclerosis in an urban setting: a population based study of inner city London. J Neurol. Dec. 2006;253(12):1642-3.
Jonsson el al., Minute quantities of misfolded mutant superoxide dismutase-1 cause amyotrophic lateral sclerosis. Brain. Jan. 2004;127(Pt 1):73-88.
Kanning et al., Motor neuron diversity in development and disease. Annu Rev Neurosci. 2010;33:409-40.
Ly CV et al., Emerging antisense oligonucleotide and viral therapies for amyotrophic lateral sclerosis. Curr Opin Neurol. Oct. 2018;31(5):648-654.
Challis et al., Systemic AAV vectors for widespread and targeted gene delivery in rodents. Nat Protoc. Feb. 2019;14 (2):379-414.
Elbashir et al., Functional anatomy of siRNAs for mediating efficient RNAi in *Drosophila melanogaster* embryo lysate. EMBO J. Dec. 3, 2001;20(23):6877-88.
Timothy M. Miller et al.: "Virus-delivered small RNA silencing sustains strength in amyotrophic lateral sclerosis", Annals of Neurology., vol. 57, No. 5, May 1, 2005 (May 1, 2005), pp. 773-776.
Chris Towne et al.: "Systemic AAV6 Delivery Mediating RNA Interference Against SOD1: Neuromuscular Transduction Does Not Alter Disease Progression in fALS Mice", Molecular Therapy: The Journal of the American Society of Gene Therapy, vol. 16, No. 6, Jun. 1, 2008 (May 6, 2008), pp. 1018-1025.
Takayuki Kubodera et al.: "In Vivo Application of an RNAi Strategy for the Selective Suppression of a Mutant Allele", Human Gene Therapy, vol. 22, No. 1, Jan. 1, 2011 (Jan. 1, 2011), pp. 27-34.
Yuki Saito et al: "Transgenic Small Interfering RNA Halts Amyotrophic Lateral Sclerosis in a Mouse Model", Journal of Biological Chemistry, vol. 280, No. 52, Oct. 12, 2005 (Oct. 12, 2005), pp. 42826-42830.
Rui Wu et al.: "Nerve Injection of Viral Vectors Efficiently Transfers Transgenes into Motor Neurons and Delivers RNAi Therapy Against ALS", Antioxidants and Redox Signaling, vol. 11, No. 7, Jul. 1, 2009 (Jul. 1, 2009), pp. 1523-1534.
H. Zhou: "An RNA polymerase II construct synthesizes short-hairpin RNA with a quantitative indicatorand mediates highly efficien RNAi", Nucleic Acids Research, vol. 33, No. 6, Mar. 23, 2005 (Mar. 23, 2005), pp. e62-e62.
Monica Nizzardo et al: "Research advances in gene therapy approaches for the treatment of amyotrophic lateral sclerosis", CMLS Cellular and Molecular Life Sciences, Birkhauser-Verlag, BA, vol. 69, No. 10, Nov. 18, 2011 (Nov. 18, 2011), pp. 1641-1650.
Extended European Search Report issued in corresponding EP Application No. 15859973.8 dated Apr. 30, 2018.
Xie J, et al. Short DNA Hairpins Compromise Recombinant Adeno-Associated Virus Genome Homogeneity. Mol Ther. Apr. 24, 2017. Epub ahead of print.
Davidsson M, et al. A novel process of viral vector barcoding and library preparation enables high-diversity library generation and recombination-free paired-end sequencing. Sci Rep. Nov. 2016;6:3563.
Chamberlain K, et al. Expressing transgenes that exceed the packaging capacity of AAV capsids. Hum Gene Ther Methods. Feb. 2016;27(1):1-12.
De Leeuw CN et al. rAAV-compatible MiniPromoters for Restricted Expression in the Brain and Eye. Mol Brain. May 10, 2016;9(1):52.

(56) References Cited

OTHER PUBLICATIONS

Hirsch ML, et al. Delivering Transgenic DNA Exceeding the Carrying Capacity of AAV Vectors Methods Mol Biol. 2016;1382:21-39.
Lu J, et al. A 5'non-coding exon containing engineered intron enhances transgene expression from recombinant AAV ectors in vivo. Hum Gene Ther. Jan. 2017;28(1):125-134.
Powell SK, et al. Viral expression cassette elements to enhance transgene target specificity and expression in gene therapy. Discov Med. Jan. 2015;19(102):49-57.
Rosario AM et al. Microglia-specific Targeting by Novel Capsid-modified AAV6 Vectors. Mol Ther Methods Clin Dev. Apr. 13, 2016;3:16026.
Wang L, et al. Productive life cycle of adeno-associated virus serotype 2 in the complete absence of a conventional polyadenylation signal. J Gen Virol. Sep. 2015;96(9):2780-7.
Yan ZY, et al. Optimization of recombinant adeno-associated virus mediated expression for large transgenes, using a synthetic promoter and tandem array enhancers. Hum Gene Ther. Jun. 2015;26(6):334-46.
Jackson KL, et al. Better Targeting, Better Efficiency for Wide-Scale Neuronal Transduction with the Synapsin Promoter and AAV-PHP. B. Front Mol Neurosci. Nov. 2016;6:116.
McClements ME, et al. A fragmented adeno-associated viral dual vector strategy for treatment of diseases caused by mutations in large genes leads to expression of hybrid transcripts. J Genet Syndr Gene Ther. Nov. 2016;7(5):311.
Parr MJ, et al. Tumor-selective transgene expression in vivo mediated by an E2F-responsive adenoviral vector. Nat Vied. Oct. 1997;3(10):1145-9.
Reid CA, et al. miRNA mediated post-transcriptional silencing of transgenes leads to increased adeno-associated viral vector yield and targeting specificity. Gene Ther. Jun. 15, 2017. Epub ahead of print.
Sawada Y et al. Inflammation-induced Reversible Switch of the Neuron-specific Enolase Promoter from Purkinje Neurons to Bergmann Glia. Sci Rep Jun. 13, 2016;6:27758.
Lukashcuk V et al. AAV9-mediated central nervous system-targeted gene delivery via cisterna magna route in mice. Mol Ther Methods Clin Dev Feb. 17, 2016;3:15055.
Tarantal AF, et al. Systemic and Persistent Muscle Gene Expression in Rhesus Monkeys with a Liver De-targeted Adeno-Associated Virus (AAV) Vector Hum Gene Ther. May 2017;28(5):385-391.
Huang LY, et al. Characterization of the Adeno-Associated Virus 1 and 6 Sialic Acid Binding Site. J Virol. May 12, 2016;90(11):5219-30.
Siu JJ, et al. Improved gene delivery to adult mouse spinal cord through the use of engineered hybrid adeno-associated viral serotypes. Gene Ther. Apr. 25, 2017. Epub ahead of print.
Deng XF, et al. Replication of an autonomous human parvovirus in non-dividing human airway epithelium is facilitated through the DNA damage and repair pathways. PLoS Pathog. Jan. 2016;12(1):e1005399.
Kailasan S, et al. Structure of an Enteric Pathogen, Bovine Parvovirus.J Virol. Mar. 2015, 89(5):2603-14.
Alton EW, et al. Repeated nebulisation of non-viral CFTR gene therapy in patients with cystic fibrosis: a randomised, double-blind, placebo-controlled, phase 2b trial. Lancet Respir Med Sep. 2015;3(9):684-91.
Baum BJ, et al. Early responses to adenoviral-mediated transfer of the aquaporin-1 cDNA for radiation-induced salivary hypofunction. Proc Natl Acad Sci U S A. Nov. 20, 2010;109(47):19403-7.
Shen W, et al. Analysis of the Cis and Trans Requirements for DNA Replication at the Right End Hairpin of the Human Bocavirus 1 Genome. J Virol. Aug. 2016;90(17):7761-77.
Crisp et al., Canine degenerative myelopathy: Biochemical characterization of superoxide dismutase 1 in the first naturally occurring. Exp Neurol. Oct. 2013; 248:1-9. Epub May 23, 2013.

Alonso et al., Incidence and lifetime risk of motor neuron disease in the United Kingdom: a population-based study. Eui J Neurol. Jun. 2009;16(6):745-51.
Haidet-Phillips et al., Astrocytes from familial and sporadic ALS patients are toxic to motor neurons. Nat Biotechnol. Aug. 1, 20110;29(9):824-8.
Murlidharan G et al. Glymphatic Fluid Transport Controls Paravascular Clearance of AAV Vectors from the Brain. JCI Insight. Sep. 8, 2016;1(14).
Neuberger EWI, et al. Establishment of two quantitative nested qPCR assays targeting the human EPO transgene. Sene Ther. Apr. 2016;23(4):330-9.
Lentz TB, et al. Insight into the Mechanism of Inhibition of Adeno-Associated Virus by the Mre11/Rad50/Nbs1 Complex. J Virol. Jan. 2015, 89(1):181-94.
Nicolson SC, et al. Identification and validation of small molecules that enhance recombinant Adeno-associated virus transduction following high throughput screen. J Virol. Jul. 2016;90(16):7019-31.
Wang M, et al. Direct interaction of human serum proteins with AAV virions to enhance AAV transduction: Immediate impacton clinical applications. Gene Ther. Jan. 2017;24(1):49-59.
Watakabe A, et al. Comparative analyses of adeno-associated viral vector serotypes 1 2 5 8 and 9 in marmoset mouse and macaque cerebral cortex. Neurosci Res.Apr. 2015, 93:144-57.
Xiao P, et al. Disruption of microtubules post virus entry enhances adeno-associated virus vector transduction. Hum Gene Ther. Apr. 2016;27(4):309-24.
Hudry EM, et al. Exosome-associated AAV vector as a robust and convenient neurosocience tool. Gene Ther. Apr. 2016,23(4):380-92.
Nery FC, et al. New methods for investigation of neuronal migration in embryonic brain explants J Neurosci Methods.Jan. 2015, 239:80-4.
Su W et al. Recombinant adeno-associated viral (rAAV) vectors mediate efficient gene transduction in cultured neonatal and adult microglia. J Neurochem. Jan. 2016;136 Suppl 1:49-62.
Ren XF, et al. Adeno-associated virus-mediated BMP-7 and SOX9 in vitro co-transfection of human degenerative intervertebral disc cells. Genet Mol Res. Apr. 22, 2015;14(2):3736-44.
Alves S et al. Ultramicroscopy as a Novel Tool to Unravel the Tropism of AAV Gene Therapy Vectors in the Brain. Sci Rep. Jun. 20, 2016;6:28272.
Kothari P, et al. Radioiodinated Capsids Facilitate In Vivo Non-Invasive Tracking of Adeno-Associated Gene Transfer Vectors. Sci Rep. Jan. 2017;7:39594.
Xie Q, et al. The 2.8 ÅElectron Microscopy Structure of Adeno-Associated Virus-DJ Bound by a Heparinoid Pentasaccharide. Mol Ther Methods Clin Dev. Mar. 8, 2017;5:1-12.
Srivastava A. Adeno-Associated Virus: The Naturally Occurring Virus Versus the Recombinant Vector. Hum Gene Ther. Jan. 2016;27(1):1-6.
Tratschin JD, et al. Adeno-associated virus vector for high-frequency integration, expression, and rescue of genes in mammalian cells. Mol Cell Biol. Nov. 1985;5(11):3251-60.
Srivastava A, et al. Nucleotide sequence and organization of the adeno-associated virus 2 genome. J Virol. Feb. 1983;45(2):555-64.
Summerford C, et al. AAVR: A multi-serotype receptor for AAV. Mol Ther. Apr. 2016;24(4):663-6.
Xie Q, et al. The atomic structure of adeno-associated virus (AAV-2), a vector for human gene therapy. Proc Natl Acad Sci U S A. Aug. 6, 2002;99(16):10405-10. Epub Jul. 22, 2002.
Wu P, et al. Mutational analysis of the adeno-associated virus type 2 (AAV2) capsid gene and construction of AAV2 vectors with altered tropism. J Virol. Sep. 2000;74(18):8635-47.
Yang C, et al. Sequential adeno-associated viral vector serotype 9-green fluorescent protein gene transfer causes massive inflammation and intense immune response in rat striatum. Hum Gene Ther. Jul. 2016;27(7):528-43.
Chandler RJ, et al. rAAV integration and genotoxicity: insights from animal models. Hum Gene Ther. Apr. 2017;28 (4):314-322.
Ye L., et al. Adeno-Associated Virus Vector Mediated Delivery of the HBV Genome Induces Chronic Hepatitis B Virus Infection and Liver Fibrosis in Mice. PLoS One. Jun. 2015, 10(6):e0130052.

(56) References Cited

OTHER PUBLICATIONS

Wang S, et al. Direct brain infusion can be enhanced with focused ultrasound and microbubbles. J Cereb Blood Flow Metab. Feb. 2016;37(2):706-714.
Wang et al., Noninvasive, neuron-specific gene therapy can be facilitated by focused ultrasound and recombinant adeno-associated virus. Gene Therapy. Nov. 22, 2014. 104-110.
Weber-Adrian D, et al. Gene delivery to the spinal cord using MRI-guided focused ultrasound. Gene Ther. Jul. 2015, 22(7):568-77.
Wu D et al. Expressing Constitutively Active Rheb in Adult Dorsal Root Ganglion Neurons Enhances the Integration of Sensory Axons that Regenerate Across a Chondroitinase-Treated Dorsal Root Entry Zone Following Dorsal Root Crush. Front Mol Neurosci. Jul. 5, 2016;9:49.
Zhu W, et al. Soluble FLT1 Gene Therapy Alleviates Brain Arteriovenous Malformation Severity. Stroke. May 2017;48 (5):1420-1423.
Watson ZL, et al. Adeno-associated Virus Vectors Efficiently Transduce Mouse and Rabbit Sensory Neurons Coinfected with Herpes Simplex Virus 1 following Peripheral Inoculation. J Virol. Aug. 12, 2016;90(17):7894-901.
Suzuki J, et al. Cochlear gene therapy with ancestral AAV in adult mice: complete transduction of inner hair cells without cochlear dysfunction. Apr. 3, 2017,7:45524.
Woodard Kt et al. Heparan Sulfate Binding Promotes Accumulation of Intravitreally Delivered Adeno-associated Viral Vectors at the Retina for Enhanced Transduction but Weakly Influences Tropism. J Virol. Oct. 14, 2016;90 (21):9878-9888.
Wang LL, et al. Comparative study of liver gene transfer with AAV vectors based on endogenous and engineered AAV capsids. Mol Ther. Dec. 2015;23(12):1877-87.
Sondhi D, et al. Genetic Modification of the Lung Directed Toward Treatment of Human Disease. Hum Gene Ther. Jan. 2017;28(1):3-84.
Yalvac ME, et al. AAV1.NT-3 gene therapy attenuates spontaneous autoimmune peripheral polyneuropathy. Gene Ther. Jan. 2016;23(1):95-102.
Srivastava A. In Vivo Tissue-tropism of Adeno-associated Viral Vectors. Curr Opin Virol. Sep. 2, 2016;21:75-80.
Adamson-Small L, et al. Sodium chloride enhances rAAV production in a serum-free suspension manufacturing platform using the Herpes Simplex Virus System. Hum Gene Ther Methods. Feb. 2017;28(1):1-14.
Al J, et al. A Scalable and Accurate Method for Quantifying Vector Genomes of Recombinant Adeno-Associated Viruses in Crude Lysate. Hum Gene Ther Methods. Apr. 13, 2017. Epub ahead of print.
Buclez PO, et al. Rapid, scalable, and low-cost purification of recombinant adeno-associated virus produced by baculovirus expression vector system. Mol Ther Methods Clin Dev. May 2016;3:16035.
Burnham B, et al. Analytical ultracentrifugation as an approach to characterize recombinant adeno-associated viral vectors. Hum Gene Ther Methods. Dec. 2015;26(6):228-42.
Clement N, et al. Manufacturing of recombinant adeno-associated viral vectors for clinical trials. Mol Ther Methods Clin Dev. Mar. 2016;3:16002.
D'Costa S, et al. Practical utilization of recombinant AAV vector reference standards: focus on vector genome titration by free ITR qPCR. Mol Ther Methods Clin Dev. Mar. 2016;5:16019.
Grieger JC, et al. Production of Recombinant Adeno-associated Virus Vectors Using Suspension HEK293 Cells and Continuous Harvest of Vector From the Culture Media for GMP FIX and FLT1 Clinical Vector. Mol Ther. Feb. 2016;24 (2):287-97.
Gruntman AM, et al. Stability and Compatibility of Recombinant Adeno-Associated Virus Under Conditions Commonly Encountered in Human Gene Therapy Trials. Hum Gene Ther Methods. Apr. 2015, 26(2):71-6.

Kajigaya S, et al. Self-assembled B19 parvovirus capsids, produced in a baculovirus system, are antigenically and immunogenically similar to native virions. Proc Natl Acad Sci U S A. Jun. 1, 1991;88(11):4646-50.
Kirnbauer R, et al. Virus-like particles of bovine papillomavirus type 4 in prophylactic and therapeutic immunization. Virology May 1, 1996;219(1):37-44.
Kohlbrenner E, et al. Production and Characterization of Vectors Based on the Cardiotropic AAV Serotype 9. Methods Mol Biol. 2017;1521:91-107.
Kotin RM, et al. Large-scale recombinant adeno-associated virus production. Hum Mol Genet. Apr. 15, 2011;20(R1): R2-6 doi: 10.1093/hmg/ddr141. Epub Apr. 29, 2011.
Merten OW, et al. Viral vectors for gene therapy and gene modification approaches. Biochem Eng J. Apr. 2016;108:98-115.
Muzyczka N, et al. AAV's Golden Jubilee. Mol Ther. May 2015;23(5):807-8.
Rutledge EA, et al. Infectious clones and vectors derived from adeno-associated virus (AAV) serotypes other than AAV type 2. J Virol. Jan. 1998;72(1):309-19.
Pillay S, et al. An essential receptor for adeno-associated virus infection. Nature. Nov. 17, 2016;539(7629):456.
Platt MP, et al. Embryonic disruption of the candidate dyslexia susceptibility gene homolog Kiaa0319-like results in neuronal migration disorders. Neuroscience. Sep. 17, 2013;248:585-93.
Poon MW, et al. Distribution of Kiaa0319-like immunoreactivity in the adult mouse brain-a novel protein encoded by the putative dyslexia susceptibility gene KIAA0319-like. Histol Histopathol. Aug. 2011;26(8):953-63.
Poon MW, et al. Dyslexia-associated kiaa0319-like protein interacts with axon guidance receptor nogo receptor 1. Cell Mol Neurobiol. Jan. 2011;31(1):27-35.
Moser, et al. Computational Molecular Biology. Oxford University Press, New York, 1988.
Kozak M. Interpreting cDNA sequences: some insights from studies on translation. Mamm Genome. Aug. 1996;7(8):563-74.
Kozak M. Point mutations define a sequence flanking the AUG initiator codon that modulates translation by eukaryotic ribosomes Cell. Jan. 31, 1986,44(2):283-92.
Kozak M. The scanning model for translation: an update. J Cell Biol. Feb. 1989;108(2):229-41.
Heim R, et al. Engineering green fluorescent protein for improved brightness, longer wavelengths and fluorescence resonance energy transfer. Curr Biol. Feb. 1, 1996;6(2):178-82.
Heim R,et al. Improved green fluorescence Nature 373, 663-664 (Feb. 23, 1995); doi:10.1038/373663b0.
Nygaard S, et al. A universal system to select gene-modified hepatocytes in vivo. Sci Transl Med. Jun. 2016;8 (342):342ra79.
Smith RH, et al. Germline viral "fossils" guide in silico reconstruction of a mid-Cenozoic era marsupial adeno-associated virus. Sci Rep. Jul. 2016;6:28965.
Li L, et al. Production and characterization of novel recombinant adeno-associated virus replicative-form genomes: a eukaryotic source of DNA for gene transfer. PLoS One. Aug. 1, 2013;8(8):e69879. doi: 10.1371/journal.pone.0069879. Print 2013.
Oliva B, et al. An automated classification of the structure of protein loops. J Mol Biol. Mar. 7, 1997;266(4):814-30.
Samaranch L, et al. MR-guided parenchymal delivery of adeno-associated viral vector serotype 5 in non-human primate brain. Gene Ther. Apr. 2017;24(4):253-261.
Petit L, et al. Rod Outer Segment Development Influences AAV-Mediated Photoreceptor Transduction After Subretinal Injection. Hum Gene Ther. May 16, 2017. Epub ahead of print.
Hinderer C et al. Delivery of an Adeno-Associated Virus Vector into CSF Attenuates Central Nervous System Disease in Mucopolysaccharidosis Type II Mice. Hum Gene Ther. Aug. 10, 2016.
Hordeaux J., et al. Efficient central nervous system AAVrh10-mediated intrathecal gene transfers in adult and neonate rats. Gene Ther.Apr. 2015, 22(4):316-24.
Merkel SF et al. Trafficking of AAV Vectors Across a Model of the Blood-Brain Barrier; a Comaparative Study of Transcytosis and Transduction Using Primary Human Brain Endothelial Cells. J Neurochem. Oct. 8, 2016.

(56) References Cited

OTHER PUBLICATIONS

Miyanohara A et al. Potent Spinal Parenchymal AAV9-mediated Gene Delivery by Subpial Injection in Adult Rats and Pigs. Mol Ther Methods Clin Dev. Jul. 13, 2016,3:16046.
Muralidharan G, et al. Unique glycan signatures regulate adeno-associated virus tropism in the developing brain. J Virol. Apr. 2015;89(7):3976-87.
Ponder K, et al. Intrathecal injection of lentiviral vector results in high expression in the brain of mucopolysaccharidosis VII dogs but the pattern of expression is different than for AAV9 or AAV-rh10. J Control Release. Dec. 2014, 196:71-8.
Salegio EA, et al. MRI-Guided Delivery of Viral Vectors. Methods Mol Viol. 2016;1382:217-30.
Samaranch L et al. Cerebellomedullary Cistern Delivery for AAV-Based Gene Therapy: A Technical Note for Nonhuman Primates. Hum Gene Ther Methods. Feb. 2016;27(1):13-6.
Saraiva J et al. Gene Therapy for the CNS Using AAVs: The Impact of Systemic Delivery by AAV9. J Control Release. Nov. 10, 2016;241:94-109.
Shen F, et al. Inhibition of pathological brain angiogenesis through systemic delivery of AAV vector expressing soluble FLT1. Gene Therapy. Nov. 22, 2015(11):893-900.
Hinderer C, et al. Neonatal Systemic AAV Induces Tolerance to CNS Gene Therapy in MPS I Dogs and Nonhuman Primates. Mol Ther. 201-307.
Ojala DS, et al. Adeno-associated virus vectors and neurological gene therapy. Neuroscientist. Feb. 2015;21(1):84-98.
Katz ML, et al. AAV gene transfer delays disease onset in a TPP1-deficient canine model of the late infantile form of Batten Disease. Sci Transl Med. Nov. 2015;7(313):313ra180.
Landegger LD, et al. A synthetic AAV vector enables safe and efficient gene transfer to the mammalian inner ear. Mat Biotechnol. Mar. 2017;35(3):280-284.
Mason JB, et al. Delivery and evaluation of recombinant adeno-associated viral vectors in the equine distal extremity for the treatment of laminitis. Equine Vet J. Jan. 2017;49(1):79-86.
Jeong D, et al. Matricellular Protein CCN5 Reverses Established Cardiac Fibrosis. J Am Coll Cardiol. Apr. 5, 2016;67(13):1556-68.
Kezevic T, et al. Adeno-associated Virus Serotype 9—Driven Expression of BAG3 Improves Left Ventricular Function in Murine Hearts with Left Ventricular Dysfunction Secondary to a Myocardial Infarction. JACC Basic Transl Sci. Dec. 2016;1(7):647-656.
Ibrahim S, et al. Stable liver specific expression of human IDOL in humanized mice raises plasma cholesterol. Cardiovasc Res. May 2016;110(1):23-9.
Lisy, et al. Efficient and targeted transduction of nonhuman primate liver with systemically delivered optimized AAV3B vectors. Mol Ther. Dec. 2015;23(12):1867-76.
Heller KN, et al. Human alpha 7 integrin gene (ITGA7) delivered by adeno-associated virus extends survival of severely affected dystrophin/utrophin deficient mice. Oct. 2015;26(1):647-56.
Mendell Jr, et al. Follistatin Gene Therapy for Sporadic Inclusion Body Myositis Improves Functional Outcomes. Mol Ther. Apr. 2017;25(4):870-879.
Schnepp BC, et al. Recombinant adeno-associated virus vector genomes take the form of long-lived transcriptionally competent episomes in human muscle. Hum Gene Ther. Jan. 2016;27(1):32-42.
Li D, et al. Slow intrathecal injection of rAAVrh10 enhances its transduction of spinal cord and therapeutic efficacy in a mutant SOD1 model of ALS. Neuroscience. Oct. 9, 2017 Epub ahead of print.
Eichler K, et al. The complete connectome of a learning and memory centre in an insect brain Nature Aug. 9, 2017;548(7666):175-182.
Le Pichon CE, et al. Loss of dual leucine zipper kinase signaling is protective in animal models of neurodegenerative disease. Sci Transl Med. Aug. 16, 2017;9(403).
Durost P, et al. Gene therapy with an AAV vector expressing human IL-2 alters immune system homeostasis in humanized mice. Hum Gene Ther. Aug. 21, 2017 Epub ahead of print.

Ahmad M, et al. Engineered Expression of Broadly Neutralizing Antibodies Against Human Immunodeficiency Virus. Annu Rev Virol. Jun. 23, 2017. Epub ahead of print.
Brady JM, et al. Antibody gene transfer with adeno-associated viral vectors as a method for HIV prevention. Immunol Rev. Jan. 2017;275(1):324-333. doi: 10.1111/imr.12478.
Magnani DM et al., Dengue virus evades AAV-mediated neutralizing antibody prophylaxis in rhesus monkeys. Mol Ther Jul. 24, 2017 Epub ahead of print.
Zhu Z, et al. Zika virus has oncolytic activity against glioblastoma stem cells. J Exp Med. Sep. 5, 2017 Epub ahead of print.
Liu Z et al. Single cell transcriptomics reconstructs fate conversion from fibroblast to cardiomyocyte. Nature. Oct. 25, 2017 Epub ahead of print.
Kurosaki F, et al. Optimization of adeno-associated virus vector-mediated gene transfer to the respiratory tract. Gene Ther. May 2017;24(5):290-297.
Tadokoro T, et al. Subpial Adeno-associated Virus 9 (AAV9) Vector Delivery in Adult Mice. J Vis Exp. Jul. 13, 2017;(125). doi: 10.3791/55770.
Merkel SF, et al. Trafficking of adeno-associated virus vectors across a model of the blood-brain barrier; a comparative study of transcytosis and transduction using primary human brain endothelial cells. J Neurochem. Jan. 2017;140(2):216-230. doi: 10.1111/jnc. 13861.
Hinderer C, et al. Delivery of an Adeno-Associated Virus Vector into Cerebrospinal Fluid Attenuates Central Nervous System Disease in Mucopolysaccharidosis Type II Mice. Hum Gene Ther. Nov. 2016;27(11):906-915. Epub Aug. 10, 2016.
Gombash SE, et al. Systemic gene delivery transduces the enteric nervous system of guinea pigs and cynomolgus macaques. Gene Ther. Aug. 3, 2017. doi: 10.1038/gt 2017.72.
Hinderer C, et al. Evaluation of intrathecal routes of administration for adeno-associated virus vectors in large animals. Hum Gene Ther. Aug. 15, 2017. doi: 10.1089/hum.2017.026.
Hordeaux J, et al. Long-term neurologic and cardiac correction by intrathecal gene therapy in Pompe disease. Acta Neuropathol Commun Sep. 6, 2017(5):66.
Tardieu M, et al. Intracerebral gene therapy in children with mucopolysaccharidosis type IIIB syndrome: an uncontrolled phase 1/2 clinical trial. Lancet Neurol. Sep. 2017;16(9):712-720.
Yazdan-Shahmorad A, et al. Widespread Optogenetic Expression in Macaque Cortex Obtained with MR-Guided, Convection Enhanced Delivery (CED) of AAV vector to the Thalamus. J Neurosci Methods. Oct. 14, 2017 Epub ahead of print.
Lee NC, et al. A neuron-specific gene therapy relieves motor deficits in pompe disease mice. Mol Neurobiol. Sep. 11, 2017 Epub ahead of print.
Carvalho LS, et al. Evaluating efficiencies of dual AAV approaches for retinal targeting. Front Neursci. Sep. 8, 2017;11:503.
Reichel FF, et al. AAV8 can induce innate and adaptive immune response in the primate eye. Mol Ther. Aug. 31, 2017 Epub ahead of print.
De Silva SR, Charbel Issa P, Singh MS, Lipinski DM, Barnea-Cramer AO, Walker NJ, Barnard AR, Hankins MW, MacLaren RE. Single residue AAV capsid mutation improves transduction of photoreceptors in the Abca4$^{-/-}$ mouse and bipolar cells in the rd1 mouse and human retina ex vivo. Gene Ther. Nov. 2016;23(11):767-774. doi 10.1038/gt.2016.54. Epub Jul. 1, 20164.
Katz MG, et al. Use of Adeno-Associated Virus Vector for Cardiac Gene Delivery in Large Animal Surgical Models of Heart Failure. Hum Gene Ther Clin Dev. Jul. 20, 2017.
Watanabe S, et al. Protein Phosphatase Inhibitor-1 Gene Therapy in a Swine Model of Nonischemic Heart Failure. Journal of the American College of Cardiology 2017.
Iwamoto N, et al. Control of phosphorothioate stereochemistry substantially increases the efficacy of antisense oligonucleotides. Nat Biotechnol Aug. 21, 2017.
Clift D, et al. A Method for the Acute and Rapid Degradation of Endogenous Proteins. Cell Nov. 16, 2017.
Boone DR, et al. Effects of AAV-mediated knockdown of nNOS and GPx-1 gene expression in rat hippocampus after traumatic brain injury. PLoS One. 2017 10;12(10):e0185943.

(56) References Cited

OTHER PUBLICATIONS

Jin X, et al. Direct LC/MS Analysis for Complete Characterization of Recombinant Adeno-Associated Virus Capsid Proteins. Hum Gene Ther Methods. Jun. 18, 2017. Epub ahead of print.

Galli A, et al. Strategies to optimize capsid protein expression and single stranded DNA formation of Adeno-associated virus in *Saccharomyces cerevisiae*. J Appl Microbiol. Jun. 13, 2017. Epub ahead of print.

Wang Z, et al. Human Bocavirus 1 is a Novel Helper for Adeno-Associated Virus Replication. J Virol. Jun. 28, 2017. Epub ahead of print.

Grobe S, et al. Relevance of assembly-activating protein for Adeno-associated virus vector production and capsid protein stability in mammalian and insect cells. J Virol. Aug. 2, 2017. pii: JVI.01198-17. doi: 10.1128/JV1.01198-17.

Kondratov O, et al. Direct head-to-head evaluation of recombinant Adeno-associated viral (rAAV) vectors manufactured in human vs insect cells. Molecular Therapy. Aug. 10, 2017.

Jungmann A, et al. Protocol for efficient generation and characterization of adeno-associated viral (AAV) vectors. Hum Gene Ther Methods Sep. 21, 2017. Epub ahead of print.

Luo Y, et al. AAVS 1-Targeted Plasmid Integration in AAV Producer Cell Lines. Hum Gene Ther Methods. Jun. 2017;28(3):124-138.

Savy A, et al. Impact of ITR integrity on rAAV8 production using baculovirus/Sf9 cells system. Hum Gene Ther Methods. Oct. 1, 2017 Epub ahead of print.

GTEx Consortium et al. Genetic effects on gene expression across human tissues. Nature. Oct. 11, 2017;550 (7675):204-213.

Li X, et al. The impact of rare variation on gene expression across tissues. Nature. Oct. 11, 2017 ;550(7675):239-243.

'Ojala DS, et al. In Vivo Selection of a Computationally Designed SCHEMA AAV Library Yields a Novel Variant for Infection of Adult Neural Stem Cells in the SVZ. Mol Ther. Sep. 8, 2017 Epub ahead of print.

Chandran JS, et al. Site Specific Modification of Adeno-Associated Virus Enables Both Fluorescent Imaging of Viral Particles and Characterization of the Capsid Interactome. Sci Rep. Nov. 7, 2017;7(1):14766.

Chai Z, et al. Application of polyploid adeno-associated virus vectors for transduction enhancement and neutralizing antibody evasion. J Control Release. Aug. 5, 2017 pii: 30168-3659(17)30772-1. doi: 10.1016/j.jconrel.2017.08.005.

Hickey DG, et al. Tropism of engineered and evolved recombinant AAV serotypes in the rd1 mouse and ex vivo primate retina. Gene Ther. Sep. 5, 2017 Epub ahead of print.

Yan Z, et al. Human Bocavirus Type-1 Capsid Facilitates the Transduction of Ferret Airways by Adeno-Associated Virus Genomes Hum Gene Ther. May 10, 2017. Epub ahead of print.

Kanaan NM, et al. Rationally Engineered AAV Capsids Improve Transduction and Volumetric Spread in the CNS. Molecular Therapy-Nucleic Acids 8:184-197 Sep. 15, 2017.

Powell SK, Khan N, Parker CL, Samulski RJ, Matsushima G, Gray SJ, McCown TJ. Characterization of a novel adeno-associated viral vector with preferential oligodendrocyte tropism. Gene Ther. Nov. 2016;23(11):807-814. doi: 10.1038/gt.2016.62. Epub Sep. 15, 2016.

Kanaan N, et al. Rationally Engineered AAV Capsids Improve Transduction and Volumetric Spread in the CNS. Molecular Therapy—Nucleic Acids, vol. 8, 184-197.

Chan Ky, et al. Engineered AAVs for efficient noninvasive gene delivery to the central and peripheral nervous systems. Nat Neurosci. Jun. 26, 2017. Epub ahead of print.

Paulk NK, et al. Bioengineered AAV Capsids with Combined High Human Liver Transduction In Vivo and Unique Humoral Seroreactivity. Mol Ther. Sep. 25, 2017 Epub ahead of print.

Hagedorn C, et al. S/MAR element facilitates episomal long-term persistence of Adeno-associated viral (AAV) vector genomes in proliferating cells. Hum Gene Ther. Jun. 30, 2017. Epub ahead of print.

Ziegler T, et al. Steerable induction of the Thymosin ß4/MRTF-A pathway via AAV-based overexpression induces therapeutic neovascularization. Hum Gene Ther. Jul. 20, 2017.

Potter RA, et al. Systemic Delivery of Dysferlin Overlap Vectors Provides Long-Term Functional Improvement for Dysferlinopathy. Hum Gene Ther. Jul. 14, 2017. Epub ahead of print.

Valdmanis P, et al. Future of rAAV gene therapy: Platform for RNAi, Gene Editing and Beyond. Hum Gene Ther. Apr. 2017;28(4):361-372.

Russian Office Action received in corresponding Russian Application No. 2017116576 dated Sep. 3, 2019.

SEQUENCE LISTING

```
<160> NUMBER OF SEQ ID NOS: 396

<210> SEQ ID NO 1
<211> LENGTH: 981
<212> TYPE: DNA
<213> ORGANISM: Homo sapiens

<400> SEQUENCE: 1
gtttggggcc agagtgggcg aggcgcggag gtctggccta taaagtagtc gcggagacgg    60
ggtgctggtt tgcgtcgtag tctcctgcag cgtctggggt ttccgttgca gtcctcggaa   120
ccaggacctc ggcgtggcct agcgagttat ggcgacgaag gccgtgtgcg tgctgaaggg   180
cgacggccca gtgcagggca tcatcaattt cgagcagaag gaaagtaatg gaccagtgaa   240
ggtgtgggga agcattaaag gactgactga aggcctgcat ggattccatg ttcatgagtt   300
tggagataat acagcaggct gtaccagtgc aggtcctcac tttaatcctc tatccagaaa   360
acacggtggg ccaaaggatg aagagaggca tgttggagac ttgggcaatg tgactgctga   420
caaagatggt gtggccgatg tgtctattga agattctgtg atctcactct caggagacca   480
ttgcatcatt ggccgcacac tggtggtcca tgaaaaagca gatgacttgg gcaaaggtgg   540
aaatgaagaa agtacaaaga caggaaacgc tggaagtcgt ttggcttgtg gtgtaattgg   600
gatcgcccaa taaacattcc cttggatgta gtctgaggcc ccttaactca tctgttatcc   660
```

```
tgctagctgt agaaatgtat cctgataaac attaaacact gtaatcttaa aagtgtaatt    720
gtgtgacttt ttcagagttg ctttaaagta cctgtagtga gaaactgatt tatgatcact    780
tggaagattt gtatagtttt ataaaactca gttaaatgt  ctgtttcaat gacctgtatt    840
ttgccagact taaatcacag atgggtatta aacttgtcag aatttctttg tcattcaagc    900
ctgtgaataa aaaccctgta tggcacttat tatgaggcta ttaaaagaat ccaaattcaa    960
actaaaaaaa aaaaaaaaa a                                               981

<210> SEQ ID NO 2
<211> LENGTH: 465
<212> TYPE: DNA
<213> ORGANISM: Macaca fascicularis

<400> SEQUENCE: 2
atggcgatga aggccgtgtg cgtgttgaag ggcgacagcc cagtgcaggg caccatcaat     60
ttcgagcaga aggaaagtaa tggaccagtg aaggtgtggg gaagcattac aggattgact    120
gaaggcctgc atggattcca tgttcatcag tttggagata atacacaagg ctgtaccagt    180
gcaggtcctc actttaatcc tctatccaga caacacggtg ggccaaagga tgaagagagg    240
catgttggag acctgggcaa tgtgactgct ggcaaagatg gtgtggccaa ggtgtctttc    300
gaagattctg tgatctcgct ctcaggagac cattccatca ttggccgcac attggtggtc    360
catgaaaaag cagatgactt gggcaaaggt ggaaatgaag aaagtaaaaa gacaggaaac    420
gctggaggtc gtctggcttg tggtgtaatt gggatcgccc aataa                    465

<210> SEQ ID NO 3
<211> LENGTH: 464
<212> TYPE: DNA
<213> ORGANISM: Macaca mulatta

<400> SEQUENCE: 3
atggcgatga aggccgtgtg cgtgttgaag ggcgacagcc cagtgcaggg caccatcaat     60
ttcgagcaga aggaaagtaa tggaccagtg aaggtgtggg gaagcattac aggattgact    120
gaaggcctgc atggattcca tgttcatcag tttggagata atacacaagg ctgtaccagt    180
gcaggtcctc actttaatcc tctatccaga caacacggtg ggccaaagga tgaagagagg    240
catgttggag acctgggcaa tgtgactgct ggcaaagatg gtgtggccaa ggtgtctttc    300
gaagattctg tgatctcgct ctcaggagac cattccatca ttggccgcac attggtggtc    360
catgaaaaag cagatgactt gggcaaaggt ggaaatgaag aaagtaaaaa gacaggaaac    420
gctggaggtc gtctggcttg tggtgtaatt gggatcgcca ataa                     464

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
cggaggucug gccuauaact t                                               21

<210> SEQ ID NO 5
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
ggaggucugg ccuauaaact t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
gaggucuggc cuauaaagct t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
aggucuggcc uauaaaguct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
ggucuggccu auaaaguact t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
ucuggccuau aaaguaguct t                                              21

<210> SEQ ID NO 10
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cuggccuaua aaguagucct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
uggccuauaa aguagucgct t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
ggccuauaaa guagucgcct t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
gccuauaaag uagucgcgct t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 14
ccuauaaagu agucgcggct t                                              21
```

```
<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
gucguagucu ccugcagcct t                                             21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
cguagucucc ugcagcguct t                                             21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
guagucuccu gcagcgucct t                                             21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
uagucuccug cagcgucuct t                                             21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
auggcgacga aggccgugct t                                             21
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cgacgaaggc cgugugcgct t                                              21

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
gaaggccgug ugcgugcuct t                                              21

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
ggccgugugc gugcugaact t                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
agggcgacgg cccagugcct t                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
ugcagggcau caucaauuct t                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 25
gcagggcauc aucaauuuct t          21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 26
agggcaucau caauuucgct t          21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 27
gggcaucauc aauuucgact t          21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 28
ggcaucauca auucgagct t          21

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 29
gcaucaucaa uuucgagcct t                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
caucaucaau uucgagcact t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
aauuucgagc agaaggaact t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
uucgagcaga aggaaaguct t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ucgagcagaa ggaaaguact t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34 aaggugugggg gaagcauuct t                                             21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
ggugugggga agcauuaact t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
gacugacuga aggccugcct t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
cugacugaag gccugcauct t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
ugacugaagg ccugcaugct t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
ugaaggccug cauggauuct t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
gaaggccugc auggauucct t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
ugcauggauu ccauguucct t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
cauggauucc auguucauct t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
ggauuccaug uucaugagct t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
uuccauguuc augaguuuct t        21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
guucaugagu uuggagauct t        21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
uucaugaguu uggagauact t        21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
ugaguuugga gauaauacct t        21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
gaguuuggag auaauacact t        21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 49
aggcuguacc agugcaggct t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
ggcuguacca gugcagguct t                                              21

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
gcagguccuc acuuuaauct t                                              21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
cagguccuca cuuuaaucct t                                              21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ucacuuuaau ccucuaucct t                                              21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

-continued

```
<223> OTHER INFORMATION: Description of Combined DNA/RNA Molecule:
      Synthetic oligonucleotide

<400> SEQUENCE: 54
cuauccagaa aacacgguct t                                                   21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
uauccagaaa acacggugct t                                                   21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
auccagaaaa cacgguggct t                                                   21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
ccagaaaaca cggugggcct t                                                   21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
gaaaacacgg ugggccaact t                                                   21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 59
aaaacacggu gggccaaact t                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
cgguggccca aaggaugact t                                              21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
aggaugaaga gaggcaugct t                                              21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
augaagagag gcauguugct t                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
gagaggcaug uuggagacct t                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
          oligonucleotide
<220> FEATURE:
<223> OTHER INFORMATION: Description of Combined DNA/RNA Molecule:
      Synthetic oligonucleotide

<400> SEQUENCE: 64
agaggcaugu uggagacuct t                                           21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
auguuggaga cuugggcact t                                           21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
guuggagacu ugggcaauct t                                           21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
ggagacuugg gcaaugugct t                                           21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
ggcaauguga cugcugacct t                                           21

<210> SEQ ID NO 69
<211> LENGTH: 21
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
caaugugacu gcugacaact t                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
cugacaaaga ugguguggct t                                              21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
ugacaaagau gguguggcct t                                              21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
cucaggagac cauugcauct t                                              21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ucaggagacc auugcaucct t                                              21

<210> SEQ ID NO 74
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74
agaccauugc aucauuggct t                                            21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
gaccauugca ucauuggcct t                                            21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
auugcaucau uggccgcact t                                            21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
cauuggccgc acacugguct t                                            21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
cgcacacugg ugguccauct t                                            21

<210> SEQ ID NO 79
<211> LENGTH: 21
<212> TYPE: DNA
```

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
cacacuggug guccaugact t                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
acacuggugg uccaugaact t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
ugguggucca ugaaaaagct t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
ugguccauga aaagcagct t                                               21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
aaagcagaug acuugggcct t                                              21

<210> SEQ ID NO 84
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
gcagaugacu ugggcaaact t                                              21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
augacuuggg caaaggugct t                                              21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
ugacuugggc aaaggtggct t                                              21

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
gacuugggca aagguggact t                                              21

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
guacaaagac aggaaacgct t                                              21

<210> SEQ ID NO 89
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
acaaagacag gaaacgcuct t                                            21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 90
caaagacagg aaacgcugct t                                            21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
aggaaacgcu ggaagucgct t                                            21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
gucguuuggc uugggugct t                                             21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
ucguuuggcu uggguguct t                                             21
```

```
<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 94
cguuuggcuu gugguguact t                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
guuuggcuug ugguguaact t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
uuggcuugug guguaauuct t                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97 ggcuguggu guaauuggct t                                               21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
gcuuguggug uaauugggct t                                              21
```

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
cuuguggugu aauugggact t                                              21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 100 uguggguaa uugggaucct t                                               21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 101
gugguguaau ugggaucgct t                                              21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 102
ugguguaauu gggaucgcct t                                              21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 103
guaauuggga ucgcccaact t                                              21

```
<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 104
uaauugggau cgcccaauct t                                               21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
aauugggauc gcccaauact t                                               21

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
auugggaucg cccaauaact t                                               21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
uugggaucgc ccaauaaact t                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
```
ugggaucgcc aauaaaacct t                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
gggaucgccc aauaaacact t                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
aucgcccaau aaacauucct t                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
ccaauaaaca uucccuugct t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
caauaaacau ucccuuggct t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113

```
aauaaacauu cccuuggact t                                              21
```

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114

```
auaaacauuc ccuuggauct t                                              21
```

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115

```
uaaacauucc cuuggaugct t                                              21
```

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 116

```
aaacauuccc uuggauguct t                                              21
```

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117

```
aacauucccu uggauguact t                                              21
```

<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 118
auucccuugg auguagucct t                                              21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
cuuggaugua gucugaggct t                                              21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
cugaggcccc uuaacucact t                                              21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121 gaggcccuu aacucaucct t                                               21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122 aggcccuua acucaucct t                                                21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 123
ccccuuaacu caucuguuct t                                               21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
cccuuaacuc aucuguuact t                                               21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
ccuuaacuca ucuguuauct t                                               21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
cuuaacucau cuguuaucct t                                               21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
uuaacucauc uguuauccct t                                               21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 128
uaacucaucu guuauccuct t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
aacucaucug uuauccugct t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
guuauccugc uagcuguact t                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131
cugcuagcug uagaaaugct t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
ugcuagcugu agaaauguct t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 133
gcuguagaaa uguauccuct t                                            21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
cuguagaaau guauccugct t                                            21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
uguagaaaug uauccugact t                                            21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
guagaaaugu auccugauct t                                            21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
aaauguaucc ugauaaacct t                                            21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 138
guauccugau aaacauuact t                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
uuaaacacug uaaucuuact t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
acuguaaucu uaaaagugct t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
cuguaaucuu aaaaguguct t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
uguaaucuua aaaguguact t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide

<400> SEQUENCE: 143
guaaucuuaa aaguguaact t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
cuuaaaagug uaauugugct t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
uaccuguagu gagaaacuct t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
uuaugaucac uuggaagact t                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
augaucacuu ggaagauuct t                                              21

<210> SEQ ID NO 148
<211> LENGTH: 21
<212> TYPE: DNA
<213> ORGANISM: Artificial Sequence
<220> FEATURE:
```

<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 148
aucacuugga agauuuguct t                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 149
uggaagauuu guauaguuct t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 150
uauaaaacuc aguuaaaact t                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 151
aaacucaguu aaaaugucct t                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 152
gucuguuuca augaccugct t                                              21

<210> SEQ ID NO 153
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
augaccugua uuuugccact t                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
accuguauuu ugccagacct t                                              21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
ccuguauuuu gccagacuct t                                              21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
uaaaucacag auggguauct t                                              21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
aucacagaug gguauuaact t                                              21

<210> SEQ ID NO 158
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
ucacagaugg guauuaaact t                                             21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
acagaugggu auuaaacuct t                                             21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
cagaugggua uuaaacuuct t                                             21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
agauggguau uaaacuugct t                                             21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162 augguauua aacuugucct t                                              21

<210> SEQ ID NO 163
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
uaaacuuguc agaauuucct t                                           21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
ucauucaagc cugugaauct t                                           21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
cauucaagcc ugugaauact t                                           21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
aauaaaaacc cguauggct t                                            21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
auaaaaaccc uguauggcct t                                           21

<210> SEQ ID NO 168
```

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
aacccuguau ggcacuuact t                                           21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
acccuguaug gcacuuauct t                                           21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
gaggcuauua aaagaaucct t                                           21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
aaagaaucca aauucaaact t                                           21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
gaauccaaau ucaaacuact t                                           21
```

```
<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
uuuauaggcc agaccuccgt t                                            21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
uuuuauaggc cagaccucct t                                            21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
ucuuuauagg ccagaccuct t                                            21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
uacuuuauag gccagaccut t                                            21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
uuacuuuaua ggccagacct t                                            21
```

```
<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
uacuacuuua uaggccagat t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
ugacuacuuu auaggccagt t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
ucgacuacuu uauaggccat t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
ugcgacuacu uuauaggcct t                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
ucgcgacuac uuuauaggct t                                              21
```

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
uccgcgacua cuuuauaggt t                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
ugcugcagga gacuacgact t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
uacgcugcag gagacuacgt t                                              21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
ugacgcugca ggagacuact t                                              21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
uagacgcugc aggagacuat t                                          21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
ucacggccuu cgucgccaut t                                          21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 189
ucgcacacgg ccuucgucgt t                                          21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
uagcacgcac acggccuuct t                                          21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
uuucagcacg cacacggcct t                                          21

<210> SEQ ID NO 192
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
ugcacugggc gucgcccut t					21

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
uaauugauga ugcccugcat t					21

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 194
uaaauugaug augcccugct t					21

<210> SEQ ID NO 195
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
ucgaaauuga ugaugcccut t					21

<210> SEQ ID NO 196
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
uucgaaauug augaugccct t					21

<210> SEQ ID NO 197
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 197
ucucgaaauu gaugaugcct t                                              21

<210> SEQ ID NO 198
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
ugcucgaaau ugaugaugct t                                              21

<210> SEQ ID NO 199
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 199
uugcucgaaa uugaugaugt t                                              21

<210> SEQ ID NO 200
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
uuuccuucug cucgaaauut t                                              21

<210> SEQ ID NO 201
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
uacuuuccuu cugcucgaat t                                              21

<210> SEQ ID NO 202
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 202
uuacuuuccu ucugcucgat t                                              21

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
uaaugcuucc ccacaccuut t                                              21

<210> SEQ ID NO 204
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
uuuaaugcuu ccccacacct t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
ugcaggccuu cagucaguct t                                              21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
uaugcaggcc uucagucagt t                                              21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 207
ucaugcaggc cuucagucat t                                              21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
uaauccaugc aggccuucat t                                              21

<210> SEQ ID NO 209
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
ugaauccaug caggccuuct t                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
ugaacaugga auccaugcat t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
uaugaacaug gaauccaugt t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 212
ucucaugaac auggaaucct t                                               21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
uaaacucaug aacauggaat t                                               21

<210> SEQ ID NO 214
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
uaucuccaaa cucaugaact t                                               21

<210> SEQ ID NO 215
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
uuaucuccaa acucaugaat t                                               21

<210> SEQ ID NO 216
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
uguauuaucu ccaaacucat t                                               21

<210> SEQ ID NO 217
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 217
uuguauuauc uccaaacuct t                                              21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
uccugcacug guacagccut t                                              21

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
uaccugcacu gguacagcct t                                              21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
uauuaaagug aggaccugct t                                              21

<210> SEQ ID NO 221
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
ugauuaaagu gaggaccugt t                                              21

<210> SEQ ID NO 222
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 222
ugauagagga uuaaagugat t                                              21

<210> SEQ ID NO 223
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
uaccguguuu ucuggauagt t                                              21

<210> SEQ ID NO 224
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 224
ucaccguguu uucuggauat t                                              21

<210> SEQ ID NO 225
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 225
uccaccgugu uuucuggaut t                                              21

<210> SEQ ID NO 226
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 226
ugcccaccgu guuuucuggt t                                              21

<210> SEQ ID NO 227
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 227
uuuggcccac cguguuuuct t                                              21

<210> SEQ ID NO 228
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 228
uuuuggccca ccguguuuut t                                              21

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
uucauccuuu ggcccaccgt t                                              21

<210> SEQ ID NO 230
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
ucaugccucu cuucauccut t                                              21

<210> SEQ ID NO 231
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
ucaacaugcc ucucuucaut t                                              21

<210> SEQ ID NO 232
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
ugucuccaac augccucuct t                                             21

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
uagucuccaa caugccucut t                                             21

<210> SEQ ID NO 234
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
uugcccaagu cuccaacaut t                                             21

<210> SEQ ID NO 235
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
uauugcccaa gucuccaact t                                             21

<210> SEQ ID NO 236
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
ucacauugcc caagucucct t                                             21

<210> SEQ ID NO 237
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
ugucagcagu cacauugcct t                                              21

<210> SEQ ID NO 238
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
uuugucagca gucacauugt t                                              21

<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
uccacaccau cuuugucagt t                                              21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
ugccacacca ucuuugucat t                                              21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
uaugcaaugg ucuccugagt t                                              21

<210> SEQ ID NO 242
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
ugaugcaaug gucuccugat t                                              21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243 uccaugaug caauggucut t                                               21

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
ugccaaugau gcaaugguct t                                              21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
uugcggccaa ugaugcaaut t                                              21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
uaccagugug cggccaaugt t                                              21

<210> SEQ ID NO 247
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
uauggaccac cagugugcgt t                                              21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
uucauggacc accagugugt t                                              21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
uuucauggac caccagugut t                                              21

<210> SEQ ID NO 250
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250 ucuuuucau ggaccaccat t                                               21

<210> SEQ ID NO 251
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
ucugcuuuuu cauggaccat t                                              21
```

```
<210> SEQ ID NO 252
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
ugcccaaguc aucugcuuut t                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
uuuugcccaa gucaucugct t                                              21

<210> SEQ ID NO 254
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 254
ucaccuuugc ccaagucaut t                                              21

<210> SEQ ID NO 255
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 255
uccaccuuug cccaagucat t                                              21

<210> SEQ ID NO 256
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 256
uuccaccuuu gcccaaguct t                                              21
```

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 257
ucguuuccug ucuuuguact t                                              21

<210> SEQ ID NO 258
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 258
uagcguuucc ugucuuugut t                                              21

<210> SEQ ID NO 259
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259
ucagcguuuc cugucuuugt t                                              21

<210> SEQ ID NO 260
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
ucgacuucca gcguuuccut t                                              21

<210> SEQ ID NO 261
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
ucaccacaag ccaaacgact t                                              21

<210> SEQ ID NO 262
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 262
uacaccacaa gccaaacgat t                                              21

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 263
uuacaccaca agccaaacgt t                                              21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 264
uuuacaccac aagccaaact t                                              21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 265
uaauuacacc acaagccaat t                                              21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 266
uccaauuaca ccacaagcct t                                    21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
ucccaauuac accacaagct t                                    21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
uucccaauua caccacaagt t                                    21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
ugaucccaau uacaccacat t                                    21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
ucgaucccaa uuacaccact t                                    21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
ugcgauccca auuacaccat t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
uuugggcgau cccaauuact t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
uauugggcga ucccaauuat t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
uuauugggcg aucccaauut t                                              21

<210> SEQ ID NO 275
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275
uuuauugggc gaucccaaut t                                              21

<210> SEQ ID NO 276
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 276
uuuuauuggg cgaucccaat t                                              21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
uguuuauugg gcgaucccat t                                              21

<210> SEQ ID NO 278
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 278
uuguuuauug ggcgauccct t                                              21

<210> SEQ ID NO 279
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279
ugaauguuua uugggcgaut t                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
ucaagggaau guuuauuggt t                                              21

<210> SEQ ID NO 281
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 281
uccaagggaa uguuuauugt t                                              21

<210> SEQ ID NO 282
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
uuccaaggga auguuuauut t                                              21

<210> SEQ ID NO 283
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 283
uauccaaggg aauguuuaut t                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
ucauccaagg gaauguuuat t                                              21

<210> SEQ ID NO 285
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
uacauccaag ggaauguuut t                                              21

<210> SEQ ID NO 286
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 286
uuacauccaa gggaauguut t                                      21

<210> SEQ ID NO 287
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
ugacuacauc caagggaaut t                                      21

<210> SEQ ID NO 288
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 288
uccucagacu acauccaagt t                                      21

<210> SEQ ID NO 289
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
uugaguuaag gggccucagt t                                      21

<210> SEQ ID NO 290
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
ugaugaguua aggggccuct t                                      21

<210> SEQ ID NO 291
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 291
uagaugaguu aagggccut t                                                    21

<210> SEQ ID NO 292
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
uaacagauga guuaaggggt t                                                   21

<210> SEQ ID NO 293
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 293
uuaacagaug aguuaagggt t                                                   21

<210> SEQ ID NO 294
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 294
uauaacagau gaguuaaggt t                                                   21

<210> SEQ ID NO 295
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 295
ugauaacaga ugaguuaagt t                                                   21

<210> SEQ ID NO 296
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 296
uggauaacag augaguuaat t                                              21

<210> SEQ ID NO 297
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
uaggauaaca gaugaguuat t                                              21

<210> SEQ ID NO 298
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
ucaggauaac agaugaguut t                                              21

<210> SEQ ID NO 299
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
uuacagcuag caggauaact t                                              21

<210> SEQ ID NO 300
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
ucauuucuac agcuagcagt t                                              21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 301
uacauuucua cagcuagcat t                                            21

<210> SEQ ID NO 302
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
uaggauacau uucuacagct t                                            21

<210> SEQ ID NO 303
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
ucaggauaca uuucuacagt t                                            21

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
uucaggauac auuucuacat t                                            21

<210> SEQ ID NO 305
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
uaucaggaua cauuucuact t                                            21

<210> SEQ ID NO 306
<211> LENGTH: 21
<212> TYPE: DNA
<213> ORGANISM: Artificial Sequence
<220> FEATURE:
```

<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 306
uguuuaucag gauacauuut t                                            21

<210> SEQ ID NO 307
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 307
uuaauguuua ucaggauact t                                            21

<210> SEQ ID NO 308
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 308
uuaagauuac aguguuuaat t                                            21

<210> SEQ ID NO 309
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 309
ucacuuuuaa gauuacagut t                                            21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 310
uacacuuuua agauuacagt t                                            21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 311
uuacacuuuu aagauuacat t                                        21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 312
uuuacacuuu uaagauuact t                                        21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 313
ucacaauuac acuuuuaagt t                                        21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 314
uaguuucuca cuacagguat t                                        21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 315
uucuuccaag ugaucauaat t                                        21

<210> SEQ ID NO 316
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
uaaucuucca agugaucaut t                                                    21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
uacaaaucuu ccaagugaut t                                                    21

<210> SEQ ID NO 318
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
uaacuauaca aaucuuccat t                                                    21

<210> SEQ ID NO 319
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
uuuuuaacug aguuuuauat t                                                    21

<210> SEQ ID NO 320
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
ugacauuuua acugaguuut t                                                    21

<210> SEQ ID NO 321
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
ucaggucauu gaaacagact t                                                   21

<210> SEQ ID NO 322
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 322
uuggcaaaau acaggucaut t                                                   21

<210> SEQ ID NO 323
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 323
ugucuggcaa aauacaggut t                                                   21

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
uagucuggca aaauacaggt t                                                   21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
uauacccauc ugugauuuat t                                                   21

<210> SEQ ID NO 326
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
uuuaauaccc aucugugaut t                                           21

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
uuuuaauacc caucugugat t                                           21

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
uaguuuaaua cccaucugut t                                           21

<210> SEQ ID NO 329
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
uaaguuuaau acccaucgt t                                            21

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
ucaaguuuaa uacccaucut t                                           21
```

```
<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
ugacaaguuu aauacccaut t                                              21

<210> SEQ ID NO 332
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
ugaaauucug acaaguuuat t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
uauucacagg cuugaaugat t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
uuauucacag gcuugaaugt t                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
uccauacagg guuuuuauut t                                              21
```

```
<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
ugccauacag gguuuuuaut t                                              21

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
uuaagugcca uacaggguut t                                              21

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
uauaagugcc auacagggut t                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
ugauucuuuu aauagccuct t                                              21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
uuuugaauuu ggauucuuut t                                              21
```

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
uuaguuugaa uuuggauuct t                                              21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
caaugugacu gcugacaacc c                                              21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
uuugucagca gucacauugu u                                              21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
caaugugacu gcugacaauc c                                              21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
caaugugacu gcugacaagc c                                              21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
caaugugacu gcugacaaac c    21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
caaugugaca gcugacaaac c    21

<210> SEQ ID NO 348
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
caaugugacu gcugacaacc    20

<210> SEQ ID NO 349
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
caaugugacu gcugacaauc cc    22

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
caaugugacu gcugacaaca c    21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
uuugucagca gucacauugu c    21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
caaugugacu gcugacaaau c					21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
caaugugacu gcugacaauu c					21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
uuugucagca gucacauuga c					21

<210> SEQ ID NO 355
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
caaugugacu gcugacaauc cc				22

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
cgacgaaggc cgugucgcc c					21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
ucgcacacgg ccuucgucgu u					21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
ugacuugggc aaagguggcc c					21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
uccaccuuug cccaagucau u                                              21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
aacucaucug uuauccugcc c                                              21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
ucaggauaac agaugaguuu u                                              21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
ccccuuaacu caucuguucc c                                              21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
uaacagauga guuaaggggu u                                              21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
cccuuaacuc aucuguuacc c                                              21

-continued

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
uuaacagaug aguuaagggu u                                              21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
aacucaucug uuaucuugcc c                                              21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
gcuguggaaa uguaucuucc c                                              21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
uaggauacau uucuacagcu u                                              21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
ugacuugggc aaaggugagc c                                              21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
ccccuuaacu caucuguugc c                                              21

```
<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
cccuuaacuc aucuguuagc c                                              21

<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aacucaucug uuaucuuagc c                                              21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
gcuguggaaa uguaucuugc c                                              21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
ugacuugggc aaagguaggc c                                              21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
ccccuuaaca caucuguuac c                                              21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
cccuuaacug aucuguuac c                                               21

<210> SEQ ID NO 377
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
aacucaucuc uuaucuugcc c                                              21

<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
gcuguggaau uguaucuugc c                                              21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
ugacuugggg aaaggugagc c                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aacucaucug uuaucuuggc c                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
ccccuuaacu cauuuguucc c                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
ugacuugggc aaagguagcc c                                              21

<210> SEQ ID NO 383
<211> LENGTH: 19
```

```
-continued

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
caaugugacu gcugacaaa                                                  19

<210> SEQ ID NO 384
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
uuugucagca gucacauugu c                                               21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
gcagguccuc acuuuaaugc c                                               21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
gauuaaagug aggaccugcu u                                               21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
ggcaauguga cugcugaccc c                                               21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
ugucagcagu cacauugccu u                                               21

<210> SEQ ID NO 389
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 389
gcagguccuc acuuuaauuc c                                              21

<210> SEQ ID NO 390
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
ggcaauguga cugcugaugc c                                              21

<210> SEQ ID NO 391
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 391
gcagguccuc acuuuaaucc c                                              21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
ggcaauguga cugcugauac c                                              21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
gcagguccug acuuuaaucc c                                              21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
ggcaaugugu cugcugauac c                                              21

<210> SEQ ID NO 395
<211> LENGTH: 22
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 395
gauuaaagug aggaccugcu uu                                              22

<210> SEQ ID NO 396
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 396
ugucagcagu cacauugccu uu                                              22
```

COMPOSITIONS AND METHODS OF TREATING AMYOTROPHIC LATERAL SCLEROSIS (ALS)

CROSS REFERENCE TO RELATED APPLICATIONS

This application is a divisional application which claims the benefit of U.S. patent application Ser. No. 16/774,493, filed Jan. 28, 2020 and entitled Compositions and Methods of Treating Amyotrophic Lateral Sclerosis (ALS); which is a divisional application which claims the benefit of U.S. patent application Ser. No. 15/526,690, filed May 12, 2017 and entitled Compositions and Methods of Treating Amyotrophic Lateral Sclerosis (ALS); which is a national stage filing under 35 U.S.C. § 371 of International Application No. PCT/US2015/060562, filed Nov. 13, 2015 and entitled Compositions and Methods of Treating Amyotrophic Lateral Sclerosis (ALS); which claims priority to U.S. Provisional Patent Application No. 62/079,588, entitled Treatment of Amyotrophic Lateral Sclerosis (ALS) with siRNAs targeting SOD-1, filed Nov. 14, 2014, U.S. Provisional Patent Application No. 62/211,992, entitled Compositions and Methods of Treating Amyotrophic Lateral Sclerosis (ALS), filed Aug. 31, 2015, U.S. Provisional Patent Application No. 62/234,466, entitled Compositions and Methods of Treating Amyotrophic Lateral Sclerosis (ALS), filed Sep. 29, 2015; the contents of each of which are herein incorporated by reference in their entirety.

REFERENCE TO THE SEQUENCE LISTING

The present application is being filed along with a Sequence Listing in electronic format. The Sequence Listing is provided as a file entitled 20571011USDIV2_SL.txt, created on Jan. 6, 2021, which is 126,990 bytes in size. The information in the electronic format of the sequence listing is incorporated herein by reference in its entirety.

FIELD OF THE INVENTION

The present invention relates to compositions, methods and processes for the design, preparation, manufacture, use and/or formulation of modulatory polynucleotides, e.g., small interfering RNA (siRNA) molecules which target the superoxide dismutase 1 (SOD1) gene. As used herein, a "modulatory polynucleotide" is any nucleic acid sequence(s) which functions to modulate (either increase or decrease) the level or amount of a target gene, e.g., mRNA or protein levels. Targeting of the SOD1 gene may interfere with SOD1 gene expression and SOD1 enzyme production. In some embodiments, the nucleic acid sequence encoding the siRNA molecule are inserted into recombinant adeno-associated virus (AAV) vectors. Methods for using the siRNA molecules to inhibit SOD1 gene expression in a subject with a neurodegenerative disease (e.g., amyotrophic lateral sclerosis (ALS)) are also disclosed.

BACKGROUND OF THE INVENTION

Amyotrophic lateral sclerosis (ALS), also known as Lou Gehrig's disease, is the most fatal progressive neurodegenerative disease, characterized by the predominant loss of motor neurons (MNs) in primary motor cortex, the brainstem, and the spinal cord. The loss of motor neurons devastates basic, fundamental movements, such as breathing, and typically causes death to patients within 2-5 years after diagnosis. Progressive deterioration of motor function in patients severely disrupts their breathing ability, requiring some form of breathing aid for survival of the patients. Other symptoms also include muscle weakness in hands, arms, legs or the muscles of swallowing. Some patients (e.g., FTD-ALS) may also develop frontotemporal dementia.

According to the ALS Association, approximately 5,600 people in the United States of America are diagnosed with ALS each year. The incidence of ALS is two per 100,000 people, and it is estimated that as many as 30,000 Americans may have the disease at any given time.

Two forms of ALS have been described: one is sporadic ALS (sALS), which is the most common form of ALS in the United States of America and accounts for 90 to 95% of all cases diagnosed; the other is familial ALS (fALS), which occurs in a family lineage mainly with a dominant inheritance and only accounts for about 5 to 10% of all cases in the United States of America. sALS and fALS are clinically indistinguishable.

Pathological studies found that disturbance of some cellular processes occur after disease onset, including increased ER stress, generation of free radicals (i.e., reactive oxygen species (ROS)), mitochondrial dysfunction, protein aggregation, apoptosis, inflammation, and glutamate excitotoxicity, specifically in the motor neurons (MNs).

The causes of ALS are complicated and heterogeneous. In general, ALS is considered to be a complex genetic disorder in which multiple genes in combination with environmental exposures combine to render a person susceptible. More than a dozen genes associated with ALS have been discovered, including, SOD-1 ($Cu^{2+}/Zn^{2+}$ superoxide dismutase), TDP-43 (TARDBP, TAR DNA binding protein-43), FUS (Fused in Sarcoma/Translocated in Sarcoma), ANG (Angiogenin), ATXN2 (Ataxin-2), valosin containing protein (VCP), OPTN (Optineurin) and an expansion of the non-coding GGGGCC hexanucleotide repeat in the chromosome 9, open reading frame 72 (C9ORF72). However, the exact mechanisms of motor neuron degeneration are still elusive.

Currently, there is no curative treatment for ALS. The only FDA approved drug is Riluzole, which antagonizes the glutamate response to reduce the pathological development of ALS. However, only about a three-month life span expansion for ALS patients in the early stages has been reported, and no therapeutic benefit for ALS patients in the late stages has been observed, indicating a lack of therapeutic options for the patients (Bensimon G et al., *J Neurol.* 2002, 249, 609-615). Therefore, a new treatment strategy that can effectively prevent the disease progression is still in demand.

Many different strategies are under investigation for potential treatment of both sporadic and familial ALS. One strategy is based on the neuroprotective and/or regenerative effect of neurotrophic factors, such as Insulin-like growth factor I (IGF-I), Glial cell line-derived neurotrophic factor (GDNF), Vascular endothelial growth factor (VEGF), Colivelin and Activity dependent neurotrophic factor (ADNF) derived peptide, which can promote neuronal survival. Several studies demonstrated that neurotrophic factors can preserve motor neuron functionality, therefore improving motor performance in the SOD1 transgenic mice. However, such treatment often fails to prolong the survival of SOD1 mice, suggesting that neurotrophic factors are not sufficient to prolong neuronal survival (See a review by Yacila and Sari, *Curr Med Chem.*, 2014, 21(31), 3583-3593).

Another strategy for ALS treatment has focused on stem cell-based therapy. Stem cells have the potential to generate motor neurons, thereby replacing degenerating motor neurons in the ALS-affected CNS such as primary motor cortex, brainstem, and spinal cord. Stem cells derived from multiple sources have been investigated, including induced pluripotent stem cells (iPSCs), mesenchymal stromal cells (MSCs) (e.g., bone marrow mesenchymal stromal cells (BMSCs) and adipocyte stem cells (ASCs)) and neural tissue origin neural stem cells (e.g., fetal spinal neural stem cells (NSCs), multipotent neural progenitor cells (NPCs)) (e.g., reviewed by Kim C et al., *Exp. Neurobiol.*, 2014, 23(3), 207-214).

Mutations in the gene of superoxide dismutase type I (SOD1; $Cu^{2+}/Zn^{2+}$ superoxide dismutase type I) are the most common cause of fALS, accounting for about 20 to 30% of all fALS cases. Recent reports indicate that SOD1 mutations may also be linked to about 4% of all sALS cases (Robberecht and Philip, *Nat. Rev. Neurosci.*, 2013, 14, 248-264). SOD1-linked fALS is most likely not caused by loss of the normal SOD1 activity, but rather by a gain of a toxic function. One of the hypotheses for mutant SOD1-linked fALS toxicity proposes that an aberrant SOD1 enzyme causes small molecules such as peroxynitrite or hydrogen peroxide to produce damaging free radicals. Other hypotheses for mutant SOD1 neurotoxicity include inhibition of the proteasome activity, mitochondrial damage, disruption of RNA processing and formation of intracellular aggregates. Abnormal accumulation of mutant SOD1 variants and/or wild-type SOD1 in ALS forms insoluble fibrillar aggregates which are identified as pathological inclusions. Aggregated SOD1 protein can induce mitochondria stress (Vehvilainen P et al., *Front Cell Neurosci.*, 2014, 8, 126) and other toxicity to cells, particularly to motor neurons.

These findings indicate that SOD1 can be a potential therapeutic target for both familial and sporadic ALS. A therapy that can reduce the SOD1 protein produced in the central nervous system of ALS patients may ameliorate the symptoms of ALS in patients such as motor neuron degeneration and muscle weakness and atrophy. Agents and methods that aim to prevent the formation of wild type and/or mutant SOD1 protein aggregation may prevent disease progression and allow for amelioration of ALS symptoms. RNA interfering (RNAi) mediated gene silencing has drawn researchers' interest in recent years. Small double stranded RNA (small interfering RNA) molecules that target the SOD1 gene haven been taught in the art for their potential in treating ALS (See, e.g., U.S. Pat. No. 7,632,938 and U.S. Patent Publication No. 20060229268, the contents of which is herein incorporated by reference in its entirety).

The present invention develops an RNA interference-based approach to inhibit or prevent the expression of SOD1 in ALS patients for treatment of the disease.

The present invention provides novel double stranded RNA (dsRNA) constructs and siRNA constructs and methods of their design. In addition, these novel siRNA constructs may be synthetic molecules or be encoded in an expression vector (one or both strands) for delivery into cells. Such vectors include, but are not limited to adeno-associated viral vectors such as vector genomes of any of the AAV serotypes or other viral delivery vehicles such as lentivirus, etc.

SUMMARY OF THE INVENTION

The present invention relates to RNA molecule mediated gene specific interference with gene expression and protein production. Methods for treating motor neuron degeneration diseases such as amyotrophic lateral sclerosis are also included in the present invention. The siRNA included in the compositions featured herein encompass a dsRNA having an antisense strand (the antisense strand) having a region that is 30 nucleotides or less, generally 19-24 nucleotides in length, that is substantially complementary to at least part of an mRNA transcript of the SOD1 gene.

The present invention provides short double stranded RNA molecules such as small interfering RNA (siRNA) duplexes that target SOD1 mRNA to interfere with SOD1 gene expression and/or SOD1 protein production. The siRNA duplexes of the present invention may interfere with both alleles of the SOD1 gene irrespective of any particular mutation in the SOD1 gene, and may particularly interact with those found in ALS disease.

In some embodiments, such siRNA molecules, or a single strand of the siRNA molecules, are inserted into adeno-associated viral vectors to be introduced into cells, specifically motor neurons and/or other surrounding cells in the central nervous system.

The siRNA duplex of the present invention comprises an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5' end of the antisense strand has a 5' phosphate group and the 3' end of the sense strand contains a 3' hydroxyl group. In other aspects, there are none, one or 2 nucleotides overhangs at the 3' end of each strand.

According to the present invention, each strand of the siRNA duplex targeting the SOD1 gene is about 19-25 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding SOD1, and the region of complementarity is 30 nucleotides or less, and at least 15 nucleotides in length. Generally, the dsRNA is 19 to 24, e.g., 19 to 21 nucleotides in length. In some embodiments the dsRNA is from about 15 to about 25 nucleotides in length, and in other embodiments the dsRNA is from about 25 to about 30 nucleotides in length.

The dsRNA, either upon contacting with a cell expressing SOD1 or upon transcription within a cell expressing SOD1, inhibits or suppresses the expression of a SOD1 gene by at least 10%, at least 20%, at least 25%, at least 30%, at least 35% or at least 40% or more, such as when assayed by a method as described herein.

According to the present invention, AAV vectors comprising the nucleic acids encoding the siRNA duplexes, one strand of the siRNA duplex or the dsRNA targeting SOD1 gene are produced, the AAV vector serotype may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and/or AAV-DJ, and variants thereof.

According to the present invention, siRNA duplexes or dsRNA targeting the SOD1 gene in ALS are selected from the siRNA duplexes listed in Table 3, 11 or 13. Preferably, the siRNA duplexes or dsRNA targeting SOD1 gene in ALS are selected from the group consisting of siRNA duplexes:

D-2757, D-2806, D-2860, D-2861, D-2875, D-2871, D-2758, D-2759, D-2866, D-2870, D-2823 and D-2858.

The present invention also provides pharmaceutical compositions comprising at least one siRNA duplex targeting the SOD1 gene and a pharmaceutically acceptable carrier. In some aspects, a nucleic acid sequence encoding the siRNA duplex is inserted into an AAV vector.

In some embodiments, the present invention provides methods for inhibiting/silencing SOD1 gene expression in a cell. Accordingly, the siRNA duplexes or dsRNA can be used to substantially inhibit SOD1 gene expression in a cell, in particular in a motor neuron. In some aspects, the inhibition of SOD1 gene expression refers to an inhibition by at least about 20%, preferably by at least about 30%, 40%, 50%, 60%, 70%, 80%, 85%, 90%, 95% and 100%. Accordingly, the protein product of the targeted gene may be inhibited by at least about 20%, preferably by at least about 30%, 40%, 50%, 60%, 70%, 80%, 85%, 90%, 95% and 100%. The SOD1 gene can be either a wild type gene or a mutated SOD1 gene with at least one mutation. Accordingly, the SOD1 protein is either wild type protein or a mutated polypeptide with at least one mutation.

In some embodiments, the present invention provides methods for treating, or ameliorating amyotrophic lateral sclerosis associated with abnormal SOD1 gene and/or SOD1 protein in a subject in need of treatment, the method comprising administering to the subject a pharmaceutically effective amount of at least one siRNA duplex targeting the SOD1 gene, delivering said siRNA duplex into targeted cells, inhibiting SOD1 gene expression and protein production, and ameliorating symptoms of ALS in the subject.

In some embodiments, an AAV vector comprising the nucleic acid sequence encoding at least one siRNA duplex targeting the SOD1 gene is administered to the subject in need for treating and/or ameliorating ALS. The AAV vector serotype may be selected from the group consisting of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10 and AAV-DJ, and variants thereof.

In some aspects, ALS is familial ALS linked to SOD1 mutations. In other aspects, ALS is sporadic ALS which is characterized by abnormal aggregation of SOD1 protein or disruption of SOD1 protein function or localization, though not necessarily as a result of genetic mutation. The symptoms of ALS ameliorated by the present method may include motor neuron degeneration, muscle weakness, stiffness of muscles, slurred speech and/or difficulty in breathing.

In some embodiments, the siRNA duplexes or dsRNA targeting SOD1 gene or the AAV vectors comprising such siRNA-encoding molecules may be introduced directly into the central nervous system of the subject, for example, by intracranial injection.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on motor neuron degeneration.

In some embodiments, the present invention provides methods for treating, or ameliorating amyotrophic lateral sclerosis by administering to a subject in need thereof a therapeutically effective amount of a plasmid or AAV vector described herein. The ALS may be familial ALS or sporadic ALS.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 11A shows the relative SOD1 expression. FIG. 11B shows the percent of guide strand. FIG. 11C shows the percent of the passenger strand.

DETAILED DESCRIPTION OF THE INVENTION

Figure 1:
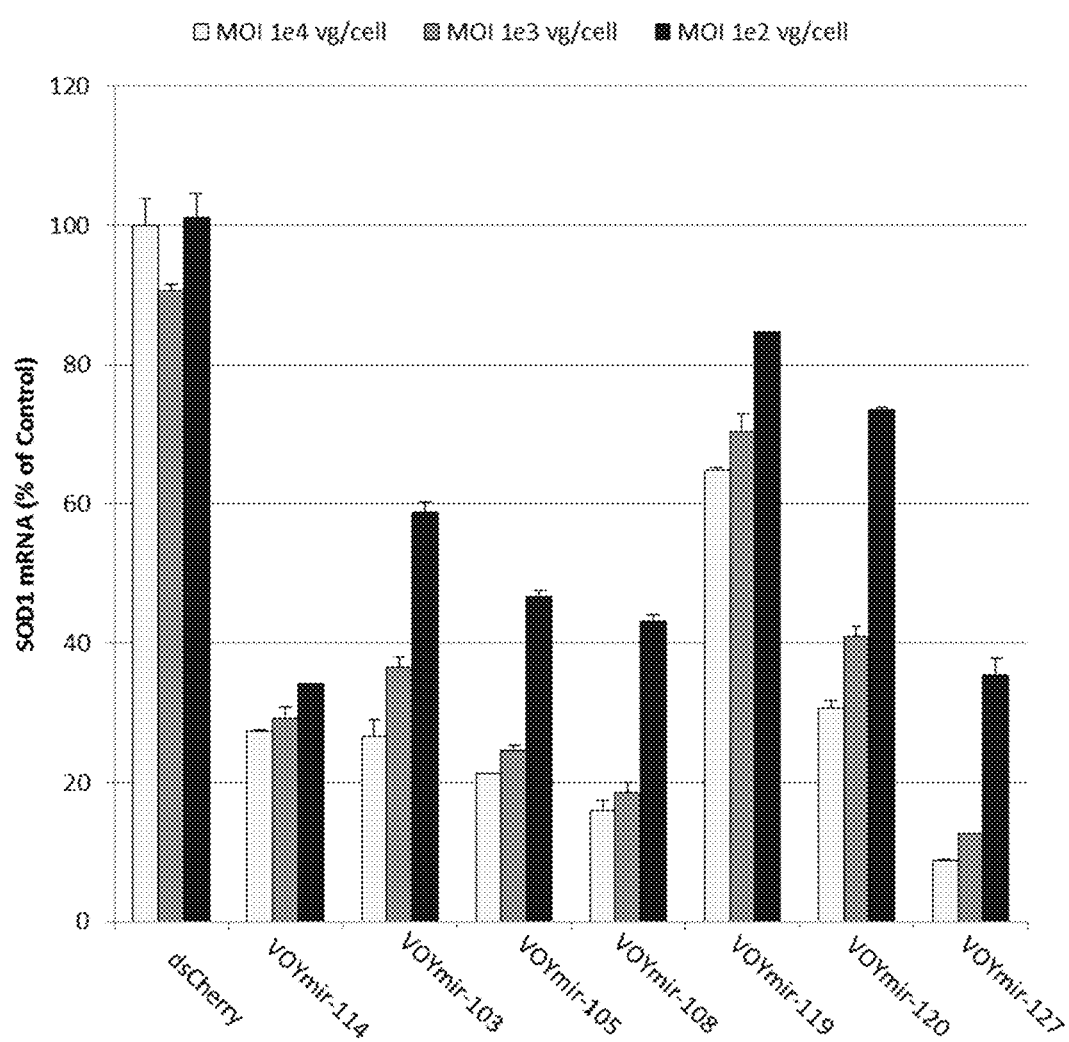
FIG. 1 is a histogram showing the activity of the constructs encoded in an AAV vector.

The present invention relates to modulatory polynucleotides, e.g., RNA or DNA molecules as therapeutic agents. RNA interfering mediated gene silencing can specifically inhibit targeted gene expression. The present invention then provides small double stranded RNA (dsRNA) molecules (small interfering RNA, siRNA) targeting the SOD1 gene, pharmaceutical compositions comprising such siRNAs, as well as processes of their design. The present invention also provides methods of their use for inhibiting SOD1 gene expression and protein production, for treating neurodegenerative disease, in particular, amyotrophic lateral sclerosis (ALS).

The present invention provides small interfering RNA (siRNA) duplexes (and modulatory polynucleotides encoding them) that target SOD1 mRNA to interfere with SOD1 gene expression and/or SOD1 protein production. The siRNA duplexes of the present invention may interfere with both alleles of the SOD1 gene irrespective of any particular mutation in the SOD1 gene, and may particularly interact with those found in ALS disease.

In some embodiments, a nucleic acid sequence encoding such siRNA molecules, or a single strand of the siRNA molecules, is inserted into adeno-associated viral vectors and introduced into cells, specifically motor neurons and/or other surrounding cells in the central nervous system.

The encoded siRNA duplex of the present invention contains an antisense strand and a sense strand hybridized together forming a duplex structure, wherein the antisense strand is complementary to the nucleic acid sequence of the targeted SOD1 gene, and wherein the sense strand is homologous to the nucleic acid sequence of the targeted SOD1 gene. In some aspects, the 5' end of the antisense strand has a 5' phosphate group and the 3' end of the sense strand contains a 3' hydroxyl group. In other aspects, there are none, one or 2 nucleotide overhangs at the 3' end of each strand.

According to the present invention, each strand of the siRNA duplex targeting the SOD1 gene is about 19 to 25, 19 to 24 or 19 to 21 nucleotides in length, preferably about 19 nucleotides, 20 nucleotides, 21 nucleotides, 22 nucleotides, 23 nucleotides, 24 nucleotides, or 25 nucleotides in length. In some aspects, the siRNAs may be unmodified RNA molecules.

In other aspects, the siRNAs may contain at least one modified nucleotide, such as base, sugar or backbone modification.

In one embodiment, an siRNA or dsRNA includes at least two sequences that are complementary to each other. The dsRNA includes a sense strand having a first sequence and an antisense strand having a second sequence. The antisense strand includes a nucleotide sequence that is substantially complementary to at least part of an mRNA encoding SOD1, and the region of complementarity is 30 nucleotides or less, and at least 15 nucleotides in length. Generally, the dsRNA is 19 to 25, 19 to 24 or 19 to 21 nucleotides in length. In some embodiments the dsRNA is from about 15 to about 25 nucleotides in length, and in other embodiments the dsRNA is from about 25 to about 30 nucleotides in length.

The dsRNA, whether directly administered or encoded in an expression vector upon contacting with a cell expressing SOD1, inhibits the expression of SOD1 by at least 10%, at least 20%, at least 25%, at least 30%, at least 35% or at least 40% or more, such as when assayed by a method as described herein.

The siRNA molecules included in the compositions featured herein comprise a dsRNA having an antisense strand (the antisense strand) having a region that is 30 nucleotides or less, generally 19 to 25, 19 to 24 or 19 to 21 nucleotides in length, that is substantially complementary to at least part of an mRNA transcript of the SOD1 gene.

According to the present invention, AAV vectors comprising the nucleic acids of the siRNA duplexes, one strand of the siRNA duplex or the dsRNA targeting SOD1 gene are produced, the AAV vector serotypes may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ, and variants thereof.

According to the present invention, siRNA duplexes or the encoded dsRNA targeting the SOD1 gene in ALS is selected from the siRNA duplexes listed in Table 3. In some embodiments, the siRNA duplexes or dsRNA targeting the SOD1 gene in ALS is selected from the group consisting of siRNA duplexes: D-2757, D-2806, D-2860, D-2861, D-2875, D-2871, D-2758, D-2759, D-2866, D-2870, D-2823 and D-2858.

The present invention also provides pharmaceutical compositions comprising at least one siRNA duplex targeting the SOD1 gene and a pharmaceutically acceptable carrier. In some aspects, the siRNA duplex is encoded by an AAV vector.

In some embodiments, the present invention provides methods for inhibiting/silencing SOD1 gene expression in a cell. Accordingly, the siRNA duplexes or encoded dsRNA can be used to substantially inhibit SOD1 gene expression in a cell, in particular in a motor neuron. In some aspects, the inhibition of SOD1 gene expression refers to an inhibition by at least about 20%, such as by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. The SOD1 gene can be either a wild type gene or a mutated SOD1 gene with at least one mutation. Accordingly, the SOD1 protein is either wild type protein or a mutated polypeptide with at least one mutation.

In one embodiment, the siRNA duplexes or encoded dsRNA may be used to reduce the expression of SOD1 protein by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of SOD1 protein expression may be reduced 50-90%.

In one embodiment, the siRNA duplexes or encoded dsRNA may be used to reduce the expression of SOD1 mRNA by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. As a non-limiting example, the expression of SOD1 mRNA expression may be reduced 50-90%.

In one embodiment, the siRNA duplexes or encoded dsRNA may be used to reduce the expression of SOD1 protein and/or mRNA in at least one region of the CNS such as, but not limited to the spinal cord, the forebrain, the midbrain or the hindbrain. The expression of SOD1 protein and/or mRNA is reduced by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in at least one region of the CNS. As a non-limiting example, the expression of SOD1 protein and mRNA in the spinal cord is reduced by 50-90%.

In some embodiments, the present invention provides methods for treating, or ameliorating amyotrophic lateral sclerosis associated with abnormal SOD1 gene and/or SOD1 protein in a subject in need of treatment, the method comprising administering to the subject a pharmaceutically effective amount of at least one siRNA duplex or a nucleic acid encoding an siRNA duplex targeting the SOD1 gene, delivering said siRNA duplex (or encoded duplex) into targeted cells, inhibiting SOD1 gene expression and protein production, and ameliorating symptoms of ALS in the subject.

In some embodiments, an AAV vector comprising the nucleic acid sequence of at least one siRNA duplex targeting the SOD1 gene is administered to the subject in need for treating and/or ameliorating ALS. The AAV vector serotype may be selected from the group consisting of AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 (AAVDJ8) and AAV-DJ (AAVDJ), and variants thereof. In one embodiment, the AAV vector serotype is AAV2. In another embodiment, the AAV vector is AAVDJ. In yet another embodiment, the AAV vector serotype is AAVDJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in their entirety, may comprise two mutations: (1) R587Q where arginine (R; arg) at amino acid 587 is changed to glutamine (Q; Gln) and (2) R590T where arginine (R; Arg) at amino acid 590 is changed to threonine (T; Thr). As another non-limiting example, may comprise three mutations: (1) K406R where lysine (K; Lys) at amino acid 406 is changed to arginine (R; Arg), (2) R587Q where arginine (R; Arg) at amino acid 587 is changed to glutamine (Q; Gln) and (3) R590T where arginine (R; Arg) at amino acid 590 is changed to threonine (T; Thr).

In some aspects, ALS is familial ALS linked to SOD1 mutations. In other aspects, ALS is sporadic ALS which is characterized by abnormal aggregation of SOD1 protein or aberrations in SOD1 protein function and localization. The symptoms of ALS ameliorated by the present method may include, but are not limited to, motor neuron degeneration, muscle weakness, stiffness of muscles, slurred speech and/or difficulty in breathing.

In some embodiments, the siRNA duplexes or encoded dsRNA targeting the SOD1 gene or the AAV vectors comprising such siRNA molecules may be introduced directly into the central nervous system of the subject, for example, by intracranial injection.

In some embodiments, the pharmaceutical composition of the present invention is used as a solo therapy. In other embodiments, the pharmaceutical composition of the present invention is used in combination therapy. The combination therapy may be in combination with one or more neuroprotective agents such as small molecule compounds, growth factors and hormones which have been tested for their neuroprotective effect on motor neuron degeneration.

In some embodiments, the present invention provides methods for treating, or ameliorating amyotrophic lateral sclerosis by administering to a subject in need thereof a therapeutically effective amount of a plasmid or AAV vector described herein. The ALS may be familial ALS or sporadic ALS.

The details of one or more embodiments of the invention are set forth in the accompanying description below. Although any materials and methods similar or equivalent to those described herein can be used in the practice or testing of the present invention, the preferred materials and methods are now described. Other features, objects and advantages of the invention will be apparent from the description. In the description, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present description will control.

Amyotrophic Lateral Sclerosis (ALS)

Amyotrophic lateral sclerosis (ALS), an adult-onset neurodegenerative disorder, is a progressive and fatal disease characterized by the selective death of motor neurons in the motor cortex, brainstem and spinal cord. The incidence of ALS is about 1.9 per 100,000. Patients diagnosed with ALS develop a progressive muscle phenotype characterized by spasticity, hyperreflexia or hyporeflexia, fasciculations, muscle atrophy and paralysis. These motor impairments are caused by the denervation of muscles due to the loss of motor neurons. The major pathological features of ALS include degeneration of the corticospinal tracts and extensive loss of lower motor neurons (LMNs) or anterior horn cells (Ghatak et al., *J Neuropathol Exp Neurol.*, 1986, 45, 385-395), degeneration and loss of Betz cells and other pyramidal cells in the primary motor cortex (Udaka et al., *Acta Neuropathol*, 1986, 70, 289-295; Maekawa et al., *Brain*, 2004, 127, 1237-1251) and reactive gliosis in the motor cortex and spinal cord (Kawamata et al., *Am J Pathol.*, 1992, 140, 691-707; and Schiffer et al., *J Neurol Sci.*, 1996, 139, 27-33). ALS is usually fatal within 3 to 5 years after the diagnosis due to respiratory defects and/or inflammation (Rowland L P and Shneibder N A, *N Engl. J Med.*, 2001, 344, 1688-1700).

A cellular hallmark of ALS is the presence of proteinaceous, ubiquitinated, cytoplasmic inclusions in degenerating motor neurons and surrounding cells (e.g., astrocytes). Ubiquitinated inclusions (i.e., Lewy body-like inclusions or Skein-like inclusions) are the most common and specific type of inclusion in ALS and are found in LMNs of the spinal cord and brainstem, and in corticospinal upper motor neurons (UMNs) (Matsumoto et al., *J Neurol Sci.*, 1993, 115, 208-213; and Sasak and Maruyama, *Acta Neuropathol.*, 1994, 87, 578-585). A few proteins have been identified to be components of the inclusions, including ubiquitin, Cu/Zn superoxide dismutase 1 (SOD1), peripherin and Dorfin. Neurofilamentous inclusions are often found in hyaline conglomerate inclusions (HCIs) and axonal 'spheroids' in spinal cord motor neurons in ALS. Other types and less specific inclusions include Bunina bodies (cystatin C-containing inclusions) and Crescent shaped inclusions (SCIs) in upper layers of the cortex. Other neuropathological features seen in ALS include fragmentation of the Golgi apparatus, mitochondrial vacuolization, and ultrastructural abnormalities of synaptic terminals (Fujita et al., *Acta Neuropathol.* 2002, 103, 243-247).

In addition, in frontotemporal dementia ALS (FTD-ALS) cortical atrophy (including the frontal and temporal lobes) is also observed, which may cause cognitive impairment in FTD-ALS patients.

ALS is a complex and multifactorial disease and multiple mechanisms hypothesized as responsible for ALS pathogenesis include, but are not limited to, dysfunction of protein degradation, glutamate excitotoxicity, mitochondrial dysfunction, apoptosis, oxidative stress, inflammation, protein misfolding and aggregation, aberrant RNA metabolism, and altered gene expression.

About 10%-15% of ALS cases have family history of the disease, and these patients are referred to as familial ALS (fALS) or inherited patients, commonly with a Mendelian dominant mode of inheritance and high penetrance. The remainder (approximately 85%-95%) is classified as sporadic ALS (sALS), as they are not associated with a documented family history, but instead are thought to be due to other risk factors including, but not limited to environmental factors, genetic polymorphisms, somatic mutations, and possibly gene-environmental interactions. In most cases, familial (or inherited) ALS is inherited as autosomal dominant disease, but pedigrees with autosomal recessive and X-linked inheritance and incomplete penetrance exist. Sporadic and familial forms are clinically indistinguishable suggesting a common pathogenesis. The precise cause of the selective death of motor neurons in ALS remains elusive. Progress in understanding the genetic factors in fALS may shed light on both forms of the disease.

Recently, an explosion to genetic causes of ALS has discovered mutations in more than 10 different genes that are known to cause fALS. The most common ones are found in the genes encoding Cu/Zn superoxide dismutase 1 (SOD1; ~20%) (Rosen D R et al., *Nature,* 1993, 362, 59-62), fused in sarcoma/translated in liposarcoma (FUS/TLS; 1-5%) and TDP-43 (TARDBP; 1-5%). Recently, a hexanucleotide repeat expansion $(GGGGCC)_n$ in the C9orF72 gene was identified as the most frequent cause of fALS (~40%) in the Western population (reviewed by Renton et al., *Nat. Neurosci.,* 2014, 17, 17-23). Other genes mutated in ALS include alsin (ALS2), senataxin (SETX), vesicle-associated membrane protein (VAPB), and angiogenin (ANG). fALS genes control different cellular mechanisms, suggesting that the pathogenesis of ALS is complicated and may be related to several different processes finally leading to motor neuron degeneration.

SOD1 is one of the three human superoxide dismutases identified and characterized in mammals: copper-zinc superoxide dismutase (Cu/ZnSOD or SOD1), manganese superoxide dismutase (MnSOD or SOD2), and extracellular superoxide dismutase (ECSOD or SOD3). SOD1 is a 32 kDa homodimer of a 153-residue polypeptide with one copper- and one zinc-binding site per subunit, which is encoded by the SOD1 gene (GeneBank access No.: NM_000454.4) on human chromosome 21 (see Table 2). SOD1 catalyzes the reaction of superoxide anion ($O^{2-}$) into molecular oxygen ($O_2$) and hydrogen peroxide ($H_2O_2$) at a bound copper ion. The intracellular concentration of SOD1 is high (ranging from 10 to 100 µM), accounting for 1% of the total protein content in the central nervous system (CNS). The protein is localized not only in the cytoplasm but also in the nucleus, lysosomes, peroxisomes, and mitochondrial intermembrane spaces in eukaryotic cells (Lindenau J et al., *Glia,* 2000, 29, 25-34).

Mutations in the SOD1 gene are carried by 15-20% of fALS patients and by 1-2% of all ALS cases. Currently, at least 170 different mutations distributed throughout the 153-amino acid SOD1 polypeptide have been found to cause ALS, and an updated list can be found at the ALS online Genetic Database (ALSOD) (Wroe R et al., *Amyotroph Lateral Scler.,* 2008, 9, 249-250). Table 1 lists some examples of mutations in SOD1 in ALS. These mutations are predominantly single amino acid substitutions (i.e. missense mutations) although deletions, insertions, and C-terminal truncations also occur. Different SOD1 mutations display different geographic distribution patterns. For instance, 40-50% of all Americans with ALS caused by SOD1 gene mutations have a particular mutation Ala4Val (or A4V). The A4V mutation is typically associated with more severe signs and symptoms and the survival period is typically 2-3 years. The I113T mutation is by far the most common mutation in the United Kingdom. The most prevalent mutation in Europe is D90A substitute and the survival period is usually greater than 10 years.

TABLE 1

Examples of SOD1 mutations in ALS

| Location | Mutations |
| --- | --- |
| Exon1 (220 bp) | Q22L; E21K, G; F20C; N19S; G16A, S; V14M, S; G12R; G10G, V, R; L8Q, V; V7E; C6G, F; V5L; A4T, V, S |
| Exon2 (97 bp) | T54R; E49K; H48R, Q; V47F, A; H46R; F45C; H43R; G41S, D; G37R; V29, insA |
| Exon3 (70 bp) | D76Y, V; G72S, C; L67R; P66A; N65S; S59I, S |
| Exon4 (118 bp) | D124G, V; V118L, InsAAAAC; L117V; T116T; R115G; G114A; I113T, F; I112M, T; G108V; L106V, F; S106L, delTCACTC; I104F; D101G, Y, H, N; E100G, K; I99V; V97L, M; D96N, V; A95T, V; G935, V, A, C, R, D; D90V, A; A89T, V; T88delACTGCTGAC; V87A, M; N86I, S, D, K; G85R, S; L84V, F; H80R |
| Exon5 (461 bp) | I151T, S; I149T; V148I, G; G147D, R; C146R, stop; A145T, G; L144F, S; G141E, stop; A140A, G; N139D, K, H, N; G138E; T137R; S134N; E133V, delGAA, insTT; E132insTT; G127R, InsTGGG; L126S, delITT, stop; D126, delTT |

To investigate the mechanism of neuronal death associated with SOD1 gene defects, several rodent models of SOD1-linked ALS were developed in the art, which express the human SOD1 gene with different mutations, including missense mutations, small deletions, or insertions. Non-limiting examples of ALS mouse models include SOD1$^{G93A}$, SOD1$^{A4V}$, SOD1$^{G37R}$, SOD1$^{G85R}$, SOD1$^{D90A}$, SOD1$^{L84V}$, SOD1$^{I113T}$, SOD1$^{H36R/H48Q}$, SOD1$^{G127X}$, SOD1$^{L126X}$, and SOD1$^{L126delTT}$. There are two transgenic rat models carrying two different human SOD1 mutations: SOD1$^{H46R}$ and SOD1$^{G93R}$. These rodent ALS models can develop muscle weakness similar to human ALS patients and other pathogenic features that reflect several characteristics of the human disease, in particular, the selective death of spinal motor neurons, aggregation of protein inclusions in motor neurons and microglial activation. It is well known in the art that the transgenic rodents are good models of human SOD1-associated ALS disease and provide models for studying disease pathogenesis and developing disease treatment.

Studies in animal and cellular models showed that SOD1 pathogenic variants cause ALS by gain of function. That is to say, the superoxide dismutase enzyme gains new but harmful properties when altered by SOD1 mutations. For example, some SOD1 mutated variants in ALS increase oxidative stress (e.g., increased accumulation of toxic superoxide radicals) by disrupting the redox cycle. Other studies also indicate that some SOD1 mutated variants in ALS might acquire toxic properties that are independent of its normal physiological function (such as abnormal aggregation of misfolded SOD1 variants. In the aberrant redox chemistry model, mutant SOD1 is unstable and through aberrant chemistry interacts with nonconventional substrates causing overproduction of reactive oxygen species (ROS). In the protein toxicity model, unstable, misfolded SOD1 aggregates into cytoplasmic inclusion bodies, sequestering proteins crucial for cellular processes. These two hypotheses are not mutually exclusive. It has been shown that oxidation of selected histidine residues that bind metals in the active site mediates SOD1 aggregation.

The aggregated mutant SOD1 protein may also induce mitochondrial dysfunction (Vehvilainen P et al., *Front Cell Neurosci.*, 2014, 8, 126), impairment of axonal transport, aberrant RNA metabolism, glial cell pathology and glutamate excitotoxicity. In some sporadic ALS cases, misfolded wild-type SOD1 protein is found in diseased motor neurons which forms a "toxic conformation" that is similar to that which is seen with familial ALS-linked SOD1 variants (Rotunno M S and Bosco D A, *Front Cell Neurosci.*, 2013, 16, 7, 253). Such evidence suggests that ALS is a protein folding diseases analogous to other neurodegenerative diseases such as Alzheimer's disease and Parkinson's disease.

Currently, no curative treatments are available for patients suffering from ALS. The only FDA approved drug Riluzole, an inhibitor of glutamate release, has a moderate effect on ALS, only extending survival by 2-3 months if it is taken for 18 months. Unfortunately, patients taking riluzole do not experience any slowing in disease progression or improvement in muscle function. Therefore, riluzole does not present a cure, or even an effective treatment. Researchers continue to search for better therapeutic agents.

Therapeutic approaches that may prevent or ameliorate SOD1 aggregation have been tested previously. For example, arimoclomol, a hydroxylamine derivative, is a drug that targets heat shock proteins, which are cellular defense mechanisms against these aggregates. Studies demonstrated that treatment with arimoclomol improved muscle function in SOD1 mouse models. Other drugs that target one or more cellular defects in ALS may include AMPA antagonists such as talampanel, beta-lactam antibiotics, which may reduce glutamate-induced excitotoxicity to motor neurons; Bromocriptine that may inhibit oxidative induced motor neuron death (e.g. U.S. Patent publication No. 20110105517; the content of which is incorporated herein by reference in its entirety); 1,3-diphenylurea derivative or multikinase inhibitor which may reduce SOD1 gene expression (e.g., U.S. Patent Publication No. 20130225642; the content of which is incorporated herein by reference in its entirety); dopamine agonist pramipexole and its anantiomer dexpramipexole, which may ameliorate the oxidative response in mitochondria; nimesulide, which inhibits cyclooxygenase enzyme (e.g., U.S. Patent Publication No. 20060041022; the content of which is incorporated herein by reference in its entirety); drugs that act as free radical scavengers (e.g. U.S. Pat. No. 6,933,310 and PCT Patent Publication No.: WO2006075434; the content of each of which is incorporated herein by reference in their entirety).

Another approach to inhibit abnormal SOD1 protein aggregation is to silence/inhibit SOD1 gene expression in ALS. It has been reported that small interfering RNAs for specific gene silencing of the mutated allele are therapeutically beneficial for the treatment of fALS (e.g., Ralgh G S et al., *Nat. Medicine*, 2005, 11(4), 429-433; and Raoul C et al., *Nat. Medicine*, 2005, 11(4), 423-428; and Maxwell M M et al., *PNAS*, 2004, 101(9), 3178-3183; and Ding H et al., *Chinese Medical J.*, 2011, 124(1), 106-110; and Scharz D S et al., *Plos Genet.*, 2006, 2(9), e140; the content of each of which is incorporated herein by reference in their entirety).

Many other RNA therapeutic agents that target the SOD1 gene and modulate SOD1 expression in ALS are taught in the art. Such RNA based agents include antisense oligonucleotides and double stranded small interfering RNAs. See, e.g., Wang H et al., *J Biol. Chem.*, 2008, 283(23), 15845-15852); U.S. Pat. Nos. 7,498,316; 7,632,938; 7,678,895; 7,951,784; 7,977,314; 8,183,219; 8,309,533 and 8, 586, 554; and U.S. Patent publication Nos. 2006/0229268 and 2011/0263680; the content of each of which is herein incorporated by reference in their entirety.

The present invention provides modulatory polynucleotides, e.g., siRNA molecules targeting the SOD1 gene and methods for their design and manufacture. Particularly, the present invention employs viral vectors such as adeno-associated viral (AAV) vectors comprising the nucleic acid sequence encoding the siRNA molecules of the present invention. The AAV vectors comprising the nucleic acid sequence encoding the siRNA molecules of the present invention may increase the delivery of active agents into motor neurons. The siRNA duplexes or encoding dsRNA targeting the SOD1 gene may be able to inhibit SOD1 gene expression (e.g., mRNA level) significantly inside cells; therefore, ameliorating SOD1 expression induced stress inside the cells such as aggregation of protein and formation of inclusions, increased free radicals, mitochondrial dysfunction, and RNA metabolism.

Such siRNA mediated SOD1 expression inhibition may be used for treating ALS. According to the present invention, methods for treating and/or ameliorating ALS in a patient comprises administering to the patient an effective amount of AAV vector comprising a nucleic acid sequence encoding the siRNA molecules of the present invention into cells. The administration of the AAV vector comprising such a nucleic acid sequence will encode the siRNA molecules which cause the inhibition/silence of SOD1 gene expression.

In one embodiment, the vectors, e.g., AAV encoding the modulatory polynucleotide, reduce the expression of mutant SOD1 in a subject. The reduction of mutant SOD1 can also reduce the formation of toxic aggregates which can cause mechanisms of toxicity such as, but not limited to, oxidative stress, mitochondrial dysfunction, impaired axonal transport, aberrant RNA metabolism, glial cell pathology and/or glutamate excitotoxicity.

In one embodiment, the vector, e.g., AAV vectors, reduces the amount of SOD1 in a subject in need thereof and thus provides a therapeutic benefit as described herein.

Compositions of the Invention siRNA Molecules

The present invention relates to RNA interference (RNAi) induced inhibition of gene expression for treating neurodegenerative disorders. Provided herein are siRNA duplexes or encoded dsRNA that target the SOD1 gene (referred to herein collectively as "siRNA molecules"). Such siRNA duplexes or encoded dsRNA can reduce or silence SOD1 gene expression in cells, for example, motor neurons, thereby, ameliorating symptoms of ALS such as, but not limited to, motor neuron death and muscle atrophy.

RNAi (also known as post-transcriptional gene silencing (PTGS), quelling, or co-suppression) is a post-transcriptional gene silencing process in which RNA molecules, in a sequence specific manner, inhibit gene expression, typically by causing the destruction of specific mRNA molecules. The active components of RNAi are short/small double stranded RNAs (dsRNAs), called small interfering RNAs (siRNAs), that typically contain 15-30 nucleotides (e.g., 19 to 25, 19 to 24 or 19-21 nucleotides) and 2 nucleotide 3' overhangs and that match the nucleic acid sequence of the target gene. These short RNA species may be naturally produced in vivo by Dicer-mediated cleavage of larger dsRNAs and they are functional in mammalian cells.

Naturally expressed small RNA molecules, named microRNAs (miRNAs), elicit gene silencing by regulating the expression of mRNAs. The miRNAs containing RNA Induced Silencing Complex (RISC) targets mRNAs presenting a perfect sequence complementarity with nucleotides 2-7 in the 5' region of the miRNA which is called the seed region, and other base pairs with its 3' region. miRNA mediated down regulation of gene expression may be caused by cleavage of the target mRNAs, translational inhibition of the target mRNAs, or mRNA decay. miRNA targeting sequences are usually located in the 3'-UTR of the target mRNAs. A single miRNA may target more than 100 transcripts from various genes, and one mRNA may be targeted by different miRNAs.

siRNA duplexes or dsRNA targeting a specific mRNA may be designed and synthesized in vitro and introduced into cells for activating RNAi processes. Elbashir et al. demonstrated that 21-nucleotide siRNA duplexes (termed small interfering RNAs) were capable of effecting potent and specific gene knockdown without inducing immune response in mammalian cells (Elbashir S M et al., *Nature*, 2001, 411, 494-498). Since this initial report, post-transcriptional gene silencing by siRNAs quickly emerged as a powerful tool for genetic analysis in mammalian cells and has the potential to produce novel therapeutics.

In vitro synthetized siRNA molecules may be introduced into cells in order to activate RNAi. An exogenous siRNA duplex, when it is introduced into cells, similar to the endogenous dsRNAs, can be assembled to form the RNA Induced Silencing Complex (RISC), a multiunit complex that facilitates searching through the genome for RNA sequences that are complementary to one of the two strands of the siRNA duplex (i.e., the antisense strand). During the process, the sense strand (or passenger strand) of the siRNA is lost from the complex, while the antisense strand (or guide strand) of the siRNA is matched with its complementary RNA. In particular, the targets of siRNA containing RISC complex are mRNAs presenting a perfect sequence complementarity. Then, siRNA mediated gene silencing occurs, cleaving, releasing and degrading the target.

The siRNA duplex comprised of a sense strand homologous to the target mRNA and an antisense strand that is complementary to the target mRNA offers much more advantage in terms of efficiency for target RNA destruction compared to the use of the single strand (ss)-siRNAs (e.g. antisense strand RNA or antisense oligonucleotides). In many cases it requires higher concentration of the ss-siRNA to achieve the effective gene silencing potency of the corresponding duplex.

Any of the foregoing molecules may be encoded by an AAV vector or vector genome.

Design and Sequences of siRNA Duplexes Targeting SOD1 Gene

Some guidelines for designing siRNAs have been proposed in the art. These guidelines generally recommend generating a 19-nucleotide duplexed region, symmetric 2-3 nucleotide 3' overhangs, 5'-phosphate and 3'-hydroxyl groups targeting a region in the gene to be silenced. Other rules that may govern siRNA sequence preference include, but are not limited to, (i) A/U at the 5' end of the antisense strand; (ii) G/C at the 5' end of the sense strand; (iii) at least five A/U residues in the 5' terminal one-third of the antisense strand; and (iv) the absence of any GC stretch of more than 9 nucleotides in length. In accordance with such consideration, together with the specific sequence of a target gene, highly effective siRNA molecules essential for suppressing mammalian target gene expression may be readily designed.

According to the present invention, siRNA molecules (e.g., siRNA duplexes or encoded dsRNA) that target the human SOD1 gene are designed. Such siRNA molecules can specifically, suppress SOD1 gene expression and protein production. In some aspects, the siRNA molecules are designed and used to selectively "knock out" SOD1 gene variants in cells, i.e., mutated SOD1 transcripts that are identified in patients with ALS disease (e.g., mutations in Table 1). In some aspects, the siRNA molecules are designed and used to selectively "knock down" SOD1 gene variants in cells. In other aspects, the siRNA molecules are able to inhibit or suppress both wild type and mutated alleles of SOD1 gene irrelevant of any particular mutations in the SOD1 gene.

In one embodiment, an siRNA molecule of the present invention comprises a sense strand and a complementary antisense strand in which both strands are hybridized together to form a duplex structure. The antisense strand has sufficient complementarity to the SOD1 mRNA sequence to direct target-specific RNAi, i.e., the siRNA molecule has a sequence sufficient to trigger the destruction of the target mRNA by the RNAi machinery or process.

In some embodiments, the antisense strand and target mRNA sequences are 100% complementary. The antisense strand may be complementary to any part of the target mRNA sequence.

In other embodiments, the antisense strand and target mRNA sequences comprise at least one mismatch. As a non-limiting example, the antisense strand and the target mRNA sequence are at least 30%, 40%, 50%, 60%, 70%, 80%, 81%, 82%, 83%, 84%, 85%, 86%, 87%, 88%, 89%, 90%, 91%, 92%, 93%, 94%, 95%, 96%, 97%, 98% or 99% or at least 20-30%, 20-40%, 20-50%, 20-60%, 20-70%, 20-80%, 20-90%, 20-95%, 20-99%, 30-40%, 30-50%, 30-60%, 30-70%, 30-80%, 30-90%, 30-95%, 30-99%, 40-50%, 40-60%, 40-70%, 40-80%, 40-90%, 40-95%, 40-99%, 50-60%, 50-70%, 50-80%, 50-90%, 50-95%, 50-99%, 60-70%, 60-80%, 60-90%, 60-95%, 60-99%, 70-80%, 70-90%, 70-95%, 70-99%, 80-90%, 80-95%, 80-99%, 90-95%, 90-99% or 95-99% complementary.

According to the present invention, the siRNA molecule has a length from about 10-50 or more nucleotides, i.e., each strand comprising 10-50 nucleotides (or nucleotide analogs). Preferably, the siRNA molecule has a length from about 15-30, e.g., 15, 16, 17, 18, 19, 20, 21, 22, 23, 24, 25, 26, 27, 28, 29, or 30 nucleotides in each strand, wherein one of the strands is sufficiently complementary to a target region. In one embodiment, the siRNA molecule has a length from about 19 to 25, 19 to 24 or 19 to 21 nucleotides.

In some embodiments, the siRNA molecules of the present invention can be synthetic RNA duplexes comprising about 19 nucleotides to about 25 nucleotides, and two overhanging nucleotides at the 3'-end. In some aspects, the siRNA molecules may be unmodified RNA molecules. In other aspects, the siRNA molecules may contain at least one modified nucleotide, such as base, sugar or backbone modifications.

In other embodiments, the siRNA molecules of the present invention can be encoded in plasmid vectors, viral vectors (e.g., AAV vectors), genome or other nucleic acid expression vectors for delivery to a cell.

DNA expression plasmids can be used to stably express the siRNA duplexes or dsRNA of the present invention in cells and achieve long-term inhibition of the target gene. In one aspect, the sense and antisense strands of a siRNA duplex are typically linked by a short spacer sequence leading to the expression of a stem-loop structure termed short hairpin RNA (shRNA). The hairpin is recognized and cleaved by Dicer, thus generating mature siRNA molecules.

According to the present invention, AAV vectors comprising the nucleic acids encoding the siRNA molecules targeting SOD1 mRNA are produced, the AAV vector serotypes may be AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ, and variants thereof.

In some embodiments, the siRNA duplexes or encoded dsRNA of the present invention suppress (or degrade) target mRNA (i.e., SOD1). Accordingly, the siRNA duplexes or encoded dsRNA can be used to substantially inhibit SOD1 gene expression in a cell, for example a motor neuron. In some aspects, the inhibition of SOD1 gene expression refers to an inhibition by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. Accordingly, the protein product of the targeted gene may be inhibited by at least about 20%, preferably by at least about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100%. The SOD1 gene can be either a wild type gene or a mutated SOD1 gene with at least one mutation. Accordingly, the protein is either wild type protein or a mutated polypeptide with at least one mutation.

According to the present invention, siRNA duplexes or encoded dsRNA targeting human SOD1 gene were designed and tested for their ability in reducing SOD1 mRNA levels in cultured cells. Such siRNA duplexes include those listed in Table 3. As a non-limiting example, the siRNA duplexes may be siRNA duplex IDs: D-2757, D-2806, D-2860, D-2861, D-2875, D-2871, D-2758, D-2759, D-2866, D-2870, D-2823 and D-2858.

In one embodiment, the 3' stem arm of the siRNA duplexes or encoded dsRNA targeting the human SOD1 gene may have 11 nucleotides downstream of the 3' end of the guide strand which have complementarity to the 11 of the 13 nucleotides upstream of the 5' end of the passenger strand in the 5' stem arm.

In one embodiment, the siRNA duplexes or encoded dsRNA targeting human SOD1 gene may have a cysteine which is 6 nucleotides downstream of the 3' end of the 3' stem arm of the modulatory polynucleotide.

In one embodiment, the siRNA duplexes or encoded dsRNA targeting human SOD1 gene comprise a miRNA seed match for the guide strand. In another embodiment, the siRNA duplexes or encoded dsRNA targeting human SOD1 gene comprise a miRNA seed match for the passenger strand. In yet another embodiment, the siRNA duplexes or encoded dsRNA targeting human SOD1 gene do not comprise a seed match for the guide or passenger strand.

In one embodiment, the siRNA duplexes or encoded dsRNA targeting human SOD1 gene may have almost no significant full-length off targets for the guide strand. In another embodiment, the siRNA duplexes or encoded dsRNA targeting human SOD1 gene may have almost no significant full-length off targets for the passenger strand. The siRNA duplexes or encoded dsRNA targeting human SOD1 gene may have less than 1%, 2%, 3%, 4%, 5%, 6%, 7%, 8%, 9%, 10%, 1-5%, 2-6%, 3-7%, 4-8%, 5-9%, 5-10% 6-10% full-length off targets for the passenger strand. In yet another embodiment, the siRNA duplexes or encoded dsRNA targeting human SOD1 gene may have almost no significant full-length off targets for the guide strand or the passenger strand. The siRNA duplexes or encoded dsRNA targeting human SOD1 gene may have less than 1%, 2%, 3%, 4%, 5%, 6%, 7%, 8%, 9%, 10%, 1-5%, 2-6%, 3-7%, 4-8%, 5- 9%, 5-10% 6-10% full-length off targets for the guide or passenger strand.

In one embodiment, the siRNA duplexes or encoded dsRNA targeting human SOD1 gene may have high activity in vitro. In another embodiment, the siRNA duplexes or encoded dsRNA targeting the human SOD1 gene may have low activity in vitro. In yet another embodiment, the siRNA duplexes or dsRNA targeting the human SOD1 gene may have high guide strand activity and low passenger strand activity in vitro.

In one embodiment, the siRNA duplexes or encoded dsRNA targeting the human SOD1 gene have a high guide strand activity and low passenger strand activity in vitro. The target knock-down (KD) by the guide strand may be at least 60%, 65%, 70%, 75%, 80%, 85%, 90%, 95%, 99%, 99.5% or 100%. The target knock-down by the guide strand may be 60-65%, 60-70%, 60-75%, 60-80%, 60-85%, 60-90%, 60-95%, 60-99%, 60-99.5%, 60-100%, 65-70%, 65-75%, 65-80%, 65-85%, 65-90%, 65-95%, 65-99%, 65-99.5%, 65-100%, 70-75%, 70-80%, 70-85%, 70-90%, 70-95%, 70-99%, 70-99.5%, 70-100%, 75-80%, 75-85%, 75-90%, 75-95%, 75-99%, 75-99.5%, 75-100%, 80-85%, 80-90%, 80-95%, 80-99%, 80-99.5%, 80-100%, 85-90%, 85-95%, 85-99%, 85-99.5%, 85-100%, 90-95%, 90-99%, 90-99.5%, 90-100%, 95-99%, 95-99.5%, 95-100%, 99-99.5%, 99-100% or 99.5-100%. As a non-limiting example, the target knock-down (KD) by the guide strand is greater than 70%.

In one embodiment, the $IC_{50}$ of the passenger strand for the nearest off target is greater than 100 multiplied by the $IC_{50}$ of the guide strand for the target. As a non-limiting example, if the $IC_{50}$ of the passenger strand for the nearest off target is greater than 100 multiplied by the $IC_{50}$ of the guide strand for the target then the siRNA duplexes or encoded dsRNA targeting the human SOD1 gene is said to have high guide strand activity and a low passenger strand activity in vitro.

In one embodiment, the 5' processing of the guide strand has a correct start (n) at the 5' end at least 75%, 80%, 85%, 90%, 95%, 99% or 100% of the time in vitro or in vivo. As a non-limiting example, the 5' processing of the guide strand is precise and has a correct start (n) at the 5' end at least 99% of the time in vitro. As a non-limiting example, the 5' processing of the guide strand is precise and has a correct start (n) at the 5' end at least 99% of the time in vivo.

In one embodiment, the guide-to-passenger (G:P) strand ratio expressed is 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, or 99:1 in vitro or in vivo. As a non-limiting example, the guide-to-passenger strand ratio is 80:20 in vitro. As a non-limiting example, the guide-to-passenger strand ratio is 80:20 in vivo.

In one embodiment, the integrity of the vector genome encoding the dsRNA is at least 60%, 65%, 70%, 75%, 80%, 85%, 90%, 95%, 99% or more than 99% of the full length of the construct.

siRNA Modification

In some embodiments, the siRNA molecules of the present invention, when not delivered as a precursor or DNA, may be chemically modified to modulate some features of RNA molecules, such as, but not limited to, increasing the stability of siRNAs in vivo. The chemically modified siRNA molecules can be used in human therapeutic applications, and are improved without compromising the RNAi activity of the siRNA molecules. As a non-limiting example, the siRNA molecules modified at both the 3' and the 5' end of both the sense strand and the antisense strand.

In some aspects, the siRNA duplexes of the present invention may contain one or more modified nucleotides such as, but not limited to, sugar modified nucleotides, nucleobase modifications and/or backbone modifications. In some aspects, the siRNA molecule may contain combined modifications, for example, combined nucleobase and backbone modifications.

In one embodiment, the modified nucleotide may be a sugar-modified nucleotide. Sugar modified nucleotides include, but are not limited to 2'-fluoro, 2'-amino and 2'-thio modified ribonucleotides, e.g., 2'-fluoro modified ribonucleotides. Modified nucleotides may be modified on the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

In one embodiment, the modified nucleotide may be a nucleobase-modified nucleotide.

In one embodiment, the modified nucleotide may be a backbone-modified nucleotide. In some embodiments, the siRNA duplexes of the present invention may further comprise other modifications on the backbone. A normal "backbone", as used herein, refers to the repeatingly alternating sugar-phosphate sequences in a DNA or RNA molecule. The deoxyribose/ribose sugars are joined at both the 3'-hydroxyl and 5'-hydroxyl groups to phosphate groups in ester links, also known as "phosphodiester" bonds/linker (PO linkage). The PO backbones may be modified as "phosphorothioate backbone (PS linkage). In some cases, the natural phosphodiester bonds may be replaced by amide bonds but the four atoms between two sugar units are kept. Such amide modifications can facilitate the solid phase synthesis of oligonucleotides and increase the thermodynamic stability of a duplex formed with siRNA complement. See e.g., Mesmaeker et al., *Pure & Appl. Chem.*, 1997, 3, 437-440; the content of which is incorporated herein by reference in its entirety.

Modified bases refer to nucleotide bases such as, for example, adenine, guanine, cytosine, thymine, uracil, xanthine, inosine, and queuosine that have been modified by the replacement or addition of one or more atoms or groups. Some examples of modifications on the nucleobase moieties include, but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any 0- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoalkyl nucleotides, and alkylcarbonylalkylated nucleotides.

In one embodiment, the modified nucleotides may be on just the sense strand.

In another embodiment, the modified nucleotides may be on just the antisense strand.

In some embodiments, the modified nucleotides may be in both the sense and antisense strands.

In some embodiments, the chemically modified nucleotide does not affect the ability of the antisense strand to pair with the target mRNA sequence, such as the SOD1 mRNA sequence.

Vectors

In some embodiments, the siRNA molecules described herein can be encoded by vectors such as plasmids or viral vectors. In one embodiment, the siRNA molecules are encoded by viral vectors. Viral vectors may be, but are not limited to, Herpesvirus (HSV) vectors, retroviral vectors, adenoviral vectors, adeno-associated viral vectors, lentiviral vectors, and the like. In some specific embodiments, the viral vectors are AAV vectors.

Retroviral Vectors

In some embodiments, the siRNA duplex targeting SOD1 gene may be encoded by a retroviral vector (See, e.g., U.S. Pat. Nos. 5,399,346; 5,124,263; 4,650,764 and 4,980,289; the content of each of which is incorporated herein by reference in their entirety).

Adenoviral Vectors

Adenoviruses are eukaryotic DNA viruses that can be modified to efficiently deliver a nucleic acid to a variety of cell types in vivo, and have been used extensively in gene therapy protocols, including for targeting genes to neural cells. Various replication defective adenovirus and minimum adenovirus vectors have been described for nucleic acid therapeutics (See, e.g., PCT Patent Publication Nos. WO199426914, WO 199502697, WO199428152, WO199412649, WO199502697 and WO199622378; the content of each of which is incorporated by reference in their entirety). Such adenoviral vectors may also be used to deliver siRNA molecules of the present invention to cells.

Adeno-Associated Viral (AAV) Vectors

An adeno-associated virus (AAV) is a dependent parvovirus (like other parvoviruses) which is a single stranded non-enveloped DNA virus having a genome of about 5000 nucleotides in length and which contains two open reading frames encoding the proteins responsible for replication (Rep) and the structural protein of the capsid (Cap). The open reading frames are flanked by two Inverted Terminal Repeat (ITR) sequences, which serve as the origin of replication of the viral genome. Furthermore, the AAV genome contains a packaging sequence, allowing packaging of the viral genome into an AAV capsid. The AAV vector requires a co-helper (e.g., adenovirus) to undergo productive infection in infected cells. In the absence of such helper functions, the AAV virions essentially enter host cells and integrate into the cells' genome.

AAV vectors have been investigated for siRNA delivery because of several unique features. Non-limiting examples of the features include (i) the ability to infect both dividing and non-dividing cells; (ii) a broad host range for infectivity, including human cells; (iii) wild-type AAV has not been associated with any disease and has not been shown to replicate in infected cells; (iv) the lack of cell-mediated immune response against the vector and (v) the non-integrative nature in a host chromosome thereby reducing potential for long-term expression. Moreover, infection with AAV vectors has minimal influence on changing the pattern of cellular gene expression (Stilwell and Samulski et al., *Biotechniques*, 2003, 34, 148).

Typically, AAV vectors for siRNA delivery may be recombinant viral vectors which are replication defective as they lack sequences encoding functional Rep and Cap proteins within the viral genome. In some cases, the defective AAV vectors may lack most or all coding sequences and essentially only contains one or two AAV ITR sequences and a packaging sequence.

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

In one embodiment, the AAV vector used in the present invention is a scAAV.

In one embodiment, the AAV vector used in the present invention is an ssAAV.

Methods for producing and/or modifying AAV vectors are disclosed in the art such as pseudotyped AAV vectors (PCT Patent Publication Nos. WO200028004; WO200123001; WO2004112727; WO 2005005610 and WO 2005072364, the content of each of which is incorporated herein by reference in their entirety).

AAV vectors comprising the nucleic acid sequence for the siRNA molecules may be prepared or derived from various serotypes of AAVs, including, but not limited to, AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ8 and AAV-DJ. In some cases, different serotypes of AAVs may be mixed together or with other types of viruses to produce chimeric AAV vectors.

In one embodiment, the AAV vectors comprising a nucleic acid sequence encoding the siRNA molecules of the present invention may be introduced into mammalian cells.

AAV vectors may be modified to enhance the efficiency of delivery. Such modified AAV vectors comprising the nucleic acid sequence encoding the siRNA molecules of the present invention can be packaged efficiently and can be used to successfully infect the target cells at high frequency and with minimal toxicity.

In some embodiments, the AAV vector comprising a nucleic acid sequence encoding the siRNA molecules of the present invention may be a human serotype AAV vector. Such human AAV vector may be derived from any known serotype, e.g., from any one of serotypes AAV1-AAV11. As non-limiting examples, AAV vectors may be vectors comprising an AAV1-derived genome in an AAV1-derived capsid; vectors comprising an AAV2-derived genome in an AAV2-derived genome; vectors comprising an AAV4-derived genome in an AAV4 derived capsid; vectors comprising an AAV6-derived genome in an AAV6 derived capsid or vectors comprising an AAV9-derived genome in an AAV9 derived capsid.

In other embodiments, the AAV vector comprising a nucleic acid sequence for encoding siRNA molecules of the present invention may be a pseudotyped hybrid or chimeric AAV vector which contains sequences and/or components originating from at least two different AAV serotypes. Pseudotyped AAV vectors may be vectors comprising an AAV genome derived from one AAV serotype and a capsid protein derived at least in part from a different AAV serotype. As non-limiting examples, such pseudotyped AAV vectors may be vectors comprising an AAV2-derived genome in an AAV1-derived capsid; or vectors comprising an AAV2-derived genome in an AAV6-derived capsid; or vectors comprising an AAV2-derived genome in an AAV4-derived capsid; or an AAV2-derived genome in an AAV9-derived capsid. In like fashion, the present invention contemplates any hybrid or chimeric AAV vector.

In other embodiments, AAV vectors comprising a nucleic acid sequence encoding the siRNA molecules of the present invention may be used to deliver siRNA molecules to the central nervous system (e.g., U.S. Pat. No. 6,180,613; the contents of which is herein incorporated by reference in its entirety).

In some aspects, the AAV vectors comprising a nucleic acid sequence encoding the siRNA molecules of the present invention may further comprise a modified capsid including peptides from non-viral origin. In other aspects, the AAV vector may contain a CNS specific chimeric capsid to facilitate the delivery of encoded siRNA duplexes into the brain and the spinal cord. For example, an alignment of cap nucleotide sequences from AAV variants exhibiting CNS tropism may be constructed to identify variable region (VR) sequence and structure.

In one embodiment, the AAV vector comprising a nucleic acid sequence encoding the siRNA molecules of the present invention may encode siRNA molecules which are polycistronic molecules. The siRNA molecules may additionally comprise one or more linkers between regions of the siRNA molecules.

In one embodiment, the encoded siRNA molecule may be located downstream of a promoter in an expression vector such as, but not limited to, CMV, U6, CBA or a CBA promoter with a SV40 intron. Further, the encoded siRNA molecule may also be located upstream of the polyadenylation sequence in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the encoded siRNA molecule may be located upstream of the polyadenylation sequence in an expression vector. Further, the encoded siRNA molecule may be located downstream of a promoter such as, but not limited to, CMV, U6, CBA or a CBA promoter with a SV40 intron in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the promoter and/or upstream of the polyadenylation sequence in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the promoter and/or upstream of the polyadenylation sequence in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides downstream from the promoter and/or upstream of the polyadenylation sequence in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the promoter and/or upstream of the polyadenylation sequence in an expression vector.

In one embodiment, the encoded siRNA molecule may be located in a scAAV.

In one embodiment, the encoded siRNA molecule may be located in an ssAAV.

In one embodiment, the encoded siRNA molecule may be located near the 5' end of the flip ITR in an expression vector. In another embodiment, the encoded siRNA molecule may be located near the 3' end of the flip ITR in an expression vector. In yet another embodiment, the encoded siRNA molecule may be located near the 5' end of the flop ITR in an expression vector. In yet another embodiment, the encoded siRNA molecule may be located near the 3' end of the flop ITR in an expression vector. In one embodiment, the encoded siRNA molecule may be located between the 5' end of the flip ITR and the 3' end of the flop ITR in an expression vector. In one embodiment, the encoded siRNA molecule may be located between (e.g., half-way between) the 5' end of the flip ITR and 3' end of the flop ITR or the 3' end of the flop ITR and the 5' end of the flip ITR), the 3' end of the flip ITR and the 5' end of the flip ITR in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides downstream from the 5' or 3' end of an ITR (e.g., Flip or Flop ITR) in an expression vector. As a non-limiting example, the encoded siRNA molecule may be located within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more than 30 nucleotides upstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 nucleotides downstream from the 5' or 3' end of an ITR (e.g., Flip or Flop ITR) in an expression vector. As another non-limiting example, the encoded siRNA molecule may be located within 1-5, 1-10, 1-15, 1-20, 1-25, 1-30, 5-10, 5-15, 5-20, 5-25, 5-30, 10-15, 10-20, 10-25, 10-30, 15-20, 15-25, 15-30, 20-25, 20-30 or 25-30 upstream from the 5' or 3' end of an ITR (e.g., Flip or Flop ITR) in an expression vector. As a non-limiting example, the encoded siRNA molecule may be located within the first 1%, 2%, 3%, 4%, 5%, 6%, 7%, 8%, 9%, 10%, 15%, 20%, 25% or more than 25% of the nucleotides upstream from the 5' or 3' end of an ITR (e.g., Flip or Flop ITR) in an expression vector. As another non-limiting example, the encoded siRNA molecule may be located with the first 1-5%, 1-10%, 1-15%, 1-20%, 1-25%, 5-10%, 5-15%, 5-20%, 5-25%, 10-15%, 10-20%, 10-25%, 15-20%, 15-25%, or 20-25% downstream from the 5' or 3' end of an ITR (e.g., Flip or Flop ITR) in an expression vector.

Expression Vector

In one embodiment, an expression vector (e.g., AAV vector) may comprise at least one of the modulatory polynucleotides comprising at least one of the expression vectors described herein.

In one embodiment, an expression vector may comprise, from ITR to ITR recited 5' to 3', an ITR, a promoter, an intron, a modulatory polynucleotide, a polyA sequence and an ITR.

Genome Size

In one embodiment, the vector genome which comprises a nucleic acid sequence encoding the modulatory polynucleotides described herein may be single stranded or double stranded vector genome. The size of the vector genome may be small, medium, large or the maximum size. Additionally, the vector genome may comprise a promoter and a polyA tail.

In one embodiment, the vector genome which comprises a nucleic acid sequence encoding the modulatory polynucleotides described herein may be a small single stranded vector genome. A small single stranded vector genome may be 2.7 to 3.5 kb in size such as about 2.7, 2.8, 2.9, 3.0, 3.1, 3.2, 3.3, 3.4, and 3.5 kb in size. As a non-limiting example, the small single stranded vector genome may be 3.2 kb in size. Additionally, the vector genome may comprise a promoter and a polyA tail.

In one embodiment, the vector genome which comprises a nucleic acid sequence encoding the modulatory polynucleotides described herein may be a small double stranded vector genome. A small double stranded vector genome may be 1.3 to 1.7 kb in size such as about 1.3, 1.4, 1.5, 1.6, and 1.7 kb in size. As a non-limiting example, the small double stranded vector genome may be 1.6 kb in size. Additionally, the vector genome may comprise a promoter and a polyA tail.

In one embodiment, the vector genome which comprises a nucleic acid sequence encoding the modulatory polynucleotides described herein e.g., siRNA or dsRNA, may be a medium single stranded vector genome. A medium single stranded vector genome may be 3.6 to 4.3 kb in size such as about 3.6, 3.7, 3.8, 3.9, 4.0, 4.1, 4.2 and 4.3 kb in size. As a non-limiting example, the medium single stranded vector genome may be 4.0 kb in size. Additionally, the vector genome may comprise a promoter and a polyA tail.

In one embodiment, the vector genome which comprises a nucleic acid sequence encoding the modulatory polynucleotides described herein may be a medium double stranded vector genome. A medium double stranded vector genome may be 1.8 to 2.1 kb in size such as about 1.8, 1.9, 2.0, and 2.1 kb in size. As a non-limiting example, the medium double stranded vector genome may be 2.0 kb in size. Additionally, the vector genome may comprise a promoter and a polyA tail.

In one embodiment, the vector genome which comprises a nucleic acid sequence encoding the modulatory polynucleotides described herein may be a large single stranded vector genome. A large single stranded vector genome may be 4.4 to 6.0 kb in size such as about 4.4, 4.5, 4.6, 4.7, 4.8, 4.9, 5.0, 5.1, 5.2, 5.3, 5.4, 5.5, 5.6, 5.7, 5.8, 5.9 and 6.0 kb in size. As a non-limiting example, the large single stranded vector genome may be 4.7 kb in size. As another non-limiting example, the large single stranded vector genome may be 4.8 kb in size. As yet another non-limiting example, the large single stranded vector genome may be 6.0 kb in size. Additionally, the vector genome may comprise a promoter and a polyA tail.

In one embodiment, the vector genome which comprises a nucleic acid sequence encoding the modulatory polynucleotides described herein may be a large double stranded vector genome. A large double stranded vector genome may be 2.2 to 3.0 kb in size such as about 2.2, 2.3, 2.4, 2.5, 2.6, 2.7, 2.8, 2.9 and 3.0 kb in size. As a non-limiting example, the large double stranded vector genome may be 2.4 kb in size. Additionally, the vector genome may comprise a promoter and a polyA tail.

Promoters

A person skilled in the art may recognize that a target cell may require a specific promoter including but not limited to a promoter that is species specific, inducible, tissue-specific, or cell cycle-specific Parr et al., *Nat. Med.* 3:1145-9 (1997); the contents of which are herein incorporated by reference in its entirety).

In one embodiment, the promoter is a promoter deemed to be efficient to drive the expression of the modulatory polynucleotide.

In one embodiment, the promoter is a promoter having a tropism for the cell being targeted.

In one embodiment, the promoter is a weak promoter which provides expression of a payload e.g., a modulatory polynucleotide, e.g., siRNA or dsRNA, for a period of time in targeted tissues such as, but not limited to, nervous system tissues. Expression may be for a period of 1 hour, 2, hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 2 days, 3 days, 4 days, 5 days, 6 days, 1 week, 8 days, 9 days, 10 days, 11 days, 12 days, 13 days, 2 weeks, 15 days, 16 days, 17 days, 18 days, 19 days, 20 days, 3 weeks, 22 days, 23 days, 24 days, 25 days, 26 days, 27 days, 28 days, 29 days, 30 days, 31 days, 1 month, 2 months, 3 months, 4 months, 5 months, 6 months, 7 months, 8 months, 9 months, 10 months, 11 months, 1 year, 13 months, 14 months, 15 months, 16 months, 17 months, 18 months, 19 months, 20 months, 21 months, 22 months, 23 months, 2 years, 3 years, 4 years, 5 years, 6 years, 7 years, 8 years, 9 years, 10 years or more than 10 years. Expression may be for 1-5 hours, 1-12 hours, 1-2 days, 1-5 days, 1-2 weeks, 1-3 weeks, 1-4 weeks, 1-2 months, 1-4 months, 1-6 months, 2-6 months, 3-6 months, 3-9 months, 4-8 months, 6-12 months, 1-2 years, 1-5 years, 2-5 years, 3-6 years, 3-8 years, 4-8 years or 5-10 years. As a non-limiting example, the promoter is a weak promoter for sustained expression of a payload in nervous tissues.

In one embodiment, the promoter may be a promoter which is less than 1 kb. The promoter may have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. The promoter may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800.

In one embodiment, the promoter may be a combination of two or more components such as, but not limited to, CMV and CBA. Each component may have a length of 200, 210, 220, 230, 240, 250, 260, 270, 280, 290, 300, 310, 320, 330, 340, 350, 360, 370, 380, 381, 382, 383, 384, 385, 386, 387, 388, 389, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 or more than 800. Each component may have a length between 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800 or 700-800. As a non-limiting example, the promoter is a combination of a 382 nucleotide CMV-enhancer sequence and a 260 nucleotide CBA-promoter sequence.

In one embodiment, the vector genome comprises at least one element to enhance the target specificity and expression (See e.g., Powell et al. *Viral Expression Cassette Elements to Enhance Transgene Target Specificity and Expression in Gene Therapy,* 2015; the contents of which are herein incorporated by reference in its entirety). Non-limiting examples of elements to enhance the transgene target specificity and expression include promoters, endogenous miR-NAs, post-transcriptional regulatory elements (PREs), polyadenylation (PolyA) signal sequences and upstream enhancers (USEs), CMV enhancers and introns.

In one embodiment, the vector genome comprises at least one element to enhance the target specificity and expression (See e.g., Powell et al. *Viral Expression Cassette Elements to Enhance Transgene Target Specificity and Expression in*

*Gene Therapy*, 2015; the contents of which are herein incorporated by reference in its entirety) such as promoters.

Promoters for which promote expression in most tissues include, but are not limited to, human elongation factor 1α-subunit (EF1α), immediate-early cytomegalovirus (CMV), chicken β-actin (CBA) and its derivative CAG, the β glucuronidase (GUSB), or ubiquitin C (UBC). Tissue-specific expression elements can be used to restrict expression to certain cell types such as, but not limited to, nervous system promoters which can be used to restrict expression to neurons, astrocytes, or oligodendrocytes. Non-limiting example of tissue-specific expression elements for neurons include neuron-specific enolase (NSE), platelet-derived growth factor (PDGF), platelet-derived growth factor B-chain (PDGF-β), the synapsin (Syn), the methyl-CpG binding protein 2 (MeCP2), CaMKII, mGluR2, NFL, NFH, nβ2, PPE, Enk and EAAT2 promoters. A non-limiting example of a tissue-specific expression elements for astrocytes include the glial fibrillary acidic protein (GFAP) and EAAT2 promoters. A non-limiting example of a tissue-specific expression element for oligodendrocytes include the myelin basic protein (MBP) promoter.

In one embodiment, the vector genome comprises a ubiquitous promoter. Non-limiting examples of ubiquitous promoters include CMV, CBA (including derivatives CAG, CBh, etc.), EF-1α, PGK, UBC, GUSB (hGBp), and UCOE (promoter of HNRPA2B1-CBX3). Yu et al. (Molecular Pain 2011, 7:63; the contents of which are herein incorporated by reference in its entirety) evaluated the expression of eGFP under the CAG, EFIα, PGK and UBC promoters in rat DRG cells and primary DRG cells using lentiviral vectors and found that UBC showed weaker expression than the other 3 promoters and there was only 10-12% glia expression seen for all promoters. Soderblom et al. (E. Neuro 2015; the contents of which are herein incorporated by reference in its entirety) the expression of eGFP in AAV8 with CMV and UBC promoters and AAV2 with the CMV promoter after injection in the motor cortex. Intranasal administration of a plasmid containing a UBC or EFIα promoter showed a sustained airway expression greater than the expression with the CMV promoter (See e.g., Gill et al., Gene Therapy 2001, Vol. 8, 1539-1546; the contents of which are herein incorporated by reference in its entirety). Husain et al. (Gene Therapy 2009; the contents of which are herein incorporated by reference in its entirety) evaluated a HβH construct with a hGUSB promoter, a HSV-1LAT promoter and a NSE promoter and found that the HβH construct showed weaker expression than NSE in mice brain. Passini and Wolfe (J. Virol. 2001, 12382-12392, the contents of which are herein incorporated by reference in its entirety) evaluated the long-term effects of the HβH vector following an intraventricular injection in neonatal mice and found that there was sustained expression for at least 1 year. Low expression in all brain regions was found by Xu et al. (Gene Therapy 2001, 8, 1323-1332; the contents of which are herein incorporated by reference in its entirety) when NF-L and NF-H promoters were used as compared to the CMV-lacZ, CMV-luc, EF, GFAP, hENK, nAChR, PPE, PPE+wpre, NSE (0.3 kb), NSE (1.8 kb) and NSE (1.8 kb+wpre). Xu et al. found that the promoter activity in descending order was NSE (1.8 kb), EF, NSE (0.3 kb), GFAP, CMV, hENK, PPE, NFL and NFH. NFL is a 650-nucleotide promoter and NFH is a 920-nucleotide promoter which are both absent in the liver but NFH is abundant in the sensory proprioceptive neurons, brain and spinal cord and NFH is present in the heart. Scn8a is a 470-nucleotide promoter which expresses throughout the DRG, spinal cord and brain with particularly high expression seen in the hippocampal neurons and cerebellar Purkinje cells, cortex, thalmus and hypothalamus (See e.g., Drews et al. 2007 and Raymond et al. 2004; the contents of each of which are herein incorporated by reference in their entireties).

In one embodiment, the vector genome comprises an UBC promoter. The UBC promoter may have a size of 300-350 nucleotides. As a non-limiting example, the UBC promoter is 332 nucleotides.

In one embodiment, the vector genome comprises a GUSB promoter. The GUSB promoter may have a size of 350-400 nucleotides. As a non-limiting example, the GUSB promoter is 378 nucleotides. As a non-limiting example, the construct may be AAV-promoter-CMV/globin intron-hFXN-RBG, where the AAV may be self-complementary and the AAV may be the DJ serotype.

In one embodiment, the vector genome comprises a NFL promoter. The NFL promoter may have a size of 600-700 nucleotides. As a non-limiting example, the NFL promoter is 650 nucleotides. As a non-limiting example, the construct may be AAV-promoter-CMV/globin intron-hFXN-RBG, where the AAV may be self-complementary and the AAV may be the DJ serotype.

In one embodiment, the vector genome comprises a NFH promoter. The NFH promoter may have a size of 900-950 nucleotides. As a non-limiting example, the NFH promoter is 920 nucleotides. As a non-limiting example, the construct may be AAV-promoter-CMV/globin intron-hFXN-RBG, where the AAV may be self-complementary and the AAV may be the DJ serotype.

In one embodiment, the vector genome comprises a scn8a promoter. The scn8a promoter may have a size of 450-500 nucleotides. As a non-limiting example, the scn8a promoter is 470 nucleotides. As a non-limiting example, the construct may be AAV-promoter-CMV/globin intron-hFXN-RBG, where the AAV may be self-complementary and the AAV may be the DJ serotype.

In one embodiment, the vector genome comprises a FXN promoter.

In one embodiment, the vector genome comprises a PGK promoter.

In one embodiment, the vector genome comprises a CBA promoter.

In one embodiment, the vector genome comprises a CMV promoter.

In one embodiment, the vector genome comprises a liver or a skeletal muscle promoter. Non-limiting examples of liver promoters include hAAT and TBG. Non-limiting examples of skeletal muscle promoters include Desmin, MCK and C5-12.

In one embodiment, the AAV vector comprises an enhancer element, a promoter and/or a 5'UTR intron. The enhancer may be, but is not limited to, a CMV enhancer, the promoter may be, but is not limited to, a CMV, CBA, UBC, GUSB, NSE, Sunapsin, MeCP2, and GFAP promoter and the 5'UTR/intron may be, but is not limited to, SV40, and CBA-MVM. As a non-limiting example, the enhancer, promoter and/or intron used in combination may be: (1) CMV enhancer, CMV promoter, SV40 5'UTR intron; (2) CMV enhancer, CBA promoter, SV 40 5'UTR intron; (3) CMV enhancer, CBA promoter, CBA-MVM 5'UTR intron; (4) UBC promoter; (5) GUSB promoter; (6) NSE promoter; (7) Synapsin promoter; (8) MeCP2 promoter and (9) GFAP promoter.

In one embodiment, the AAV vector has an engineered promoter.

Introns

In one embodiment, the vector genome comprises at least one element to enhance the transgene target specificity and expression (See e.g., Powell et al. *Viral Expression Cassette Elements to Enhance Transgene Target Specificity and Expression in Gene Therapy*, 2015; the contents of which are herein incorporated by reference in its entirety) such as an intron. Non-limiting examples of introns include, MVM (67-97 bps), F. IX truncated intron 1 (300 bps), β-globin SD/immunoglobulin heavy chain splice acceptor (250 bps), adenovirus splice donor/immunoglobin splice acceptor (500 bps), SV40 late splice donor/splice acceptor (19S/16S) (180 bps) and hybrid adenovirus splice donor/IgG splice acceptor (230 bps).

In one embodiment, the intron may be 100-500 nucleotides in length. The intron may have a length of 80, 90, 100, 110, 120, 130, 140, 150, 160, 170, 171, 172, 173, 174, 175, 176, 177, 178, 179, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500. The promoter may have a length between 80-100, 80-120, 80-140, 80-160, 80-180, 80-200, 80-250, 80-300, 80-350, 80-400, 80-450, 80-500, 200-300, 200-400, 200-500, 300-400, 300-500, or 400-500.

In one embodiment, the AAV vector genome may comprise a promoter such as, but not limited to, CMV or U6. As a non-limiting example, the promoter for the AAV comprising the nucleic acid sequence for the siRNA molecules of the present invention is a CMV promoter. As another non-limiting example, the promoter for the AAV comprising the nucleic acid sequence for the siRNA molecules of the present invention is a U6 promoter.

In one embodiment, the AAV vector may comprise a CMV and a U6 promoter.

In one embodiment, the AAV vector may comprise a CBA promoter.

Introduction into Cells—Synthetic dsRNA

To ensure the chemical and biological stability of siRNA molecules (e.g., siRNA duplexes and dsRNA), it is important to deliver siRNA molecules inside the target cells. In some embodiments, the cells may include, but are not limited to, cells of mammalian origin, cells of human origins, embryonic stem cells, induced pluripotent stem cells, neural stem cells, and neural progenitor cells.

Nucleic acids, including siRNA, carry a net negative charge on the sugar-phosphate backbone under normal physiological conditions. In order to enter the cell, a siRNA molecule must come into contact with a lipid bilayer of the cell membrane, whose head groups are also negatively charged.

The siRNA duplexes can be complexed with a carrier that allows them to traverse cell membranes such as package particles to facilitate cellular uptake of the siRNA. The package particles may include, but are not limited to, liposomes, nanoparticles, cationic lipids, polyethylenimine derivatives, dendrimers, carbon nanotubes and the combination of carbon-made nanoparticles with dendrimers. Lipids may be cationic lipids and/or neutral lipids. In addition to well established lipophilic complexes between siRNA molecules and cationic carriers, siRNA molecules can be conjugated to a hydrophobic moiety, such as cholesterol (e.g., U.S. Patent Publication No. 20110110937; the content of which is herein incorporated by reference in its entirety). This delivery method holds a potential of improving in vitro cellular uptake and in vivo pharmacological properties of siRNA molecules. The siRNA molecules of the present invention may also be conjugated to certain cationic cell-penetrating peptides (CPPs), such as MPG, transportan or penetratin covalently or non-covalently (e.g., U.S. Patent Publication No. 20110086425; the content of which is herein incorporated by reference in its entirety).

Introduction into Cells—AAV Vectors

The siRNA molecules (e.g., siRNA duplexes) of the present invention may be introduced into cells using any of a variety of approaches such as, but not limited to, viral vectors (e.g., AAV vectors). These viral vectors are engineered and optimized to facilitate the entry of siRNA molecule into cells that are not readily amendable to transfection. Also, some synthetic viral vectors possess an ability to integrate the shRNA into the cell genome, thereby leading to stable siRNA expression and long-term knockdown of a target gene. In this manner, viral vectors are engineered as vehicles for specific delivery while lacking the deleterious replication and/or integration features found in wild-type virus.

In some embodiments, the siRNA molecules of the present invention are introduced into a cell by contacting the cell with a composition comprising a lipophilic carrier and a vector, e.g., an AAV vector, comprising a nucleic acid sequence encoding the siRNA molecules of the present invention. In other embodiments, the siRNA molecule is introduced into a cell by transfecting or infecting the cell with a vector, e.g., an AAV vector, comprising nucleic acid sequences capable of producing the siRNA molecule when transcribed in the cell. In some embodiments, the siRNA molecule is introduced into a cell by injecting into the cell a vector, e.g., an AAV vector, comprising a nucleic acid sequence capable of producing the siRNA molecule when transcribed in the cell.

In some embodiments, prior to transfection, a vector, e.g., an AAV vector, comprising a nucleic acid sequence encoding the siRNA molecules of the present invention may be transfected into cells.

In other embodiments, the vectors, e.g., AAV vectors, comprising the nucleic acid sequence encoding the siRNA molecules of the present invention may be delivered into cells by electroporation (e.g., U.S. Patent Publication No. 20050014264; the content of which is herein incorporated by reference in its entirety).

Other methods for introducing vectors, e.g., AAV vectors, comprising the nucleic acid sequence for the siRNA molecules described herein may include photochemical internalization as described in U. S. Patent publication No. 20120264807; the content of which is herein incorporated by reference in its entirety.

In some embodiments, the formulations described herein may contain at least one vector, e.g., AAV vectors, comprising the nucleic acid sequence encoding the siRNA molecules described herein. In one embodiment, the siRNA molecules may target the SOD1 gene at one target site. In another embodiment, the formulation comprises a plurality of vectors, e.g., AAV vectors, each vector comprising a nucleic acid sequence encoding a siRNA molecule targeting the SOD1 gene at a different target site. The SOD1 may be targeted at 2, 3, 4, 5 or more than 5 sites.

In one embodiment, the vectors, e.g., AAV vectors, from any relevant species, such as, but not limited to, human, dog, mouse, rat or monkey may be introduced into cells.

In one embodiment, the vectors, e.g., AAV vectors, may be introduced into cells which are relevant to the disease to be treated. As a non-limiting example, the disease is ALS and the target cells are motor neurons and astrocytes.

In one embodiment, the vectors, e.g., AAV vectors, may be introduced into cells which have a high level of endogenous expression of the target sequence.

In another embodiment, the vectors, e.g., AAV vectors, may be introduced into cells which have a low level of endogenous expression of the target sequence.

In one embodiment, the cells may be those which have a high efficiency of AAV transduction.

Pharmaceutical Compositions and Formulation

In addition to the pharmaceutical compositions (vectors, e.g., AAV vectors, comprising a nucleic acid sequence encoding the siRNA molecules), provided herein are pharmaceutical compositions which are suitable for administration to humans, it will be understood by the skilled artisan that such compositions are generally suitable for administration to any other animal, e.g., to non-human animals, e.g., non-human mammals. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as poultry, chickens, ducks, geese, and/or turkeys.

In some embodiments, compositions are administered to humans, human patients, or subjects. For the purposes of the present disclosure, the phrase "active ingredient" generally refers either to the synthetic siRNA duplexes, the vector, e.g., AAV vector, encoding the siRNA duplexes, or to the siRNA molecule delivered by a vector as described herein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, dividing, shaping and/or packaging the product into a desired single- or multi-dose unit.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered.

The vectors e.g., AAV vectors, comprising the nucleic acid sequence encoding the siRNA molecules of the present invention can be formulated using one or more excipients to: (1) increase stability; (2) increase cell transfection or transduction; (3) permit the sustained or delayed release; or (4) alter the biodistribution (e.g., target the viral vector to specific tissues or cell types such as brain and motor neurons).

Formulations of the present invention can include, without limitation, saline, lipidoids, liposomes, lipid nanoparticles, polymers, lipoplexes, core-shell nanoparticles, peptides, proteins, cells transfected with viral vectors (e.g., for transplantation into a subject), nanoparticle mimics and combinations thereof. Further, the viral vectors of the present invention may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient. By way of example, the composition may comprise between 0.1% and 100%, e.g., between 0.5 and 50%, between 1-30%, between 5-80%, at least 80% (w/w) active ingredient.

In some embodiments, a pharmaceutically acceptable excipient may be at least 95%, at least 96%, at least 97%, at least 98%, at least 99%, or 100% pure. In some embodiments, an excipient is approved for use for humans and for veterinary use. In some embodiments, an excipient may be approved by United States Food and Drug Administration. In some embodiments, an excipient may be of pharmaceutical grade. In some embodiments, an excipient may meet the standards of the United States Pharmacopoeia (USP), the European Pharmacopoeia (EP), the British Pharmacopoeia, and/or the International Pharmacopoeia.

Excipients, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired. Various excipients for formulating pharmaceutical compositions and techniques for preparing the composition are known in the art (see Remington: The Science and Practice of Pharmacy, 21$^{st}$ Edition, A. R. Gennaro, Lippincott, Williams & Wilkins, Baltimore, Md., 2006; incorporated herein by reference in its entirety). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

In some embodiments, the formulations may comprise at least one inactive ingredient. As used herein, the term "inactive ingredient" refers to one or more inactive agents included in formulations. In some embodiments, all, none, or some of the inactive ingredients which may be used in the formulations of the present invention may be approved by the US Food and Drug Administration (FDA).

Formulations of vectors comprising the nucleic acid sequence for the siRNA molecules of the present invention may include cations or anions. In one embodiment, the formulations include metal cations such as, but not limited to, Zn2+, Ca2+, Cu2+, Mg+ and combinations thereof.

As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977); the content of each of which is incorporated herein by reference in their entirety.

The term "pharmaceutically acceptable solvate," as used herein, means a compound of the invention wherein molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

According to the present invention, the vector, e.g., AAV vector, comprising the nucleic acid sequence for the siRNA molecules of the present invention may be formulated for CNS delivery. Agents that cross the brain blood barrier may be used. For example, some cell penetrating peptides that can target siRNA molecules to the brain blood barrier endothelium may be used to formulate the siRNA duplexes targeting the SOD1 gene (e.g., Mathupala, *Expert Opin Ther Pat.*, 2009, 19, 137-140; the content of which is incorporated herein by reference in its entirety).

Administration

The vector, e.g., AAV vector, comprising a nucleic acid sequence encoding the siRNA molecules of the present invention may be administered by any route which results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electro-osmosis, endocervical, endosinusial, endotracheal, extracorporeal, hemodialysis, infiltration, interstitial, intra-abdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corpus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratumor (within a tumor), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration which is then covered by a dressing which occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal.

In specific embodiments, compositions of vector, e.g., AAV vector, comprising a nucleic acid sequence encoding the siRNA molecules of the present invention may be administered in a way which facilitates the vectors or siRNA molecule to enter the central nervous system and penetrate into motor neurons.

In some embodiments, the vector, e.g., AAV vector, comprising a nucleic acid sequence encoding the siRNA molecules of the present invention may be administered by muscular injection. Rizvanov et al. demonstrated for the first time that siRNA molecules, targeting mutant human SOD1 mRNA, is taken up by the sciatic nerve, retrogradely transported to the perikarya of motor neurons, and inhibits mutant SOD1 mRNA in SOD1$^{G93A}$ transgenic ALS mice (Rizvanov A A et al., *Exp. Brain Res.*, 2009, 195(1), 1-4; the content of which is incorporated herein by reference in its entirety). Another study also demonstrated that muscle delivery of AAV expressing small hairpin RNAs (shRNAs) against the mutant SOD1 gene, led to significant mutant SOD1 knockdown in the muscle as well as innervating motor neurons (Towne C et al., *Mol Ther.*, 2011; 19(2): 274-283; the content of which is incorporated herein by reference in its entirety).

In some embodiments, AAV vectors that express siRNA duplexes of the present invention may be administered to a subject by peripheral injections and/or intranasal delivery. It was disclosed in the art that the peripheral administration of AAV vectors for siRNA duplexes can be transported to the central nervous system, for example, to the motor neurons (e.g., U.S. Patent Publication Nos. 20100240739; and 20100130594; the content of each of which is incorporated herein by reference in their entirety).

In other embodiments, compositions comprising at least one vector, e.g., AAV vector, comprising a nucleic acid sequence encoding the siRNA molecules of the present invention may be administered to a subject by intracranial delivery (See, e.g., U.S. Pat. No. 8,119,611; the content of which is incorporated herein by reference in its entirety).

The vector, e.g., AAV vector, comprising a nucleic acid sequence encoding the siRNA molecules of the present invention may be administered in any suitable form, either as a liquid solution or suspension, as a solid form suitable for liquid solution or suspension in a liquid solution. The siRNA duplexes may be formulated with any appropriate and pharmaceutically acceptable excipient.

The vector, e.g., AAV vector, comprising a nucleic acid sequence encoding the siRNA molecules of the present invention may be administered in a "therapeutically effective" amount, i.e., an amount that is sufficient to alleviate and/or prevent at least one symptom associated with the disease, or provide improvement in the condition of the subject.

In one embodiment, the vector, e.g., AAV vector, may be administered to the CNS in a therapeutically effective amount to improve function and/or survival for a subject with ALS. As a non-limiting example, the vector may be administered intrathecally.

In one embodiment, the vector, e.g., AAV vector, may be administered to a subject (e.g., to the CNS of a subject via intrathecal administration) in a therapeutically effective amount for the siRNA duplexes or dsRNA to target the motor neurons and astrocytes in the spinal cord and/or brain steam. As a non-limiting example, the siRNA duplexes or dsRNA may reduce the expression of SOD1 protein or mRNA. As another non-limiting example, the siRNA duplexes or dsRNA can suppress SOD1 and reduce SOD1 mediated toxicity. The reduction of SOD1 protein and/or mRNA as well as SOD1 mediated toxicity may be accomplished with almost no enhanced inflammation.

In one embodiment, the vector, e.g., AAV vector, may be administered to a subject (e.g., to the CNS of a subject) in a therapeutically effective amount to slow the functional decline of a subject (e.g., determined using a known evaluation method such as the ALS functional rating scale (ALSFRS)) and/or prolong ventilator-independent survival of subjects (e.g., decreased mortality or need for ventilation support). As a non-limiting example, the vector may be administered intrathecally.

In one embodiment, the vector, e.g., AAV vector, may be administered to the cisterna magna in a therapeutically effective amount to transduce spinal cord motor neurons and/or astrocytes. As a non-limiting example, the vector may be administered intrathecally.

In one embodiment, the vector, e.g., AAV vector, may be administered using intrathecal infusion in a therapeutically effective amount to transduce spinal cord motor neurons and/or astrocytes. As a non-limiting example, the vector may be administered intrathecally.

In one embodiment, the vector, e.g., AAV vector, comprising a modulatory polynucleotide may be formulated. As a non-limiting example the baricity and/or osmolality of the formulation may be optimized to ensure optimal drug distribution in the central nervous system or a region or component of the central nervous system.

In one embodiment, the vector, e.g., AAV vector, comprising a modulatory polynucleotide may be delivered to a subject via a single route administration.

In one embodiment, the vector, e.g., AAV vector, comprising a modulatory polynucleotide may be delivered to a subject via a multi-site route of administration. A subject may be administered the vector, e.g., AAV vector, comprising a modulatory polynucleotide at 2, 3, 4, 5 or more than 5 sites.

In one embodiment, a subject may be administered the vector, e.g., AAV vector, comprising a modulatory polynucleotide described herein using a bolus infusion.

In one embodiment, a subject may be administered the vector, e.g., AAV vector, comprising a modulatory polynucleotide described herein using sustained delivery over a period of minutes, hours, or days. The infusion rate may be changed depending on the subject, distribution, formulation, or another delivery parameter.

In one embodiment, the catheter may be located at more than one site in the spine for multi-site delivery. The vector, e.g., AAV vector, comprising a modulatory polynucleotide may be delivered in a continuous and/or bolus infusion. Each site of delivery may be a different dosing regimen or the same dosing regimen may be used for each site of delivery. As a non-limiting example, the sites of delivery may be in the cervical and the lumbar region. As another non-limiting example, the sites of delivery may be in the cervical region. As another non-limiting example, the sites of delivery may be in the lumbar region.

In one embodiment, a subject may be analyzed for spinal anatomy and pathology prior to delivery of the vector, e.g., AAV vector, comprising a modulatory polynucleotide described herein. As a non-limiting example, a subject with scoliosis may have a different dosing regimen and/or catheter location compared to a subject without scoliosis.

In one embodiment, the orientation of the spine of the subject during delivery of the vector, e.g., AAV vector, comprising a modulatory polynucleotide may be vertical to the ground.

In another embodiment, the orientation of the spine of the subject during delivery of the vector, e.g., AAV vector, comprising a modulatory polynucleotide may be horizontal to the ground.

In one embodiment, the spine of the subject may be at an angle as compared to the ground during the delivery of the vector, e.g., AAV vector, comprising a modulatory polynucleotide. The angle of the spine of the subject as compared to the ground may be at least 10, 20, 30, 40, 50, 60, 70, 80, 90, 100, 110, 120, 130, 140, 150 or 180 degrees.

In one embodiment, the delivery method and duration is chosen to provide broad transduction in the spinal cord. As a non-limiting example, intrathecal delivery is used to provide broad transduction along the rostral-caudal length of the spinal cord. As another non-limiting example, multi-site infusions provide a more uniform transduction along the rostral-caudal length of the spinal cord. As yet another non-limiting example, prolonged infusions provide a more uniform transduction along the rostral-caudal length of the spinal cord.

Dosing

The pharmaceutical compositions of the present invention may be administered to a subject using any amount effective for reducing, preventing and/or treating a SOD1 associated disorder (e.g., ALS). The exact amount required will vary from subject to subject, depending on the species, age, and general condition of the subject, the severity of the disease, the particular composition, its mode of administration, its mode of activity, and the like.

The compositions of the present invention are typically formulated in unit dosage form for ease of administration and uniformity of dosage. It will be understood, however, that the total daily usage of the compositions of the present invention may be decided by the attending physician within the scope of sound medical judgment. The specific therapeutic effectiveness for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the siRNA duplexes employed; the duration of the treatment; drugs used in combination or coincidental with the specific compound employed; and like factors well known in the medical arts.

In one embodiment, the age and sex of a subject may be used to determine the dose of the compositions of the present invention. As a non-limiting example, a subject who is older may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a younger subject. As another non-limiting example, a subject who is younger may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to an older subject. As yet another non-limiting example, a subject who is female may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a male subject. As yet another non-limiting example, a subject who is male may receive a larger dose (e.g., 5-10%, 10-20%, 15-30%, 20-50%, 25-50% or at least 1%, 2%, 3%, 4%, 5%, 10%, 20%, 30%, 40%, 50%, 60%, 70%, 80%, 90% or more than 90% more) of the composition as compared to a female subject In some specific embodiments, the doses of AAV vectors for delivering siRNA duplexes of the present invention may be adapted dependent on the disease condition, the subject, and the treatment strategy.

In one embodiment, delivery of the compositions in accordance with the present invention to cells comprises a rate of delivery defined by [VG/hour=mL/hour*VG/mL] wherein VG is viral genomes, VG/mL is composition concentration, and mL/hour is rate of prolonged delivery.

In one embodiment, delivery of compositions in accordance with the present invention to cells may comprise a total concentration per subject between about $1 \times 10^6$ VG and about $1 \times 10^{16}$ VG. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $5 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $3 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{12}$, $8.8 \times 10^{12}$, $8.9 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/subject.

In one embodiment, delivery of compositions in accordance with the present invention to cells may comprise a total concentration per subject between about $1 \times 10^6$ VG/kg and about $1 \times 10^{16}$ VG/kg. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $2.1 \times 10^{11}$, $2.2 \times 10^{11}$, $2.3 \times 10^{11}$, $2.4 \times 10^{11}$, $2.5 \times 10^{11}$, $2.6 \times 10^{11}$, $2.7 \times 10^{11}$, $2.8 \times 10^{11}$, $2.9 \times 10^{11}$, $3 \times 10^{11}$, $4 \times 10^{11}$, $5 \times 10^{11}$, $6 \times 10^{11}$, $7 \times 10^{11}$, $7.1 \times 10^{11}$, $7.2 \times 10^{11}$, $7.3 \times 10^{11}$, $7.4 \times 10^{11}$, $7.5 \times 10^{11}$, $7.6 \times 10^{11}$, $7.7 \times 10^{11}$, $7.8 \times 10^{11}$, $7.9 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $3 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $8.1 \times 10^{12}$, $8.2 \times 10^{12}$, $8.3 \times 10^{12}$, $8.4 \times 10^{12}$, $8.5 \times 10^{12}$, $8.6 \times 10^{12}$, $8.7 \times 10^{'2}$, $8.8 \times 10^{12}$, $8.9 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{13}$, $6.7 \times 10^{13}$, $7 \times 10^{13}$, $8 \times 10^{13}$, $9 \times 10^{13}$, $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, $9 \times 10^{15}$, or $1 \times 10^{16}$ VG/kg.

In one embodiment, about $10^5$ to $10^6$ viral genome (unit) may be administered per dose.

In one embodiment, delivery of the compositions in accordance with the present invention to cells may comprise a total concentration between about $1 \times 10^6$ VG/mL and about $1 \times 10^{16}$ VG/mL. In some embodiments, delivery may comprise a composition concentration of about $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, $4 \times 10^7$, $5 \times 10^7$, $6 \times 10^7$, $7 \times 10^7$, $8 \times 10^7$, $9 \times 10^7$, $1 \times 10^8$, $2 \times 10^8$, $3 \times 10^8$, $4 \times 10^8$, $5 \times 10^8$, $6 \times 10^8$, $7 \times 10^8$, $8 \times 10^8$, $9 \times 10^8$, $1 \times 10^9$, $2 \times 10^9$, $3 \times 10^9$, $4 \times 10^9$, $5 \times 10^9$, $6 \times 10^9$, $7 \times 10^9$, $8 \times 10^9$, $9 \times 10^9$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, $9 \times 10^{11}$, $1 \times 10^{12}$, $1.1 \times 10^{12}$, $1.2 \times 10^{12}$, $1.3 \times 10^{12}$, $1.4 \times 10^{12}$, $1.5 \times 10^{12}$, $1.6 \times 10^{12}$, $1.7 \times 10^{12}$, $1.8 \times 10^{12}$, $1.9 \times 10^{12}$, $2 \times 10^{12}$, $2.1 \times 10^{12}$, $2.2 \times 10^{12}$, $2.3 \times 10^{12}$, $2.4 \times 10^{12}$, $2.5 \times 10^{12}$, $2.6 \times 10^{12}$, $2.7 \times 10^{12}$, $2.8 \times 10^{12}$, $2.9 \times 10^{12}$, $3 \times 10^{12}$, $3.1 \times 10^{12}$, $3.2 \times 10^{12}$, $3.3 \times 10^{12}$, $3.4 \times 10^{12}$, $3.5 \times 10^{12}$, $3.6 \times 10^{12}$, $3.7 \times 10^{12}$, $3.8 \times 10^{12}$, $3.9 \times 10^{12}$, $4 \times 10^{12}$, $4.1 \times 10^{12}$, $4.2 \times 10^{12}$, $4.3 \times 10^{12}$, $4.4 \times 10^{12}$, $4.5 \times 10^{12}$, $4.6 \times 10^{12}$, $4.7 \times 10^{12}$, $4.8 \times 10^{12}$, $4.9 \times 10^{12}$, $5 \times 10^{12}$, $6 \times 10^{12}$, $7 \times 10^{12}$, $8 \times 10^{12}$, $9 \times 10^{12}$, $1 \times 10^{13}$, $2 \times 10^{13}$, $3 \times 10^{13}$, $4 \times 10^{13}$, $5 \times 10^{13}$, $6 \times 10^{i3}$, $6.7 \times 10^{13}$, $7 \times 10^{13}$, $8 \times 10^{i3}$, $9 \times 10^{13}$, $1 \times 10^{14}$, $2 \times 10^{14}$, $3 \times 10^{i4}$, $4 \times 10^{14}$, $5 \times 10^{14}$, $6 \times 10^{14}$, $7 \times 10^{14}$, $8 \times 10^{14}$, $9 \times 10^{14}$, $1 \times 10^{15}$, $2 \times 10^{15}$, $3 \times 10^{15}$, $4 \times 10^{15}$, $5 \times 10^{15}$, $6 \times 10^{15}$ $7 \times 10^{15}$, $8 \times 10^{15}$, $9 \times 10^{15}$, or $1 \times 10^{16}$ VG/mL.

In certain embodiments, the desired siRNA duplex dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. As used herein, a "split dose" is the division of single unit dose or total daily dose into two or more doses, e.g., two or more administrations of the single unit dose. As used herein, a "single unit dose" is a dose of any modulatory polynucleotide therapeutic administered in one dose/at one time/single route/single point of contact, i.e., single administration event. As used herein, a "total daily dose" is an amount given or prescribed in 24-hour period. It may be administered as a single unit dose. In one embodiment, the viral vectors comprising the modulatory polynucleotides of the present invention are administered to a subject in split doses. They may be formulated in buffer only or in a formulation described herein.

Methods of Treatment of ALS

Provided in the present invention are methods for introducing the vectors, e.g., AAV vectors, comprising a nucleic acid sequence encoding the siRNA molecules of the present invention into cells, the method comprising introducing into said cells any of the vectors in an amount sufficient for degradation of target SOD1 mRNA to occur, thereby activating target-specific RNAi in the cells. In some aspects, the cells may be stem cells, neurons such as motor neurons, muscle cells and glial cells such as astrocytes.

Disclosed in the present invention are methods for treating ALS associated with abnormal SOD1 function in a subject in need of treatment. The method optionally comprises administering to the subject a therapeutically effective amount of a composition comprising at least vectors, e.g., AAV vectors, comprising a nucleic acid sequence encoding the siRNA molecules of the present invention. As a non-limiting example, the siRNA molecules can silence SOD1 gene expression, inhibit SOD1 protein production, and reduce one or more symptoms of ALS in the subject such that ALS is therapeutically treated.

In some embodiments, the composition comprising the vectors, e.g., AAV vectors, comprising a nucleic acid sequence encoding the siRNA molecules of the present invention is administered to the central nervous system of the subject. In other embodiments, the composition comprising the vectors, e.g., AAV vectors, comprising a nucleic acid sequence encoding the siRNA molecules of the present invention is administered to the muscles of the subject In particular, the vectors, e.g., AAV vectors, comprising a nucleic acid sequence encoding the siRNA molecules of the present invention may be delivered into specific types of targeted cells, including motor neurons; glial cells including oligodendrocyte, astrocyte, and microglia; and/or other cells surrounding neurons such as T cells. Studies in human ALS patients and animal SOD1 ALS models implicate glial cells as playing an early role in the dysfunction and death of motor neurons. Normal SOD1 in the surrounding, protective glial cells can prevent the motor neurons from dying even though mutant SOD1 is present in motor neurons (e.g., reviewed by Philips and Rothstein, *Exp. Neurol.*, 2014, May 22. pii: S0014-4886(14)00157-5; the content of which is incorporated herein by reference in its entirety).

In some specific embodiments, the vectors, e.g., AAV vectors, comprising a nucleic acid sequence encoding the siRNA molecules of the present invention may be used as a therapy for ALS.

In some embodiments, the present composition is administered as a solo therapeutics or combination therapeutics for the treatment of ALS.

The vectors, e.g., AAV vectors, encoding siRNA duplexes targeting the SOD1 gene may be used in combination with one or more other therapeutic agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent.

Therapeutic agents that may be used in combination with the vectors, e.g., AAV vectors, encoding the nucleic acid sequence for the siRNA molecules of the present invention can be small molecule compounds which are antioxidants, anti-inflammatory agents, anti-apoptosis agents, calcium regulators, antiglutamatergic agents, structural protein inhibitors, and compounds involved in metal ion regulation.

Compounds tested for treating ALS which may be used in combination with the vectors described herein include, but are not limited to, antiglutamatergic agents: Riluzole, Topiramate, Talampanel, Lamotrigine, Dextromethorphan, Gabapentin and AMPA antagonist; Anti-apoptosis agents: Minocycline, Sodium phenylbutyrate and Arimoclomol; Anti-inflammatory agent: ganglioside, Celecoxib, Cyclosporine, Azathioprine, Cyclophosphamide, Plasmaphoresis, Glatiramer acetate and thalidomide; Ceftriaxone (Berry et al., *Plos One,* 2013, 8(4)); Beat-lactam antibiotics; Pramipexole (a dopamine agonist) (Wang et al., *Amyotrophic Lateral Scler.,* 2008, 9(1), 50-58); Nimesulide in U.S. Patent Publication No. 20060074991; Diazoxide disclosed in U.S. Patent Publication No. 20130143873); pyrazolone derivatives disclosed in US Patent Publication No. 20080161378; free radical scavengers that inhibit oxidative stress-induced cell death, such as bromocriptine (US. Patent Publication No. 20110105517); phenyl carbamate compounds discussed in PCT Patent Publication No. 2013100571; neuroprotective compounds disclosed in U.S. Pat. Nos. 6,933,310 and 8,399,514 and US Patent Publication Nos. 20110237907 and 20140038927; and glycopeptides taught in U.S. Patent Publication No. 20070185012; the content of each of which is incorporated herein by reference in their entirety.

Therapeutic agents that may be used in combination therapy with the vectors, e.g., AAV vectors, encoding the nucleic acid sequence for the siRNA molecules of the present invention may be hormones or variants that can protect neuronal loss, such as adrenocorticotropic hormone (ACTH) or fragments thereof (e.g., U.S. Patent Publication No. 20130259875); Estrogen (e.g., U.S. Pat. Nos. 6,334,998 and 6,592,845); the content of each of which is incorporated herein by reference in their entirety.

Neurotrophic factors may be used in combination therapy with the vectors, e.g., AAV vectors, encoding the nucleic acid sequence for the siRNA molecules of the present invention for treating ALS. Generally, a neurotrophic factor is defined as a substance that promotes survival, growth, differentiation, proliferation and/or maturation of a neuron, or stimulates increased activity of a neuron. In some embodiments, the present methods further comprise delivery of one or more trophic factors into the subject in need of treatment. Trophic factors may include, but are not limited to, IGF-I, GDNF, BDNF, CTNF, VEGF, Colivelin, Xaliproden, Thyrotrophin-releasing hormone and ADNF, and variants thereof.

In one aspect, the vector, e.g., AAV vector, encoding the nucleic acid sequence for the at least one siRNA duplex targeting the SOD1 gene may be co-administered with AAV vectors expressing neurotrophic factors such as AAV-IGF-I (Vincent et al., *Neuromolecular medicine,* 2004, 6, 79-85; the content of which is incorporated herein by reference in its entirety) and AAV-GDNF (Wang et al., *J Neurosci.,* 2002, 22, 6920-6928; the content of which is incorporated herein by reference in its entirety).

In some embodiments, the composition of the present invention for treating ALS is administered to the subject in need intravenously, intramuscularly, subcutaneously, intraperitoneally, intrathecally and/or intraventricularly, allowing the siRNA molecules or vectors comprising the siRNA molecules to pass through one or both the blood-brain barrier and the blood spinal cord barrier. In some aspects, the method includes administering (e.g., intraventricularly administering and/or intrathecally administering) directly to the central nervous system (CNS) of a subject (using, e.g., an infusion pump and/or a delivery scaffold) a therapeutically effective amount of a composition comprising vectors, e.g., AAV vectors, encoding the nucleic acid sequence for the siRNA molecules of the present invention. The vectors may be used to silence or suppress SOD1 gene expression, and/or reducing one or more symptoms of ALS in the subject such that ALS is therapeutically treated.

In certain aspects, the symptoms of ALS include, but are not limited to, motor neuron degeneration, muscle weakness, muscle atrophy, the stiffness of muscle, difficulty in breathing, slurred speech, fasciculation development, frontotemporal dementia and/or premature death are improved in the subject treated. In other aspects, the composition of the present invention is applied to one or both of the brain and the spinal cord. In other aspects, one or both of muscle coordination and muscle function are improved. In other aspects, the survival of the subject is prolonged.

In one embodiment, administration of the vectors, e.g., AAV vectors encoding a siRNA of the invention, to a subject may lower mutant SOD1 in the CNS of a subject. In another embodiment, administration of the vectors, e.g., AAV vectors, to a subject may lower wild-type SOD1 in the CNS of a subject. In yet another embodiment, administration of the vectors, e.g., AAV vectors, to a subject may lower both mutant SOD1 and wild-type SOD1 in the CNS of a subject. The mutant and/or wild-type SOD1 may be lowered by about 30%, 40%, 50%, 60%, 70%, 80%, 85%, 90%, 95% and 100%, or at least 20-30%, 20-40%, 20-50%, 20-60%, 20-70%, 20-80%, 20-90%, 20-95%, 20-100%, 30-40%, 30-50%, 30-60%, 30-70%, 30-80%, 30-90%, 30-95%, 30-100%, 40-50%, 40-60%, 40-70%, 40-80%, 40-90%, 40-95%, 40-100%, 50-60%, 50-70%, 50-80%, 50-90%, 50-95%, 50-100%, 60-70%, 60-80%, 60-90%, 60-95%, 60-100%, 70-80%, 70-90%, 70-95%, 70-100%, 80-90%, 80-95%, 80-100%, 90-95%, 90-100% or 95-100% in the CNS, a region of the CNS, or a specific cell of the CNS of a subject. As a non-limiting example, the vectors, e.g., AAV vectors may lower the expression of wild-type SOD1 by at least 50% in the motor neurons (e.g., ventral horn motor neurons) and/or astrocytes. As another non-limiting example, the vectors, e.g., AAV vectors may lower the expression of mutant SOD1 by at least 50% in the motor neurons (e.g., ventral horn motor neurons) and/or astrocytes. As yet another non-limiting example, the vectors, e.g., AAV vectors may lower the expression of wild-type SOD1 and mutant SOD1 by at least 50% in the motor neurons (e.g., ventral horn motor neurons) and/or astrocytes.

In one embodiment, administration of the vectors, e.g., AAV vectors, to a subject will reduce the expression of mutant and/or wild-type SOD1 in the spinal cord and the reduction of expression of the mutant and/or wild-type SOD1 will reduce the effects of ALS in a subject.

In one embodiment, the vectors, e.g., AAV vectors, may be administered to a subject who is in the early stages of ALS. Early-stage symptoms include, but are not limited to, muscles which are weak and soft or stiff, tight and spastic, cramping and twitching (fasciculations) of muscles, loss of muscle bulk (atrophy), fatigue, poor balance, slurred words, weak grip, and/or tripping when walking. The symptoms may be limited to a single body region or a mild symptom may affect more than one region. As a non-limiting example, administration of the vectors, e.g., AAV vectors, may reduce the severity and/or occurrence of the symptoms of ALS.

In one embodiment, the vectors, e.g., AAV vectors, may be administered to a subject who is in the middle stages of ALS. The middle stage of ALS includes, but is not limited to, more widespread muscle symptoms as compared to the early stage, some muscles are paralyzed while others are weakened or unaffected, continued muscle twitchings (fasciculations), unused muscles may cause contractures where the joints become rigid, painful and sometimes deformed, weakness in swallowing muscles may cause choking and greater difficulty eating and managing saliva, weakness in breathing muscles can cause respiratory insufficiency which can be prominent when lying down, and/or a subject may have bouts of uncontrolled and inappropriate laughing or crying (pseudobulbar affect). As a non-limiting example, administration of the vectors, e.g., AAV vectors, may reduce the severity and/or occurrence of the symptoms of ALS.

In one embodiment, the vectors, e.g., AAV vectors, may be administered to a subject who is in the late stages of ALS. The late stage of ALS includes, but is not limited to, voluntary muscles which are mostly paralyzed, the muscles that help move air in and out of the lungs are severely compromised, mobility is extremely limited, poor respiration may cause fatigue, fuzzy thinking, headaches and susceptibility to infection or diseases (e.g., pneumonia), speech is difficult and eating or drinking by mouth may not be possible.

In one embodiment, the vectors, e.g., AAV vectors, may be used to treat a subject with ALS who has a C9orf72 mutation.

In one embodiment, the vectors, e.g., AAV vectors, may be used to treat a subject with ALS who has TDP-43 mutations.

In one embodiment, the vectors, e.g., AAV vectors, may be used to treat a subject with ALS who has FUS mutations.

DEFINITIONS

Unless stated otherwise, the following terms and phrases have the meanings described below. The definitions are not meant to be limiting in nature and serve to provide a clearer understanding of certain aspects of the present invention.

As used herein, the term "nucleic acid", "polynucleotide" and 'oligonucleotide" refer to any nucleic acid polymers composed of either polydeoxyribonucleotides (containing 2-deoxy-D-ribose), or polyribonucleotides (containing D-ribose), or any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA.

As used herein, the term "RNA" or "RNA molecule" or "ribonucleic acid molecule" refers to a polymer of ribonucleotides; the term "DNA" or "DNA molecule" or "deoxyribonucleic acid molecule" refers to a polymer of deoxyribonucleotides. DNA and RNA can be synthesized naturally, e.g., by DNA replication and transcription of DNA, respectively; or be chemically synthesized. DNA and RNA can be single-stranded (i.e., ssRNA or ssDNA, respectively) or multi-stranded (e.g., double stranded, i.e., dsRNA and dsDNA, respectively). The term "mRNA" or "messenger RNA", as used herein, refers to a single stranded RNA that encodes the amino acid sequence of one or more polypeptide chains.

As used herein, the term "RNA interfering" or "RNAi" refers to a sequence specific regulatory mechanism mediated by RNA molecules which results in the inhibition or interfering or "silencing" of the expression of a corresponding protein-coding gene. RNAi has been observed in many types of organisms, including plants, animals and fungi. RNAi occurs in cells naturally to remove foreign RNAs (e.g., viral RNAs). Natural RNAi proceeds via fragments cleaved from free dsRNA which direct the degradative mechanism to other similar RNA sequences. RNAi is controlled by the RNA-induced silencing complex (RISC) and is initiated by short/small dsRNA molecules in cell cytoplasm, where they interact with the catalytic RISC component argonaute. The dsRNA molecules can be introduced into cells exogenously. Exogenous dsRNA initiates RNAi by activating the ribonuclease protein Dicer, which binds and cleaves dsRNAs to produce double-stranded fragments of 21-25 base pairs with a few unpaired overhang bases on each end. These short double stranded fragments are called small interfering RNAs (siRNAs).

As used herein, the terms "short interfering RNA," "small interfering RNA" or "siRNA" refer to an RNA molecule (or RNA analog) comprising between about 5-60 nucleotides (or nucleotide analogs) which is capable of directing or mediating RNAi. Preferably, a siRNA molecule comprises between about 15-30 nucleotides or nucleotide analogs, such as between about 16-25 nucleotides (or nucleotide analogs), between about 18-23 nucleotides (or nucleotide analogs), between about 19-22 nucleotides (or nucleotide analogs) (e.g., 19, 20, 21 or 22 nucleotides or nucleotide analogs), between about 19-25 nucleotides (or nucleotide analogs), and between about 19-24 nucleotides (or nucleotide analogs). The term "short" siRNA refers to a siRNA comprising 5-23 nucleotides, preferably 21 nucleotides (or nucleotide analogs), for example, 19, 20, 21 or 22 nucleotides. The term "long" siRNA refers to a siRNA comprising 24-60 nucleotides, preferably about 24-25 nucleotides, for example, 23, 24, 25 or 26 nucleotides. Short siRNAs may, in some instances, include fewer than 19 nucleotides, e.g., 16, 17 or 18 nucleotides, or as few as 5 nucleotides, provided that the shorter siRNA retains the ability to mediate RNAi. Likewise, long siRNAs may, in some instances, include more than 26 nucleotides, e.g., 27, 28, 29, 30, 35, 40, 45, 50, 55, or even 60 nucleotides, provided that the longer siRNA retains the ability to mediate RNAi or translational repression absent further processing, e.g., enzymatic processing, to a short siRNA. siRNAs can be single stranded RNA molecules (ss-siRNAs) or double stranded RNA molecules (ds-siRNAs) comprising a sense strand and an antisense strand which hybridized to form a duplex structure called siRNA duplex.

As used herein, the term "the antisense strand" or "the first strand" or "the guide strand" of a siRNA molecule refers to a strand that is substantially complementary to a section of about 10-50 nucleotides, e.g., about 15-30, 16-25, 18-23 or 19-22 nucleotides of the mRNA of the gene targeted for silencing. The antisense strand or first strand has sequence sufficiently complementary to the desired target mRNA sequence to direct target-specific silencing, e.g., complementarity sufficient to trigger the destruction of the desired target mRNA by the RNAi machinery or process.

As used herein, the term "the sense strand" or "the second strand" or "the passenger strand" of a siRNA molecule refers to a strand that is complementary to the antisense strand or first strand. The antisense and sense strands of a siRNA molecule are hybridized to form a duplex structure. As used herein, a "siRNA duplex" includes a siRNA strand having sufficient complementarity to a section of about 10-50 nucleotides of the mRNA of the gene targeted for silencing and a siRNA strand having sufficient complementarity to form a duplex with the siRNA strand.

As used herein, the term "complementary" refers to the ability of polynucleotides to form base pairs with one another. Base pairs are typically formed by hydrogen bonds between nucleotide units in antiparallel polynucleotide strands. Complementary polynucleotide strands can form base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated. Perfect complementarity or 100% complementarity refers to the situation in which each nucleotide unit of one polynucleotide strand can form hydrogen bond with a nucleotide unit of a second polynucleotide strand. Less than perfect complementarity refers to the situation in which some, but not all, nucleotide units of two strands can form hydrogen bond with each other. For example, for two 20-mers, if only two base pairs on each strand can form hydrogen bond with each other, the polynucleotide strands exhibit 10% complementarity. In the same example, if 18 base pairs on each strand can form hydrogen bonds with each other, the polynucleotide strands exhibit 90% complementarity.

As used herein, the term "substantially complementary" means that the siRNA has a sequence (e.g., in the antisense strand) which is sufficient to bind the desired target mRNA, and to trigger the RNA silencing of the target mRNA.

As used herein, "targeting" means the process of design and selection of nucleic acid sequence that will hybridize to a target nucleic acid and induce a desired effect.

The term "gene expression" refers to the process by which a nucleic acid sequence undergoes successful transcription and in most instances translation to produce a protein or peptide. For clarity, when reference is made to measurement of "gene expression", this should be understood to mean that measurements may be of the nucleic acid product of transcription, e.g., RNA or mRNA or of the amino acid product of translation, e.g., polypeptides or peptides. Methods of measuring the amount or levels of RNA, mRNA, polypeptides, and peptides are well known in the art.

As used herein, the term "mutation" refers to any changing of the structure of a gene, resulting in a variant (also called "mutant") form that may be transmitted to subsequent generations. Mutations in a gene may be caused by the alternation of single base in DNA, or the deletion, insertion, or rearrangement of larger sections of genes or chromosomes.

As used herein, the term "vector" means any molecule or moiety which transports, transduces or otherwise acts as a carrier of a heterologous molecule such as the siRNA molecule of the invention. A "viral vector" is a vector which comprises one or more polynucleotide regions encoding or comprising a molecule of interest, e.g., a transgene, a polynucleotide encoding a polypeptide or multi-polypeptide or a modulatory nucleic acid such as small interfering RNA (siRNA). Viral vectors are commonly used to deliver genetic materials into cells. Viral vectors are often modified for specific applications. Types of viral vectors include retroviral vectors, lentiviral vectors, adenoviral vectors and adeno-associated viral vectors.

The term "adeno-associated virus" or "AAV" or "AAV vector" as used herein refers to any vector which comprises or derives from components of an adeno-associated vector and is suitable to infect mammalian cells, preferably human cells. The term AAV vector typically designates an AAV type viral particle or virion comprising a nucleic acid molecule encoding a siRNA duplex. The AAV vector may be derived from various serotypes, including combinations of serotypes (i.e., "pseudotyped" AAV) or from various genomes (e.g., single stranded or self-complementary). In addition, the AAV vector may be replication defective and/or targeted.

As used herein, the phrase "inhibit expression of a gene" means to cause a reduction in the amount of an expression product of the gene. The expression product can be a RNA molecule transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "modified" refers to a changed state or structure of a molecule of the invention. Molecules may be modified in many ways including chemically, structurally, and functionally.

As used herein, the term "synthetic" means produced, prepared, and/or manufactured by the hand of man. Synthesis of polynucleotides or polypeptides or other molecules of the present invention may be chemical or enzymatic.

As used herein, the term "transfection" refers to methods to introduce exogenous nucleic acids into a cell. Methods of transfection include, but are not limited to, chemical methods, physical treatments and cationic lipids or mixtures. The list of agents that can be transfected into a cell is large and includes, but is not limited to, siRNA, sense and/or antisense sequences, DNA encoding one or more genes and organized into an expression plasmid, proteins, protein fragments, and more.

As used herein, "off target" refers to any unintended effect on any one or more target, gene, or cellular transcript.

As used herein, the phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "effective amount" of an agent is that amount sufficient to effect beneficial or desired results, for example, clinical results, and, as such, an "effective amount" depends upon the context in which it is being applied. For example, in the context of administering an agent that treats ALS, an effective amount of an agent is, for example, an amount sufficient to achieve treatment, as defined herein, of ALS, as compared to the response obtained without administration of the agent.

As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates such as chimpanzees and other apes and monkey species, and humans) and/or plants.

As used herein, the term "preventing" or "prevention" refers to delaying or forestalling the onset, development or progression of a condition or disease for a period of time, including weeks, months, or years.

The term "treatment" or "treating," as used herein, refers to the application of one or more specific procedures used for the cure or amelioration of a disease. In certain embodiments, the specific procedure is the administration of one or more pharmaceutical agents. In the context of the present invention, the specific procedure is the administration of one or more siRNA duplexes or encoded dsRNA targeting SOD1 gene.

As used herein, the term "amelioration" or "ameliorating" refers to a lessening of severity of at least one indicator of a condition or disease. For example, in the context of neurodegeneration disorder, amelioration includes the reduction of neuron loss.

As used herein, the term "administering" refers to providing a pharmaceutical agent or composition to a subject.

As used herein, the term "neurodegeneration" refers to a pathologic state which results in neural cell death. A large number of neurological disorders share neurodegeneration as a common pathological state. For example, Alzheimer's disease, Parkinson's disease, Huntington's disease, and amyotrophic lateral sclerosis (ALS) all cause chronic neurodegeneration, which is characterized by a slow, progressive neural cell death over a period of several years, whereas acute neurodegeneration is characterized by a sudden onset of neural cell death as a result of ischemia, such as stroke, or trauma, such as traumatic brain injury, or as a result of axonal transection by demyelination or trauma caused, for example, by spinal cord injury or multiple sclerosis. In some neurological disorders, mainly one type of neuron cells are degenerative, for example, motor neuron degeneration in ALS.

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or the entire group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any antibiotic, therapeutic or active ingredient; any method of production; any method of use; etc.) can be excluded from any one or more claims, for any reason, whether or not related to the existence of prior art.

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

EXAMPLES

Example 1. SOD1 siRNA Design and Synthesis

SOD1 siRNA Design siRNA design was carried out to identify siRNAs targeting human SOD1 gene. The design used the SOD1 transcripts for human ((Genebank access NO. NM_000454.4 (SEQ ID NO: 1)), cynomolgus ((Genebank access NO. XM_005548833.1) from the NCBI Refseq collection (release 63) (SEQ ID NO: 2)) and rhesus (SOD1 transcript ENSMMUT00000002415 (SEQ ID NO: 3) from the Ensembl project (release 75)) as described in Table 2.

TABLE 2

| SOD1 gene sequences | | |
|---|---|---|
| SOD1 transcripts | Access No. | SEQ ID NO. |
| Human SOD1 cDNA (981 bp) | NM_000454.4 | 1 |
| cynomolgus SOD1 cDNA (465 bp) | XM_005548833.1 | 2 |
| rhesus SOD1 cDNA (464 bp) | ENSMMUT00000002415 | 3 |

The siRNA duplexes were designed to have 100% identity to the human SOD1 transcript for positions 2-18 of the antisense strand, and partial or 100% identity to the nonhuman primate SOD1 transcript for positions 2-18 of the antisense strand. In all siRNA duplexes, position 1 of the antisense strand was engineered to a U and position 19 of the sense strand was engineered to a C, in order to unpair the duplex at this position.

SOD1 siRNA Sequence Selection

Based on predicted selectivity of the antisense strand for human, cynomolgus and rhesus SOD1 genes, and lack of match of the seed sequence at positions 2-7 of the antisense strand to human sequences in miRBase20.0, a total of 169 antisense and 169 sense human SOD1 derived oligonucleotides were synthesized and formed into duplexes (Table 3). The siRNA duplexes were then tested for in vitro inhibitory activity on endogenous SOD1 gene expression (SOD1 mRNA levels).

TABLE 3

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 26 D-2741 | 7414 | CGGAGGUCUGGCCUAUAACdTdT | 4 | 7415 | UUUAUAGGCCAGACCUCCGdTdT | 173 |
| 27 D-2742 | 7416 | GGAGGUCUGGCCUAUAAACdTdT | 5 | 7417 | UUUUAUAGGCCAGACCUCCdTdT | 174 |
| 28 D-2743 | 7418 | GAGGUCUGGCCUAUAAAGCdTdT | 6 | 7419 | UCUUUAUAGGCCAGACCUCdTdT | 175 |
| 29 D-2744 | 7420 | AGGUCUGGCCUAUAAAGUCdTdT | 7 | 7421 | UACUUUAUAGGCCAGACCUdTdT | 176 |
| 30 D-2745 | 7422 | GGUCUGGCCUAUAAAGUACdTdT | 8 | 7423 | UUACUUUAUAGGCCAGACCdTdT | 177 |
| 32 D-2746 | 7424 | UCUGGCCUAUAAAGUAGUCdTdT | 9 | 7425 | UACUACUUUAUAGGCCAGAdTdT | 178 |
| 33 D-2747 | 7426 | CUGGCCUAUAAAGUAGUCCdTdT | 10 | 7427 | UGACUACUUUAUAGGCCAGdTdT | 179 |
| 34 D-2748 | 7428 | UGGCCUAUAAAGUAGUCGCdTdT | 11 | 7429 | UCGACUACUUUAUAGGCCAdTdT | 180 |
| 35 D-2749 | 7430 | GGCCUAUAAAGUAGUCGCCdTdT | 12 | 7431 | UGCGACUACUUUAUAGGCCdTdT | 181 |
| 36 D-2750 | 7432 | GCCUAUAAAGUAGUCGCGCdTdT | 13 | 7433 | UCGCGACUACUUUAUAGGCdTdT | 182 |
| 37 D-2751 | 7434 | CCUAUAAAGUAGUCGCGGCdTdT | 14 | 7435 | UCCGCGACUACUUUAUAGGdTdT | 183 |
| 74 D-2752 | 7436 | GUCGUAGUCUCCUGCAGCCdTdT | 15 | 7437 | UGCUGCAGGAGACUACGACdTdT | 184 |
| 76 D-2753 | 7438 | CGUAGUCUCCUGCAGCGUCdTdT | 16 | 7439 | UACGCUGCAGGAGACUACGdTdT | 185 |
| 77 D-2754 | 7440 | GUAGUCUCCUGCAGCGUCCdTdT | 17 | 7441 | UGACGCUGCAGGAGACUACdTdT | 186 |
| 78 D-2755 | 7442 | UAGUCUCCUGCAGCGUCUCdTdT | 18 | 7443 | UAGACGCUGCAGGAGACUAdTdT | 187 |
| 149 D-2756 | 7444 | AUGGCGACGAAGGCCGUGCdTdT | 19 | 7445 | UCACGGCCUUCGUCGCCAUdTdT | 188 |
| 153 D-2757 | 7446 | CGACGAAGGCCGUGUGCGCdTdT | 20 | 7447 | UCGCACACGGCCUUCGUCGdTdT | 189 |
| 157 D-2758 | 7448 | GAAGGCCGUGUGCGUGCUCdTdT | 21 | 7449 | UAGCACGCACACGGCCUUCdTdT | 190 |
| 160 D-2759 | 7450 | GGCCGUGUGCGUGCUGAACdTdT | 22 | 7451 | UUUCAGCACGCACACGGCCdTdT | 191 |
| 177 D-2760 | 7452 | AGGGCGACGGCCCAGUGCCdTdT | 23 | 7453 | UGCACUGGGCCGUCGCCCUdTdT | 192 |
| 192 D-2761 | 7454 | UGCAGGGCAUCAUCAAUUCdTdT | 24 | 7455 | UAAUUGAUGAUGCCCUGCAdTdT | 193 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 193 | D-2762 | 7456 GCAGGGCAUCAUCAA UUUCdTdT | 25 | 7457 | UAAAUUGAUGAUGCCCUG CdTdT | 194 |
| 195 | D-2763 | 7458 AGGGCAUCAUCAAUU UCGCdTdT | 26 | 7459 | UCGAAAUUGAUGAUGCCC UdTdT | 195 |
| 196 | D-2764 | 7460 GGGCAUCAUCAAUUU CGACdTdT | 27 | 7461 | UUCGAAAUUGAUGAUGCC CdTdT | 196 |
| 197 | D-2765 | 7462 GGCAUCAUCAAUUUC GAGCdTdT | 28 | 7463 | UCUCGAAAUUGAUGAUGC CdTdT | 197 |
| 198 | D-2766 | 7464 GCAUCAUCAAUUUCG AGCCdTdT | 29 | 7465 | UGCUCGAAAUUGAUGAUG CdTdT | 198 |
| 199 | D-2767 | 7466 CAUCAUCAAUUUCGA GCACdTdT | 30 | 7467 | UUGCUCGAAAUUGAUGAU GdTdT | 199 |
| 206 | D-2768 | 7468 AAUUUCGAGCAGAAG GAACdTdT | 31 | 7469 | UUUCCUUCUGCUCGAAAU UdTdT | 200 |
| 209 | D-2769 | 7470 UUCGAGCAGAAGGAA AGUCdTdT | 32 | 7471 | UACUUUCCUUCUGCUCGA AdTdT | 201 |
| 210 | D-2770 | 7472 UCGAGCAGAAGGAAA GUACdTdT | 33 | 7473 | UUACUUUCCUUCUGCUCG AdTdT | 202 |
| 239 | D-2771 | 7474 AAGGUGUGGGGAAGC AUUCdTdT | 34 | 7475 | UAAUGCUUCCCCACACCU UdTdT | 203 |
| 241 | D-2772 | 7476 GGUGUGGGGAAGCAU UAACdTdT | 35 | 7477 | UUUAAUGCUUCCCCACAC CdTdT | 204 |
| 261 | D-2773 | 7478 GACUGACUGAAGGCC UGCCdTdT | 36 | 7479 | UGCAGGCCUUCAGUCAGU CdTdT | 205 |
| 263 | D-2774 | 7480 CUGACUGAAGGCCUG CAUCdTdT | 37 | 7481 | UAUGCAGGCCUUCAGUCA GdTdT | 206 |
| 264 | D-2775 | 7482 UGACUGAAGGCCUGC AUGCdTdT | 38 | 7483 | UCAUGCAGGCCUUCAGUC AdTdT | 207 |
| 268 | D-2776 | 7484 UGAAGGCCUGCAUGG AUUCdTdT | 39 | 7485 | UAAUCCAUGCAGGCCUUC AdTdT | 208 |
| 269 | D-2777 | 7486 GAAGGCCUGCAUGGA UUCCdTdT | 40 | 7487 | UGAAUCCAUGCAGGCCUU CdTdT | 209 |
| 276 | D-2778 | 7488 UGCAUGGAUUCCAUG UUCCdTdT | 41 | 7489 | UGAACAUGGAAUCCAUGC AdTdT | 210 |
| 278 | D-2779 | 7490 CAUGGAUUCCAUGUU CAUCdTdT | 42 | 7491 | UAUGAACAUGGAAUCCAU GdTdT | 211 |
| 281 | D-2780 | 7492 GGAUUCCAUGUUCAU GAGCdTdT | 43 | 7493 | UCUCAUGAACAUGGAAUC CdTdT | 212 |
| 284 | D-2781 | 7494 UUCCAUGUUCAUGAG UUUCdTdT | 44 | 7495 | UAAACUCAUGAACAUGGA AdTdT | 213 |
| 290 | D-2782 | 7496 GUUCAUGAGUUUGGA GAUCdTdT | 45 | 7497 | UAUCUCCAAACUCAUGAA CdTdT | 214 |
| 291 | D-2783 | 7498 UUCAUGAGUUUGGAG AUACdTdT | 46 | 7499 | UUAUCUCCAAACUCAUGA AdTdT | 215 |
| 295 | D-2784 | 7500 UGAGUUUGGAGAUAA UACCdTdT | 47 | 7501 | UGUAUUAUCUCCAAACUC AdTdT | 216 |
| 296 | D-2785 | 7502 GAGUUUGGAGAUAAU ACACdTdT | 48 | 7503 | UUGUAUUAUCUCCAAACU CdTdT | 217 |
| 316 | D-2786 | 7504 AGGCUGUACCAGUGC AGGCdTdT | 49 | 7505 | UCCUGCACUGGUACAGCC UdTdT | 218 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 317 D-2787 | 7506 | GGCUGUACCAGUGCAGGUCdTdT | 50 | 7507 | UACCUGCACUGGUACAGCCdTdT | 219 |
| 329 D-2788 | 7508 | GCAGGUCCUCACUUUAAUCdTdT | 51 | 7509 | UAUUAAAGUGAGGACCUGCdTdT | 220 |
| 330 D-2789 | 7510 | CAGGUCCUCACUUUAAUCCdTdT | 52 | 7511 | UGAUUAAAGUGAGGACCUGdTdT | 221 |
| 337 D-2790 | 7512 | UCACUUUAAUCCUCUAUCCdTdT | 53 | 7513 | UGAUAGAGGAUUAAAGUGAdTdT | 222 |
| 350 D-2791 | 7514 | CUAUCCAGAAAACACGGUCdTdT | 54 | 7515 | UACCGUGUUUUCUGGAUAGdTdT | 223 |
| 351 D-2792 | 7516 | UAUCCAGAAAACACGGUGCdTdT | 55 | 7517 | UCACCGUGUUUUCUGGAUAdTdT | 224 |
| 352 D-2793 | 7518 | AUCCAGAAAACACGGUGGCdTdT | 56 | 7519 | UCCACCGUGUUUUCUGGAUdTdT | 225 |
| 354 D-2794 | 7520 | CCAGAAAACACGGUGGGCCdTdT | 57 | 7521 | UGCCCACCGUGUUUUCUGGdTdT | 226 |
| 357 D-2795 | 7522 | GAAAACACGGUGGGCCAACdTdT | 58 | 7523 | UUUGGCCCACCGUGUUUUCdTdT | 227 |
| 358 D-2796 | 7524 | AAAACACGGUGGGCCAAAdTdT | 59 | 7525 | UUUUGGCCCACCGUGUUUUdTdT | 228 |
| 364 D-2797 | 7526 | CGGUGGGCCAAAGGAUGAdTdT | 60 | 7527 | UUCAUCCUUUGGCCCACCGdTdT | 229 |
| 375 D-2798 | 7528 | AGGAUGAAGAGAGGCAUGCdTdT | 61 | 7529 | UCAUGCCUCUCUUCAUCCUdTdT | 230 |
| 378 D-2799 | 7530 | AUGAAGAGAGGCAUGUUGCdTdT | 62 | 7531 | UCAACAUGCCUCUCUUCAUdTdT | 231 |
| 383 D-2800 | 7532 | GAGAGGCAUGUUGGAGACCdTdT | 63 | 7533 | UGUCUCCAACAUGCCUCUCdTdT | 232 |
| 384 D-2801 | 7534 | AGAGGCAUGUUGGAGACUCdTdT | 64 | 7535 | UAGUCUCCAACAUGCCUCUdTdT | 233 |
| 390 D-2802 | 7536 | AUGUUGGAGACUUGGGCACdTdT | 65 | 7537 | UUGCCCAAGUCUCCAACAUdTdT | 234 |
| 392 D-2803 | 7538 | GUUGGAGACUUGGGCAAUCdTdT | 66 | 7539 | UAUUGCCCAAGUCUCCAACdTdT | 235 |
| 395 D-2804 | 7540 | GGAGACUUGGGCAAUGUGCdTdT | 67 | 7541 | UCACAUUGCCCAAGUCUCCdTdT | 236 |
| 404 D-2805 | 7542 | GGCAAUGUGACUGCUGACCdTdT | 68 | 7543 | UGUCAGCAGUCACAUUGCCdTdT | 237 |
| 406 D-2806 | 7544 | CAAUGUGACUGCUGACAACdTdT | 69 | 7545 | UUUGUCAGCAGUCACAUUGdTdT | 238 |
| 417 D-2807 | 7546 | CUGACAAAGAUGGUGUGGCdTdT | 70 | 7547 | UCCACACCAUCUUUGUCAGdTdT | 239 |
| 418 D-2808 | 7548 | UGACAAAGAUGGUGUGGCCdTdT | 71 | 7549 | UGCCACACCAUCUUUGUCAdTdT | 240 |
| 469 D-2809 | 7550 | CUCAGGAGACCAUUGCAUCdTdT | 72 | 7551 | UAUGCAAUGGUCUCCUGAGdTdT | 241 |
| 470 D-2810 | 7552 | UCAGGAGACCAUUGCAUCdTdT | 73 | 7553 | UGAUGCAAUGGUCUCCUGAdTdT | 242 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 475 D-2811 | 7554 | AGACCAUUGCAUCAU UGGCdTdT | 74 | 7555 | UCCAAUGAUGCAAUGGUC UdTdT | 243 |
| 476 D-2812 | 7556 | GACCAUUGCAUCAUU GGCCdTdT | 75 | 7557 | UGCCAAUGAUGCAAUGGU CdTdT | 244 |
| 480 D-2813 | 7558 | AUUGCAUCAUUGGCC GCACdTdT | 76 | 7559 | UUGCGGCCAAUGAUGCAA UdTdT | 245 |
| 487 D-2814 | 7560 | CAUUGGCCGCACACU GGUCdTdT | 77 | 7561 | UACCAGUGUGCGGCCAAU GdTdT | 246 |
| 494 D-2815 | 7562 | CGCACACUGGUGGUC CAUCdTdT | 78 | 7563 | UAUGGACCACCAGUGUGC GdTdT | 247 |
| 496 D-2816 | 7564 | CACACUGGUGGUCCA UGACdTdT | 79 | 7565 | UUCAUGGACCACCAGUGU GdTdT | 248 |
| 497 D-2817 | 7566 | ACACUGGUGGUCCAU GAACdTdT | 80 | 7567 | UUUCAUGGACCACCAGUG UdTdT | 249 |
| 501 D-2818 | 7568 | UGGUGGUCCAUGAAA AAGCdTdT | 81 | 7569 | UCUUUUUCAUGGACCACC AdTdT | 250 |
| 504 D-2819 | 7570 | UGGUCCAUGAAAAAG CAGCdTdT | 82 | 7571 | UCUGCUUUUUCAUGGACC AdTdT | 251 |
| 515 D-2820 | 7572 | AAAGCAGAUGACUUG GCCdTdT | 83 | 7573 | UGCCCAAGUCAUCUGCUU UdTdT | 252 |
| 518 D-2821 | 7574 | GCAGAUGACUUGGGC AAACdTdT | 84 | 7575 | UUUUGCCCAAGUCAUCUG CdTdT | 253 |
| 522 D-2822 | 7576 | AUGACUUGGGCAAAG GUGCdTdT | 85 | 7577 | UCACCUUUGCCCAAGUCA UdTdT | 254 |
| 523 D-2823 | 7578 | UGACUUGGGCAAAGG UGGCdTdT | 86 | 7579 | UCCACCUUUGCCCAAGUC AdTdT | 255 |
| 524 D-2824 | 7580 | GACUUGGGCAAAGGU GGACdTdT | 87 | 7581 | UUCCACCUUUGCCCAAGU CdTdT | 256 |
| 552 D-2825 | 7582 | GUACAAAGACAGGAA ACGCdTdT | 88 | 7583 | UCGUUUCCUGUCUUUGUA CdTdT | 257 |
| 554 D-2826 | 7584 | ACAAAGACAGGAAAC GCUCdTdT | 89 | 7585 | UAGCGUUUCCUGUCUUUG UdTdT | 258 |
| 555 D-2827 | 7586 | CAAAGACAGGAAACG CUGCdTdT | 90 | 7587 | UCAGCGUUUCCUGUCUUU GdTdT | 259 |
| 562 D-2828 | 7588 | AGGAAACGCUGGAAG UCGCdTdT | 91 | 7589 | UCGACUUCCAGCGUUUCC UdTdT | 260 |
| 576 D-2829 | 7590 | GUCGUUUGGCUUGUG GUGCdTdT | 92 | 7591 | UCACCACAAGCCAAACGA CdTdT | 261 |
| 577 D-2830 | 7592 | UCGUUUGGCUUGUGG UGUCdTdT | 93 | 7593 | UACACCAAGCCAAACG AdTdT | 262 |
| 578 D-2831 | 7594 | CGUUUGGCUUGUGGU GUACdTdT | 94 | 7595 | UUACACCACAAGCCAAAC GdTdT | 263 |
| 579 D-2832 | 7596 | GUUUGGCUUGUGGUG UAACdTdT | 95 | 7597 | UUUACACCACAAGCCAAA CdTdT | 264 |
| 581 D-2833 | 7598 | UUGGCUUGUGGUGUA AUUCdTdT | 96 | 7599 | UAAUUACACCACAAGCCA AdTdT | 265 |
| 583 D-2834 | 7600 | GGCUUGUGGUGUAAU UGGCdTdT | 97 | 7601 | UCCAAUUACACCACAAGC CdTdT | 266 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 584 | D-2835 | 7602 | GCUUGUGGUGUAAUU GGGCdTdT | 98 | 7603 | UCCCAAUUACACCACAAG CdTdT | 267 |
| 585 | D-2836 | 7604 | CUUGUGGUGUAAUUG GGACdTdT | 99 | 7605 | UUCCCAAUUACACCACAA GdTdT | 268 |
| 587 | D-2837 | 7606 | UGUGGUGUAAUUGGG AUCCdTdT | 100 | 7607 | UGAUCCCAAUUACACCAC AdTdT | 269 |
| 588 | D-2838 | 7608 | GUGGUGUAAUUGGGA UCGCdTdT | 101 | 7609 | UCGAUCCCAAUUACACCA CdTdT | 270 |
| 589 | D-2839 | 7610 | UGGUGUAAUUGGGAU CGCCdTdT | 102 | 7611 | UGCGAUCCCAAUUACACC AdTdT | 271 |
| 593 | D-2840 | 7612 | GUAAUUGGGAUCGCC CAACdTdT | 103 | 7613 | UUUGGGCGAUCCCAAUUA CdTdT | 272 |
| 594 | D-2841 | 7614 | UAAUUGGGAUCGCCC AAUCdTdT | 104 | 7615 | UAUUGGGCGAUCCCAAUU AdTdT | 273 |
| 595 | D-2842 | 7616 | AAUUGGGAUCGCCCA AUACdTdT | 105 | 7617 | UUAUUGGGCGAUCCCAAU UdTdT | 274 |
| 596 | D-2843 | 7618 | AUUGGGAUCGCCCAA UAACdTdT | 106 | 7619 | UUUAUUGGGCGAUCCCAA UdTdT | 275 |
| 597 | D-2844 | 7620 | UUGGGAUCGCCCAAU AAACdTdT | 107 | 7621 | UUUUAUUGGGCGAUCCCA AdTdT | 276 |
| 598 | D-2845 | 7622 | UGGGAUCGCCCAAUA AACCdTdT | 108 | 7623 | UGUUUAUUGGGCGAUCCC AdTdT | 277 |
| 599 | D-2846 | 7624 | GGGAUCGCCCAAUAA ACACdTdT | 109 | 7625 | UUGUUUAUUGGGCGAUCC CdTdT | 278 |
| 602 | D-2847 | 7626 | AUCGCCCAAUAAACA UUCCdTdT | 110 | 7627 | UGAAUGUUUAUUGGGCGA UdTdT | 279 |
| 607 | D-2848 | 7628 | CCAAUAAACAUUCCC UUGCdTdT | 111 | 7629 | UCAAGGGAAUGUUUAUUG GdTdT | 280 |
| 608 | D-2849 | 7630 | CAAUAAACAUUCCCU UGGCdTdT | 112 | 7631 | UCCAAGGGAAUGUUUAUU GdTdT | 281 |
| 609 | D-2850 | 7632 | AAUAAACAUUCCCUU GGACdTdT | 113 | 7633 | UUCCAAGGGAAUGUUUAU UdTdT | 282 |
| 610 | D-2851 | 7634 | AUAAACAUUCCCUUG GAUCdTdT | 114 | 7635 | UAUCCAAGGGAAUGUUUA UdTdT | 283 |
| 611 | D-2852 | 7636 | UAAACAUUCCCUUGG AUGCdTdT | 115 | 7637 | UCAUCCAAGGGAAUGUUU AdTdT | 284 |
| 612 | D-2853 | 7638 | AAACAUUCCCUUGGA UGUCdTdT | 116 | 7639 | UACAUCCAAGGGAAUGUU UdTdT | 285 |
| 613 | D-2854 | 7640 | AACAUUCCCUUGGAU GUACdTdT | 117 | 7641 | UUACAUCCAAGGGAAUGU UdTdT | 286 |
| 616 | D-2855 | 7642 | AUUCCCUUGGAUGUA GUCCdTdT | 118 | 7643 | UGACUACAUCCAAGGGAA UdTdT | 287 |
| 621 | D-2856 | 7644 | CUUGGAUGUAGUCUG AGGCdTdT | 119 | 7645 | UCCUCAGACUACAUCCAA GdTdT | 288 |
| 633 | D-2857 | 7646 | CUGAGGCCCCUUAAC UCACdTdT | 120 | 7647 | UUGAGUUAAGGGGCCUCA GdTdT | 289 |
| 635 | D-2858 | 7648 | GAGGCCCCUUAACUC AUCCdTdT | 121 | 7649 | UGAUGAGUUAAGGGGCCU CdTdT | 290 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 636 | D-2859 | 7650 AGGCCCCUUAACUCA UCUCdTdT | 122 | 7651 | UAGAUGAGUUAAGGGGCC UdTdT | 291 |
| 639 | D-2860 | 7652 CCCCUUAACUCAUCU GUUCdTdT | 123 | 7653 | UAACAGAUGAGUUAAGGG GdTdT | 292 |
| 640 | D-2861 | 7654 CCCUUAACUCAUCUG UUACdTdT | 124 | 7655 | UUAACAGAUGAGUUAAGG GdTdT | 293 |
| 641 | D-2862 | 7656 CCUUAACUCAUCUGU UAUCdTdT | 125 | 7657 | UAUAACAGAUGAGUUAAG GdTdT | 294 |
| 642 | D-2863 | 7658 CUUAACUCAUCUGUU AUCCdTdT | 126 | 7659 | UGAUAACAGAUGAGUUAA GdTdT | 295 |
| 643 | D-2864 | 7660 UUAACUCAUCUGUUA UCCCdTdT | 127 | 7661 | UGGAUAACAGAUGAGUUA AdTdT | 296 |
| 644 | D-2865 | 7662 UAACUCAUCUGUUAU CCUCdTdT | 128 | 7663 | UAGGAUAACAGAUGAGUU AdTdT | 297 |
| 645 | D-2866 | 7664 AACUCAUCUGUUAUC CUGCdTdT | 129 | 7665 | UCAGGAUAACAGAUGAGU UdTdT | 298 |
| 654 | D-2867 | 7666 GUUAUCCUGCUAGCU GUACdTdT | 130 | 7667 | UUACAGCUAGCAGGAUAA CdTdT | 299 |
| 660 | D-2868 | 7668 CUGCUAGCUGUAGAA AUGCdTdT | 131 | 7669 | UCAUUUCUACAGCUAGCA GdTdT | 300 |
| 661 | D-2869 | 7670 UGCUAGCUGUAGAAA UGUCdTdT | 132 | 7671 | UACAUUUCUACAGCUAGC AdTdT | 301 |
| 666 | D-2870 | 7672 GCUGUAGAAAUGUAU CCUCdTdT | 133 | 7673 | UAGGAUACAUUUCUACAG CdTdT | 302 |
| 667 | D-2871 | 7674 CUGUAGAAAUGUAUC CUGCdTdT | 134 | 7675 | UCAGGAUACAUUUCUACA GdTdT | 303 |
| 668 | D-2872 | 7676 UGUAGAAAUGUAUCC UGACdTdT | 135 | 7677 | UUCAGGAUACAUUUCUAC AdTdT | 304 |
| 669 | D-2873 | 7678 GUAGAAAUGUAUCCU GAUCdTdT | 136 | 7679 | UAUCAGGAUACAUUUCUA CdTdT | 305 |
| 673 | D-2874 | 7680 AAAUGUAUCCUGAUA AACCdTdT | 137 | 7681 | UGUUUAUCAGGAUACAUU UdTdT | 306 |
| 677 | D-2875 | 7682 GUAUCCUGAUAAACA UUACdTdT | 138 | 7683 | UUAAUGUUUAUCAGGAUA CdTdT | 307 |
| 692 | D-2876 | 7684 UUAAACACUGUAAUC UUACdTdT | 139 | 7685 | UUAAGAUUACAGUGUUUA AdTdT | 308 |
| 698 | D-2877 | 7686 ACUGUAAUCUUAAAA GUGCdTdT | 140 | 7687 | UCACUUUUAAGAUUACAG UdTdT | 309 |
| 699 | D-2878 | 7688 CUGUAAUCUUAAAAG UGUCdTdT | 141 | 7689 | UACACUUUUAAGAUUACA GdTdT | 310 |
| 700 | D-2879 | 7690 UGUAAUCUUAAAAGU GUACdTdT | 142 | 7691 | UUACACUUUUAAGAUUAC AdTdT | 311 |
| 701 | D-2880 | 7692 GUAAUCUUAAAAGUG UAACdTdT | 143 | 7693 | UUUACACUUUUAAGAUUA CdTdT | 312 |
| 706 | D-2881 | 7694 CUUAAAAGUGUAAUU GUGCdTdT | 144 | 7695 | UCACAAUUACACUUUUAA GdTdT | 313 |
| 749 | D-2882 | 7696 UACCUGUAGUGAGAA ACUCdTdT | 145 | 7697 | UAGUUUCUCACUACAGGU AdTdT | 314 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 770 | D-2883 | 7698 UUAUGAUCACUUGGA AGACdTdT | 146 | 7699 | UUCUUCCAAGUGAUCAUA AdTdT | 315 |
| 772 | D-2884 | 7700 AUGAUCACUUGGAAG AUUCdTdT | 147 | 7701 | UAAUCUUCCAAGUGAUCA UdTdT | 316 |
| 775 | D-2885 | 7702 AUCACUUGGAAGAUU UGUCdTdT | 148 | 7703 | UACAAAUCUUCCAAGUGA UdTdT | 317 |
| 781 | D-2886 | 7704 UGGAAGAUUUGUAUA GUUCdTdT | 149 | 7705 | UAACUAUACAAAUCUUCC AdTdT | 318 |
| 800 | D-2887 | 7706 UAUAAAACUCAGUUA AAACdTdT | 150 | 7707 | UUUUUAACUGAGUUUUAU AdTdT | 319 |
| 804 | D-2888 | 7708 AAACUCAGUUAAAAU GUCCdTdT | 151 | 7709 | UGACAUUUUAACUGAGUU UdTdT | 320 |
| 819 | D-2889 | 7710 GUCUGUUUCAAUGAC CUGCdTdT | 152 | 7711 | UCAGGUCAUUGAAACAGA CdTdT | 321 |
| 829 | D-2890 | 7712 AUGACCUGUAUUUUG CCACdTdT | 153 | 7713 | UUGGCAAAAUACAGGUCA UdTdT | 322 |
| 832 | D-2891 | 7714 ACCUGUAUUUUGCCA GACCdTdT | 154 | 7715 | UGUCUGGCAAAAUACAGG UdTdT | 323 |
| 833 | D-2892 | 7716 CCUGUAUUUUGCCAG ACUCdTdT | 155 | 7717 | UAGUCUGGCAAAAUACAG GdTdT | 324 |
| 851 | D-2893 | 7718 UAAAUCACAGAUGGG UAUCdTdT | 156 | 7719 | UAUACCCAUCUGUGAUUU AdTdT | 325 |
| 854 | D-2894 | 7720 AUCACAGAUGGGUAU UAACdTdT | 157 | 7721 | UUUAAUACCCAUCUGUGA UdTdT | 326 |
| 855 | D-2895 | 7722 UCACAGAUGGGUAUU AAACdTdT | 158 | 7723 | UUUUAAUACCCAUCUGUG AdTdT | 327 |
| 857 | D-2896 | 7724 ACAGAUGGGUAUUAA ACUCdTdT | 159 | 7725 | UAGUUUAAUACCCAUCUG UdTdT | 328 |
| 858 | D-2897 | 7726 CAGAUGGGUAUUAAA CUUCdTdT | 160 | 7727 | UAAGUUUAAUACCCAUCU GdTdT | 329 |
| 859 | D-2898 | 7728 AGAUGGGUAUUAAAC UUGCdTdT | 161 | 7729 | UCAAGUUUAAUACCCAUC UdTdT | 330 |
| 861 | D-2899 | 7730 AUGGGUAUUAAACUU GUCCdTdT | 162 | 7731 | UGACAAGUUUAAUACCCA UdTdT | 331 |
| 869 | D-2900 | 7732 UAAACUUGUCAGAAU UUCCdTdT | 163 | 7733 | UGAAAUUCUGACAAGUUU AdTdT | 332 |
| 891 | D-2901 | 7734 UCAUUCAAGCCUGUG AAUCdTdT | 164 | 7735 | UAUUCACAGGCUUGAAUG AdTdT | 333 |
| 892 | D-2902 | 7736 CAUUCAAGCCUGUGA AUACdTdT | 165 | 7737 | UUAUUCACAGGCUUGAAU GdTdT | 334 |
| 906 | D-2903 | 7738 AAUAAAAACCCUGUA UGGCdTdT | 166 | 7739 | UCCAUACAGGGUUUUUAU UdTdT | 335 |
| 907 | D-2904 | 7740 AUAAAAACCCUGUAU GGCCdTdT | 167 | 7741 | UGCCAUACAGGGUUUUUA UdTdT | 336 |
| 912 | D-2905 | 7742 AACCCUGUAUGGCAC UUACdTdT | 168 | 7743 | UUAAGUGCCAUACAGGGU UdTdT | 337 |
| 913 | D-2906 | 7744 ACCCUGUAUGGCACU UAUCdTdT | 169 | 7745 | UAUAAGUGCCAUACAGGG UdTdT | 338 |

TABLE 3-continued

Sense and antisense strand sequences of human SOD1 dsRNA

| siRNA duplex StartID | SS ID | sense strand sequence (5'-3') | SEQ ID NO | AS ID | antisense strand sequence (5'-3') | SEQ ID NO |
|---|---|---|---|---|---|---|
| 934 D-2907 | 7746 | GAGGCUAUUAAAAGA AUCCdTdT | 170 | 7747 | UGAUUCUUUUAAUAGCCU CdTdT | 339 |
| 944 D-2908 | 7748 | AAAGAAUCCAAAUUC AAACdTdT | 171 | 7749 | UUUUGAAUUUGGAUUCUU UdTdT | 340 |
| 947 D-2909 | 7750 | GAAUCCAAAUUCAAA CUACdTdT | 172 | 7751 | UUAGUUUGAAUUUGGAUU CdTdT | 341 |

SOD1 siRNA Synthesis

Oligoribonucleotides were assembled on an ABI 3900 synthesizer (Applied Biosystems) according to the phosphoramidite oligomerization chemistry. The solid support was polystyrene loaded with 2'-deoxy-thymidine (purchased from Glen Research, Sterling, Va., USA) to give a synthesis scale of 0.2 µmol. Ancillary synthesis reagents, DNA and RNA phosphoramidites were obtained from SAFC Proligo (Hamburg, Germany). Specifically, 5'-O-(4,4'-dimethoxytrityl)-3'-O-(2-cyanoethyl-N,N-diisopropyl) phosphoramidite monomers of uridine (U), thymidine (dT), 4-N-acetylcytidine ($C^{Ac}$), 6-N-benzoyladenosine ($A^{bz}$) and 2-N-isobutyrlguanosine ($G^{iBu}$) with 2'-O-t-butyldimethylsilyl were used to build the oligomers sequence. Coupling time for all phosphoramidites (70 mM in Acetonitrile) was 3 min employing 5-Ethylthio-1H-tetrazole (ETT) as activator (0.5 M in Acetonitrile). Sequences were synthesized with removal of the final dimetoxytrityl protecting group on the synthesizer ("DMT off" synthesis). Upon completion of the solid phase synthesis oligoribonucleotides were cleaved from the solid support and de-protected using a 1:1 (v/v) mixture of aqueous methylamine (40%) and methylamine in ethanol (33%). After 90 minutes at 45° C. the solution was diluted with N,N-Dimethyl formamide (DMF) and triethylamine trihydrofluoride (TEA.HF) was added. After incubation at 45° C. for 2 hours the oligoribonucleotides were precipitated with 1 M NaOAc and a mixture of acetone and ethanol 4:1 (v/v). The pellets were dissolved in 1 M aqueous NaCl solution and desalted by size exclusion chromatography. This was accomplished using an AKTA Purifier HPLC System (GE Healthcare, Freiburg, Germany) equipped with a HiTrap 5 mL column (GE Healthcare). Identity of the oligoribonucleotides was confirmed by MALDI mass spectrometry or ESI mass spectrometry. To generate siRNAs from RNA single strands, equimolar amounts of complementary sense and antisense strands were mixed and annealed in a 20 mM NaCl, 4 mM sodium phosphate pH 6.8 buffer. siRNAs were stored frozen until use.

Example 2. In Vitro Screening of SOD1 siRNAs for Human SOD1 mRNA Suppression

Human SOD1 targeting siRNAs (described in Table 3) were assayed for inhibition of endogenous SOD1 expression in HeLa cells, using the bDNA (branched DNA) assay to quantify SOD1 mRNA. Results from two dose assays were used to select a subset of SOD1 dsRNA duplexes for dose response experiments in 4 types of cultured cells to calculate IC50's.

Cell Culture and Transfection

HeLa cells were obtained from ATCC (ATCC in Partnership with LGC Standards, Wesel, Germany) and cultured in HAM's F-12 Medium (Biochrom GmbH, Berlin, Germany) supplemented to contain 10% fetal calf serum (Ultra-low IgG from GIBCO/Life Technologies) and 1% Pen/Strep (Biochrom GmbH, Berlin, Germany) at 37° C. in an atmosphere with 5% $CO_2$ in a humidified incubator.

For transfection with siRNA, HeLa cells were seeded at a density of 19,000-20,000 cells/well in 96-well plates. Transfection of siRNA was carried out with Lipofectamine 2000 (Invitrogen/Life Technologies) according to the manufacturer's instructions. For the two-dose screen, SOD1 siRNA concentrations of 1 nM or 0.1 nM were used. Dose response experiments were done with SOD1 siRNA concentrations of 10, 2.5, 0.6, 0.16, 0.039, 0.0098, 0.0024, 0.0006, 0.00015, and 0.000038 nM. Control wells were transfected with luciferase siRNA, Aha-1 siRNA, PLGF siRNA, or a control mix of unrelated siRNAs.

Branched DNA Assays—QuantiGene 2.0

After a 24-hour incubation with siRNA, media was removed and cells were lysed in 150 µl Lysis Mixture (1 volume lysis mixture, 2 volumes nuclease-free water) then incubated at 53° C. for 60 minutes. 80 µl Working Probe Set SOD1 (gene target) and 90 µl Working Probe Set GAPDH (endogenous control) and 20 µl or 10 µl of cell-lysate were then added to the Capture Plates. Capture Plates were incubated at 55° C. (for SOD1) and 53° C. (for GAPDH) (approx. 16-20 hrs). The next day, the Capture Plates were washed 3 times with at least 300 l of 1× Wash Buffer (nuclease-free water, Buffer Component 1 and Wash Buffer Component 2) (after the last wash, invert the plate and blot it against clean paper towels). 100 µl of pre-Amplifier Working Reagent was added to the SOD1 Capture Plates, which were sealed with aluminum foil and incubated for 1 hour at 55° C. Following a 1-hour incubation, the wash step was repeated, then 100 µl Amplifier Working Reagent was added to both SOD1 and GAPDH capture plates. After 1 hour of incubation at 55° C. (SOD1) or 53° C. (GAPDH), the wash and dry steps were repeated, and 100 µl Label Probe was added. Capture plates were incubated at 50° C. (SOD1) or 53° C. (GAPDH) for 1 hour. The plates were then washed with 1× Wash Buffer and dried, and then 100 µl Substrate was added to the Capture Plates. Luminescence was read using 1420 Luminescence Counter (WALLAC VICTOR Light, Perkin Elmer, Rodgau-Jügesheim, Germany) following 30 minutes incubation in the dark.

bDNA Data Analysis

For each SOD1 siRNA or control siRNA, four wells were transfected in parallel, and individual datapoints were collected from each well. For each well, the SOD1 mRNA level was normalized to the GAPDH mRNA level. The activity of a given SOD1 siRNA was expressed as percent SOD1 mRNA concentration (normalized to GAPDH mRNA) in treated cells, relative to the SOD1 mRNA concentration (normalized to GAPDH mRNA) averaged across control wells.

Table 4 provides the results from the in vitro HeLa screen where the SOD1 siRNAs, the sequences of which are given in Table 3, were tested at either 1 nM or 0.1 nM. The mean percentage of SOD1 mRNA (normalized to GAPDH mRNA) remaining in treated cells relative to controls, as well as the standard deviation, is shown in Table 4 for each SOD1 siRNA. A number of SOD1 siRNAs at 1 nM were effective at reducing SOD1 mRNA levels by more than 80% in HeLa cells. Furthermore, a number of SOD1 siRNAs at 0.1 nM were effective at reducing SOD1 mRNA levels by more than 80% in HeLa cells.

TABLE 4

Two dose results of in vitro screen of SOD1 siRNAs in HeLa cells for SOD1 gene expression inhibiting activity

| siRNA duplex ID | Remaining SOD1 mRNA [% of Control] 24 hr After 1 nM SOD1 siRNA | SD [%] | Remaining SOD1 mRNA [% of Control] 24 hr After 0.1 nM SOD1 siRNA | SD [%] |
|---|---|---|---|---|
| D-2741 | 87.2 | 2.7 | 70.6 | 3 |
| D-2742 | 86.9 | 4.3 | 79.5 | 8.5 |
| D-2743 | 89.6 | 3.6 | 80.6 | 8.8 |
| D-2744 | 83.8 | 7.2 | 75.9 | 8.5 |
| D-2745 | 95.1 | 9.1 | 84.1 | 6.8 |
| D-2746 | 111.3 | 3.6 | 92.0 | 7.2 |
| D-2747 | 100.0 | 6.1 | 92.9 | 4.4 |
| D-2748 | 100.4 | 3.1 | 91.6 | 12 |
| D-2749 | 87.1 | 2.9 | 96.4 | 13 |
| D-2750 | 94.2 | 7.1 | 93.1 | 8 |
| D-2751 | 85.4 | 7.2 | 96.1 | 8 |
| D-2752 | 27.2 | 3.6 | 70.2 | 6.5 |
| D-2753 | 25.5 | 4.8 | 67.5 | 4.5 |
| D-2754 | 23.2 | 4 | 70.2 | 2.3 |
| D-2755 | 36.6 | 3.7 | 75.5 | 11 |
| D-2756 | 9.1 | 0.7 | 29.2 | 2.6 |
| D-2757 | 3.9 | 0.6 | 9.0 | 1.8 |
| D-2758 | 6.4 | 1.1 | 13.9 | 2.8 |
| D-2759 | 6.7 | 1.1 | 14.1 | 1 |
| D-2760 | 32.3 | 3.4 | 61.9 | 8.8 |
| D-2761 | 12.9 | 3.6 | 41.7 | 8.3 |
| D-2762 | 16.9 | 2.6 | 41.2 | 10 |
| D-2763 | 5.7 | 1.3 | 10.5 | 3.4 |
| D-2764 | 9.2 | 2.7 | 19.5 | 4.9 |
| D-2765 | 13.6 | 1.9 | 29.4 | 8.8 |
| D-2766 | 8.7 | 1.1 | 28.1 | 6.6 |
| D-2767 | 10.4 | 1.6 | 24.7 | 5.9 |
| D-2768 | 13.0 | 1.4 | 27.7 | 7.3 |
| D-2769 | 25.3 | 1.9 | 57.4 | 7.5 |
| D-2770 | 14.9 | 1.6 | 35.5 | 4.4 |
| D-2771 | 11.4 | 1.8 | 32.6 | 8.6 |
| D-2772 | 10.6 | 1.3 | 27.9 | 4.7 |
| D-2773 | 14.3 | 1.4 | 35.7 | 3.1 |
| D-2774 | 7.1 | 1.3 | 23.0 | 1.5 |
| D-2775 | 9.8 | 0.9 | 31.3 | 3.3 |
| D-2776 | 11.1 | 2.9 | 31.3 | 5.3 |
| D-2777 | 47.8 | 5.5 | 80.9 | 4.6 |
| D-2778 | 7.4 | 0.6 | 26.5 | 4.2 |
| D-2779 | 7.9 | 0.6 | 17.9 | 3 |
| D-2780 | 12.5 | 1.3 | 31.7 | 5.6 |
| D-2781 | 16.3 | 2.3 | 39.1 | 8 |
| D-2782 | 10.2 | 3.1 | 25.4 | 3 |
| D-2783 | 13.5 | 3.5 | 33.4 | 6.5 |
| D-2784 | 12.3 | 2.5 | 36.3 | 5.4 |
| D-2785 | 14.6 | 3 | 30.5 | 7.4 |
| D-2786 | 16.2 | 3.5 | 42.6 | 8 |
| D-2787 | 14.4 | 4.2 | 37.3 | 6.5 |
| D-2788 | 9.8 | 3 | 21.6 | 6.6 |
| D-2789 | 18.5 | 5.9 | 48.9 | 12 |
| D-2790 | 11.6 | 3.8 | 28.1 | 5.6 |
| D-2791 | 8.9 | 1.8 | 26.6 | 5.6 |
| D-2792 | 8.1 | 1.4 | 25.6 | 5.3 |
| D-2793 | 9.3 | 1.6 | 26.6 | 3 |
| D-2794 | 8.9 | 1.9 | 25.8 | 4.2 |
| D-2795 | 22.6 | 3.4 | 59.5 | 9.9 |
| D-2796 | 15.1 | 0.7 | 43.0 | 1.9 |
| D-2797 | 21.1 | 2.5 | 43.0 | 1.3 |
| D-2798 | 10.4 | 1.2 | 28.0 | 5.1 |
| D-2799 | 11.0 | 1.2 | 29.8 | 3.3 |
| D-2800 | 21.3 | 2.4 | 52.4 | 4.7 |
| D-2801 | 12.3 | 3.3 | 28.7 | 4 |
| D-2802 | 8.4 | 1.8 | 18.8 | 3.7 |
| D-2803 | 5.9 | 1 | 12.1 | 4.1 |
| D-2804 | 11.8 | 1.6 | 28.9 | 7.5 |
| D-2805 | 13.5 | 2.6 | 34.5 | 7.5 |
| D-2806 | 5.5 | 1.1 | 10.4 | 2.5 |
| D-2807 | 8.5 | 1.3 | 24.2 | 6.6 |
| D-2808 | 9.5 | 1.5 | 26.0 | 1.4 |
| D-2809 | 7.5 | 0.9 | 17.7 | 2.8 |
| D-2810 | 12.1 | 2 | 43.1 | 8.3 |
| D-2811 | 5.6 | 0.8 | 16.7 | 7 |
| D-2812 | 14.2 | 1.4 | 42.5 | 8.2 |
| D-2813 | 29.0 | 3.4 | 66.7 | 13 |
| D-2814 | 35.7 | 3.5 | 73.4 | 15 |
| D-2815 | 30.3 | 1.9 | 74.3 | 12 |
| D-2816 | 14.6 | 2.1 | 47.2 | 5.1 |
| D-2817 | 27.5 | 1.8 | 70.5 | 6.6 |
| D-2818 | 9.6 | 0.8 | 32.9 | 7.2 |
| D-2819 | 9.0 | 0.8 | 29.1 | 3 |
| D-2820 | 10.8 | 1.4 | 38.7 | 3.5 |
| D-2821 | 5.8 | 0.4 | 19.4 | 6.1 |
| D-2822 | 10.5 | 2.5 | 46.3 | 6.8 |
| D-2823 | 3.5 | 1.1 | 18.8 | 3.5 |
| D-2824 | 9.9 | 3.2 | 43.8 | 0.8 |
| D-2825 | 6.6 | 2.6 | 29.7 | 1.1 |
| D-2826 | 8.0 | 1.9 | 40.6 | 7.2 |
| D-2827 | 7.0 | 1.2 | 25.2 | 4.5 |
| D-2828 | 6.4 | 2.2 | 22.4 | 1.7 |
| D-2829 | 14.8 | 2.7 | 45.5 | 7.4 |
| D-2830 | 9.4 | 2 | 28.5 | 6.5 |
| D-2831 | 8.6 | 2.8 | 28.4 | 6.6 |
| D-2832 | 12.3 | 3.2 | 43.4 | 3.2 |
| D-2833 | 20.5 | 5.2 | 66.7 | 9.1 |
| D-2834 | 10.7 | 2.5 | 35.9 | 2.2 |
| D-2835 | 11.6 | 2.4 | 37.7 | 4 |
| D-2836 | 24.1 | 3.3 | 57.0 | 4.2 |
| D-2837 | 98.7 | 12 | 96.7 | 4.3 |
| D-2838 | 20.5 | 4 | 49.5 | 1.4 |
| D-2839 | 10.0 | 2.4 | 31.9 | 4.3 |
| D-2840 | 50.2 | 8.3 | 89.2 | 7.4 |
| D-2841 | 70.8 | 11 | 87.1 | 7.9 |
| D-2842 | 79.7 | 21 | 90.9 | 3.6 |
| D-2843 | 24.2 | 1.2 | 57.2 | 8.4 |
| D-2844 | 21.5 | 6.4 | 51.4 | 1 |
| D-2845 | 12.9 | 2.2 | 39.4 | 7.3 |
| D-2846 | 10.2 | 2.6 | 30.5 | 2.6 |
| D-2847 | 40.5 | 9.7 | 70.0 | 6.5 |
| D-2848 | 41.8 | 7 | 63.7 | 6 |
| D-2849 | 24.7 | 6.8 | 51.3 | 8.1 |
| D-2850 | 79.4 | 7.5 | 76.5 | 16 |
| D-2851 | 28.1 | 6.5 | 72.0 | 8.8 |
| D-2852 | 13.8 | 2.1 | 56.9 | 4.8 |
| D-2853 | 32.1 | 9.5 | 72.2 | 12 |
| D-2854 | 21.5 | 3.9 | 58.8 | 10 |
| D-2855 | 39.8 | 10 | 75.4 | 5.5 |

TABLE 4-continued

Two dose results of in vitro screen of SOD1 siRNAs in
HeLa cells for SOD1 gene expression inhibiting activity

| siRNA duplex ID | Remaining SOD1 mRNA [% of Control] 24 hr After 1 nM SOD1 siRNA | SD [%] | Remaining SOD1 mRNA [% of Control] 24 hr After 0.1 nM SOD1 siRNA | SD [%] |
|---|---|---|---|---|
| D-2856 | 14.4 | 3.4 | 40.4 | 5.8 |
| D-2857 | 8.6 | 1 | 18.4 | 4.5 |
| D-2858 | 10.1 | 1.1 | 19.1 | 4.8 |
| D-2859 | 10.9 | 1.3 | 20.9 | 5.4 |
| D-2860 | 7.4 | 1.3 | 11.7 | 3.8 |
| D-2861 | 5.0 | 1.4 | 12.6 | 2.6 |
| D-2862 | 5.5 | 1 | 13.8 | 2.7 |
| D-2863 | 8.2 | 1.3 | 26.5 | 4.3 |
| D-2864 | 9.1 | 1.6 | 40.2 | 3.4 |
| D-2865 | 6.3 | 0.6 | 22.8 | 3.4 |
| D-2866 | 7.0 | 1.7 | 17.8 | 4.3 |
| D-2867 | 9.3 | 0.8 | 31.7 | 6.2 |
| D-2868 | 10.3 | 2.5 | 30.8 | 6.5 |
| D-2869 | 9.4 | 4.3 | 34.7 | 4.6 |
| D-2870 | 5.9 | 0.6 | 18.1 | 2.6 |
| D-2871 | 6.5 | 1.1 | 13.5 | 1.5 |
| D-2872 | 10.5 | 1 | 31.3 | 5.3 |
| D-2873 | 7.0 | 1.1 | 20.8 | 3.7 |
| D-2874 | 9.4 | 2.4 | 35.3 | 5.7 |
| D-2875 | 5.4 | 1.1 | 13.5 | 2.4 |
| D-2876 | 14.1 | 4.6 | 45.9 | 5.2 |
| D-2877 | 64.5 | 9.8 | 64.0 | 9 |
| D-2878 | 57.0 | 14 | 62.9 | 8.1 |
| D-2879 | 71.4 | 12 | 79.4 | 8.6 |
| D-2880 | 79.7 | 11 | 100.9 | 4.9 |
| D-2881 | 72.8 | 12 | 82.8 | 5.6 |
| D-2882 | 64.4 | 8.8 | 73.2 | 6.9 |
| D-2883 | 80.1 | 4.9 | 86.3 | 13 |
| D-2884 | 69.6 | 5.8 | 74.2 | 13 |
| D-2885 | 76.9 | 2 | 76.7 | 18 |
| D-2886 | 74.0 | 0.7 | 80.4 | 3.4 |
| D-2887 | 77.7 | 8.7 | 88.6 | 16 |
| D-2888 | 70.3 | 5.1 | 66.2 | 2.2 |
| D-2889 | 71.2 | 3 | 67.3 | 7.3 |
| D-2890 | 75.3 | 7.9 | 71.2 | 6.4 |
| D-2891 | 74.6 | 8.4 | 72.4 | 4.3 |
| D-2892 | 72.5 | 6.9 | 71.6 | 5.7 |
| D-2893 | 73.9 | 3.8 | 83.7 | 2.9 |
| D-2894 | 66.9 | 5.7 | 72.4 | 4.9 |
| D-2895 | 71.6 | 8.9 | 72.1 | 9 |
| D-2896 | 71.0 | 5.6 | 74.4 | 1.3 |
| D-2897 | 74.4 | 7.9 | 78.0 | 3.8 |
| D-2898 | 74.0 | 5.8 | 73.5 | 1.6 |
| D-2899 | 71.0 | 10 | 74.1 | 9.7 |
| D-2900 | 71.3 | 4.1 | 77.8 | 5.8 |
| D-2901 | 64.8 | 9.4 | 82.0 | 11 |
| D-2902 | 53.6 | 5.2 | 82.7 | 15 |
| D-2903 | 66.8 | 2.6 | 101.1 | 13 |
| D-2904 | 62.6 | 7.8 | 87.5 | 20 |
| D-2905 | 67.1 | 14 | 74.0 | 4.1 |
| D-2906 | 64.0 | 3.2 | 73.9 | 12 |
| D-2907 | 66.4 | 7.3 | 82.0 | 11 |
| D-2908 | 72.6 | 20 | 85.2 | 23 |
| D-2909 | 80.0 | 7.3 | 77.2 | 12 |

Twelve of the most active SOD1 siRNAs at 0.1 nM in HeLa cells were evaluated in dose-response experiments. Table 5 provides the IC50 concentrations resulting in 50% SOD1 mRNA suppression relative to control for these twelve selected SOD1 siRNAs in HeLa cells. These twelve SOD1 siRNAs were particularly potent in this experimental paradigm, and exhibited IC50 values between 1 and 8 pM.

TABLE 5

IC50 results of in vitro assay of SOD1 siRNAs in HeLa cells for SOD1 gene expression inhibiting activity

| siRNA duplex ID | IC50 Mean (pM) |
|---|---|
| D-2757 | 1 |
| D-2806 | 4 |
| D-2860 | 2 |
| D-2861 | 2 |
| D-2875 | 4 |
| D-2871 | 5 |
| D-2758 | 5 |
| D-2759 | 5 |
| D-2866 | 4 |
| D-2870 | 4 |
| D-2823 | 6 |
| D-2858 | 8 |

The dose response data from HeLa cells used to identify the IC50s for these twelve SOD1 siRNAs are presented in detail below in Table 6. All twelve siRNAs were determined to have pM IC50s in HeLa cells. The IC50 data for the SOD1 siRNAs in Table 5 are a summary of the data presented in Table 6 below.

TABLE 6

Dose response data for 12 SOD1 siRNAs in HeLa cells

| siRNA duplex ID | Remaining SOD1 mRNA (% of control) | | | | | | | | | | IC50 (nM) |
|---|---|---|---|---|---|---|---|---|---|---|---|
| | 10 nM | 2.5 nM | 0.6 nM | 0.16 nM | 0.039 nM | 0.0098 nM | 0.0024 nM | 0.0006 nM | 0.00015 nM | 0.000038 nM | |
| D-2757 | 2 | 2 | 2 | 3 | 6 | 16 | 33 | 57 | 77 | 86 | 0.001 |
| D-2806 | 2 | 3 | 3 | 6 | 13 | 32 | 59 | 83 | 90 | 105 | 0.004 |
| D-2860 | 5 | 5 | 5 | 6 | 10 | 22 | 50 | 68 | 87 | 92 | 0.002 |
| D-2861 | 4 | 4 | 4 | 5 | 10 | 25 | 51 | 73 | 81 | 92 | 0.002 |
| D-2875 | 4 | 4 | 4 | 7 | 15 | 34 | 62 | 78 | 82 | 92 | 0.004 |
| D-2871 | 4 | 5 | 4 | 8 | 18 | 43 | 62 | 78 | 87 | 90 | 0.005 |
| D-2758 | 5 | 5 | 5 | 9 | 17 | 41 | 70 | 81 | 97 | 111 | 0.005 |
| D-2759 | 4 | 4 | 4 | 7 | 15 | 35 | 63 | 82 | 87 | 94 | 0.005 |
| D-2866 | 3 | 3 | 4 | 8 | 17 | 39 | 54 | 79 | 80 | 76 | 0.004 |
| D-2870 | 4 | 5 | 5 | 8 | 18 | 41 | 59 | 77 | 93 | 101 | 0.004 |

TABLE 6-continued

Dose response data for 12 SOD1 siRNAs in HeLa cells

Remaining SOD1 mRNA (% of control)

| siRNA duplex ID | 10 nM | 2.5 nM | 0.6 nM | 0.16 nM | 0.039 nM | 0.0098 nM | 0.0024 nM | 0.0006 nM | 0.00015 nM | 0.000038 nM | IC50 (nM) |
|---|---|---|---|---|---|---|---|---|---|---|---|
| D-2823 | 3 | 3 | 4 | 7 | 20 | 42 | 65 | 81 | 86 | 92 | 0.006 |
| D-2858 | 5 | 5 | 5 | 9 | 21 | 46 | 72 | 82 | 88 | 94 | 0.008 |

Example 3. In Vitro Screen of Selected SOD1 siRNAs Against Endogenous SOD1 mRNA Expression in SH-SY5Y Cells, U87 Cells and Primary Human Astrocytes SH-SY5Y cells were obtained from ATCC (ATCC in Partnership with LGC Standards, Wesel, Germany) and cultured in Dulbecco's MEM (Biochrom GmbH, Berlin, Germany) supplemented to contain 15% FCS (Ultra-low IgG from GIBCO/Life Technologies), 1% L-Glutamine (Biochrom GmbH, Berlin, Germany) and 1% Pen/Strep (Biochrom GmbH, Berlin, Germany) at 37° C. in an atmosphere with 5% $CO_2$ in a humidified incubator.

U87MG cells were obtained from ATCC (ATCC in Partnership with LGC Standards, Wesel, Germany) and cultured in ATCC-formulated Eagle's Minimum Essential Medium (ATCC in Partnership with LGC Standards, Wesel, Germany) supplemented to contain 10% FCS (Ultra-low IgG from GIBCO/Life Technologies) and 1% Pen/Strep (Biochrom GmbH, Berlin, Germany) at 37° C. in an atmosphere with 5% $CO_2$ in a humidified incubator.

Primary human astrocytes were obtained from LONZA (Lonza Sales Ltd, Basel, Switzerland) and cultured in ABM Basal Medium (Lonza Sales Ltd, Basel, Switzerland) supplemented with AGM SingleQuot Kit (Lonza Sales Ltd, Basel, Switzerland) at 37° C. in an atmosphere with 5% $CO_2$ in a humidified incubator.

Transfection of SH-SY5Y cells, U87MG cells and primary human astrocytes with twelve selected siRNAs (D-2757, D-2806, D-2860, D-2861, D-2875, D-2871, D-2758, D-2759, D-2866, D-2870, D-2823, D-2858), and quantitation of SOD1 and GAPDH mRNA levels with bDNA were performed in a similar manner to that described for HeLa cells, except that the transfection reagents were Lipofectamine2000 (Invitrogen/Life Technologies) for SH-SY5Y cells, RNAiMAX (Invitrogen/Life Technologies) for U87 cells, and Lipofectamine2000 (Invitrogen/Life Technologies) for primary human astrocytes.

The dose response data from SH-SY5Y cells, U87MG cells and primary human astrocytes used to identify the IC50s for these twelve SOD1 siRNAs (D-2757, D-2806, D-2860, D-2861, D-2875, D-2871, D-2758, D-2759, D-2866, D-2870, D-2823, D-2858), are presented in detail below in Tables 7, 8 and 9, respectively. All twelve siRNAs were determined to have pM IC50s in U87 cells.

IC50 values are provided in Table 10. In primary human astrocytes, IC50s were higher than in SH-SY5Y and U87MG cells, in general.

TABLE 7

Dose response data for 12 SOD1 siRNAs in SH-SY5Y cells

| siRNA duplex ID | Remaining SOD1 mRNA (% of control) | | | | | | | | | | IC50 (nM) |
|---|---|---|---|---|---|---|---|---|---|---|---|
| | 10 nM | 2.5 nM | 0.6 nM | 0.16 nM | 0.039 nM | 0.0098 nM | 0.0024 nM | 0.0006 nM | 0.00015 nM | 0.000038 nM | |
| D-2757 | 8 | 13 | 16 | 22 | 36 | 55 | 72 | 92 | 107 | 114 | 0.013 |
| D-2806 | 11 | 12 | 15 | 26 | 40 | 71 | 103 | 121 | 117 | 131 | 0.025 |
| D-2860 | 11 | 15 | 17 | 26 | 42 | 63 | 79 | 86 | 92 | 96 | 0.022 |
| D-2861 | 12 | 14 | 16 | 19 | 37 | 60 | 82 | 83 | 87 | 94 | 0.017 |
| D-2875 | 20 | 25 | 35 | 59 | 79 | 92 | 96 | 95 | 99 | 104 | 0.234 |
| D-2871 | 15 | 19 | 23 | 42 | 71 | 87 | 95 | 94 | 99 | 96 | 0.103 |
| D-2758 | 24 | 35 | 36 | 58 | 91 | 96 | 134 | 123 | 105 | 94 | 0.369 |
| D-2759 | 10 | 11 | 16 | 25 | 43 | 67 | 85 | 94 | 104 | 108 | 0.026 |
| D-2866 | 17 | 19 | 24 | 42 | 72 | 93 | 93 | 102 | 103 | 101 | 0.105 |
| D-2870 | 19 | 22 | 26 | 40 | 62 | 88 | 100 | 105 | 105 | 105 | 0.078 |
| D-2823 | 11 | 16 | 25 | 47 | 64 | 84 | 91 | 98 | 105 | 95 | 0.099 |
| D-2858 | 16 | 21 | 25 | 46 | 68 | 91 | 92 | 95 | 103 | 116 | 0.106 |

TABLE 8

Dose response data for 12 SOD1 siRNAs in U87MG cells

| siRNA duplex ID | Remaining SOD1 mRNA (% of control) | | | | | | | | | | IC50 (nM) |
|---|---|---|---|---|---|---|---|---|---|---|---|
| | 10 nM | 2.5 nM | 0.6 nM | 0.16 nM | 0.039 nM | 0.0098 nM | 0.0024 nM | 0.0006 nM | 0.00015 nM | 0.000038 nM | |
| D-2757 | 3 | 4 | 3 | 4 | 5 | 8 | 19 | 50 | 86 | 99 | 0.001 |
| D-2806 | 4 | 3 | 3 | 3 | 4 | 8 | 18 | 49 | 81 | 106 | 0.001 |
| D-2860 | 4 | 4 | 5 | 5 | 6 | 8 | 20 | 46 | 72 | 93 | 0.001 |

TABLE 8-continued

Dose response data for 12 SOD1 siRNAs in U87MG cells

| siRNA duplex ID | Remaining SOD1 mRNA (% of control) | | | | | | | | | | IC50 (nM) |
|---|---|---|---|---|---|---|---|---|---|---|---|
| | 10 nM | 2.5 nM | 0.6 nM | 0.16 nM | 0.039 nM | 0.0098 nM | 0.0024 nM | 0.0006 nM | 0.00015 nM | 0.000038 nM | |
| D-2861 | 5 | 6 | 6 | 6 | 8 | 15 | 39 | 67 | 87 | 93 | 0.001 |
| D-2875 | 4 | 5 | 5 | 5 | 6 | 9 | 19 | 45 | 76 | 99 | 0.001 |
| D-2871 | 5 | 5 | 5 | 5 | 6 | 11 | 24 | 50 | 77 | 86 | 0.001 |
| D-2758 | 7 | 9 | 6 | 7 | 10 | 25 | 64 | 99 | 103 | 112 | 0.004 |
| D-2759 | 6 | 6 | 5 | 6 | 8 | 21 | 50 | 80 | 93 | 104 | 0.002 |
| D-2866 | 4 | 4 | 4 | 5 | 8 | 17 | 38 | 64 | 86 | 94 | 0.001 |
| D-2870 | 5 | 5 | 5 | 5 | 7 | 7 | 13 | 31 | 63 | 85 | 0.003 |
| D-2823 | 4 | 4 | 4 | 4 | 6 | 13 | 34 | 61 | 74 | 94 | 0.001 |
| D-2858 | 7 | 6 | 6 | 7 | 8 | 14 | 33 | 54 | 71 | 94 | 0.001 |

TABLE 9

Dose response data for 12 SOD1 siRNAs in Primary Human Astrocytes

| siRNA duplex ID | Remaining SOD1 mRNA (% of control) | | | | | | | | | | IC50 (nM) |
|---|---|---|---|---|---|---|---|---|---|---|---|
| | 10 nM | 2.5 nM | 0.6 nM | 0.16 nM | 0.039 nM | 0.0098 nM | 0.0024 nM | 0.0006 nM | 0.00015 nM | 0.000038 nM | |
| D-2757 | 29 | 30 | 35 | 48 | 66 | 87 | 95 | 101 | 95 | 103 | 0.123 |
| D-2806 | 26 | 32 | 35 | 47 | 63 | 78 | 87 | 95 | 95 | 98 | 0.113 |
| D-2860 | 29 | 38 | 39 | 51 | 68 | 82 | 94 | 93 | 94 | 101 | 0.192 |
| D-2861 | 27 | 33 | 38 | 47 | 62 | 73 | 88 | 93 | 96 | 102 | 0.114 |
| D-2875 | 25 | 28 | 39 | 47 | 72 | 80 | 100 | 105 | 105 | 118 | 0.151 |
| D-2871 | 25 | 34 | 42 | 52 | 63 | 83 | 97 | 100 | 97 | 108 | 0.182 |
| D-2758 | 27 | 29 | 31 | 41 | 51 | 71 | 86 | 91 | 95 | 98 | 0.049 |
| D-2759 | 34 | 39 | 41 | 53 | 70 | 83 | 97 | 101 | 98 | 103 | 0.219 |
| D-2866 | 30 | 32 | 35 | 46 | 65 | 78 | 84 | 87 | 92 | 95 | 0.118 |
| D-2870 | 34 | 34 | 38 | 48 | 71 | 74 | 82 | 91 | 92 | 98 | 0.163 |
| D-2823 | 27 | 31 | 40 | 53 | 67 | 80 | 84 | 86 | 92 | 97 | 0.186 |
| D-2858 | 29 | 30 | 37 | 55 | 72 | 91 | 93 | 100 | 104 | 104 | 0.197 |

The IC50 data for SOD1 siRNAs in Table 10 is a summary of the data presented in Tables 7, 8 and 9.

TABLE 10

IC50 results of in vitro assays of SOD1 siRNAs in SH-SY5Y cells, U87MG cells and primary human astrocytes for SOD1 gene expression inhibiting activity

| siRNA duplex ID | SH-SY5Y IC50 Mean (pM) | U87MG IC50 Mean (pM) | Primary Human Astrocytes IC 50 Mean (pM) |
|---|---|---|---|
| D-2757 | 13 | 1 | 123 |
| D-2806 | 25 | 1 | 113 |
| D-2860 | 22 | 1 | 192 |
| D-2861 | 17 | 1 | 114 |
| D-2875 | 234 | 1 | 151 |
| D-2871 | 103 | 1 | 182 |
| D-2758 | 369 | 4 | 49 |
| D-2759 | 26 | 2 | 219 |
| D-2866 | 105 | 1 | 118 |
| D-2870 | 78 | 3 | 163 |
| D-2823 | 99 | 1 | 186 |
| D-2858 | 106 | 1 | 197 |

Example 4. siRNA Targeting SOD1

The passenger-guide strand duplexes of the SOD1 siRNA found to be efficacious are engineered into expression vectors and transfected into cells of the central nervous system or neuronal cell lines. Even though overhang utilized in the siRNA knockdown study is a canonical dTdT for siRNA, the overhang in the constructs may comprise any dinucleotide overhang.

The cells used may be primary cells or derived from induced pluripotent stem cells (iPS cells).

SOD1 knockdown is then measured and deep sequencing performed to determine the exact passenger and guide strand processed from each construct administered in the expression vector.

A guide to passenger strand ratio is calculated to determine the efficiency of knockdown, e.g., of RNA Induced Silencing Complex (RISC) processing.

The N-terminus is sequenced to determine the cleavage site and to determine the percent homogeneous cleavage of the target. It is expected that cleavage will be higher than 90 percent.

HeLa cells are co-transfected in a parallel study to analyze in vitro knockdown of SOD1. A luciferase construct is used as a control to determine off-target effects.

Deep sequencing is again performed.

Example 5. Passenger and Guide Sequences Targeting SOD1

According to the present invention, SOD1 siRNAs were designed. These are given in Tables 11A and 11B. The passenger and guide strands are described in the tables. In Tables 11A and 11B, the "miR" component of the name of the sequence does not necessarily correspond to the sequence numbering of miRNA genes (e.g., VOYmiR-101 is the name of the sequence and does not necessarily mean that miR-101 is part of the sequence).

TABLE 11A

| Passenger and Guide Sequences (5'-3') | | | | | | | |
|---|---|---|---|---|---|---|---|
| Name | Duplex ID | SS ID | Passenger | Passenger SEQ ID | AS ID | Guide | Guide SEQ ID |
| VOYpre-001_D - 2806_Starting construct (18 native nucleotides and position 19 is C; 3' terminal CC dinucleotide) | D-2910 | 7752 | CAAUGUG ACUGCUG ACAACCC | 342 | 7753 | UUUGU CAGCA GUCAC AUUGU U | 343 |
| VOYpre-002_D-2806_p19MMU (position 19 U to form mismatch) | D-2911 | 7754 | CAAUGUG ACUGCUG ACAAUCC | 344 | 7753 | UUUGU CAGCA GUCAC AUUGU U | 343 |
| VOYpre-003_D-2806_p19GUpair (position 19 is G to form GU pair) | D-2912 | 7755 | CAAUGUG ACUGCUG ACAAGCC | 345 | 7753 | UUUGU CAGCA GUCAC AUUGU U | 343 |
| VOYpre-004_D-2806_p19AUpair (position 19 is A to form AU pair) | D-2913 | 7756 | CAAUGUG ACUGCUG ACAAACC | 346 | 7753 | UUUGU CAGCA GUCAC AUUGU U | 343 |
| VOYpre-005_D-2806_CMM (central mismatch) | D-2914 | 7757 | CAAUGUG ACAGCUG ACAAACC | 347 | 7753 | UUUGU CAGCA GUCAC AUUGU U | 343 |
| VOYpre-006_D-2806_p19DEL (position 19 deleted) | D-2915 | 7758 | CAAUGUG ACUGCUG ACAACC | 348 | 7753 | UUUGU CAGCA GUCAC AUUGU U | 343 |
| VOYpre-007_D-2806_p19ADD (nucleotide added at position 19; addition is U; keep C and terminal CC dinucleotide) | D-2916 | 7759 | CAAUGUG ACUGCUG ACAAUCC C | 349 | 7753 | UUUGU CAGCA GUCAC AUUGU U | 343 |
| VOYpre-008_D-2806_Uloop | D-2917 | 7752 | CAAUGUG ACUGCUG ACAACCC | 342 | 7753 | UUUGU CAGCA GUCAC AUUGU U | 343 |
| VOYpre-009_D-2806_AUloop | D-2918 | 7752 | CAAUGUG ACUGCUG ACAACCC | 342 | 7753 | UUUGU CAGCA GUCAC AUUGU U | 343 |
| VOYpre-010_D -2806_mir-22-loop | D-2919 | 7760 | CAAUGUG ACUGCUG ACAACAC | 350 | 7753 | UUUGU CAGCA GUCAC AUUGU U | 343 |
| VOYmiR-101_pre-001 hsa-mir-155; D-2806 | D-2923 | 7752 | CAAUGUG ACUGCUG ACAACCC | 342 | 7753 | UUUGU CAGCA GUCAC AUUGU U | 343 |
| VOYmiR-102_pre-001 Engineered; D-2806; let-7b stem | D-2924 | 7752 | CAAUGUG ACUGCUG ACAACCC | 342 | 7753 | UUUGU CAGCA GUCAC AUUGU U | 343 |

TABLE 11A-continued

Passenger and Guide Sequences (5'-3')

| Name | Duplex ID | SS ID | Passenger | Passenger SEQ ID | AS ID | Guide | Guide SEQ ID |
|---|---|---|---|---|---|---|---|
| VOYmiR-103_pre-002 Engineered; D-2806_p19M MU; let-7b stem | D-2925 | 7754 | CAAUGUG ACUGCUG ACAAUCC | 344 | 7753 | UUUGU CAGCA GUCAC AUUGU U | 343 |
| VOYmiR-104_pre-003 Engineered; D-2806_p19GUpair; let-7b stem | D-2926 | 7755 | CAAUGUG ACUGCUG ACAAGCC | 345 | 7753 | UUUGU CAGCA GUCAC AUUGU U | 343 |
| VOYmiR-105_pre-004 Engineered; D-2806_p19AUpair; let-7b stem | D-2927 | 7756 | CAAUGUG ACUGCUG ACAAACC | 346 | 7753 | UUUGU CAGCA GUCAC AUUGU U | 343 |
| VOYmiR-106_pre-005 Engineered; D-stem 2806_CMM; let-7b | D-2928 | 7757 | CAAUGUG ACAGCUG ACAAACC | 347 | 7753 | UUUGU CAGCA GUCAC AUUGU U | 343 |
| VOYmiR-107_pre-006 Engineered; D-2806_p19DEL; let-7b stem | D-2929 | 7758 | CAAUGUG ACUGCUG ACAACC | 348 | 7753 | UUUGU CAGCA GUCAC AUUGU U | 343 |
| VOYmiR-108_pre-007 Engineered; D-2806_p19ADD; let-7b stem | D-2930 | 7765 | CAAUGUG ACUGCUG ACAAUCC C | 355 | 7753 | UUUGU CAGCA GUCAC AUUGU U | 343 |
| VOYmiR-109_pre-008 Engineered; D-2806_Uloop; let-7b stem | D-2931 | 7752 | CAAUGUG ACUGCUG ACAACCC | 342 | 7753 | UUUGU CAGCA GUCAC AUUGU U | 343 |
| VOYmiR-110_pre-009 Engineered; D-2806_AUloop; let-7b stem | D-2932 | 7752 | CAAUGUG ACUGCUG ACAACCC | 342 | 7753 | UUUGU CAGCA GUCAC AUUGU U | 343 |
| VOYmiR-111_pre-010 Engineered; D-2806_mir-22-loop; let-7b stem | D-2933 | 7760 | CAAUGUG ACUGCUG ACAACAC | 350 | 7753 | UUUGU CAGCA GUCAC AUUGU U | 343 |
| VOYmiR-112_pre-001 Engineered; PD; D-2806; let-7b basal-stem instability | D-2934 | 7752 | CAAUGUG ACUGCUG ACAACCC | 342 | 7753 | UUUGU CAGCA GUCAC AUUGU U | 343 |
| VOYmiR-113_pre-002 Engineered; D-2806_p19M MU; let-7b basal-stem instability | D-2935 | 7754 | CAAUGUG ACUGCUG ACAAUCC | 344 | 7753 | UUUGU CAGCA GUCAC AUUGU U | 343 |
| VOYmiR-114_pre-005 Engineered; D-2806_CMM; let-7b basal-stem instability | D-2936 | 7757 | CAAUGUG ACAGCUG ACAAACC | 347 | 7753 | UUUGU CAGCA GUCAC AUUGU U | 343 |
| VOYmiR-115_pre-010 Engineered; D- | D-2937 | 7760 | CAAUGUG ACUGCUG | 350 | 7753 | UUUGU CAGCA | 343 |

TABLE 11A-continued

Passenger and Guide Sequences (5'-3')

| Name | Duplex ID | SS ID | Passenger | Passenger SEQ ID | AS ID | Guide | Guide SEQ ID |
|---|---|---|---|---|---|---|---|
| 2806_mir-22-loop; let-7b basal-stem instability | | | ACAACAC | | | GUCACAUUGUU | |
| VOYmiR-116_pre-003 Engineered; D-2806_p19GUpair; let-7b basal-stem instability | D-2938 | 7755 | CAAUGUGACUGCUGACAAGCC | 345 | 7753 | UUUGUCAGCAGUCACAUUGUU | 343 |
| VOYmiR-117_pre-001 Engineered; D-2757; let-7b stem | D-2939 | 7766 | CGACGAAGGCCGUGUGCGCCC | 356 | 7767 | UCGCACACGGCCUUCGUCGUU | 357 |
| VOYmiR-118_pre-001 Engineered; D-2823; let-7b stem | D-2940 | 7768 | UGACUUGGGCAAAGGUGGCCC | 358 | 7769 | UCCACCUUUGCCCAAGUCAUU | 359 |
| VOYmiR-119_pre-001 Engineered; D-2866; let-7b stem | D-2941 | 7770 | AACUCAUCUGUUAUCCUGCCC | 360 | 7771 | UCAGGAUAACAGAUGAGUUUU | 361 |
| VOYmiR-127 | D-2942 | 7752 | CAAUGUGACUGCUGACAACCC | 342 | 7753 | UUUGUCAGCAGUCACAUUGUU | 343 |
| VOYmiR-102.860 | D-2943 | 7772 | CCCCUUAACUCAUCUGUUCCC | 362 | 7773 | UAACAGAUGAGUUAAGGGGU | 363 |
| VOYmiR102.861 | D-2944 | 7774 | CCCUUAACUCAUCUGUUACCC | 364 | 7775 | UUAACAGAUGAGUUAAGGGU | 365 |
| VOYmiR-102.866 | D-2945 | 7776 | AACUCAUCUGUUAUCUUGCCC | 366 | 7771 | UCAGGAUAACAGAUGAGUUUU | 361 |
| VOYmiR-102.870 | D-2946 | 7777 | GCUGUGGAAAUGUAUCUUCCC | 367 | 7778 | UAGGAUACAUUUCUACAGCUU | 368 |
| VOYmiR-102.823 | D-2947 | 7779 | UGACUUGGGCAAAGGUGAGCC | 369 | 7769 | UCCACCUUUGCCCAAGUCAUU | 359 |
| VOYmiR-104.860 | D-2948 | 7780 | CCCCUUAACUCAUCUGUUGCC | 370 | 7773 | UAACAGAUGAGUUAAGGGGU | 363 |
| VOYmiR-104.861 | D-2949 | 7781 | CCCUUAACUCAUCUGUUAGCC | 371 | 7775 | UUAACAGAUGAGUUAAGGGU | 365 |

TABLE 11A-continued

Passenger and Guide Sequences (5'-3')

| Name | Duplex ID | SS ID | Passenger | Passenger SEQ ID | AS ID | Guide | Guide SEQ ID |
|---|---|---|---|---|---|---|---|
| VOYmiR-104.866 | D-2950 | 7782 | AACUCAUCUGUUAUCUUAGCC | 372 | 7771 | UCAGGAUAACAGAUGAGUUUU | 361 |
| VOYmiR-104.870 | D-2951 | 7783 | GCUGUGGAAAUGUAUCUUGCC | 373 | 7778 | UAGGAUACAUUUCUACAGCUU | 368 |
| VOYmiR-104.823 | D-2952 | 7784 | UGACUUGGGCAAAGGUAGGCC | 374 | 7769 | UCCACCUUUGCCCAAGUCAUU | 359 |
| VOYmiR-109.860 | D-2953 | 7772 | CCCCUUAACUCAUCUGUUCCC | 362 | 7773 | UAACAGAUGAGUUAAGGGGUU | 363 |
| VOYmiR-104.861 | D-2954 | 7774 | CCCUUAACUCAUCUGUUACCC | 364 | 7775 | UUAACAGAUGAGUUAAGGGUU | 365 |
| VOYmiR-104.866 | D-2955 | 7776 | AACUCAUCUGUUAUCUUGCCC | 366 | 7771 | UCAGGAUAACAGAUGAGUUUU | 361 |
| VOYmiR-109.870 | D-2956 | 7777 | GCUGUGGAAAUGUAUCUUCCC | 367 | 7778 | UAGGAUACAUUUCUACAGCUU | 368 |
| VOYmiR-109.823 | D-2957 | 7779 | UGACUUGGGCAAAGGUGAGCC | 369 | 7769 | UCCACCUUUGCCCAAGUCAUU | 359 |
| VOYmiR-114.860 | D-2958 | 7785 | CCCCUUAACACAUCUGUUACC | 375 | 7773 | UAACAGAUGAGUUAAGGGGUU | 363 |
| VOYmiR-114.861 | D-2959 | 7786 | CCCUUAACUGAUCUGUUACC | 376 | 7775 | UUAACAGAUGAGUUAAGGGUU | 365 |
| VOYmiR-114.866 | D-2960 | 7787 | AACUCAUCUCUUAUCUUGCCC | 377 | 7771 | UCAGGAUAACAGAUGAGUUUU | 361 |
| VOYmiR-114.870 | D-2961 | 7788 | GCUGUGGAAUUGUAUCUUGCC | 378 | 7778 | UAGGAUACAUUUCUACAGCUU | 368 |
| VOYmiR-114.823 | D-2962 | 7789 | UGACUUGGGGAAAG... | 379 | 7769 | UCCACCUUUG... | 359 |

TABLE 11A-continued

| Name | Duplex ID | SS ID | Passenger | Passenger SEQ ID | AS ID | Guide | Guide SEQ ID |
|---|---|---|---|---|---|---|---|
| | | | GUGAGCC | | | CCCAA GUCAU U | |
| VOYmiR-116.860 | D-2963 | 7780 | CCCCUUA ACUCAUC UGUUGCC | 370 | 7773 | UAACA GAUGA GUUAA GGGGU U | 363 |
| VOYmiR-116.861 | D-2964 | 7781 | CCCUUAA CUCAUCU GUUAGCC | 371 | 7775 | UUAAC AGAUG AGUUA AGGGU U | 365 |
| VOYmiR-116.866 | D-2965 | 7790 | AACUCAU CUGUUAU CUUGGCC | 380 | 7771 | UCAGG AUAAC AGAUG AGUUU U | 361 |
| VOYmiR-116.870 | D-2966 | 7783 | GCUGUGG AAAUGUA UCUUGCC | 373 | 7778 | UAGGA UACAU UUCUA CAGCU U | 368 |
| VOYmiR-116.823 | D-2967 | 7784 | UGACUUG GGCAAAG GUAGGCC | 374 | 7769 | UCCAC CUUUG CCCAA GUCAU U | 359 |
| VoymiR-127.860 | D-2968 | 7791 | CCCCUUA ACUCAUU UGUUCCC | 381 | 7773 | UAACA GAUGA GUUAA GGGGU U | 363 |
| VoymiR-127.861 | D-2969 | 7774 | CCCUUAA CUCAUCU GUUACCC | 364 | 7775 | UUAAC AGAUG AGUUA AGGGU U | 365 |
| VoymiR-127.866 | D-2970 | 7776 | AACUCAU CUGUUAU CUUGCCC | 366 | 7771 | UCAGG AUAAC AGAUG AGUUU U | 361 |
| VoymiR-127.870 | D-2971 | 7777 | GCUGUGG AAAUGUA UCUUCCC | 367 | 7778 | UAGGA UACAU UUCUA CAGCU U | 368 |
| VoymiR-127.823 | D-2972 | 7792 | UGACUUG GGCAAAG GUAGCCC | 382 | 7769 | UCCAC CUUUG CCCAA GUCAU U | 359 |
| VOYmiR-120 | D-2973 | 7793 | CAAUGUG ACUGCUG ACAAA | 383 | 7794 | UUUGU CAGCA GUCAC AUUGU C | 384 |

TABLE 11B

Passenger and Guide Sequences (5'-3')

| Name | Duplex ID | SS ID | Passenger | Passenger SEQ ID | AS ID | Guide | Guide SEQ ID |
|---|---|---|---|---|---|---|---|
| VOYpre-011_D-2806_passenger-guide strand swap with terminal 3' C on passenger strand | D-2920 | 7761 | UUUGUCA GCAGUCA CAUUGUC | 351 | 7762 | CAAUG UGACU GCUGA CAAAU C | 352 |
| VOYpre-012_D-2806_passenger-guide strand swap with terminal 3' C on passenger strand | D-2921 | 7761 | UUUGUCA GCAGUCA CAUUGUC | 351 | 7763 | CAAUG UGACU GCUGA CAAUU C | 353 |
| VOYpre -013_D-2806_passenger-guide strand swap with terminal 3' C on passenger strand | D-2922 | 7764 | UUUGUCA GCAGUCA CAUUGAC | 354 | 7762 | CAAUG UGACU GCUGA CAAAU C | 352 |

Example 6. SOD1 siRNA Constructs in AAV-miRNA Vectors

The passenger-guide strand duplexes of the SOD1 siRNA listed in Table 11 are engineered into AAV-miRNA expression vectors. The construct from ITR to ITR, recited 5' to 3', comprises a mutant ITR, a promoter (either a CMV, a U6 or the CB6 promoter (which includes a CMVie enhancer, a CBA promoter and an SV40 intron), the passenger and guide strand (with a loop between the passenger and guide strand, a 5' flanking region before the passenger strand and a 3' flanking region after the guide strand) from Table 11, a rabbit globin polyA and wild type ITR. In vitro and in vivo studies are performed to test the efficacy of the AAV-miRNA expression vectors.

Example 7. Activity of Constructs in HeLa Cells

Seven of the SOD1 siRNA constructs described in Example 6 (VOYmiR-103, VOYmiR-105, VOYmiR-108, VOYmiR-114, VOYmiR-119, VOYmiR-120, and VOYmiR-127) and a control of double stranded mCherry were transfected in HeLa to test the activity of the constructs.

A. Passenger and Guide Strand Activity

The seven SOD1 siRNA constructs and a control of double stranded mCherry were transfected into HeLa cells. After 48 hours the endogenous mRNA expression was evaluated. All seven of the SOD1 siRNA constructs showed high activity of the guide strand with 75-80% knock-down and low to no activity of the passenger strand. Guide strands of the SOD1 siRNA candidate vectors showed high activity, yielding 75-80% knockdown of SOD1, while passenger strands demonstrated little to no activity.

B. Activity of Constructs on SOD1

The seven SOD1 siRNA constructs and a control of double stranded mCherry (dsCherry) were transfected into HeLa cells at a MOI of 1e4 vg/cell, 1e3 vg/cell, or 1e2 vg/cell. After 72 hours the endogenous mRNA expression was evaluated. All seven of the SOD1 siRNA constructs showed efficient knock-down at 1e3 vg/cell. Most of the SOD1 siRNA constructs showed high activity (75-80% knock-down) as shown in FIG. 1.

Example 8. Activity of Constructs in HEK Cells

Thirty of the SOD1 siRNA constructs described in Example 6 (VOYmiR-102.860, VOYmiR-102.861, VOYmiR-102.866, VOYmiR-102.870, VOYmiR-102.823, VOYmiR-104.860, VOYmiR-104.861, VOYmiR-104.866, VOYmiR-104.870, VOYmiR-104.823, VOYmiR-109.860, VOYmiR-109.861, VOYmiR-109.866, VOYmiR-109.870, VOYmiR-109.823, VOYmiR-114.860, VOYmiR-114.861, VOYmiR-114.866, VOYmiR-114.870, VOYmiR-114.823, VOYmiR-116.860, VOYmiR-116.861, VOYmiR-116.866, VOYmiR-116.870, VOYmiR-116.823, VOYmiR-127.860, VOYmiR-127.861, VOYmiR-127.866, VOYmiR-127.870, VOYmiR-127.823) and a control of VOYmiR-114 and double stranded mCherry were transfected in cells to test the activity of the constructs.

A. Passenger and Guide Strand Activity in HEK293

Figure 2:
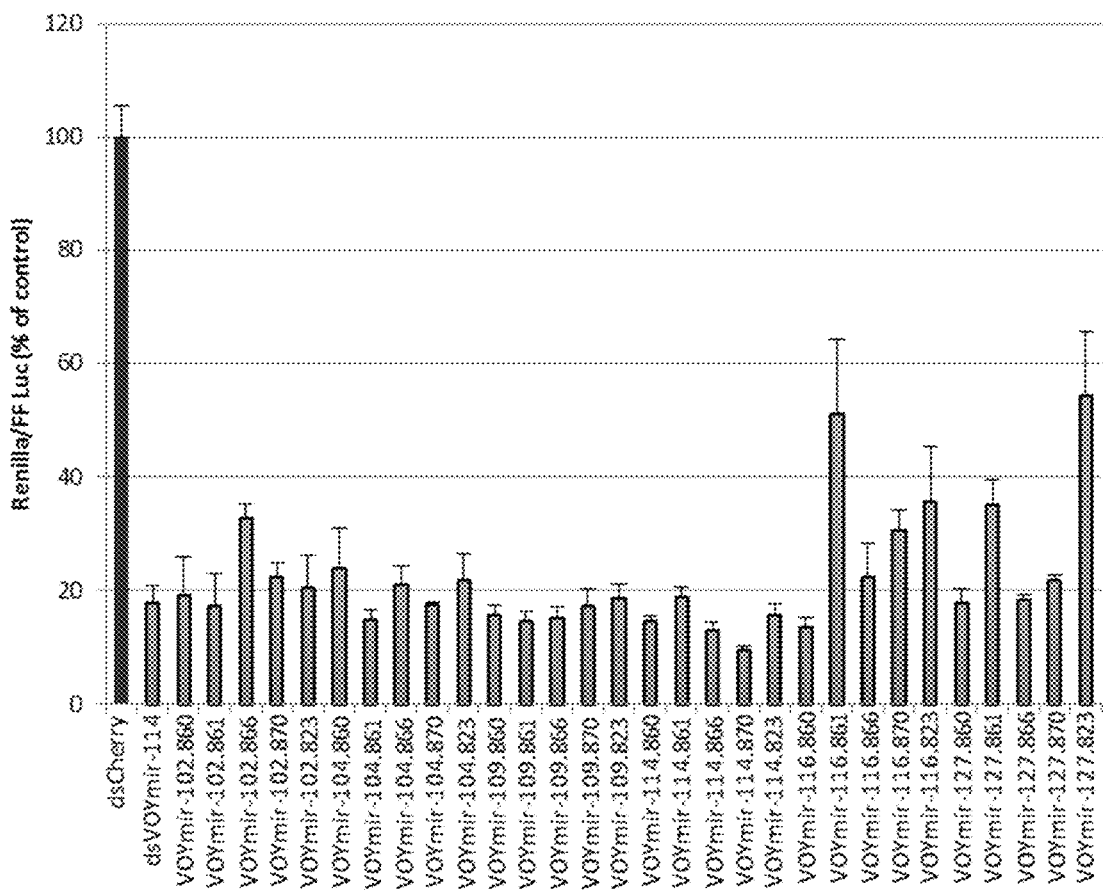
FIG. 2 is a histogram showing the activity of the guide strand of the modulatory polynucleotides encoded in an AAV vector in HEK293T cells.
Figure 3:
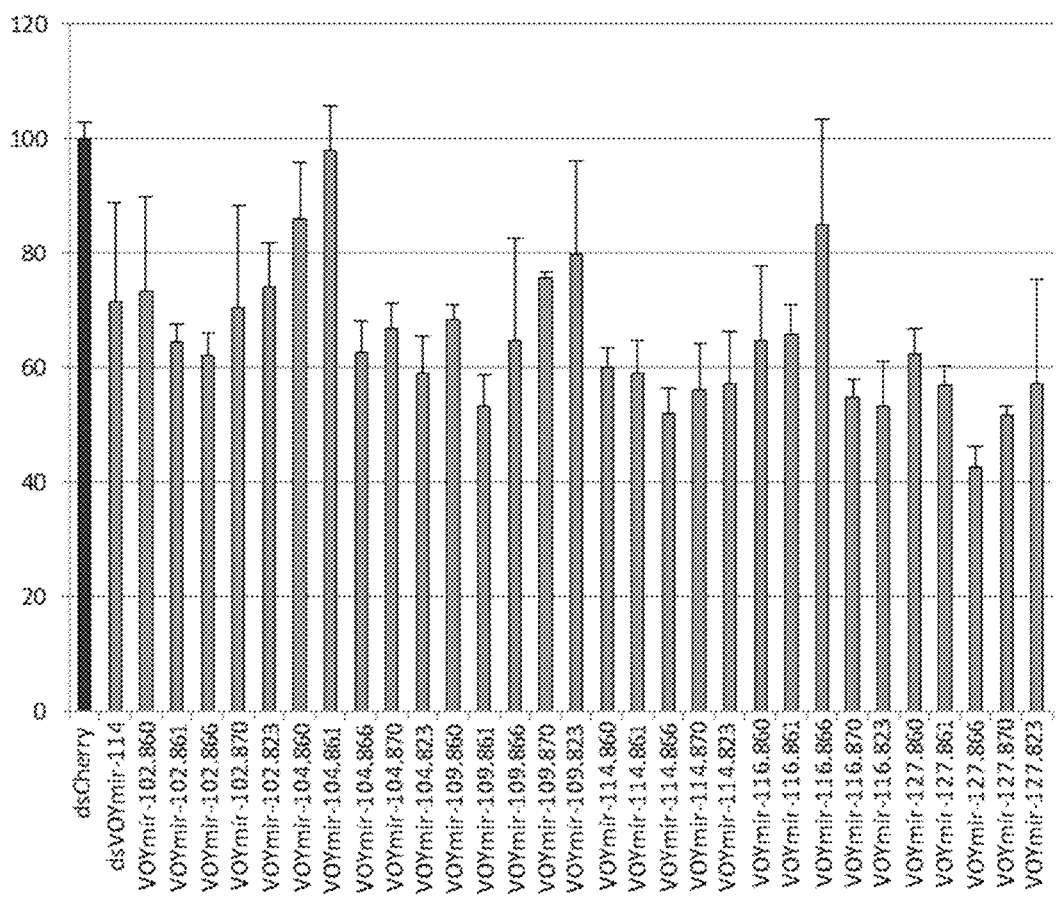
FIG. 3 is a histogram showing the activity of the passenger strand of the modulatory polynucleotides encoded in an AAV vector in HEK293T cells.

The thirty constructs and two controls were transfected into HEK293T cells. After 24 hours the endogenous mRNA expression was evaluated. Most of the constructs showed high activity of the guide strand (FIG. 2) and low to no activity of the passenger strand (FIG. 3).

B. Passenger and Guide Strand Activity in HeLa

Figure 4:
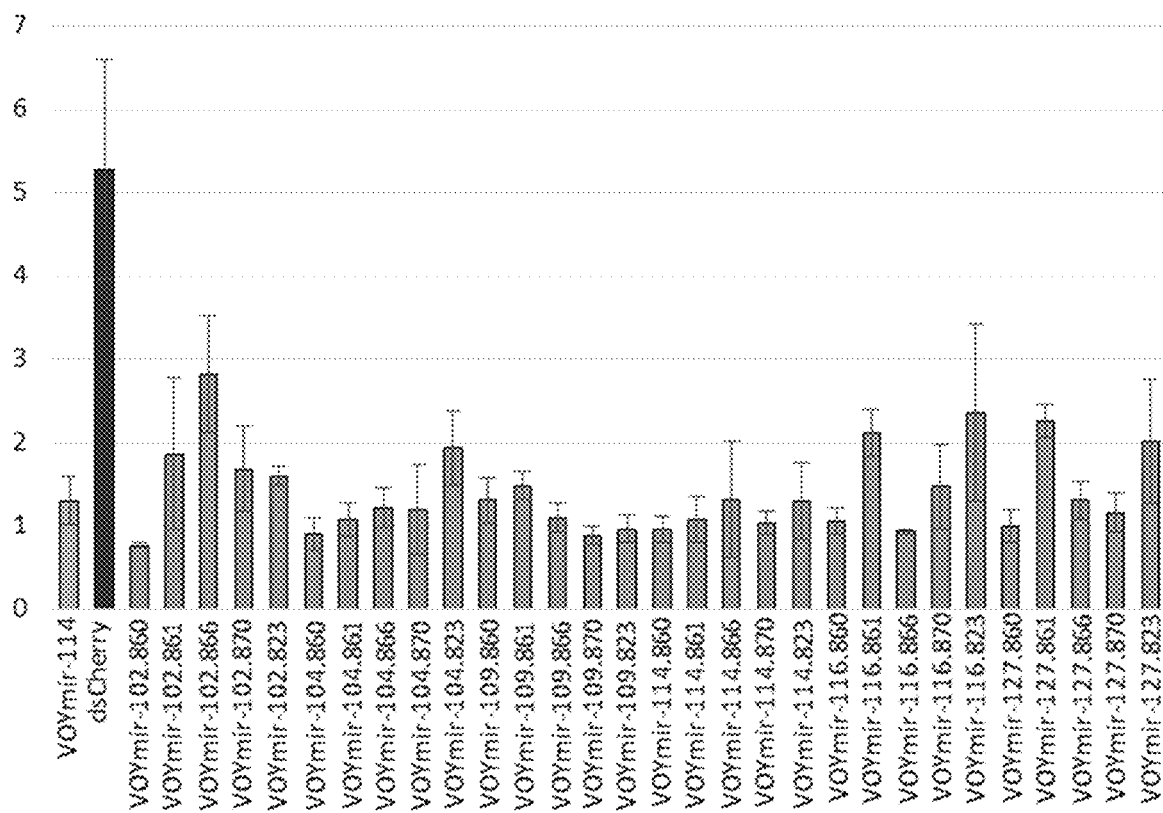
FIG. 4 is a histogram showing the activity of the guide strand of the modulatory polynucleotides encoded in an AAV vector in HeLa cells.
Figure 5:
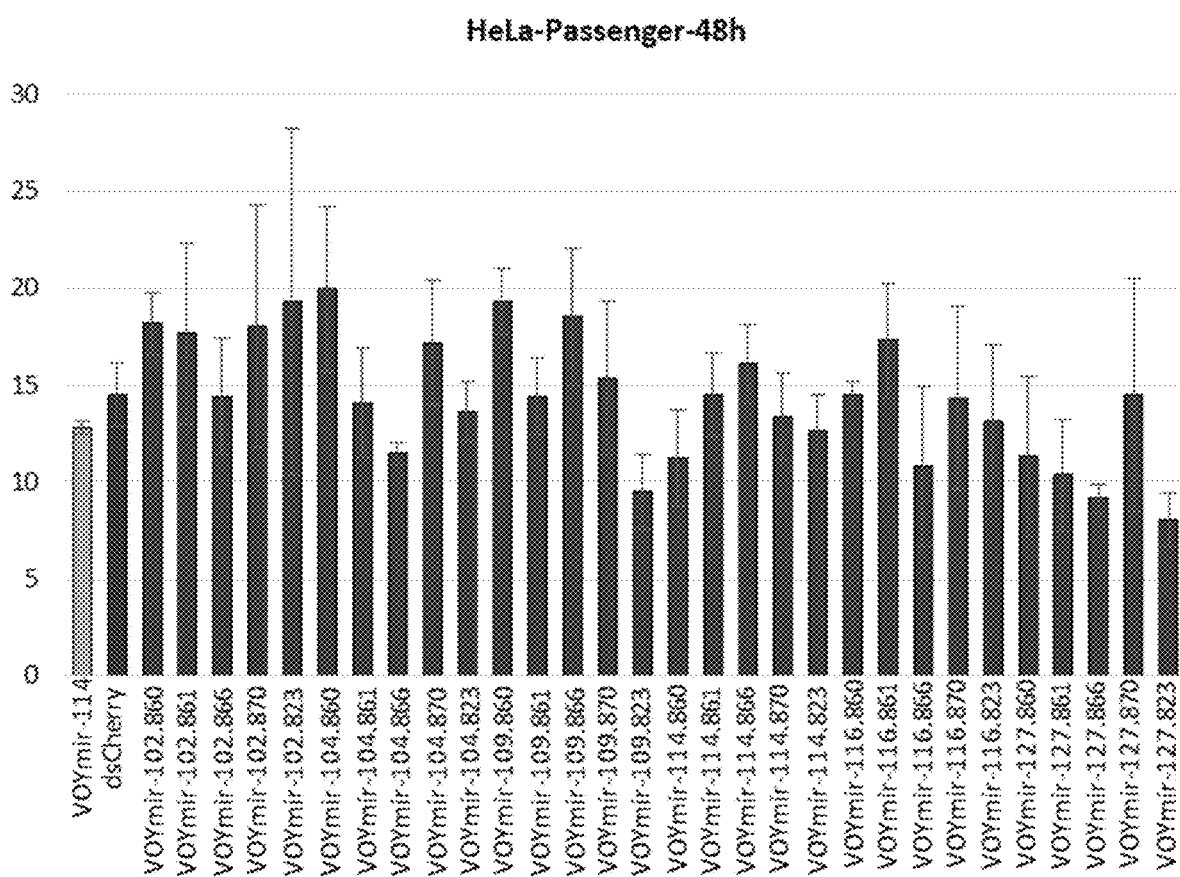
FIG. 5 is a histogram showing the activity of the passenger strand of the modulatory polynucleotides encoded in an AAV vector in HeLa cells.

The thirty constructs and two controls were transfected into HeLa cells. After 48 hours the endogenous mRNA expression was evaluated. Most of the constructs showed high activity of the guide strand (FIG. 4) and low to no activity of the passenger strand (FIG. 5).

C. HeLa and HEK293 Correlation

The knock-down of the thirty constructs were similar between the HeLa and HEK293 cells. The thirty constructs showed knock-down for the guide strand for the constructs (See FIGS. 2 and 4). Most of the guide strands of the constructs showed 70-90% knock-down.

D. Capsid Selection

The top constructs from the HeLa and HEK293 are packaged in AAVs and will undergo HeLa infection. To determine the best AAV to package the constructs, mCherry packaged in either AAV2 or AAV-DJ8 was infected into HeLa cells at a MOI of 10 vg/cell, 1e2 vg/cell, 1e3 vg/cell, 1e4 vg/cell or 1e5 vg/cell and the expression was evaluated at 40 hours. AAV2 was selected as the capsid to package the top constructs.

E. AAV2 Production

The top constructs from the HeLa and HEK293 are packaged in AAV2 (1.6 kb) and a control of double stranded mCherry (dsmCherry) was also packaged. The packaged constructs underwent Idoixanol purification prior to analysis. The AAV titer is shown in Table 12.

TABLE 12

AAV Titer

| Construct | AAV Titer (genomes per ul) |
|---|---|
| VOYmir-102.860 | 5.5E+08 |
| VOYmir-102.861 | 1.0E+09 |
| VOYmir-102.823 | 9.1E+08 |
| VOYmir-104.861 | 1.2E+09 |
| VOYmir-104.866 | 8.0E+08 |
| VOYmir-104.823 | 5.7E+08 |
| VOYmir-109.860 | 3.1E+08 |
| VOYmir-109.861 | 8.9E+08 |
| VOYmir-109.866 | 6.0E+08 |
| VOYmir-109.823 | 6.0E+08 |
| VOYmir-114.860 | 4.7E+08 |
| VOYmir-114.861 | 3.7E+08 |
| VOYmir-114.866 | 1.0E+09 |
| VOYmir-144.823 | 1.7E+09 |
| VOYmir-116.860 | 1.0E+09 |
| VOYmir-116.866 | 9.1E+08 |
| VOYmir-127.860 | 1.2E+09 |
| VOYmir-127.866 | 9.0E+08 |
| dsmCherry | 1.2E+09 |

Figure 6:
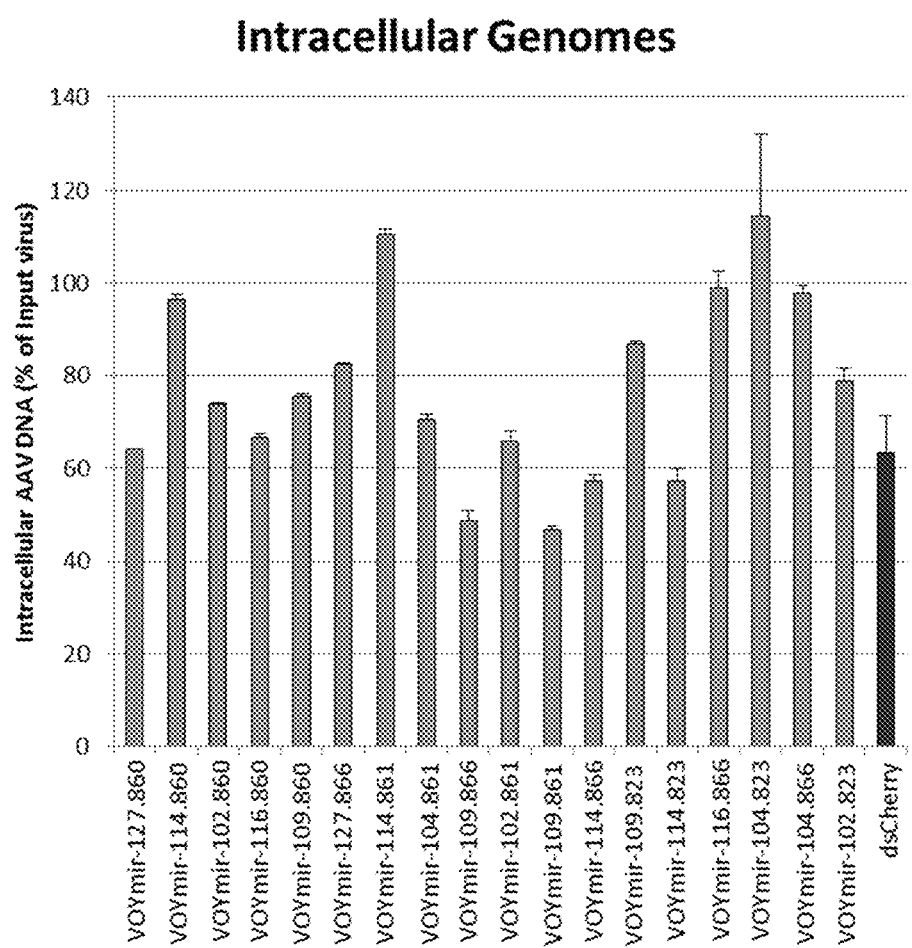
FIG. 6 is a histogram for the intracellular AAV DNA.

The effect of transduction on SOD1 knock-down in HeLa cells is shown in FIG. 6. In addition, in HeLa cells, a larger MOI (1.0E+04 compared to 1.0E+05) did not show increased knock-down for every construct.

F. Activity of Constructs in Human Motor Neuron Progenitors (HMNPs)

Figure 7:
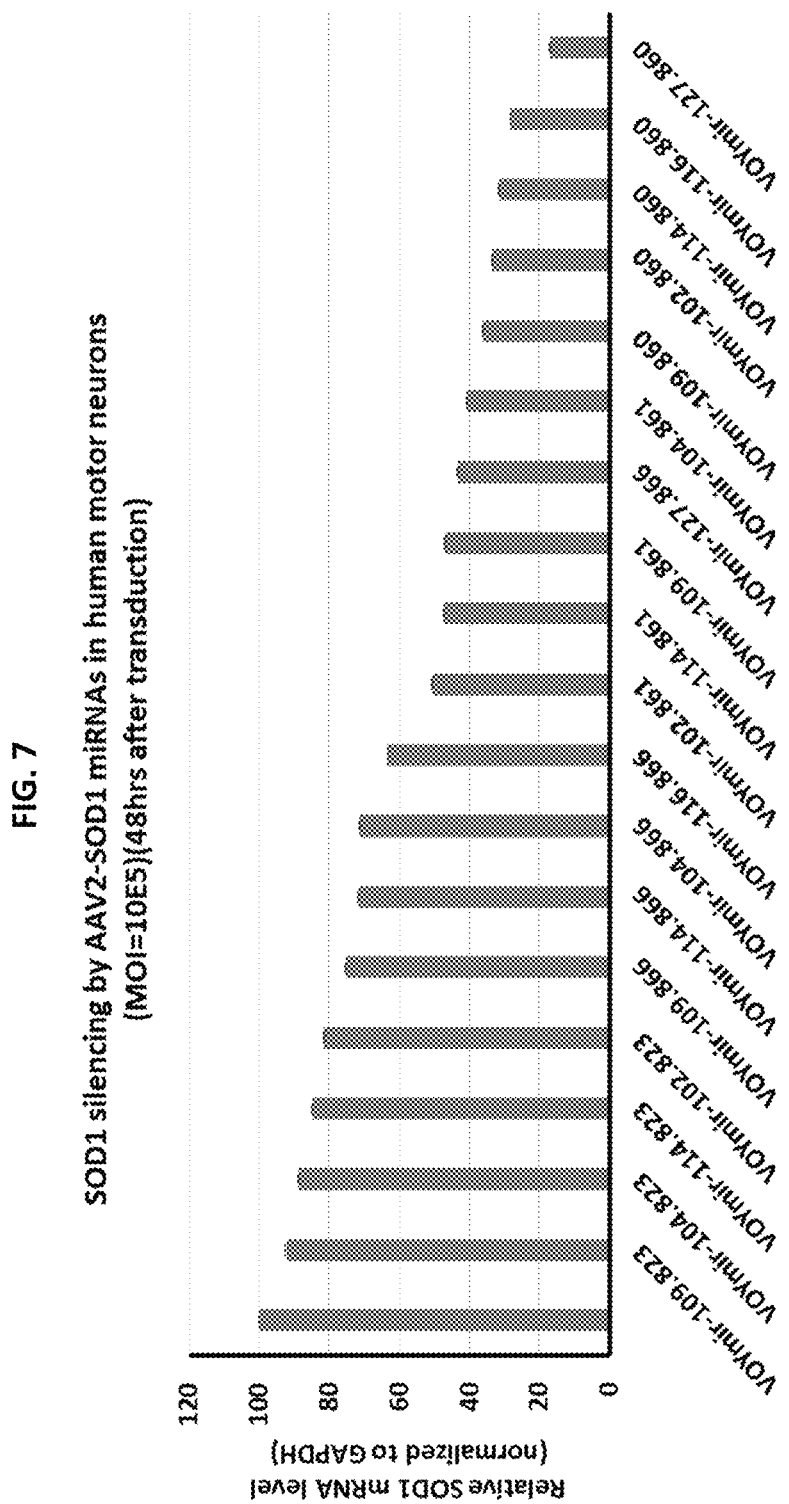
FIG. 7 is a histogram showing the activity of the constructs encoded in an AAV vector in human motor neurons.

The top 18 pri-miRNA constructs as described in Example 8E and a control of mCherry were infected into human motor neuron progenitor (HMNP) cells at a MOI of 10E5. After 48 hours the endogenous mRNA expression was evaluated. About half of the constructs gave greater than 50% silencing of SOD1 in HMNPs and 4 of those gave greater than 70% silencing (FIG. 7).

G. Construct Selection for In Vivo Studies

The top twelve constructs are selected which had a major effect on the target sequence and a minor effect on the cassette. These constructs packaged in AAV-rh10 capsids are formulated for injection and administered in mammals to study the in vivo effects of the constructs.

Example 9. In Vitro Study of Constructs

The 18 constructs and mCherry control described in Example 8D packaged in AAV2 were used for this study. For this study, HEK293T cells (Fisher Scientific, Cat. #HCL4517) in culture medium (500 ml of DMEM/F-12 GLUTAMAX™ supplement (Life Technologies, Cat #. 10565-018), 50 ml FBS (Life Technologies, Cat #. 16000-044, lot:1347556), 5 ml MEM Non-essential amino acids solution (100×) (Cat. #11140-050) and 5 ml HEPES (1M) (Life Technologies, Cat #. 15630-080)), U251MG cells (P18) (Sigma, Cat #. 09063001-1VL) in culture medium (500 ml of DMEM/F-12 GLUTAMAX™ supplement (Life Technologies, Cat #. 10565-018), 50 ml FBS (Life Technologies, Cat #. 16000-044, lot:1347556), 5 ml MEM Non-essential amino acids solution (100×) (Cat. #11140-050) and 5 ml HEPES (1M) (Life Technologies, Cat #. 15630-080)) or normal human astrocyte (HA) (Lonza, Cat #CC-2565) in culture medium (ABM Basal Medium 500 ml (Lonza, Cat #. CC-3186) supplemented with AGM SingleQuot Kit Suppl. & Growth Factors (Lonza, Cat #. CC-4123)) were used to test the constructs. HEK293T cells (5×10E4 cells/well in 96 well plate), U251MG cells (2×10E4 cells/well in 96 well plate) and HA cells (2×10E4 cells/well in 96 well plate) were seeded and the MOI used for infection of cells was 1.0E+05. After 48 hours the cells were analyzed and the results are shown in Table 13.

TABLE 13

Relative SOD1 mRNA level

| | Relative SOD1 mRNA Level (%) (Normalized to GAPDH) | | |
|---|---|---|---|
| Construct | HEK293T | U251MG | HA |
| VOYmiR-102.823 | 19.5 | 49.6 | 87.3 |
| VOYmiR-102.860 | 1.7 | 5.3 | 19.2 |
| VOYmiR-102.861 | 1.1 | 13.9 | 42.6 |
| VOYmiR-104.823 | 49.9 | 69.6 | 102.7 |
| VOYmiR-104.861 | 1.0 | 10.7 | 36.3 |
| VOYmiR-104.866 | 12.3 | 54.6 | 85.5 |
| VOYmiR-109.823 | 23.0 | 46.1 | 84.6 |
| VOYmiR-109.860 | 1.9 | 8.3 | 35.6 |
| VOYmiR-109.861 | 1.9 | 22.7 | 57.3 |
| VOYmiR-109.866 | 4.1 | 38.5 | 67.9 |
| VOYmiR-114.823 | 19.3 | 44.7 | 82.3 |
| VOYmiR-114.860 | 1.4 | 4.7 | 17.6 |
| VOYmiR-114.861 | 1.1 | 9.7 | 48.1 |
| VOYmiR-114.866 | 4.0 | 38.7 | 78.2 |
| VOYmiR-116.860 | 1.1 | 4.8 | 15.8 |
| VOYmiR-116.866 | 5.5 | 40.2 | 73.7 |
| VOYmiR-127.860 | 1.0 | 2.1 | 7.4 |
| VOYmiR-127.866 | 1.0 | 15.4 | 43.8 |
| mCherry | 100.0 | 100.2 | 100.1 |

Greater than 80% knock-down was seen in the HEK293T cells for most constructs. More than half of the constructs showed greater than 80% knock-down in the U251MG cells and in the HA cells.

Example 10. Dose Dependent SOD1 Lowering

Figure 8:
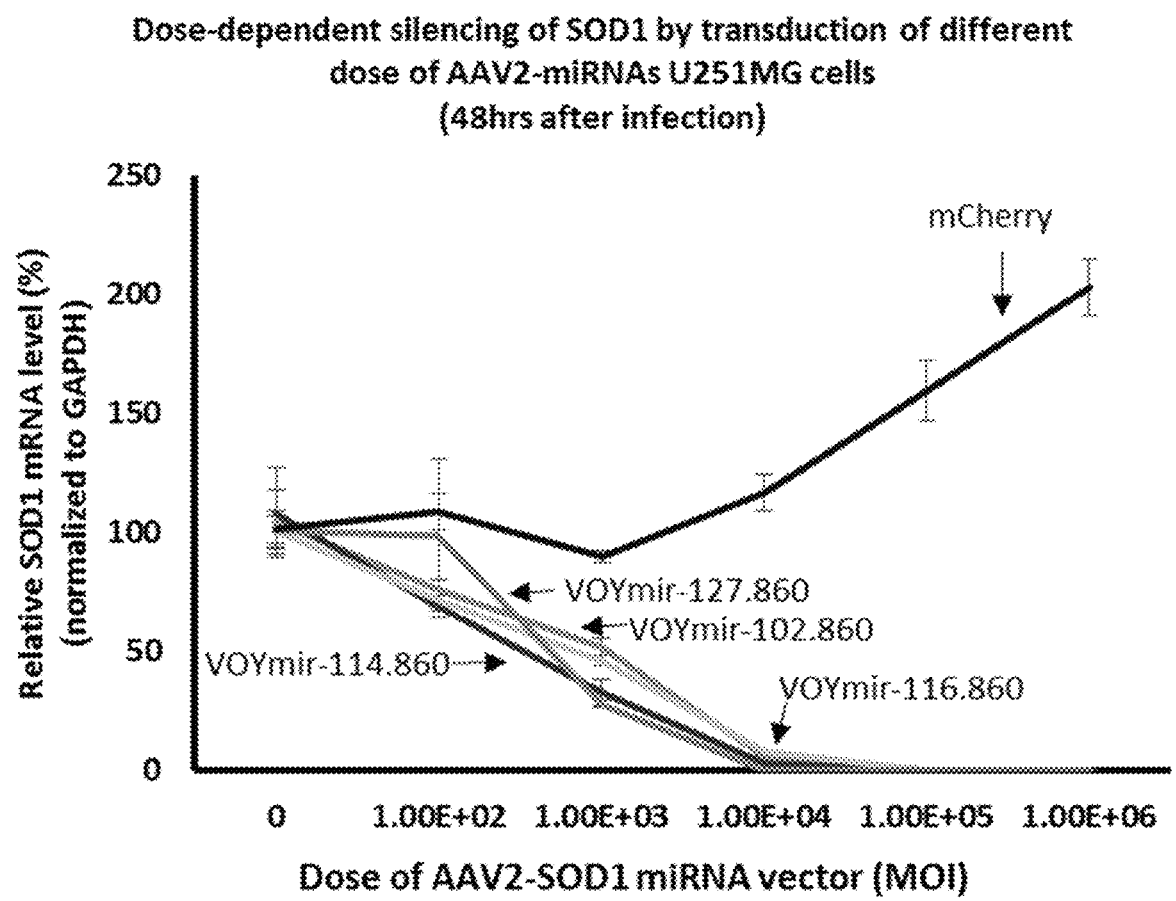
FIG. 8 is a chart showing the dose-dependent silencing of SOD1 in U251MG cells.
Figure 9:
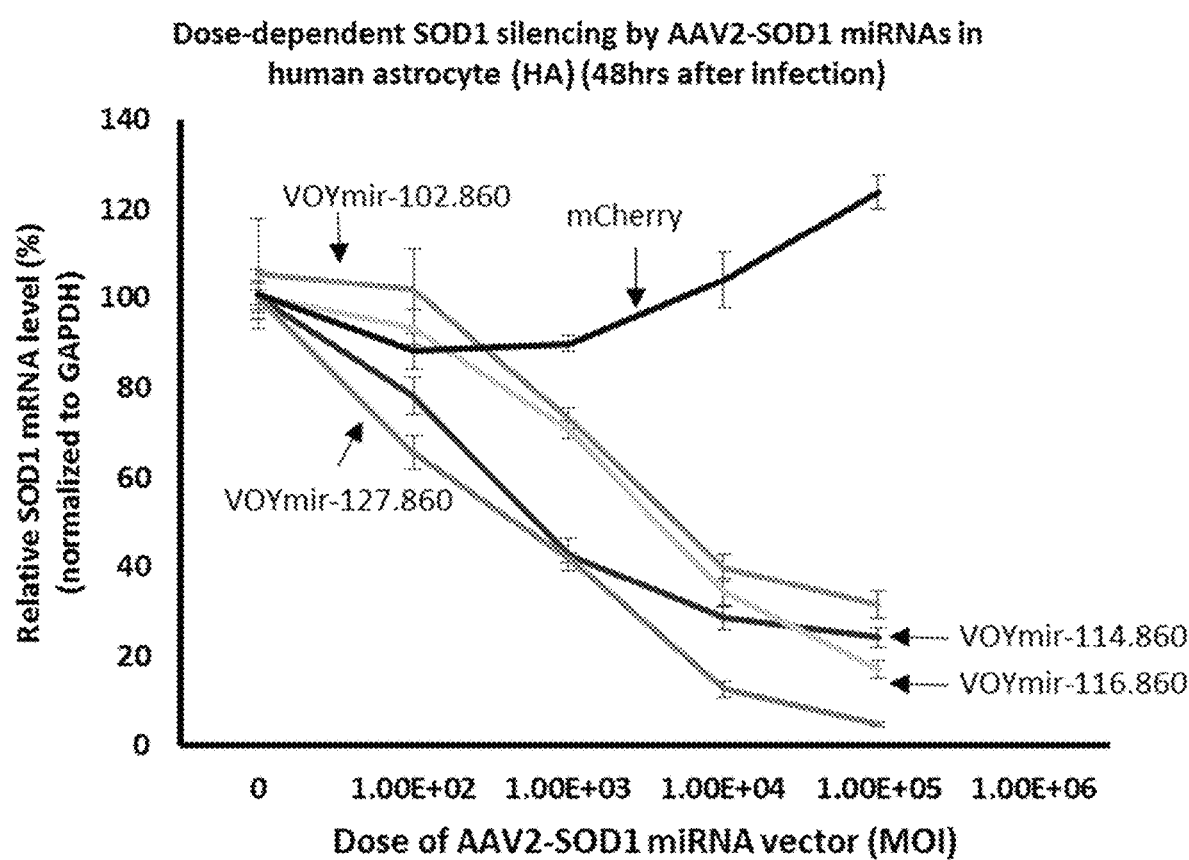
FIG. 9 is a chart showing the dose-dependent silencing of SOD1 in human astrocyte cells.

Four of the top 18 pri-miRNA constructs as described in Example 8E and a control of mCherry were transfected into a human astrocyte cell line (U251MG) or a primary human astrocyte (HA) at an MOI of 1.0E+02, 1.0E+03, 1.0E+04, 1.0E+05 or 1.0E+06. After 48 hours the endogenous mRNA expression was evaluated and the dose-dependent silencing are shown in FIG. 8 (U251MG) and FIG. 9 (HA). For all constructs, the increase in dose also correlated to an increase in the amount of SOD1 mRNA that was knocked-down.

Example 11. Time Course of SOD1 Knock-Down

Figure 10:
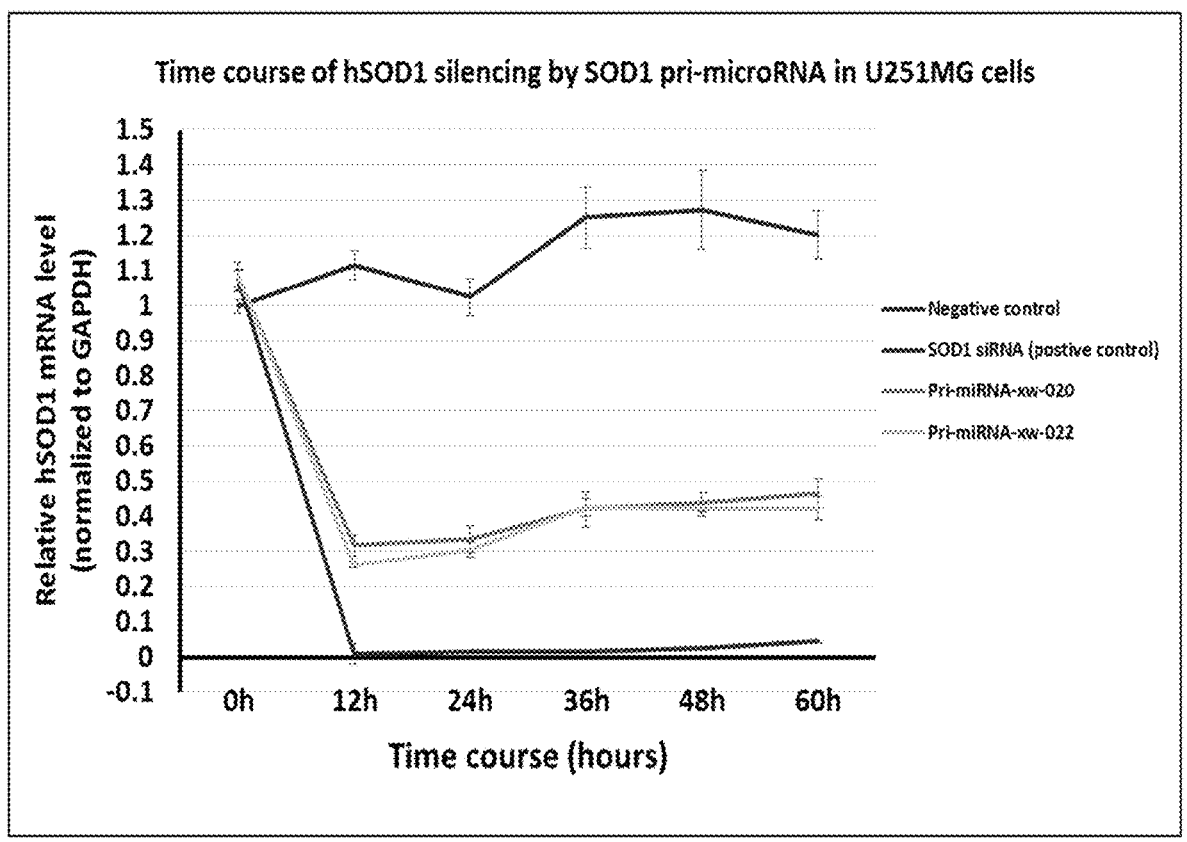
FIG. 10 is a chart showing the time course of the silencing of SOD1 in U251MG cells.

Two pri-miRNA constructs (VOYmiR-120 and VOYmiR-122), a negative control and a positive control of SOD1 siRNA were transfected into a human astrocyte cell line (U251MG). The relative SOD1 mRNA was determined for 60 hours as shown in FIG. 10. 70-75% knock-down of hSOD1 was seen for both pri-miR constructs after Nucleofector transfection, with the greatest knock-down seen in the 12-24 hour window.

Example 12. SOD1 Knock-Down and Stand Percentages

Figure 11A:
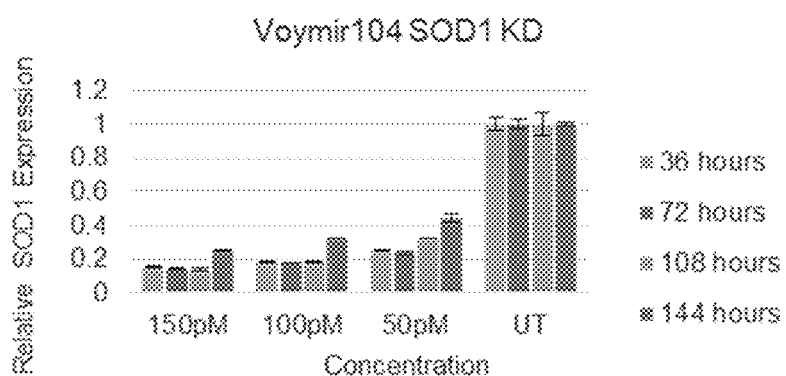
FIG. 11A, FIG. 11B and FIG. 11C are charts showing the dose-dependent effects of a construct.
Figure 11B:
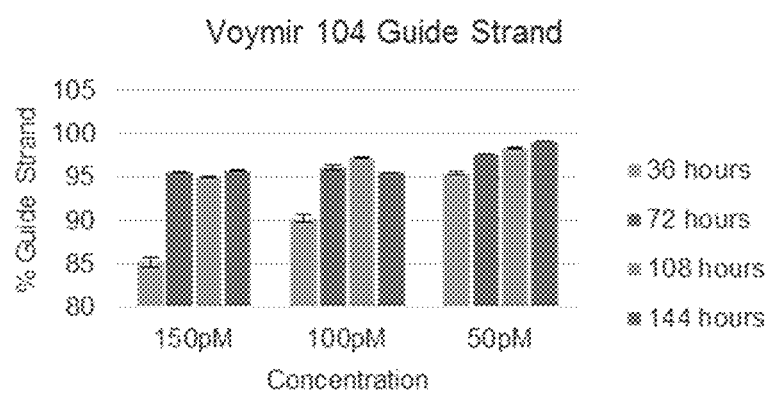
Figure 11C:
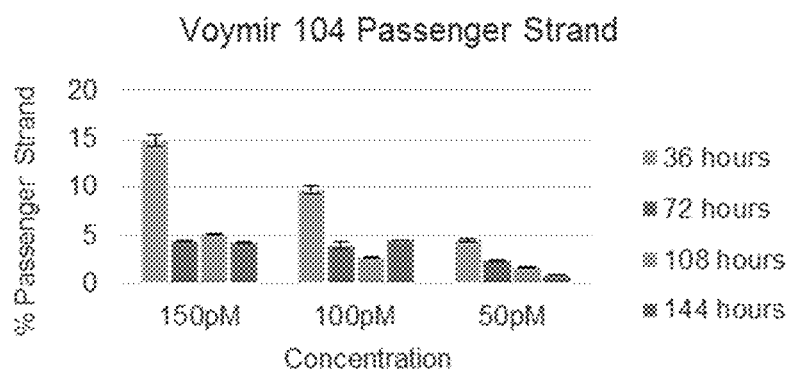

VOYmiR-104 was transfected into HeLa cells at a concentration of 50 pM, 100 pM and 150 pM and compared to untreated (UT) cells. The relative SOD1 mRNA, the percent of the guide strand and the percent of the passenger strand was determined at 36, 72, 108 and 144 hours as shown in FIGS. 11A-11C. The highest concentration (150 pM) showed the greatest reduction in expression, but all three doses showed a significant reduction in the expression of SOD1.

Example 13. Constructs Targeting SOD1

Constructs were designed for Dog SOD1 and the constructs are given in Table 14. Dog SOD1 is 100% conserved with human in the region targeted in the present invention. The passenger and guide sequences are described in the table. In Table 14, the "miR" component of the name of the sequence does not necessarily correspond to the sequence numbering of miRNA genes (e.g., dVOYmiR-102 is the name of the sequence and does not necessarily mean that miR-102 is part of the sequence).

TABLE 14

Dog sequences (5'-3')

| Name | Duplex ID | SS ID | Passenger | Passenger SEQ ID | AS ID | Guide | Guide SEQ ID |
|---|---|---|---|---|---|---|---|
| dVOYmiR-102.788 | D-2974 | 7795 | GCAGGUCC UCACUUUA AUGCC | 385 | 7796 | GAUUAAAG UGAGGACC UGCUU | 386 |
| dVOYmiR-102.805 | D-2975 | 7797 | GGCAAUGU GACUGCUG ACCCC | 387 | 7798 | UGUCAGCA GUCACAUU GCCUU | 388 |
| dVOYmiR-104.788 | D-2976 | 7799 | GCAGGUCC UCACUUUA AUUCC | 389 | 7796 | GAUUAAAG UGAGGACC UGCUU | 386 |
| dVOYmiR-104.805 | D-2977 | 7800 | GGCAAUGU GACUGCUG AUGCC | 390 | 7798 | UGUCAGCA GUCACAUU GCCUU | 388 |
| dVOYmiR-109.788 | D-2978 | 7801 | GCAGGUCC UCACUUUA AUCCC | 391 | 7796 | GAUUAAAG UGAGGACC UGCUU | 386 |
| dVOYmiR-109.805 | D-2979 | 7802 | GGCAAUGU GACUGCUG AUACC | 392 | 7798 | UGUCAGCA GUCACAUU GCCUU | 388 |
| dVOYmiR-114.788 | D-2980 | 7803 | GCAGGUCC UGACUUUA AUCCC | 393 | 7796 | GAUUAAAG UGAGGACC UGCUU | 386 |
| dVOYmiR-114.805 | D-2981 | 7804 | GGCAAUGU GUCUGCUG AUACC | 394 | 7798 | UGUCAGCA GUCACAUU GCCUU | 388 |
| dVOYmiR-116.788 | D-2982 | 7801 | GCAGGUCC UCACUUUA AUCCC | 391 | 7796 | GAUUAAAG UGAGGACC UGCUU | 386 |
| dVOYmiR-116.805 | D-2983 | 7802 | GGCAAUGU GACUGCUG AUACC | 392 | 7798 | UGUCAGCA GUCACAUU GCCUU | 388 |
| dVoymiR-127.788 | D-2984 | 7801 | GCAGGUCC UCACUUUA AUCCC | 391 | 7805 | GAUUAAAG UGAGGACC UGCUUU | 395 |
| dVoymiR-127.805 | D-2985 | 7802 | GGCAAUGU GACUGCUG AUACC | 392 | 7806 | UGUCAGCA GUCACAUU GCCUUU | 396 |

Example 14. Effect of the Position of Modulatory Polynucleotides

A. Effect on Viral Titers

Figure 12:
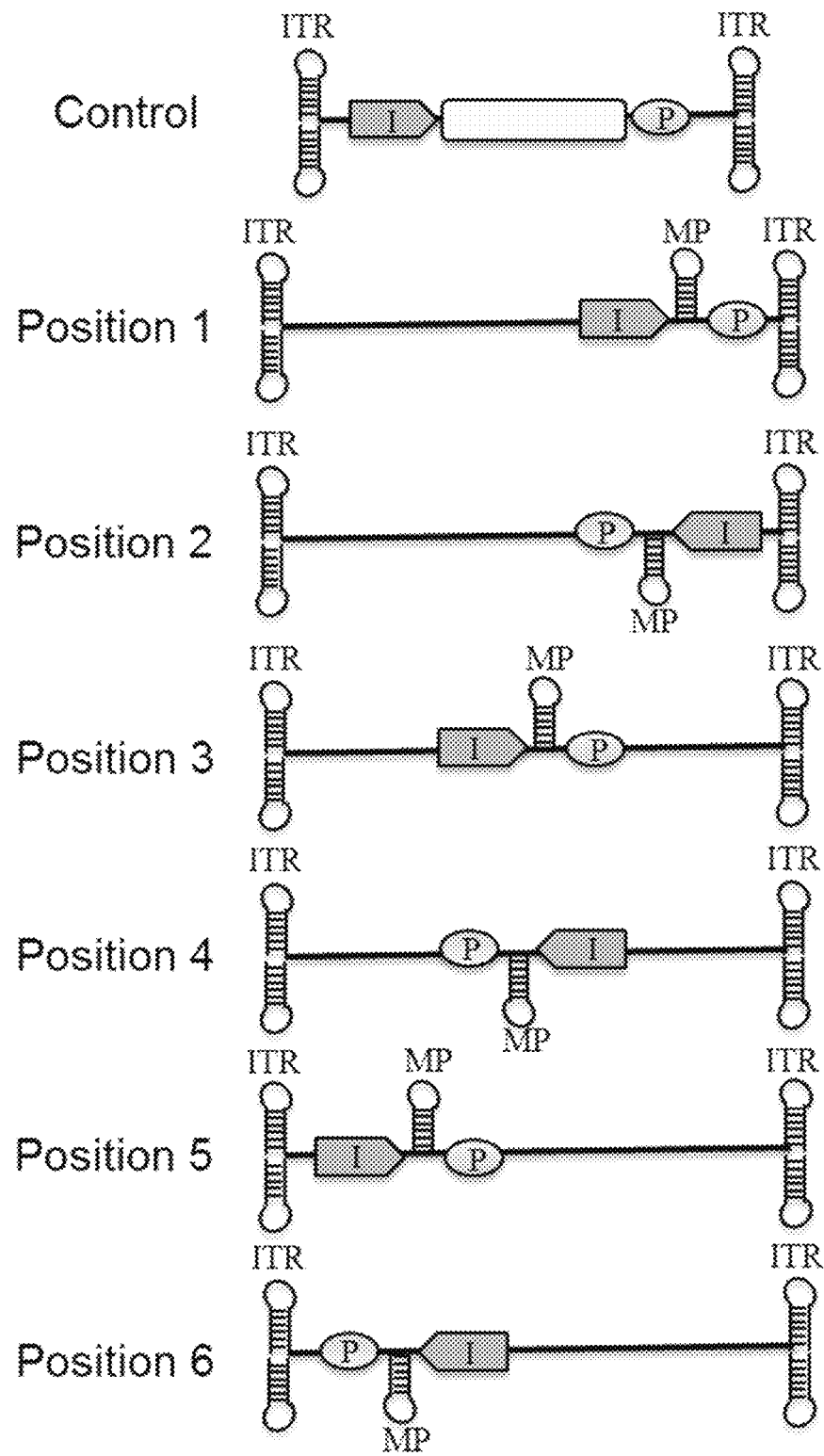
FIG. 12 is a diagram showing the location of the modulatory polynucleotide (MP) in relation to the ITRs, the intron (I) and the polyA (P).

A siRNA molecule (VOYmiR-114 or VOYmiR-126) was inserted into an expression vector (genome size 2400 nucleotides; scAAV) at six different locations as shown in FIG. 12. In FIG. 12, "ITR" is the inverted terminal repeat, "I" represents intron, "P" is the polyA and "MP" is the modulatory polynucleotide comprising the siRNA molecule. The viral titers were evaluated using TaqMan PCR for the 6 position and for a control (construct without a modulatory polynucleotide; scAAV) and the results are shown in Table 15.

TABLE 15

Viral Titers

| siRNA Molecule | siRNA Molecule Position | Virus Titer (VG per 15-cm dish) |
|---|---|---|
| VOYmiR-114 | Position 1 | 5.5E+10 |
| VOYmiR-114 | Position 2 | 5.5E+10 |
| VOYmiR-114 | Position 3 | 4.5E+10 |
| VOYmiR-114 | Position 4 | 3.7E+10 |
| VOYmiR-114 | Position 5 | 6.5E+10 |
| VOYmiR-114 | Position 6 | 2.5E+10 |
| VOYmiR-126 | Position 1 | 1.6E+10 |
| VOYmiR-126 | Position 2 | 3.2E+10 |
| VOYmiR-126 | Position 3 | 6.0E+10 |
| VOYmiR-126 | Position 4 | 1.6E+10 |
| VOYmiR-126 | Position 5 | 9.5E+09 |
| VOYmiR-126 | Position 6 | 6.0E+10 |
| — | Control | 2.1E+11 |

B. Effect on Genome Integrity

A siRNA molecule (VOYmiR-114) was inserted into an expression vector (genome size 2400 nucleotides; scAAV) at six different locations and a control without a modulatory polynucleotide (scAAV) as shown in FIG. 12. In FIG. 12, "ITR" is the inverted terminal repeat, "I" represents intron, "P" is the polyA and "MP" is the modulatory polynucleotide comprising the siRNA molecule. Viral genomes were extracted from purified AAV preparations and run on a neutral agarose gel. Truncated genomes were seen in all constructs and the approximate percent of the truncated genomes (percent of the total) is shown in Table 16.

TABLE 16

Truncated Genomes

| Construct | % of total |
|---|---|
| Position 1 | 50 |
| Position 2 | 41 |
| Position 3 | 49 |
| Position 4 | 34 |
| Position 5 | 33 |
| Position 6 | 59 |
| Control | 9 |

Position 6 had the greatest number of truncated genomes with Position 4 and 5 having the least amount of truncated genomes.

C. Effect on Knock-Down Efficiency

A siRNA molecule (VOYmiR-114) was inserted into an expression vector (AAV2) (genome size 2400 nucleotides; scAAV) at six different locations as shown in FIG. 12. In FIG. 12, "ITR" is the inverted terminal repeat, "I" represents intron, "P" is the polyA and "MP" is the modulatory polynucleotide comprising the siRNA molecule. Transduction of HeLa cells was conducted at $1\times10^4$ vg/cell, $1\times10^3$ vg/cell and $1\times10^2$ vg/cell. The SOD1 mRNA expression (as % of control (eGFP)) was determined 72 hours post-infection and the results are shown in Table 17.

TABLE 17

SOD1 Expression

| Construct | SOD1 mRNA expression (% of control) | | |
|---|---|---|---|
| | $1 \times 10^4$ vg/cell | $1 \times 10^3$ vg/cell | $1 \times 10^2$ vg/cell |
| Position 1 | 40 | 59 | 69 |
| Position 2 | 31 | 46 | 75 |

TABLE 17-continued

SOD1 Expression

| Construct | SOD1 mRNA expression (% of control) | | |
|---|---|---|---|
| | $1 \times 10^4$ vg/cell | $1 \times 10^3$ vg/cell | $1 \times 10^2$ vg/cell |
| Position 3 | 50 | 66 | 81 |
| Position 4 | 21 | 34 | 55 |
| Position 5 | 49 | 52 | 67 |
| Position 6 | 31 | 37 | 62 |
| Control (eGFP) | 100 | 100 | 94 |

Position 3 had the highest SOD1 mRNA expression (as % of control) and Position 4 had the lowest SOD1 mRNA expression (as % of control).

Example 15. Effect of Genome Size

A. Effect on Viral Titers

A siRNA molecule (VOYmiR-114) was inserted into an expression vector (genome size 2 kb; scAAV) at positions 1, 2, 5 and 6 as shown in FIG. 12. In FIG. 12, "ITR" is the inverted terminal repeat, "I" represents intron, "P" is the polyA and "MP" is the modulatory polynucleotide comprising the siRNA molecule. A double stranded control without a siRNA molecule (genome size 1.6 kb; scAAV ctrl) and a double stranded expression vector (scAAV miR114; ITR (105 nucleotide)—Promoter (~900 nucleotides)—modulatory polynucleotide comprising the siRNA molecule (158 nucleotides)—polyA sequence (127 nucleotides) and ITR) was compared as well as a control (eGFP; scAAV) with no siRNA molecule. The viral titers were evaluated using TaqMan PCR and the results are shown in Table 18.

TABLE 18

Viral Titers

| Construct | Size | Virus Titer (VG per 15-cm dish) |
|---|---|---|
| Position 1 | 2 kb | 9.5E+10 |
| Position 2 | 2 kb | 1.2E+11 |
| scAAV miR114 | 1.6 kb | 1.1E+11 |
| Position 5 | 2 kb | 2.4E+10 |
| Position 6 | 2 kb | 1.1E+11 |
| Control | 2 kb | 2.2E+11 |

The lowest viral titers were seen with the position 5 construct and the greatest was with the position 2 construct.

B. Effect on Genome Integrity

A siRNA molecule (VOYmiR-114) was inserted into an expression vector (genome size 2 kb; scAAV) at positions 1, 2, 5 and 6 as shown in FIG. 12. In FIG. 12, "ITR" is the inverted terminal repeat, "I" represents intron, "P" is the polyA and "MP" is the modulatory polynucleotide comprising the siRNA molecule. A double stranded control without a siRNA molecule (genome size 1.6 kb; scAAV ctrl) and a double stranded expression vector (scAAV miR114; ITR (105 nucleotide)—Promoter (~900 nucleotides)—modulatory polynucleotide comprising the siRNA molecule (158 nucleotides)—polyA sequence (127 nucleotides) and ITR) was compared as well as a control (eGFP; scAAV) with no siRNA molecule. Truncated genomes were seen in all constructs and the approximate percent of the truncated genomes (percent of the total) is shown in Table 19.

TABLE 19

| Truncated Genomes | | |
|---|---|---|
| Construct | Size | % of total |
| Position 1 | 2 kb | 34 |
| Position 2 | 2 kb | 30 |
| scAAV miR114 | 1.6 kb | 20 |
| Position 5 | 2 kb | 21 |
| Position 6 | 2 kb | 46 |
| Control | 2 kb | 5 |

All constructs were determined to have some truncated genomes.

An additional study was conducted to determine the effect of different siRNA molecules. VOYmiR-114 and VOYmiR-126 were inserted into separate expression vectors (genome size 1.6 kb; scAAV) at position 3 as shown in FIG. 12. In FIG. 12, "ITR" is the inverted terminal repeat, "I" represents intron, "P" is the polyA and "MP" is the modulatory polynucleotide comprising the siRNA molecule. For the VOYmiR-114 construct the distance between the 5' end of the vector genome (1526 nucleotides) and the center of the modulatory polynucleotide (middle of the flexible loop) is 1115 nucleotides. For the VOYmiR-126 construct the distance between the 5' end of the vector genome (1626 nucleotides) and the center of the modulatory polynucleotide (middle of the flexible loop) is 1164 nucleotides.

For the VOYmiR-114 construct, the viral titer (VG per 15-cm dish) was about 1.1E+11. For the VOYmiR-126 construct, the intron probe viral titer (VG per 15-cm dish) was about 1.2E+12. The control was about 2.1E+11 (VG per 15-cm dish). VOYmir-114 had about 20% truncated genomes, VOYmiR-126 has about 15% truncated genomes and the control had about 5% truncated genomes.

Example 16. Effect of Single Stranded Constructs

A. Effect on Viral Titers

A siRNA polynucleotide (VOYmiR-114) was inserted into an expression vector (genome size 4.7 kb; ssAAV) at positions 1, 3 and 5 as shown in FIG. 12 and there was a control also tested without a siRNA polynucleotide (genome size 2 kb; ssAAV). In FIG. 12, "ITR" is the inverted terminal repeat, "I" represents intron, "P" is the polyA and "MP" is the modulatory polynucleotide comprising the siRNA molecule. The viral titers were evaluated using TaqMan PCR and the results are shown in Table 20.

TABLE 20

| Viral Titers | |
|---|---|
| Construct | Virus Titer (VG per 15-cm dish) |
| Position 1 | 5.0E+11 |
| Position 3 | 7.5E+11 |
| Position 5 | 3.5E+11 |
| Control | 2.5E+11 |

Position 3 showed the greatest viral titers followed by position 1 and then position 5.

B. Effect on Genome Integrity

A siRNA molecule (VOYmiR-114) was inserted into an expression vector (genome size 4.7 kb; ssAAV) at positions 1, 3 and 5 as shown in FIG. 12 and there was a control also tested without a modulatory polynucleotide (genome size 2 kb; ssAAV). In FIG. 12, "ITR" is the inverted terminal repeat, "I" represents intron, "P" is the polyA and "MP" is the modulatory polynucleotide comprising the siRNA molecule. Viral genomes were extracted from purified AAV preparations and run on a neutral agarose gel. Truncated genomes were seen in all constructs and the approximate percent of the truncated genomes (percent of the total) is shown in Table 21.

TABLE 21

| Truncated Genomes | |
|---|---|
| Construct | % of total |
| Position 1 | 48 |
| Position 3 | 30 |
| Position 5 | 72 |
| Control | 0 |

Position 5 had the greatest number of truncated genomes with Position 3 having the least amount of truncated genomes.

C. Effect on Knock-Down Efficiency

A siRNA molecule (VOYmiR-114) was inserted into an expression vector (genome size 4.7 kb; ssAAV) at positions 1, 3 and 5 as shown in FIG. 12 and there was a single stranded control without a siRNA molecule (genome size 2 kb; ssAAV ctrl), a double stranded control without a siRNA molecule (genome size 1.6 kb; scAAV ctrl) and a double stranded expression vector (genome size 2.4 kb; scAAV miR114) with a siRNA molecule. In FIG. 12, "ITR" is the inverted terminal repeat, "I" represents intron, "P" is the polyA and "MP" is the modulatory polynucleotide comprising the siRNA molecule. Transduction of HeLa cells was conducted at $1\times10^4$ vg/cell, $1\times10^3$ vg/cell and $1\times10^2$ vg/cell. The SOD1 mRNA expression (as % of control (eGFP)) was determined 72 hours post-infection and the results are shown in Table 22.

TABLE 22

| SOD1 Expression | | | |
|---|---|---|---|
| | SOD1 mRNA expression (% of control) | | |
| Construct | $1 \times 10^4$ vg/cell | $1 \times 10^3$ vg/cell | $1 \times 10^2$ vg/cell |
| Position 1 | 62 | 85 | 87 |
| Position 3 | 77 | 93 | 99 |
| Position 5 | 59 | 82 | 84 |
| ssAAV ctrl | 100 | 101 | 108 |
| scAAV ctrl | 95 | 97 | 102 |
| scAAV miR114 | 23 | 33 | 62 |

Position 3 had the highest SOD1 mRNA expression (as % of control), then position 1 and the single stranded constructs with the lowest SOD1 mRNA expression (as % of control) was Position 5. None of the single stranded constructs had knock-down efficiency that was as low as the double stranded control with a siRNA polynucleotide.

Example 17. SOD1 Knock-Down In Vivo

To evaluate the in vivo biological activity of pri-miRNAs, self-complementary pri-miRNAs (VOYmiR-114.806, VOYmiR127.806, VOYmiR102.860, VOYmiR109.860, VOYmiR114.860, VOYmiR116.860, VOYmiR127.860, VOYmiR102.861, VOYmiR104.861, VOYmiR109.861, VOYmiR114.861, VOYmiR109.866, VOYmiR116.866, or VOYmiR127.866) are packaged in AAV-DJ with a CBA promoter.

In mice, these packaged pri-miRNAs or a control of vehicle only (phosphate-buffered saline with 5% sorbitol and 0.001% F-68) were administered by a 10-minute intrastriatal infusion. Female or male Tg(SOD1)3Cje/J mice (Jackson Laboratory, Bar Harbor, Me.), which express human SOD1, and of approximately 20-30 g body weight, receive unilateral injections of 5 uL test article which is targeted to the striatum (anteroposterior+0.5 mm, mediolateral+2 mm, relative to bregma; dorsoventral 3.8 mm, relative to skull surface). Test articles are injected (5 animals per test article) at 0.5 uL/min. using pre-filled, pump-regulated Hamilton micro-syringes (1701 model, 10 μl) with 33-gauge needles. At 1, 2, 3, 4 or 6 weeks following the injection, animals are sacrificed, brains are removed, and ipsilateral striata encompassing the infusion site from a 1 mm coronal slab, as well as striatal tissue from the adjacent 1 mm coronal slabs are dissected and flash frozen. Mouse tissue samples are lysed, and human SOD1 protein levels, and SOD1 and mouse GAPDH (mGAPDH) mRNA levels are quantified. SOD1 protein levels are quantified by ELISA (eBioscience (Affymetrix, San Diego, Calif.)), and total protein levels are quantified by BCA analysis (ThermoFisher Scientific, Waltham, Mass.). For each tissue sample, the level of SOD1 protein normalized to total protein is calculated as an average of 2 determinations. These normalized SOD1 protein levels are further normalized to the vehicle group, then averaged to obtain a group (treatment) average. SOD1 and mGAPDH mRNA levels are quantified by qRT-PCR. For each tissue sample, the ratio of SOD1/mGAPDH (normalized SOD1 mRNA level) is calculated as an average of 3 determinations. These ratios are then averaged to obtain a group (treatment) average. These group averages are further normalized to the vehicle group.

In non-human primates, test articles ($1 \times 10^{13}$-$3 \times 10^{13}$ vg of pri-miRNA packaged in AAV-DJ with a CBA promoter) or vehicle are administered by intrathecal lumbar bolus. Female cynomolgus monkeys (*Macaca fascicularis*, CR Research Model Houston, Houston, Tex.) of approximately 2.5-8.5 kg body weight, receive implanted single intrathecal catheters with the tip of the catheter located at the lumbar spine. Test articles are administered (4 animals per test article) comprising three 1 mL bolus injections (1 mL/minute), at approximately 60-minute intervals. At 4 to 6 weeks following the administration, animals are sacrificed, and selected tissues harvested for bioanalytical and histological evaluation. SOD1 protein and mRNA levels are assessed for suppression after treatment with pri-miRNA packaged in AAV-DJ with a CBA promoter, relative to the vehicle group.

Example 18. SOD1 Knock-Down In Vivo Using VOYmiR-114.806

In Tg(SOD1)3Cje/J mice, VOYmiR-114.806 packaged in AAVDJ with a CBA promoter as described in Example 17. The mice were administered by unilateral intrastriatal administration a dose of $3.7 \times 10^9$ vg. After 1 or 2 weeks, there was no significant reduction in normalized SOD1 protein levels; normalized SOD1 protein levels were 98±11% (standard deviation) and 98±10% of the vehicle control group after 1 and 2 weeks, respectively. By week 3, VOYmiR-114.806 reduced the normalized SOD1 protein level to 84±9.0% of the vehicle control group, which was statistically significant ($p<0.05$, One-way ANOVA with Dunnett's post-hoc analysis). By weeks 4 and 6, VOYmiR-114.806 reduced the normalized SOD1 protein level to 73±7.9% ($p<0.0001$) and 75±7.4% ($p<0.0001$), respectively, of the vehicle control group. These results demonstrate that VOYmiR-114.806 packaged in AAV-DJ with a CBA promoter, is efficacious in vivo in down-modulating SOD1 protein levels. In addition, these results demonstrate that a total intrastriatal dose as low as $3.7 \times 10^9$ vg of VOYmiR-114.806 packaged in AAVDJ with a CBA promoter resulted in significant down-modulation of SOD1 protein levels.

We claim:

1. An adeno-associated viral (AAV) vector genome comprising a nucleic acid sequence positioned between two inverted terminal repeats (ITRs); wherein said nucleic acid sequence encodes a sense strand sequence and an antisense strand sequence of an siRNA duplex; wherein the antisense strand sequence comprises nucleotides 1-18 of SEQ ID NO. 261; and wherein the sense strand sequence comprises nucleotides 1-17 of SEQ ID NO. 93.

2. The AAV vector genome of claim 1, wherein the sense strand sequence and the antisense strand sequence are, independently, between 19-22 nucleotides in length.

3. The AAV vector genome of claim 1, wherein the antisense strand sequence comprises nucleotides 1-19 of SEQ ID NO. 261.

4. The AAV vector genome of claim 1, wherein the sense strand sequence comprises nucleotides 1-18 of SEQ ID NO. 93.

5. The AAV vector genome of claim 1, wherein the sense strand sequence comprises nucleotides 1-19 of SEQ ID NO. 93.

6. The AAV vector genome of claim 1, wherein the antisense strand sequence comprises nucleotides 1-19 of SEQ ID NO. 261, and wherein the sense strand sequence comprises nucleotides 1-18 of SEQ ID NO. 93.

7. The AAV vector genome of claim 6, wherein the sense strand sequence comprises nucleotides 1-19 of SEQ ID NO. 93.

8. The AAV vector genome of claim 7, wherein the sense strand sequence and the antisense strand sequence are, independently, between 19-22 nucleotides in length.

9. The AAV vector genome of claim 1, wherein the sense strand sequence comprises nucleotides 1-18 of SEQ ID NO. 92.

10. The AAV vector genome of claim 1, wherein the sense strand sequence comprises nucleotides 1-19 of SEQ ID NO. 92.

11. The AAV vector genome of claim 1, wherein the antisense strand sequence comprises nucleotides 1-19 of SEQ ID NO. 261, and wherein the sense strand sequence comprises nucleotides 1-18 of SEQ ID NO. 92.

12. The AAV vector genome of claim 11, wherein the sense strand sequence comprises nucleotides 1-19 of SEQ ID NO. 92.

13. The AAV vector genome of claim 12, wherein the sense strand sequence and the antisense strand sequence are, independently, between 19-22 nucleotides in length.

14. The AAV vector genome of claim 1, wherein at least one of the sense strand sequence and the antisense strand sequence comprise a 3' overhang of at least 1 nucleotide.

15. The AAV vector genome of claim 14, wherein the 3' overhang is a deoxyribonucleotide.

16. An AAV particle comprising the AAV vector genome of claim 1.

17. The AAV particle of claim 16, comprising an AAVrh10 capsid.

18. A method for inhibiting the expression of SOD1 gene in a cell comprising administering to the cell a composition comprising an AAV particle of claim 16.

19. The method of claim 18, wherein the cell is a mammalian motor neuron or astrocyte.

20. A method for treating amyotrophic lateral sclerosis (ALS) in a subject, the method comprising administering to the subject a therapeutically effective amount of a composition comprising an AAV particle of claim 16.

21. The method of claim 20, wherein the expression of SOD1 mRNA in a target cell is inhibited or suppressed by about 50% to about 93%.

22. The method of claim 20, wherein the administration of the composition comprises intraparenchymal spinal administration.

23. An siRNA duplex comprising a sense strand sequence and an antisense strand sequence; wherein the antisense strand sequence comprises nucleotides 1-18 of SEQ ID NO. 261; and wherein the sense strand sequence comprises nucleotides 1-17 of SEQ ID NO. 93.

24. The siRNA duplex of claim 23, wherein the antisense strand sequence comprises nucleotides 1-19 of SEQ ID NO. 261.

25. The siRNA duplex of claim 23, wherein the sense strand sequence comprises nucleotides 1-19 of SEQ ID NO. 93.

26. The siRNA duplex of claim 23, wherein the antisense strand sequence comprises nucleotides 1-19 of SEQ ID NO. 261, and wherein the sense strand sequence comprises nucleotides 1-19 of SEQ ID NO. 93.

27. The siRNA duplex of claim 26, wherein the sense strand sequence and the antisense strand sequence are, independently, between 19-22 nucleotides in length.

28. The siRNA duplex of claim 23, wherein the sense strand sequence comprises nucleotides 1-19 of SEQ ID NO. 92.

29. The siRNA duplex of claim 23, wherein the antisense strand sequence comprises nucleotides 1-19 of SEQ ID NO. 261, and wherein the sense strand sequence comprises nucleotides 1-19 of SEQ ID NO. 92.

30. The siRNA duplex of claim 29, wherein the sense strand sequence and the antisense strand sequence are, independently, between 19-22 nucleotides in length.

* * * * *